US012187796B2

(12) United States Patent
Crawley et al.

(10) Patent No.: US 12,187,796 B2
(45) Date of Patent: Jan. 7, 2025

(54) ILT3-BINDING AGENTS AND METHODS OF USE THEREOF

(71) Applicant: NGM Biopharmaceuticals, Inc., South San Francisco, CA (US)

(72) Inventors: Suzanne Christine Crawley, Brisbane, CA (US); Jer-Yuan Hsu, San Bruno, CA (US); Daniel David Kaplan, San Mateo, CA (US); Betty Chan Li, Millbrae, CA (US); Vicky Yi-Bing Lin, Cupertino, CA (US); Seth Malmersjö, Menlo Park, CA (US); Kevin James Paavola, San Francisco, CA (US); Julie Michelle Roda, Pacifica, CA (US); Yan Wang, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 18/364,285

(22) Filed: Aug. 2, 2023

(65) Prior Publication Data
US 2024/0043533 A1 Feb. 8, 2024

Related U.S. Application Data

(62) Division of application No. 17/125,734, filed on Dec. 17, 2020, now Pat. No. 11,760,802.

(60) Provisional application No. 62/950,434, filed on Dec. 19, 2019.

(51) Int. Cl.
*A61K 39/00* (2006.01)
*A61P 35/00* (2006.01)
*C07K 16/28* (2006.01)

(52) U.S. Cl.
CPC .... *C07K 16/2803* (2013.01); *A61K 2039/505* (2013.01); *C07K 2317/565* (2013.01)

(58) Field of Classification Search
CPC .......... C07K 16/2802; A61K 2039/505; A61P 35/00
See application file for complete search history.

(56) References Cited

U.S. PATENT DOCUMENTS

| | | | |
|---|---|---|---|
| 7,777,008 B2 | 8/2010 | Ponath et al. |
| 7,834,157 B2 | 11/2010 | Cosman |
| 9,696,312 B2 | 7/2017 | Suciu-Foca et al. |
| 10,428,143 B2 | 10/2019 | Krummel et al. |
| 2004/0241167 A1 | 12/2004 | Sucio-Foca et al. |
| 2007/0041982 A1 | 2/2007 | Ponath et al. |
| 2007/0071675 A1 | 3/2007 | Wu et al. |
| 2007/0166318 A1 | 7/2007 | Macina et al. |
| 2009/0202544 A1 | 8/2009 | Sucio-Foca et al. |
| 2009/0226457 A1 | 9/2009 | Cosman |
| 2009/0280109 A1 | 11/2009 | Sucio-Foca et al. |
| 2011/0034675 A1 | 2/2011 | Ponath et al. |
| 2015/0110714 A1 | 4/2015 | Sucio-Foca et al. |
| 2015/0139986 A1 | 5/2015 | Ponath et al. |
| 2015/0174203 A1 | 6/2015 | Chen et al. |
| 2016/0244525 A1 | 8/2016 | Yin et al. |
| 2017/0291946 A1 | 10/2017 | Krummel et al. |
| 2017/0327591 A1 | 11/2017 | Sucio-Foca et al. |
| 2018/0086829 A1 | 3/2018 | Zhang et al. |
| 2018/0177847 A1 | 6/2018 | Chen et al. |
| 2018/0201676 A1 | 7/2018 | Blaser et al. |
| 2019/0153093 A1 | 5/2019 | Meehl et al. |
| 2019/0241655 A1 | 8/2019 | Cua et al. |
| 2019/0255107 A1 | 8/2019 | Kuchroo et al. |
| 2022/0324950 A1 | 10/2022 | Takai et al. |

FOREIGN PATENT DOCUMENTS

| | | |
|---|---|---|
| DE | 3743402 A1 | 7/1988 |
| EP | 2041180 B1 | 1/2014 |
| EP | 1907001 B1 | 7/2015 |
| EP | 2937360 A1 | 10/2015 |
| EP | 3265113 A2 | 1/2018 |
| JP | S63-219393 A | 9/1988 |
| JP | 2018-025554 A | 2/2018 |
| JP | 2008-514621 A | 5/2018 |
| WO | WO 2001/077342 A1 | 10/2001 |
| WO | WO 2003/000199 A2 | 1/2003 |
| WO | WO 2006/036813 A2 | 4/2006 |
| WO | WO 2006/036813 A3 | 4/2006 |
| WO | WO 2014/055897 A2 | 4/2014 |
| WO | WO 2014/116846 A2 | 7/2014 |
| WO | WO 2014/179664 A2 | 11/2014 |
| WO | WO 2016/144728 A2 | 9/2016 |
| WO | WO 2017/069958 A2 | 4/2017 |
| WO | WO 2018/022881 A2 | 2/2018 |
| WO | WO 2018/067991 A1 | 4/2018 |
| WO | WO 2018/089300 A1 | 5/2018 |
| WO | WO 2018/148494 A1 | 8/2018 |
| WO | WO 2018/234367 A1 | 12/2018 |

(Continued)

OTHER PUBLICATIONS

Almagro et al., 2008, "Humanitzation of Antibodies", Front Biosci. 13:1619-1633.
Brandish et al., "Antibodies to IL T3 (LILRB4) abrogate myeloid immunosuppression and combine with PD1 blockade to enable T cell activation and function", Journal for Immuno Therapy of Cancer, 2019, 7(Suppl 1): 283, p. 137 of 237.
Carsons, 1987, "High Levels of Fibronectin Fragments in the Plasma of a Patient with Active Systemic Lupus Erythematosus," The Journal of Rheumatology, 14(5):1052-1054.
Cella et al., "A Novel Inhibitory Receptor (IL T3) Expressed on Monocytes, Macrophages, and Dendritic Cells Involved in Antigen Processing", J. Exp. Med., May 19, 1997, 185(10): 1743-1751.

(Continued)

*Primary Examiner* — Aurora M Fontainhas
*Assistant Examiner* — Jennifer A Benavides
(74) *Attorney, Agent, or Firm* — Jones Day

(57) ABSTRACT

The present disclosure provides binding agents, such as antibodies, that specifically bind ILT3, including human ILT3, as well as compositions comprising the binding agents, and methods of their use. The disclosure also provides related polynucleotides and vectors encoding the binding agents and cells comprising the binding agents.

26 Claims, 28 Drawing Sheets

Specification includes a Sequence Listing.

(56) References Cited

FOREIGN PATENT DOCUMENTS

| WO | WO 2019/099597 A2 | 5/2019 |
|---|---|---|
| WO | WO 2019/144052 A1 | 7/2019 |
| WO | WO 2019/185792 A1 | 10/2019 |
| WO | WO 2021/029318 A1 | 2/2021 |

OTHER PUBLICATIONS

Chen et al., 1995, "Enhancement and destruction of anitbody function by somatic mutation: unequal occurrence is controlled by V gene combinatorial assocations", EMBO J. 14(12):2784-2794.
Condurso et al., 2022, "483. Preclinical Evaluation of JTX-1484, an ANTILILRB4 Antagonist Antibody, for Reprogramming of Immunosuppressive Myeloid Cells", Journal for Immunotherapy of Cancer, Biomed Central, 10(2):A504.
Deng et al., A motif in LILRB2 critical for Angpt12 binding and activation, BLOOD, Aug. 7, 2014, vol. 124, No. 6, pp. 924-935.
Deng et al., LILRB4 signaling in leukemia cells mediates T cell suppression and tumor infiltration, Nature. Oct. 2018 ; 562(7728): 605-609.
Gribskov et al., "Sigma factors from *E. coli*, B. subtilis, phage SP01, and phage T4 are homologous proteins", Nucleic Acids Research, 1986, 14(16): 6745-6763.
Gui et al., 2019, "Disrupting LILRB4/APOE interaction by an efficacious humanized 3 antibody reverses T-cell suppression and blocks AML development", Cancer Immunol Res 1(8):1244-1257.
Harakal et al., 2016, "Regulatory T Cells Control Th2-Dominant Murine Autoimmune Gastritis", J. Immunol 197(1):27-41.
International Searching Authority, English translation of International Search Report and Written Opinion for International Patent Application No. PCT/JP2020/030175, Publication No. WO2021029318 A1, mailed Sep. 24, 2020 (13 pages).
International Searching Authority, International Search Report and Written Opinion for PCT International Application No. PCT/US2020/065642, Publication No. WO2021127200, mailed Apr. 6, 2021 (21 pages).
Kussie et al., 1994, "A single engineered amino acid substitution changes antibody fine specificity", J. Immunol 152(1):145-152.
Lefranc et al., "IMGT unique numbering for immunoglobulin and T cell receptor variable domains and Ig superfamily V-like domains", Developmental and Comparative Immunology 27 (2003) pp. 55-77.
Lu et al., Leukocyte Ig-like Receptor B4 (LILRB4) is a Potent Inhibitor of FcγRI-mediated Monocyte Activation via Dephosphorylation of Multiple Kinases, The Journal of Biological Chemistry, Dec. 11, 2009, 284(50): 34839-34848.
Meng et al., 2009, "Characterisation of fibronectin-mediated FAK signalling pathways in lung cancer cell migration and invasion," British Journal of Cancer, 101(2):327-334.
Mori et al., 2007, "Analysis of differentiation regulation mechanism of human osteoclast cells by LILRB4", The Journal of Japanese Orthopaedic Surgical Society, 81(8):S980, 1-Pf-2 (in Japanese with machine English translation).
Mori et al., 2008, "Inhibitory Immunoglobulin-Like Receptors LILRB and PIR-B Negatively Regulate Osteoclast Development,:" J. Immunol., 181(7):4742-4751.

NCBI Reference Sequence: XP_015297198.1, "Leukocyte immunoglobulin-like receptor subfamily B member 4 isoform X1 [Macaca fasscicularis]", Jan. 25, 2016.
Paavola et al., 2021, "The Fibronectin-ILT3 Interaction Functions as a Stromal Checkpoint that Suppreses Myeloid Cells", Cancer Immunology Research 9:1283-1297.
Penna et al., "Expression of the inhibitory receptor ILT3 on dendritic cells is dispensable for induction of CD4+Foxp3+ regulatory T cells by 1,25-dihydroxyvitamin D3", Blood, 2005, 106(10):3490-3497.
Przybysz et al., 2013, "Fibronectin molecular status determination useful to differentiate between rheumatoid arthritis and systemic lupus erythematosus patients," Rheumatol Int., 33(1):37-43 (Epub 2012).
Przybysz et al., 2007, "Synovial fibronectin fragmentation and domain expressions in relation to rheumatoid arthritis progression," Rheumatology, 46(7):1071-1075.
Resources.rndsystems.com, "Human LILRB4/CD85k/ILT3 Antibody," Monoclonal Mouse IgG2A Clone # 293623, Catalog No. MAB24251, Feb. 7, 2018.
Rudikoff et al., 1982, "Single amino acid substitution altering antigen-binding specificity", Proc Natl Acad Sci USA 79(6):1979-1983.
Sekiguchi et al., 1983, "Differences in domain structure between pericellular matrix and plasma fibronectins as revealed by domain-specific antibodies combined with limited proteolysis and S-cyanylation: A preliminary note.," Biochemical and Biophysical Research Communications, 116(2):534-540.
Stahl et al., "The Tripartite CNTF Receptor Complex: Activation and Signaling Involves Components Shared with Other Cytokines", Journal of Neurobiology, 1994, 25(11): 1454-1466.
Su et al., 2021, "Blockade of checkpoint, ILT3/LILRB4/gp49B binding to fibronectin ameliorates autoimmune disease in BXSB/Yaa mice", International Immunology 33(8):447-458.
UniProtKB/Swiss-Prot: P02751.4, ID: FINC_HUMAN, Dec. 5, 2018.
UniProtKB/Swiss-Prot: P26992.2, ID: CNTFR_HUMAN, Dec. 5, 2018.
UniProtKB/Swiss-Prot: Q8NHJ6.3, ID: LIRB4_HUMAN, Sep. 12, 2018.
Wong et al., 2019, "Gp49B is a pathogenic marker for autoantibody-producing plasma cells in lupus-prone BXSB/Yaa mice", International Immunology 31(6):397-406.
Wu et al., 1999, "Humanization of a murine monoclonal antibody by simultaneous optimization of framework and CDR residues", J Mol Biol 294(1):151-162.
Xu et al., 2018, "ILT3.Fc-CD166 Interaction Induces Inactivation of p70 S6 Kinase and Inhibits Tumor Cell Growth," The Journal of Immunology, 200(3):1207-1219 and Supplemental Material (15 pages).
Badri et al., 2015, "Optimization of radiation dosing schedules for proneural glioblastoma," J. Math. Biol. pp. 1-36.
Baylot et al., 2017, "TCTP has a Crucial Role in the Different Stages of Prostate Cancer Malignant Progression," Spring International Publishing AG 2017, Chapter 13, 255-261.
Keskinov et al., 2016, "Pathophysiology of Dendritic Cells in Cancer," Russian Journal of Biotherapy 15:25-33.
Muller et al., 2008, "Spliceosomal Peptide P140 for Immunotherapy of Systemic Lupus Erythematosus," Arthritis & Rheumatism 58(12):3873-3883.

```
                         SEQUENCE LISTING

Sequence total quantity: 164
SEQ ID NO: 1              moltype = AA  length = 448
FEATURE                   Location/Qualifiers
source                    1..448
                          mol_type = protein
                          organism = Homo sapiens
SEQUENCE: 1
MIPTFTALLC LGLSLGPRTH MQAGPLPKPT LWAEPGSVIS WGNSVTIWCQ GTLEAREYRL   60
DKEESPAPWD RQNPLEPKNK ARFSIPSMTE DYAGRYRCYY RSPVGWSQPS DPLELVMTGA  120
YSKPTLSALP SPLVTSGKSV TLLCQSRSPM DTFLLIKERA AHPLLHLRSE HGAQQHQAEF  180
PMSPVTSVHG GTYRCFSSHG FSHYLLSHPS DPLELIVSGS LEDPRPSPTR SVSTAAGPED  240
QPLMPTGSVP HSGLRRHWEV LIGVLVVSIL LLSLLLFLLL QHWRQGKHRT LAQRQADFQR  300
PPGAAEPEPK DGGLQRRSSP AADVQGENFC AAVKNTQPED GVEMDTRQSP HDEDPQAVTY  360
AKVKHSRPRR EMASPPSPLS GEFLDTKDRQ AEEDRQMDTE AAASEAPQDV TYAQLHSFTL  420
RQKATEPPPS QEGASPAEPS VYATLAIH                                    448

SEQ ID NO: 2              moltype = AA  length = 427
FEATURE                   Location/Qualifiers
source                    1..427
                          mol_type = protein
                          organism = Homo sapiens
SEQUENCE: 2
QAGPLPKPTL WAEPGSVISW GNSVTIWCQG TLEAREYRLD KEESPAPWDR QNPLEPKNKA   60
RFSIPSMTED YAGRYRCYYR SPVGWSQPSD PLELVMTGAY SKPTLSALPS PLVTSGKSVT  120
LLCQSRSPMD TFLLIKERAA HPLLHLRSEH GAQQHQAEFP MSPVTSVHGG TYRCFSSHGF  180
SHYLLSHPSD PLELIVSGSL EDPRPSPTRS VSTAAGPEDQ PLMPTGSVPH SGLRRHWEVL  240
IGVLVVSILL LSLLLFLLLQ HWRQGKHRTL AQRQADFQRP PGAAEPEPKD GGLQRRSSPA  300
ADVQGENFCA AVKNTQPEDG VEMDTRQSPH DEDPQAVTYA KVKHSRPRRE MASPPSPLSG  360
EFLDTKDRQA EEDRQMDTEA AASEAPQDVT YAQLHSFTLR QKATEPPPSQ EGASPAEPSV  420
YATLAIH                                                           427

SEQ ID NO: 3              moltype = AA  length = 238
FEATURE                   Location/Qualifiers
source                    1..238
                          mol_type = protein
```

```
                        organism = Homo sapiens
SEQUENCE: 3
QAGPLPKPTL WAEPGSVISW GNSVTIWCQG TLEAREYRLD KEESPAPWDR QNPLEPKNKA   60
RFSIPSMTED YAGRYRCYYR SPVGWSQPSD PLELVMTGAY SKPTLSALPS PLVTSGKSVT  120
LLCQSRSPMD TFLLIKERAA HPLLHLRSEH GAQQHQAEFP MSPVTSVHGG TYRCFSSHGF  180
SHYLLSHPSD PLELIVSGSL EDPRPSPTRS VSTAAGPEDQ PLMPTGSVPH SGLRRHWE    238

SEQ ID NO: 4            moltype = AA  length = 92
FEATURE                 Location/Qualifiers
source                  1..92
                        mol_type = protein
                        organism = Homo sapiens
SEQUENCE: 4
PKPTLWAEPG SVISWGNSVT IWCQGTLEAR EYRLDKEESP APWDRQNPLE PKNKARFSIP   60
SMTEDYAGRY RCYYRSPVGW SQPSDPLELV MT                                 92

SEQ ID NO: 5            moltype = AA  length = 95
FEATURE                 Location/Qualifiers
source                  1..95
                        mol_type = protein
                        organism = Homo sapiens
SEQUENCE: 5
PTLSALPSPL VTSGKSVTLL CQSRSPMDTF LLIKERAAHP LLHLRSEHGA QQHQAEFPMS   60
PVTSVHGGTY RCFSSHGFSH YLLSHPSDPL ELIVS                              95

SEQ ID NO: 6            moltype = AA  length = 448
FEATURE                 Location/Qualifiers
source                  1..448
                        mol_type = protein
                        organism = Macaca fascicularis
SEQUENCE: 6
MTPPLTVLFC LGLSLGPRTC VQAGPLPKPT VWAEPGSVIS WGSPVTIWCQ GTLDAQEYHL   60
DKEGSPAPWD TQNPLEPRNK AKFSIPSMTQ HYAGRYRCYY HSHPDWSEDS DPLDLVMTGA  120
YSKPILSVLP SPLVTSGESV TLLCQSQSPM DTFLLFKEGA AHPLPRLRSQ HGAQLHWAEF  180
PMGPVTSVHG GTYRCISSRS FSHYLLSRPS DPVELTVLGS LESPSPSPTR SISAAAGPED  240
QSLMPTGSDP QSGLRRHWEV LIGVLVVSIL LLSLVFFLLL QHWRQGKHRT SAQRQADFQR  300
PPGAAEPEPK DGGLQRRSRP AADVQGENPN AAMKDTQPED GVELDSRQRP HDEDPQAVTY  360
ARVKHSGPRR EMASPPSPLS EEFLDTKDTQ AEEDRQMDTQ AATSEAPQDV TYAQLQSLTL  420
RREATEPPPP QKREPSAEPS VYATLAIH                                     448

SEQ ID NO: 7            moltype = AA  length = 427
FEATURE                 Location/Qualifiers
source                  1..427
                        mol_type = protein
                        organism = Macaca fascicularis
SEQUENCE: 7
QAGPLPKPTV WAEPGSVISW GSPVTIWCQG TLDAQEYHLD KEGSPAPWDT QNPLEPRNKA   60
KFSIPSMTQH YAGRYRCYYH SHPDWSEDSD PLDLVMTGAY SKPILSVLPS PLVTSGESVT  120
LLCQSQSPMD TFLLFKEGAA HPLPRLRSQH GAQLHWAEFP MGPVTSVHGG TYRCISSRSF  180
SHYLLSRPSD PVELTVLGSL ESPSPSPTRS ISAAAGPEDQ SLMPTGSDPQ SGLRRHWEVL  240
IGVLVVSILL LSLVFFLLLQ HWRQGKHRTS AQRQADFQRP PGAAEPEPKD GGLQRRSRPA  300
ADVQGENPNA AMKDTQPEDG VELDSRQRPH DEDPQAVTYA RVKHSGPRRE MASPPSPLSE  360
EFLDTKDTQA EEDRQMDTQA ATSEAPQDVT YAQLQSLTLR REATEPPPPQ KREPSAEPSV  420
YATLAIH                                                            427

SEQ ID NO: 8            moltype = AA  length = 238
FEATURE                 Location/Qualifiers
source                  1..238
                        mol_type = protein
                        organism = Macaca fascicularis
SEQUENCE: 8
QAGPLPKPTV WAEPGSVISW GSPVTIWCQG TLDAQEYHLD KEGSPAPWDT QNPLEPRNKA   60
KFSIPSMTQH YAGRYRCYYH SHPDWSEDSD PLDLVMTGAY SKPILSVLPS PLVTSGESVT  120
LLCQSQSPMD TFLLFKEGAA HPLPRLRSQH GAQLHWAEFP MGPVTSVHGG TYRCISSRSF  180
SHYLLSRPSD PVELTVLGSL ESPSPSPTRS ISAAAGPEDQ SLMPTGSDPQ SGLRRHWE    238

SEQ ID NO: 9            moltype = AA  length = 92
FEATURE                 Location/Qualifiers
source                  1..92
                        mol_type = protein
                        organism = Macaca fascicularis
SEQUENCE: 9
PKPTVWAEPG SVISWGSPVT IWCQGTLDAQ EYHLDKEGSP APWDTQNPLE PRNKAKFSIP   60
SMTQHYAGRY RCYYHSHPDW SEDSDPLDLV MT                                 92

SEQ ID NO: 10           moltype = AA  length = 95
FEATURE                 Location/Qualifiers
source                  1..95
                        mol_type = protein
```

```
                              organism = Macaca fascicularis
SEQUENCE: 10
PILSVLPSPL VTSGESVTLL CQSQSPMDTF LLFKEGAAHP LPRLRSQHGA QLHWAEFPMG   60
PVTSVHGGTY RCISSRSFSH YLLSRPSDPV ELTVL                             95

SEQ ID NO: 11           moltype = AA  length = 10
FEATURE                 Location/Qualifiers
source                  1..10
                        mol_type = protein
                        note = Description of Artificial Sequence: Synthetic peptide
                        organism = synthetic construct
SEQUENCE: 11
GFSLTSYGVH                                                         10

SEQ ID NO: 12           moltype = AA  length = 16
FEATURE                 Location/Qualifiers
source                  1..16
                        mol_type = protein
                        note = Description of Artificial Sequence: Synthetic peptide
                        organism = synthetic construct
SEQUENCE: 12
VIWPGGTINY NSALMS                                                  16

SEQ ID NO: 13           moltype = AA  length = 10
FEATURE                 Location/Qualifiers
source                  1..10
                        mol_type = protein
                        note = Description of Artificial Sequence: Synthetic peptide
                        organism = synthetic construct
SEQUENCE: 13
DKYDGGWFAY                                                         10

SEQ ID NO: 14           moltype = AA  length = 11
FEATURE                 Location/Qualifiers
source                  1..11
                        mol_type = protein
                        note = Description of Artificial Sequence: Synthetic peptide
                        organism = synthetic construct
SEQUENCE: 14
KASQNVRTAV A                                                       11

SEQ ID NO: 15           moltype = AA  length = 7
FEATURE                 Location/Qualifiers
source                  1..7
                        mol_type = protein
                        note = Description of Artificial Sequence: Synthetic peptide
                        organism = synthetic construct
SEQUENCE: 15
LASNRHT                                                            7

SEQ ID NO: 16           moltype = AA  length = 9
FEATURE                 Location/Qualifiers
source                  1..9
                        mol_type = protein
                        note = Description of Artificial Sequence: Synthetic peptide
                        organism = synthetic construct
SEQUENCE: 16
LQHLNYPLT                                                          9

SEQ ID NO: 17           moltype = AA  length = 7
FEATURE                 Location/Qualifiers
source                  1..7
                        mol_type = protein
                        note = Description of Artificial Sequence: Synthetic peptide
                        organism = synthetic construct
SEQUENCE: 17
GFSLTSY                                                            7

SEQ ID NO: 18           moltype = AA  length = 5
FEATURE                 Location/Qualifiers
source                  1..5
                        mol_type = protein
                        note = Description of Artificial Sequence: Synthetic peptide
                        organism = synthetic construct
SEQUENCE: 18
WPGGT                                                              5

SEQ ID NO: 19           moltype = AA  length = 9
FEATURE                 Location/Qualifiers
```

```
source                  1..9
                        mol_type = protein
                        note = Description of Artificial Sequence: Synthetic peptide
                        organism = synthetic construct
SEQUENCE: 19
VIWPGGTIN                                                                        9

SEQ ID NO: 20           moltype = AA   length = 5
FEATURE                 Location/Qualifiers
source                  1..5
                        mol_type = protein
                        note = Description of Artificial Sequence: Synthetic peptide
                        organism = synthetic construct
SEQUENCE: 20
SYGVH                                                                            5

SEQ ID NO: 21           moltype = AA   length = 6
FEATURE                 Location/Qualifiers
source                  1..6
                        mol_type = protein
                        note = Description of Artificial Sequence: Synthetic peptide
                        organism = synthetic construct
SEQUENCE: 21
TSYGVH                                                                           6

SEQ ID NO: 22           moltype = AA   length = 12
FEATURE                 Location/Qualifiers
source                  1..12
                        mol_type = protein
                        note = Description of Artificial Sequence: Synthetic peptide
                        organism = synthetic construct
SEQUENCE: 22
WLGVIWPGGT IN                                                                   12

SEQ ID NO: 23           moltype = AA   length = 11
FEATURE                 Location/Qualifiers
source                  1..11
                        mol_type = protein
                        note = Description of Artificial Sequence: Synthetic peptide
                        organism = synthetic construct
SEQUENCE: 23
ASDKYDGGWF A                                                                    11

SEQ ID NO: 24           moltype = AA   length = 7
FEATURE                 Location/Qualifiers
source                  1..7
                        mol_type = protein
                        note = Description of Artificial Sequence: Synthetic peptide
                        organism = synthetic construct
SEQUENCE: 24
RTAVAWY                                                                          7

SEQ ID NO: 25           moltype = AA   length = 10
FEATURE                 Location/Qualifiers
source                  1..10
                        mol_type = protein
                        note = Description of Artificial Sequence: Synthetic peptide
                        organism = synthetic construct
SEQUENCE: 25
ALIYLASNRH                                                                      10

SEQ ID NO: 26           moltype = AA   length = 8
FEATURE                 Location/Qualifiers
source                  1..8
                        mol_type = protein
                        note = Description of Artificial Sequence: Synthetic peptide
                        organism = synthetic construct
SEQUENCE: 26
LQHLNYPL                                                                         8

SEQ ID NO: 27           moltype = AA   length = 10
FEATURE                 Location/Qualifiers
source                  1..10
                        mol_type = protein
                        note = Description of Artificial Sequence: Synthetic peptide
                        organism = synthetic construct
SEQUENCE: 27
GFTFSSYGMS                                                                      10
```

```
SEQ ID NO: 28            moltype = AA  length = 17
FEATURE                  Location/Qualifiers
source                   1..17
                         mol_type = protein
                         note = Description of Artificial Sequence: Synthetic peptide
                         organism = synthetic construct
SEQUENCE: 28
TISGGGSYTN YPDSVKG                                                          17

SEQ ID NO: 29            moltype = AA  length = 12
FEATURE                  Location/Qualifiers
source                   1..12
                         mol_type = protein
                         note = Description of Artificial Sequence: Synthetic peptide
                         organism = synthetic construct
SEQUENCE: 29
REWRMTLYAM DY                                                               12

SEQ ID NO: 30            moltype = AA  length = 15
FEATURE                  Location/Qualifiers
source                   1..15
                         mol_type = protein
                         note = Description of Artificial Sequence: Synthetic peptide
                         organism = synthetic construct
SEQUENCE: 30
RASESVDSYG NSFMH                                                            15

SEQ ID NO: 31            moltype = AA  length = 7
FEATURE                  Location/Qualifiers
source                   1..7
                         mol_type = protein
                         note = Description of Artificial Sequence: Synthetic peptide
                         organism = synthetic construct
SEQUENCE: 31
LTSNLES                                                                      7

SEQ ID NO: 32            moltype = AA  length = 9
FEATURE                  Location/Qualifiers
source                   1..9
                         mol_type = protein
                         note = Description of Artificial Sequence: Synthetic peptide
                         organism = synthetic construct
SEQUENCE: 32
QQNNEDPFT                                                                    9

SEQ ID NO: 33            moltype = AA  length = 7
FEATURE                  Location/Qualifiers
source                   1..7
                         mol_type = protein
                         note = Description of Artificial Sequence: Synthetic peptide
                         organism = synthetic construct
SEQUENCE: 33
GFTFSSY                                                                      7

SEQ ID NO: 34            moltype = AA  length = 6
FEATURE                  Location/Qualifiers
source                   1..6
                         mol_type = protein
                         note = Description of Artificial Sequence: Synthetic peptide
                         organism = synthetic construct
SEQUENCE: 34
SGGGSY                                                                       6

SEQ ID NO: 35            moltype = AA  length = 10
FEATURE                  Location/Qualifiers
source                   1..10
                         mol_type = protein
                         note = Description of Artificial Sequence: Synthetic peptide
                         organism = synthetic construct
SEQUENCE: 35
TISGGGSYTN                                                                  10

SEQ ID NO: 36            moltype = AA  length = 5
FEATURE                  Location/Qualifiers
source                   1..5
                         mol_type = protein
                         note = Description of Artificial Sequence: Synthetic peptide
                         organism = synthetic construct
SEQUENCE: 36
```

```
SYGMS                                                                    5

SEQ ID NO: 38          moltype = AA  length = 6
FEATURE                Location/Qualifiers
source                 1..6
                       mol_type = protein
                       note = Description of Artificial Sequence: Synthetic peptide
                       organism = synthetic construct
SEQUENCE: 37
SSYGMS                                                                   6

SEQ ID NO: 38          moltype = AA  length = 13
FEATURE                Location/Qualifiers
source                 1..13
                       mol_type = protein
                       note = Description of Artificial Sequence: Synthetic peptide
                       organism = synthetic construct
SEQUENCE: 38
WVATISGGGS YTN                                                          13

SEQ ID NO: 39          moltype = AA  length = 13
FEATURE                Location/Qualifiers
source                 1..13
                       mol_type = protein
                       note = Description of Artificial Sequence: Synthetic peptide
                       organism = synthetic construct
SEQUENCE: 39
ARREWRMTLY AMD                                                          13

SEQ ID NO: 40          moltype = AA  length = 11
FEATURE                Location/Qualifiers
source                 1..11
                       mol_type = protein
                       note = Description of Artificial Sequence: Synthetic peptide
                       organism = synthetic construct
SEQUENCE: 40
DSYGNSFMHW Y                                                            11

SEQ ID NO: 41          moltype = AA  length = 10
FEATURE                Location/Qualifiers
source                 1..10
                       mol_type = protein
                       note = Description of Artificial Sequence: Synthetic peptide
                       organism = synthetic construct
SEQUENCE: 41
LLIYLTSNLE                                                              10

SEQ ID NO: 42          moltype = AA  length = 8
FEATURE                Location/Qualifiers
source                 1..8
                       mol_type = protein
                       note = Description of Artificial Sequence: Synthetic peptide
                       organism = synthetic construct
SEQUENCE: 42
QQNNEDPF                                                                 8

SEQ ID NO: 43          moltype = AA  length = 10
FEATURE                Location/Qualifiers
source                 1..10
                       mol_type = protein
                       note = Description of Artificial Sequence: Synthetic peptide
                       organism = synthetic construct
SEQUENCE: 43
GYTFTDYNMD                                                              10

SEQ ID NO: 44          moltype = AA  length = 17
FEATURE                Location/Qualifiers
source                 1..17
                       mol_type = protein
                       note = Description of Artificial Sequence: Synthetic peptide
                       organism = synthetic construct
SEQUENCE: 44
YIYPNNGGTG YNQKFNS                                                      17

SEQ ID NO: 45          moltype = AA  length = 14
FEATURE                Location/Qualifiers
source                 1..14
                       mol_type = protein
                       note = Description of Artificial Sequence: Synthetic peptide
```

```
                              -continued
                        organism = synthetic construct
SEQUENCE: 45
SPYYDYVGSY AMDY                                                 14

SEQ ID NO: 46           moltype = AA  length = 12
FEATURE                 Location/Qualifiers
source                  1..12
                        mol_type = protein
                        note = Description of Artificial Sequence: Synthetic peptide
                        organism = synthetic construct
SEQUENCE: 46
TASSSVSSSY LH                                                   12

SEQ ID NO: 47           moltype = AA  length = 7
FEATURE                 Location/Qualifiers
source                  1..7
                        mol_type = protein
                        note = Description of Artificial Sequence: Synthetic peptide
                        organism = synthetic construct
SEQUENCE: 47
STSNLAS                                                         7

SEQ ID NO: 48           moltype = AA  length = 9
FEATURE                 Location/Qualifiers
source                  1..9
                        mol_type = protein
                        note = Description of Artificial Sequence: Synthetic peptide
                        organism = synthetic construct
SEQUENCE: 48
HQYHRSPRT                                                       9

SEQ ID NO: 49           moltype = AA  length = 7
FEATURE                 Location/Qualifiers
source                  1..7
                        mol_type = protein
                        note = Description of Artificial Sequence: Synthetic peptide
                        organism = synthetic construct
SEQUENCE: 49
GYTFTDY                                                         7

SEQ ID NO: 50           moltype = AA  length = 6
FEATURE                 Location/Qualifiers
source                  1..6
                        mol_type = protein
                        note = Description of Artificial Sequence: Synthetic peptide
                        organism = synthetic construct
SEQUENCE: 50
YPNNGG                                                          6

SEQ ID NO: 51           moltype = AA  length = 10
FEATURE                 Location/Qualifiers
source                  1..10
                        mol_type = protein
                        note = Description of Artificial Sequence: Synthetic peptide
                        organism = synthetic construct
SEQUENCE: 51
YIYPNNGGTG                                                      10

SEQ ID NO: 52           moltype = AA  length = 5
FEATURE                 Location/Qualifiers
source                  1..5
                        mol_type = protein
                        note = Description of Artificial Sequence: Synthetic peptide
                        organism = synthetic construct
SEQUENCE: 52
DYNMD                                                           5

SEQ ID NO: 53           moltype = AA  length = 6
FEATURE                 Location/Qualifiers
source                  1..6
                        mol_type = protein
                        note = Description of Artificial Sequence: Synthetic peptide
                        organism = synthetic construct
SEQUENCE: 53
TDYNMD                                                          6

SEQ ID NO: 54           moltype = AA  length = 13
FEATURE                 Location/Qualifiers
source                  1..13
```

```
                        mol_type = protein
                        note = Description of Artificial Sequence: Synthetic peptide
                        organism = synthetic construct
SEQUENCE: 54
WIGYIYPNNG GTG                                                          13

SEQ ID NO: 55           moltype = AA   length = 15
FEATURE                 Location/Qualifiers
source                  1..15
                        mol_type = protein
                        note = Description of Artificial Sequence: Synthetic peptide
                        organism = synthetic construct
SEQUENCE: 55
ASSPYYDYVG SYAMD                                                        15

SEQ ID NO: 56           moltype = AA   length = 8
FEATURE                 Location/Qualifiers
source                  1..8
                        mol_type = protein
                        note = Description of Artificial Sequence: Synthetic peptide
                        organism = synthetic construct
SEQUENCE: 56
SSSYLHWY                                                                8

SEQ ID NO: 57           moltype = AA   length = 10
FEATURE                 Location/Qualifiers
source                  1..10
                        mol_type = protein
                        note = Description of Artificial Sequence: Synthetic peptide
                        organism = synthetic construct
SEQUENCE: 57
LWIYSTSNLA                                                              10

SEQ ID NO: 58           moltype = AA   length = 8
FEATURE                 Location/Qualifiers
source                  1..8
                        mol_type = protein
                        note = Description of Artificial Sequence: Synthetic peptide
                        organism = synthetic construct
SEQUENCE: 58
HQYHRSPR                                                                8

SEQ ID NO: 59           moltype = AA   length = 17
FEATURE                 Location/Qualifiers
source                  1..17
                        mol_type = protein
                        note = Description of Artificial Sequence: Synthetic peptide
                        organism = synthetic construct
SEQUENCE: 59
YIYPSNGGTG YNQKFKS                                                      17

SEQ ID NO: 60           moltype = AA   length = 14
FEATURE                 Location/Qualifiers
source                  1..14
                        mol_type = protein
                        note = Description of Artificial Sequence: Synthetic peptide
                        organism = synthetic construct
SEQUENCE: 60
VPYYDYLYYY AMDY                                                         14

SEQ ID NO: 61           moltype = AA   length = 10
FEATURE                 Location/Qualifiers
source                  1..10
                        mol_type = protein
                        note = Description of Artificial Sequence: Synthetic peptide
                        organism = synthetic construct
SEQUENCE: 61
RASSSVSFMH                                                              10

SEQ ID NO: 62           moltype = AA   length = 7
FEATURE                 Location/Qualifiers
source                  1..7
                        mol_type = protein
                        note = Description of Artificial Sequence: Synthetic peptide
                        organism = synthetic construct
SEQUENCE: 62
ATSNLAS                                                                 7

SEQ ID NO: 63           moltype = AA   length = 11
```

| | |
|---|---|
| FEATURE | Location/Qualifiers |
| source | 1..11<br>mol_type = protein<br>note = Description of Artificial Sequence: Synthetic peptide<br>organism = synthetic construct |
| SEQUENCE: 63<br>QQWSTNPYMY T | 11 |
| SEQ ID NO: 64<br>FEATURE<br>source | moltype = AA  length = 6<br>Location/Qualifiers<br>1..6<br>mol_type = protein<br>note = Description of Artificial Sequence: Synthetic peptide<br>organism = synthetic construct |
| SEQUENCE: 64<br>YPSNGG | 6 |
| SEQ ID NO: 65<br>FEATURE<br>source | moltype = AA  length = 10<br>Location/Qualifiers<br>1..10<br>mol_type = protein<br>note = Description of Artificial Sequence: Synthetic peptide<br>organism = synthetic construct |
| SEQUENCE: 65<br>YIYPSNGGTG | 10 |
| SEQ ID NO: 66<br>FEATURE<br>source | moltype = AA  length = 13<br>Location/Qualifiers<br>1..13<br>mol_type = protein<br>note = Description of Artificial Sequence: Synthetic peptide<br>organism = synthetic construct |
| SEQUENCE: 66<br>WIGYIYPSNG GTG | 13 |
| SEQ ID NO: 67<br>FEATURE<br>source | moltype = AA  length = 15<br>Location/Qualifiers<br>1..15<br>mol_type = protein<br>note = Description of Artificial Sequence: Synthetic peptide<br>organism = synthetic construct |
| SEQUENCE: 67<br>ARVPYYDYLY YYAMD | 15 |
| SEQ ID NO: 68<br>FEATURE<br>source | moltype = AA  length = 6<br>Location/Qualifiers<br>1..6<br>mol_type = protein<br>note = Description of Artificial Sequence: Synthetic peptide<br>organism = synthetic construct |
| SEQUENCE: 68<br>SFMHWY | 6 |
| SEQ ID NO: 69<br>FEATURE<br>source | moltype = AA  length = 10<br>Location/Qualifiers<br>1..10<br>mol_type = protein<br>note = Description of Artificial Sequence: Synthetic peptide<br>organism = synthetic construct |
| SEQUENCE: 69<br>PWIYATSNLA | 10 |
| SEQ ID NO: 70<br>FEATURE<br>source | moltype = AA  length = 10<br>Location/Qualifiers<br>1..10<br>mol_type = protein<br>note = Description of Artificial Sequence: Synthetic peptide<br>organism = synthetic construct |
| SEQUENCE: 70<br>QQWSTNPYMY | 10 |
| SEQ ID NO: 71<br>FEATURE<br>source | moltype = AA  length = 10<br>Location/Qualifiers<br>1..10<br>mol_type = protein<br>note = Description of Artificial Sequence: Synthetic peptide<br>organism = synthetic construct |
| SEQUENCE: 71<br>GFTFSDYGMH | 10 |

```
SEQ ID NO: 72          moltype = AA   length = 17
FEATURE                Location/Qualifiers
source                 1..17
                       mol_type = protein
                       note = Description of Artificial Sequence: Synthetic peptide
                       organism = synthetic construct
SEQUENCE: 72
YIFSGSSTIY YADTVKG                                                        17

SEQ ID NO: 73          moltype = AA   length = 9
FEATURE                Location/Qualifiers
source                 1..9
                       mol_type = protein
                       note = Description of Artificial Sequence: Synthetic peptide
                       organism = synthetic construct
SEQUENCE: 73
ADGRGAMDY                                                                  9

SEQ ID NO: 74          moltype = AA   length = 11
FEATURE                Location/Qualifiers
source                 1..11
                       mol_type = protein
                       note = Description of Artificial Sequence: Synthetic peptide
                       organism = synthetic construct
SEQUENCE: 74
RASQDISKFL N                                                              11

SEQ ID NO: 75          moltype = AA   length = 7
FEATURE                Location/Qualifiers
source                 1..7
                       mol_type = protein
                       note = Description of Artificial Sequence: Synthetic peptide
                       organism = synthetic construct
SEQUENCE: 75
YTSRLHS                                                                    7

SEQ ID NO: 76          moltype = AA   length = 9
FEATURE                Location/Qualifiers
source                 1..9
                       mol_type = protein
                       note = Description of Artificial Sequence: Synthetic peptide
                       organism = synthetic construct
SEQUENCE: 76
QQGNTLPWT                                                                  9

SEQ ID NO: 77          moltype = AA   length = 7
FEATURE                Location/Qualifiers
source                 1..7
                       mol_type = protein
                       note = Description of Artificial Sequence: Synthetic peptide
                       organism = synthetic construct
SEQUENCE: 77
GFTFSDY                                                                    7

SEQ ID NO: 78          moltype = AA   length = 6
FEATURE                Location/Qualifiers
source                 1..6
                       mol_type = protein
                       note = Description of Artificial Sequence: Synthetic peptide
                       organism = synthetic construct
SEQUENCE: 78
FSGSST                                                                     6

SEQ ID NO: 79          moltype = AA   length = 10
FEATURE                Location/Qualifiers
source                 1..10
                       mol_type = protein
                       note = Description of Artificial Sequence: Synthetic peptide
                       organism = synthetic construct
SEQUENCE: 79
YIFSGSSTIY                                                                10

SEQ ID NO: 80          moltype = AA   length = 5
FEATURE                Location/Qualifiers
source                 1..5
                       mol_type = protein
                       note = Description of Artificial Sequence: Synthetic peptide
                       organism = synthetic construct
```

| | | |
|---|---|---|
| SEQUENCE: 80 | | |
| DYGMH | | 5 |
| | | |
| SEQ ID NO: 81 | moltype = AA   length = 6 | |
| FEATURE | Location/Qualifiers | |
| source | 1..6 | |
| | mol_type = protein | |
| | note = Description of Artificial Sequence: Synthetic peptide | |
| | organism = synthetic construct | |
| | | |
| SEQUENCE: 81 | | |
| SDYGMH | | 6 |
| | | |
| SEQ ID NO: 82 | moltype = AA   length = 13 | |
| FEATURE | Location/Qualifiers | |
| source | 1..13 | |
| | mol_type = protein | |
| | note = Description of Artificial Sequence: Synthetic peptide | |
| | organism = synthetic construct | |
| | | |
| SEQUENCE: 82 | | |
| WVAYIFSGSS TIY | | 13 |
| | | |
| SEQ ID NO: 83 | moltype = AA   length = 10 | |
| FEATURE | Location/Qualifiers | |
| source | 1..10 | |
| | mol_type = protein | |
| | note = Description of Artificial Sequence: Synthetic peptide | |
| | organism = synthetic construct | |
| | | |
| SEQUENCE: 83 | | |
| ARADGRGAMD | | 10 |
| | | |
| SEQ ID NO: 84 | moltype = AA   length = 7 | |
| FEATURE | Location/Qualifiers | |
| source | 1..7 | |
| | mol_type = protein | |
| | note = Description of Artificial Sequence: Synthetic peptide | |
| | organism = synthetic construct | |
| | | |
| SEQUENCE: 84 | | |
| SKFLNWY | | 7 |
| | | |
| SEQ ID NO: 85 | moltype = AA   length = 10 | |
| FEATURE | Location/Qualifiers | |
| source | 1..10 | |
| | mol_type = protein | |
| | note = Description of Artificial Sequence: Synthetic peptide | |
| | organism = synthetic construct | |
| | | |
| SEQUENCE: 85 | | |
| LLIYYTSRLH | | 10 |
| | | |
| SEQ ID NO: 86 | moltype = AA   length = 8 | |
| FEATURE | Location/Qualifiers | |
| source | 1..8 | |
| | mol_type = protein | |
| | note = Description of Artificial Sequence: Synthetic peptide | |
| | organism = synthetic construct | |
| | | |
| SEQUENCE: 86 | | |
| QQGNTLPW | | 8 |
| | | |
| SEQ ID NO: 87 | moltype = AA   length = 17 | |
| FEATURE | Location/Qualifiers | |
| source | 1..17 | |
| | mol_type = protein | |
| | note = Description of Artificial Sequence: Synthetic peptide | |
| | organism = synthetic construct | |
| | | |
| SEQUENCE: 87 | | |
| TISSGGTYTF YPDSVKG | | 17 |
| | | |
| SEQ ID NO: 88 | moltype = AA   length = 12 | |
| FEATURE | Location/Qualifiers | |
| source | 1..12 | |
| | mol_type = protein | |
| | note = Description of Artificial Sequence: Synthetic peptide | |
| | organism = synthetic construct | |
| | | |
| SEQUENCE: 88 | | |
| RGWLLHYYAM DY | | 12 |
| | | |
| SEQ ID NO: 89 | moltype = AA   length = 15 | |
| FEATURE | Location/Qualifiers | |
| source | 1..15 | |
| | mol_type = protein | |

```
                    note = Description of Artificial Sequence: Synthetic peptide
                    organism = synthetic construct
SEQUENCE: 89
RPSESVDSFG NSFMH                                                       15

SEQ ID NO: 90       moltype = AA  length = 7
FEATURE             Location/Qualifiers
source              1..7
                    mol_type = protein
                    note = Description of Artificial Sequence: Synthetic peptide
                    organism = synthetic construct
SEQUENCE: 90
LSSKLES                                                                7

SEQ ID NO: 91       moltype = AA  length = 9
FEATURE             Location/Qualifiers
source              1..9
                    mol_type = protein
                    note = Description of Artificial Sequence: Synthetic peptide
                    organism = synthetic construct
SEQUENCE: 91
QQHNEDPFT                                                              9

SEQ ID NO: 92       moltype = AA  length = 6
FEATURE             Location/Qualifiers
source              1..6
                    mol_type = protein
                    note = Description of Artificial Sequence: Synthetic peptide
                    organism = synthetic construct
SEQUENCE: 92
SSGGTY                                                                 6

SEQ ID NO: 93       moltype = AA  length = 10
FEATURE             Location/Qualifiers
source              1..10
                    mol_type = protein
                    note = Description of Artificial Sequence: Synthetic peptide
                    organism = synthetic construct
SEQUENCE: 93
TISSGGTYTF                                                             10

SEQ ID NO: 94       moltype = AA  length = 13
FEATURE             Location/Qualifiers
source              1..13
                    mol_type = protein
                    note = Description of Artificial Sequence: Synthetic peptide
                    organism = synthetic construct
SEQUENCE: 94
WVATISSGGT YTF                                                         13

SEQ ID NO: 95       moltype = AA  length = 13
FEATURE             Location/Qualifiers
source              1..13
                    mol_type = protein
                    note = Description of Artificial Sequence: Synthetic peptide
                    organism = synthetic construct
SEQUENCE: 95
ARRGWLLHYY AMD                                                         13

SEQ ID NO: 96       moltype = AA  length = 11
FEATURE             Location/Qualifiers
source              1..11
                    mol_type = protein
                    note = Description of Artificial Sequence: Synthetic peptide
                    organism = synthetic construct
SEQUENCE: 96
DSFGNSFMHW F                                                           11

SEQ ID NO: 97       moltype = AA  length = 10
FEATURE             Location/Qualifiers
source              1..10
                    mol_type = protein
                    note = Description of Artificial Sequence: Synthetic peptide
                    organism = synthetic construct
SEQUENCE: 97
LLIYLSSKLE                                                             10

SEQ ID NO: 98       moltype = AA  length = 8
FEATURE             Location/Qualifiers
```

```
source                     1..8
                           mol_type = protein
                           note = Description of Artificial Sequence: Synthetic peptide
                           organism = synthetic construct
SEQUENCE: 98
QQHNEDPF                                                                            8

SEQ ID NO: 99              moltype = AA  length = 17
FEATURE                    Location/Qualifiers
source                     1..17
                           mol_type = protein
                           note = Description of Artificial Sequence: Synthetic peptide
                           organism = synthetic construct
SEQUENCE: 99
YISTGIITVY YADTVKG                                                                 17

SEQ ID NO: 100             moltype = AA  length = 11
FEATURE                    Location/Qualifiers
source                     1..11
                           mol_type = protein
                           note = Description of Artificial Sequence: Synthetic peptide
                           organism = synthetic construct
SEQUENCE: 100
RASQDISNFL N                                                                       11

SEQ ID NO: 101             moltype = AA  length = 6
FEATURE                    Location/Qualifiers
source                     1..6
                           mol_type = protein
                           note = Description of Artificial Sequence: Synthetic peptide
                           organism = synthetic construct
SEQUENCE: 101
STGIIT                                                                              6

SEQ ID NO: 102             moltype = AA  length = 10
FEATURE                    Location/Qualifiers
source                     1..10
                           mol_type = protein
                           note = Description of Artificial Sequence: Synthetic peptide
                           organism = synthetic construct
SEQUENCE: 102
YISTGIITVY                                                                         10

SEQ ID NO: 103             moltype = AA  length = 13
FEATURE                    Location/Qualifiers
source                     1..13
                           mol_type = protein
                           note = Description of Artificial Sequence: Synthetic peptide
                           organism = synthetic construct
SEQUENCE: 103
WVAYISTGII TVY                                                                     13

SEQ ID NO: 104             moltype = AA  length = 7
FEATURE                    Location/Qualifiers
source                     1..7
                           mol_type = protein
                           note = Description of Artificial Sequence: Synthetic peptide
                           organism = synthetic construct
SEQUENCE: 104
SNFLNWY                                                                             7

SEQ ID NO: 105             moltype = AA  length = 12
FEATURE                    Location/Qualifiers
source                     1..12
                           mol_type = protein
                           note = Description of Artificial Sequence: Synthetic peptide
                           organism = synthetic construct
SEQUENCE: 105
REWRYTLYAM DY                                                                      12

SEQ ID NO: 106             moltype = AA  length = 15
FEATURE                    Location/Qualifiers
source                     1..15
                           mol_type = protein
                           note = Description of Artificial Sequence: Synthetic peptide
                           organism = synthetic construct
SEQUENCE: 106
RASESVESYG SSFMH                                                                   15
```

| | |
|---|---|
| SEQ ID NO: 107 | moltype = AA length = 13 |
| FEATURE | Location/Qualifiers |
| source | 1..13 |
| | mol_type = protein |
| | note = Description of Artificial Sequence: Synthetic peptide |
| | organism = synthetic construct |

SEQUENCE: 107
ARREWRYTLY AMD                                                    13

| | |
|---|---|
| SEQ ID NO: 108 | moltype = AA length = 11 |
| FEATURE | Location/Qualifiers |
| source | 1..11 |
| | mol_type = protein |
| | note = Description of Artificial Sequence: Synthetic peptide |
| | organism = synthetic construct |

SEQUENCE: 108
ESYGSSFMHW Y                                                      11

| | |
|---|---|
| SEQ ID NO: 109 | moltype = AA length = 118 |
| FEATURE | Location/Qualifiers |
| source | 1..118 |
| | mol_type = protein |
| | note = Description of Artificial Sequence: Synthetic polypeptide |
| | organism = synthetic construct |

SEQUENCE: 109
QVQLKESGPG LVAPSQSLSI TCTVSGFSLT SYGVHWVRQP PGKGLEWLGV IWPGGTINYN    60
SALMSRLSIS KDNSKSQVFL KLNSLQTDDT AMYYCASDKY DGGWFAYWGQ GTLVTVSA    118

| | |
|---|---|
| SEQ ID NO: 110 | moltype = AA length = 107 |
| FEATURE | Location/Qualifiers |
| source | 1..107 |
| | mol_type = protein |
| | note = Description of Artificial Sequence: Synthetic polypeptide |
| | organism = synthetic construct |

SEQUENCE: 110
DIVMTQSQKF MSTSVGDRVS ITCKASQNVR TAVAWYQQKP GQSPEALIYL ASNRHTGVPD    60
RFTGSGSGTD FSLSISNVQS EDLADYFCLQ HLNYPLTFGS GTKLEIK               107

| | |
|---|---|
| SEQ ID NO: 111 | moltype = AA length = 121 |
| FEATURE | Location/Qualifiers |
| source | 1..121 |
| | mol_type = protein |
| | note = Description of Artificial Sequence: Synthetic polypeptide |
| | organism = synthetic construct |

SEQUENCE: 111
EVKLVESGGG LVKPGGSLKL SCAASGFTFS SYGMSWVRQT PEKRLEWVAT ISGGGSYTNY    60
PDSVKGRLTI SRDNAKKNLY LEMSSLRSED TALYYCARRE WRMTLYAMDY WGQGTSVTVS   120
S                                                                121

| | |
|---|---|
| SEQ ID NO: 112 | moltype = AA length = 111 |
| FEATURE | Location/Qualifiers |
| source | 1..111 |
| | mol_type = protein |
| | note = Description of Artificial Sequence: Synthetic polypeptide |
| | organism = synthetic construct |

SEQUENCE: 112
NIVLTQSPAS LAVSLGQRAT ISCRASESVD SYGNSFMHWY QQKPGQAPKL LIYLTSNLES    60
GVPARFSGSG SRTDFTLTID PVEADDAATY YCQQNNEDPF TFGSGTKLEI K           111

| | |
|---|---|
| SEQ ID NO: 113 | moltype = AA length = 123 |
| FEATURE | Location/Qualifiers |
| source | 1..123 |
| | mol_type = protein |
| | note = Description of Artificial Sequence: Synthetic polypeptide |
| | organism = synthetic construct |

SEQUENCE: 113
EVQLQQSGPE LVKPGASVKI SCKASGYTFT DYNMDWVKQS HGKSLEWIGY IYPNNGGTGY    60
NQKFNSKATL TVDKSSSTAY MELHSLTSED SAVYYCASSP YDYVGSYAM DYWGQGTSVT   120
VSS                                                               123

| | |
|---|---|
| SEQ ID NO: 114 | moltype = AA length = 108 |
| FEATURE | Location/Qualifiers |
| source | 1..108 |
| | mol_type = protein |

```
                            note = Description of Artificial Sequence: Synthetic
                               polypeptide
                            organism = synthetic construct
SEQUENCE: 114
QIVLTQSPAI MSASLGERVT MTCTASSSVS SSYLHWYQQK PGSSPKLWIY STSNLASGVP    60
ARFSGSGSGT SYSLTISSME AEDAATYYCH QHRSPRTFG GGTKLEIK                108

SEQ ID NO: 115          moltype = AA  length = 123
FEATURE                 Location/Qualifiers
source                  1..123
                        mol_type = protein
                        note = Description of Artificial Sequence: Synthetic
                           polypeptide
                        organism = synthetic construct
SEQUENCE: 115
EVQLQQSGPE LVKPGASVKI SCKASGYTFT DYNMDWVKQS HGKSLEWIGY IYPSNGGTGY    60
NQKFKSKATL TVDKSSNTAY MELHSLTSED SAVYYCARVP YYDYLYYYAM DYWGQGTSVT   120
VSS                                                                123

SEQ ID NO: 116          moltype = AA  length = 108
FEATURE                 Location/Qualifiers
source                  1..108
                        mol_type = protein
                        note = Description of Artificial Sequence: Synthetic
                           polypeptide
                        organism = synthetic construct
SEQUENCE: 116
QIVLSQSPAI LSASPGEKVT MACRASSSVS FMHWYQQKPG SSPQPWIYAT SNLASGVPAR    60
FSGSGSGTSY SLTISRVEAE DAATYYCQQW STNPYMYTFG GGTKLEIK                108

SEQ ID NO: 117          moltype = AA  length = 118
FEATURE                 Location/Qualifiers
source                  1..118
                        mol_type = protein
                        note = Description of Artificial Sequence: Synthetic
                           polypeptide
                        organism = synthetic construct
SEQUENCE: 117
EVQLVESGGG LVKPGGSLKL SCAASGFTFS DYGMHWVRQA PEKGLEWVAY IFSGSSTIYY    60
ADTVKGRFTI SRDNAKNTLF LQMTSLRSED TAMYYCARAD GRGAMDYWGQ GTSVTVSS    118

SEQ ID NO: 118          moltype = AA  length = 107
FEATURE                 Location/Qualifiers
source                  1..107
                        mol_type = protein
                        note = Description of Artificial Sequence: Synthetic
                           polypeptide
                        organism = synthetic construct
SEQUENCE: 118
DVQMTQTTSS LSASLGDRVT ISCRASQDIS KFLNWYQQKP DGTVTLLIYY TSRLHSGVPS    60
RFSGSGSGTD YSLTISNLDQ EDIATYFCQQ GNTLPWTFGG GTKLEIK                 107

SEQ ID NO: 119          moltype = AA  length = 121
FEATURE                 Location/Qualifiers
source                  1..121
                        mol_type = protein
                        note = Description of Artificial Sequence: Synthetic
                           polypeptide
                        organism = synthetic construct
SEQUENCE: 119
EVQLVESGGD LMKPGGSLKL SCAASGFTFS SYGMSWVRQT PDKRLEWVAT ISSGGTYTFY    60
PDSVKGRFTI SRDNAKNTLY LQMSSLKSED TAMYYCARRG WLLHYYAMDY WGQGTSVTVS  120
S                                                                  121

SEQ ID NO: 120          moltype = AA  length = 111
FEATURE                 Location/Qualifiers
source                  1..111
                        mol_type = protein
                        note = Description of Artificial Sequence: Synthetic
                           polypeptide
                        organism = synthetic construct
SEQUENCE: 120
NIVLTQSPAS LAVSLGQRAT ISCRPSESVD SFGNSFMHWF QQKPGQPPKL LIYLSSKLES    60
GVPARFSGSG SRTDFTLTID PVEADDAATY YCQQHNEDPF TFGSGTKLEI K            111

SEQ ID NO: 121          moltype = AA  length = 118
FEATURE                 Location/Qualifiers
source                  1..118
                        mol_type = protein
```

```
                            note = Description of Artificial Sequence: Synthetic
                              polypeptide
                            organism = synthetic construct
SEQUENCE: 121
EVQVVESGGG LVKPGGSLKL SCAASGFTFS DYGMHWVRQA PEKGLEWVAY ISTGIITVYY    60
ADTVKGRFTM SRDNAKNTLF LQMTSLRSED TAIYYCARAD GRGAMDYWGQ GTSVIVSS    118

SEQ ID NO: 122              moltype = AA   length = 107
FEATURE                     Location/Qualifiers
source                      1..107
                            mol_type = protein
                            note = Description of Artificial Sequence: Synthetic
                              polypeptide
                            organism = synthetic construct
SEQUENCE: 122
DIQMTQTTSS LSASLGDRVT ISCRASQDIS NFLNWYQQKP DGTVTLLIYY TSRLHSGVPS    60
RFSGSGSGTD YSLTISNLEQ EDFATYFCQQ GNTLPWTFGG GTKLEIK                107

SEQ ID NO: 123              moltype = AA   length = 121
FEATURE                     Location/Qualifiers
source                      1..121
                            mol_type = protein
                            note = Description of Artificial Sequence: Synthetic
                              polypeptide
                            organism = synthetic construct
SEQUENCE: 123
EVQLVESGGG LVQPGGSLRL SCAASGFTFS SYGMSWVRQA PGKGLEWVAT ISGGGSYTNY    60
PDSVKGRFTI SRDNAKNSLY LQMNSLRAED TAVYYCARRE WRYTLYAMDY WGQGTTVTVS   120
S                                                                  121

SEQ ID NO: 124              moltype = AA   length = 111
FEATURE                     Location/Qualifiers
source                      1..111
                            mol_type = protein
                            note = Description of Artificial Sequence: Synthetic
                              polypeptide
                            organism = synthetic construct
SEQUENCE: 124
DIQLTQSPSF LSASVGDRVT ITCRASESVE SYGSSFMHWY QQKPGKAPKL LIYLTSNLES    60
GVPSRFSGSG SGTEFTLTIS SLQPEDFATY YCQQNNEDPF TFGQGTKLEI K            111

SEQ ID NO: 125              moltype = AA   length = 473
FEATURE                     Location/Qualifiers
source                      1..473
                            mol_type = protein
                            note = Description of Artificial Sequence: Synthetic
                              polypeptide
                            organism = synthetic construct
SEQUENCE: 125
MDMRVPAQLL GLLLLWLRGA RCEVQLVESG GGLVQPGGSL RLSCAASGFT FSSYGMSWVR    60
QAPGKGLEWV ATISGGGSYT NYPDSVKGRF TISRDNAKNS LYLQMNSLRA EDTAVYYCAR   120
REWRYTLYAM DYWGQGTTVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYGSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 126              moltype = AA   length = 451
FEATURE                     Location/Qualifiers
source                      1..451
                            mol_type = protein
                            note = Description of Artificial Sequence: Synthetic
                              polypeptide
                            organism = synthetic construct
SEQUENCE: 126
EVQLVESGGG LVQPGGSLRL SCAASGFTFS SYGMSWVRQA PGKGLEWVAT ISGGGSYTNY    60
PDSVKGRFTI SRDNAKNSLY LQMNSLRAED TAVYYCARRE WRYTLYAMDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
GSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 127              moltype = AA   length = 240
FEATURE                     Location/Qualifiers
source                      1..240
                            mol_type = protein
```

```
                        note = Description of Artificial Sequence: Synthetic
                          polypeptide
                        organism = synthetic construct
SEQUENCE: 127
MDMRVPAQLL GLLLLWLRGA RCDIQLTQSP SFLSASVGDR VTITCRASES VESYGSSFMH    60
WYQQKPGKAP KLLIYLTSNL ESGVPSRFSG SGSGTEFTLT ISSLQPEDFA TYYCQQNNED   120
PFTFGQGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 128          moltype = AA   length = 218
FEATURE                 Location/Qualifiers
source                  1..218
                        mol_type = protein
                        note = Description of Artificial Sequence: Synthetic
                          polypeptide
                        organism = synthetic construct
SEQUENCE: 128
DIQLTQSPSF LSASVGDRVT ITCRASESVE SYGSSFMHWY QQKPGKAPKL LIYLTSNLES    60
GVPSRFSGSG SGTEFTLTIS SLQPEDFATY YCQQNNEDPF TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 129          moltype = AA   length = 330
FEATURE                 Location/Qualifiers
source                  1..330
                        mol_type = protein
                        organism = Homo sapiens
SEQUENCE: 129
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 130          moltype = AA   length = 330
FEATURE                 Location/Qualifiers
source                  1..330
                        mol_type = protein
                        organism = Homo sapiens
SEQUENCE: 130
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPALAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 131          moltype = AA   length = 330
FEATURE                 Location/Qualifiers
source                  1..330
                        mol_type = protein
                        organism = Homo sapiens
SEQUENCE: 131
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 132          moltype = AA   length = 330
FEATURE                 Location/Qualifiers
source                  1..330
                        mol_type = protein
                        organism = Homo sapiens
SEQUENCE: 132
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 133          moltype = AA   length = 330
FEATURE                 Location/Qualifiers
source                  1..330
                        mol_type = protein
                        organism = Homo sapiens
```

```
SEQUENCE: 133
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKKVEP  KSCDKTHTCP  PCPAPELLGG   120
PSVFLFPPKP  KDTLMISRTP  EVTCVVVDVS  HEDPEVKFNW  YVDGVEVHNA  KTKPREEQYG   180
STYRVVSVLT  VLHQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPGK                                      330

SEQ ID NO: 134          moltype = AA  length = 330
FEATURE                 Location/Qualifiers
source                  1..330
                        mol_type = protein
                        organism = Homo sapiens
SEQUENCE: 134
ASTKGPSVFP  LAPSSKSTSG  GTAALGCLVK  DYFPEPVTVS  WNSGALTSGV  HTFPAVLQSS    60
GLYSLSSVVT  VPSSSLGTQT  YICNVNHKPS  NTKVDKKVEP  KSCDKTHTCP  PCPAPELLGG   120
PSVFLFPPKP  KDTLMISRTP  EVTCVVVDVS  HEDPEVKFNW  YVDGVEVHNA  KTKPREEQYG   180
STYRVVSVLT  VLAQDWLNGK  EYKCKVSNKA  LPAPIEKTIS  KAKGQPREPQ  VYTLPPSREE   240
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPGK                                      330

SEQ ID NO: 135          moltype = AA  length = 107
FEATURE                 Location/Qualifiers
source                  1..107
                        mol_type = protein
                        organism = Homo sapiens
SEQUENCE: 135
RTVAAPSVFI  FPPSDEQLKS  GTASVVCLLN  NFYPREAKVQ  WKVDNALQSG  NSQESVTEQD    60
SKDSTYSLSS  TLTLSKADYE  KHKVYACEVT  HQGLSSPVTK  SFNRGEC                 107

SEQ ID NO: 136          moltype = AA  length = 106
FEATURE                 Location/Qualifiers
source                  1..106
                        mol_type = protein
                        organism = Homo sapiens
SEQUENCE: 136
GQPKAAPSVT  LFPPSSEELQ  ANKATLVCLI  SDFYPGAVTV  AWKADSSPVK  AGVETTTPSK    60
QSNNKYAASS  YLSLTPEQWK  SHRSYSCQVT  HEGSTVEKTV  APTECS                  106

SEQ ID NO: 137          moltype = AA  length = 197
FEATURE                 Location/Qualifiers
source                  1..197
                        mol_type = protein
                        organism = Homo sapiens
SEQUENCE: 137
QAGPLPKPTL  WAEPGSVISW  GNSVTIWCQG  TLEAREYRLD  KEESPAPWDR  QNPLEPKNKA    60
RFSIPSMTED  YAGRYRCYYR  SPVGWSQPSD  PLELVMTGAY  SKPTLSALPS  PLVTSGKSVT   120
LLCQSRSPMD  TFLLIKERAA  HPLLHLRSEH  GAQQHQAEFP  MSPVTSVHGG  TYRCFSSHGF   180
SHYLLSHPSD  PLELIVS                                                     197

SEQ ID NO: 138          moltype = AA  length = 2477
FEATURE                 Location/Qualifiers
source                  1..2477
                        mol_type = protein
                        organism = Homo sapiens
SEQUENCE: 138
MLRGPGPGLL  LLAVQCLGTA  VPSTGASKSK  RQAQQMVQPQ  SPVAVSQSKP  GCYDNGKHYQ    60
INQQWERTYL  GNALVCTCYG  GSRGFNCESK  PEAEETCFDK  YTGNTYRVGD  TYERPKDSMI   120
WDCTCIGAGR  GRISCTIANR  CHEGGQSYKI  GDTWRRPHET  GGYMLECVCL  GNGKGEWTCK   180
PIAEKCFDHA  AGTSYVVGET  WEKPYQGWMM  VDCTCLGEGS  GRITCTSRNR  CNDQDTRTSY   240
RIGDTWSKKD  NRGNLLQCIC  TGNGRGEWKC  ERHTSVQTTS  SGSGPFTDVR  AAVYQPQPHP   300
QPPPYGHCVT  DSGVVYSVGM  QWLKTQGNKQ  MLCTCLGNGV  SCQETAVTQT  YGGNSNGEPC   360
VLPFTYNGRT  FYSCTTEGRQ  DGHLWCSTTS  NYEQDQKYSF  CTDHTVLVQT  RGGNSNGALC   420
HFPFLYNNHN  YTDCTSEGRR  DNMKWCGTTQ  NYDADQKFGF  CPMAAHEEIC  TTNEGVMYRI   480
GDQWDKQHDM  GHMMRCTCVG  NGRGEWTCIA  YSQLRDQCIV  DDITYNVNDT  FHKRHEEGHM   540
LNCTCFGQGR  GRWKCDPVDQ  CQDSETGTFY  QIGDSWEKYV  HGVRYQCYCY  GRGIGEWHCQ   600
PLQTYPSSSG  PVEVFITETP  SQPNSHPIQW  NAPQPSHISK  YILRWRPKNS  VGRWKEATIP   660
GHLNSYTIKG  LKPGVVYEGQ  LISIQQYGHQ  EVTRFDFTTS  STSTPVTSNT  VGETTPFSP    720
LVATSESVTE  ITASSFVVSW  VSASDTVSGF  RVEYELSEEG  DEPQYLDLPS  TATSVNIPDL   780
LPGRKYIVNV  YQISEDGEQS  LILSTSQTTA  PDAPPDTTVD  QVDDTSIVVR  WSRPQAPITG   840
YRIVYSPSVE  GSSTELNLPE  TANSVTLSDL  QPGVQYNITI  YAVEENQEST  PVVIQQETTG   900
TPRSDTVPSP  RDLQFVEVTD  VKVTIMWTPP  ESAVTGYRVD  VIPVNLPGEH  GQRLPISRNT   960
FAEVTGLSPG  VTYYFKVFAV  SHGRESKPLT  AQQTTKLDAP  TNLQFVNETD  STVLVRWTPP  1020
RAQITGYRLT  VGLTRRGQPR  QYNVGPSVSK  YPLRNLQPAS  EYTVSLVAIK  GNQESPKATG  1080
VFTTLQPGSS  IPPYNTEVTE  TTIVITWTPA  PRIGFKLGVR  PSQGGEAPRE  VTSDSGSIVV  1140
SGLTPGVEYV  YTIQVLRDGQ  ERDAPIVNKV  VTPLSPPTNL  HLEANPDTGV  LTVSWERSTT  1200
PDITGYRITT  TPTNGQQGNS  LEEVVHADQS  SCTFDNLSPG  LEYNVSVYTV  KDDKESVPIS  1260
DTIIPEVPQL  TDLSFVDITD  SSIGLRWTPL  NSSTIIGYRI  TVVAAGEGIP  IFEDFVDSSV  1320
GYYTVTGLEP  GIDYDISVIT  LINGGESAPT  TLTQQTAVPP  PTDLRFTNIG  PDTMRVTWAP  1380
```

```
PPSIDLTNFL VRYSPVKNEE DVAELSISPS DNAVVLTNLL PGTEYVVSVS SVYEQHESTP      1440
LRGRQKTGLD SPTGIDFSDI TANSFTVHWI APRATITGYR IRHHPEHFSG RPREDRVPHS      1500
RNSITLTNLT PGTEYVVSIV ALNGREESPL LIGQQSTVSD VPRDLEVVAA TPTSLLISWD      1560
APAVTVRYYR ITYGETGGNS PVQEFTVPGS KSTATISGLK PGVDYTITVY AVTGRGDSPA      1620
SSKPISINYR TEIDKPSQMQ VTDVQDNSIS VKWLPSSSPV RYRVTTTPK NGPGPTKTKT       1680
AGPDQTEMTI EGLQPTVEYV VSVYAQNPSG ESQPLVQTAV TNIDRPKGLA FTDVDVDSIK      1740
IAWESPQGQV SRYRVTYSSP EDGIHELFPA PDGEEDTAEL QGLRPGSEYT VSVVALHDDM      1800
ESQPLIGTQS TAIPAPTDLK FTQVTPTSLS AQWTPPNVQL TGYRVRVTPK EKTGPMKEIN      1860
LAPDSSSVVV SGLMVATKYE VSVYALKDTL TSRPAQGVVT TLENVSPPRR ARVTDATETT      1920
ITISWRTKTE TITGFQVDAV PANGQTPIQR TIKPDVRSYT ITGLQPGTDY KIYLYTLNDN      1980
ARSSPVVIDA STAIDAPSNL RFLATTPNSL LVSWQPPRAR ITGYIIKYEK PGSPPREVVP      2040
RPRPGVTEAT ITGLEPGTEY TIYVIALKNN QKSEPLIGRK KTDELPQLVT LPHPNLHGPE      2100
ILDVPSTVQK TPFVTHPGYD TGNGIQLPGT SGQQPSVGQQ MIFEEHGFRR TTPPTTATPI      2160
RHRPRPYPPN VGEEIQIGHI PREDVDYHLY PHGPGLNPNA STGQEALSQT TISWAPFQDT      2220
SEYIISCHPV GTDEEPLQFR VPGTSTSATL TGLTRGATYN VIVEALKDQQ RHKVREEVVT      2280
VGNSVNEGLN QPTDDSCFDP YTVSHYAVGD EWERMSESGF KLLCQCLGFG SGHFRCDSSR      2340
WCHDNGVNYK IGEKWDRQGE NGQMMSCTCL GNGKGEFKCD PHEATCYDDG KTYHVGEQWQ      2400
KEYLGAICSC TCFGGQRGWR CDNCRRPGGE PSPEGTTGQS YNQYSQRYHQ RTNTNVNCPI      2460
ECFMPLDVQA DREDSRE                                                    2477

SEQ ID NO: 139           moltype = AA  length = 2446
FEATURE                  Location/Qualifiers
source                   1..2446
                         mol_type = protein
                         organism = Homo sapiens
SEQUENCE: 139
QAQQMVPQS PVAVSQSKPG CYDNGKHYQI NQQWERTYLG NALVCTCYGG SRGFNCESKP       60
EAEETCFDKY TGNTYRVGDT YERPKDSMIW DCTCIGAGRG RISCTIANRC HEGGQSYKIG      120
DTWRRPHETG GYMLECVCLG NGKGEWTCKP IAEKCFDHAA GTSYVVGETW EKPYQGWMMV     180
DCTCLGEGSG RITCTSRNRC NDQDTRTSYR IGDTWSKKDN RGNLLQCICT GNRGEWKCE      240
RHTSVQTTSS GSGPFTDVRA AVYQPQPHPQ PPPYGHCVTD SGVVYSVGMQ WLKTQGNKQM    300
LCTCLGNGVS CQETAVTQTY GGNSNGEPCV LPFTYNGRTF YSCTTEGRQD GHLWCSTTSN    360
YEQDQKYSFC TDHTVLVQTR GGNSNGALCH FPFLYNNHNY TDCTSEGRRD NMKWCGTTQN    420
YDADQKFGFC PMAAHEEICT TNEGVMYRIG DQWDKQHMDG HMMRCTCVGN GRGEWTCIAY    480
SQLRDQCIVD DITYNVNDTF HKRHEEGHML NCTCFGQGRG RWKCDPVDQC QDSETGTFYQ   540
IGDSWEKYVH GVRYQCYCYG RGIGEWHCQP LQTYPSSSGP VEVFITETPS QPNSHPIQWN    600
APQPSHISKY ILRWRPKNSV GRWKEATIPG HLNSYTIKGL KPGVVYEGQL ISIQQYGHQE    660
VTRFDFTTTS TSTPVTSNTV TGETTPFSPL VATSESVTEI TASSFVVSWV SASDTVSGFR    720
VEYELSEEGD EPQYLDLPST ATSVNIPDLL PGRKYIVNVY QISEDGEQSL ILSTSQTTAP    780
DAPPDTTVDQ VDDTSIVVRW SRPQAPITGY RIVYSPSVEG SSTELNLPET ANSVTLSDLQ    840
PGVQYNITIY AVEENQESTP VVIQQETTGT PRSDTVPSPR DLQFVEVTDV KVTIMWTPPE    900
SAVTGYRVDV IPVNLPGEHG QRLPISRNTF AEVTGLSPGV TYYFKVFAVS HGRESKPLTA    960
QQTTKLDAPT NLQFVNETDS TVLVRWTPPR AQITGYRLTV GLTRRGQPRQ YNVGPSVSKY   1020
PLRNLQPASE YTVSLVAIKG NQESPKATGV FTTLQPGSSI PPYNTEVTET TIVITWTPAP   1080
RIGFKLGVRP SQGGEAPREV TSDSGSIVVS GLTPGVEYVY TIQVLRDGQE RDAPIVNKVV   1140
TPLSPPTNLH LEANPDTGVL TVSWERSTTP DITGYRITTT PTNGQQGNSL EEVVHADQSS   1200
CTFDNLSPGL EYNVSVYTVK DDKESVPISD TIIPEVPLDT DLSFVDITDS SIGLRWTPLN   1260
SSTIIGYRIT VVAAGEGIPI FEDFVDSSVG YYTVTGLEPG IDYDISVITL INGGESAPTT   1320
LTQQTAVPPP TDLRFTNIGP DTMRVTWAPP PSIDLTNFLV RYSPVKNEED VAELSISPSD   1380
NAVVLTNLLP GTEYVVSVSS VYEQHESTPL RGRQKTGLDS PTGIDFSDIT ANSFTVHWIA   1440
PRATITGYRI RHHPEHFSGR PREDRVPHSR NSITLTNLTP GTEYVVSIVA LNGREESPLL   1500
IGQQSTVSDV PRDLEVVAAT PTSLLISWDA PAVTVRYYRI TYGETGGNSP VQEFTVPGSK   1560
STATISGLKP GVDYTITVYA VTGRGDSPAS SKPISINYRT EIDKPSQMQV TDVQDNSISV   1620
KWLPSSSPVT GYRVTTTPKN GPGPTKTKTA GPDQTEMTIE GLQPTVEYVV SVYAQNPSGE   1680
SQPLVQTAVT NIDRPKGLAF TDVDVDSIKI AWESPQGQVS RYRVTYSSPE DGIHELFPAP   1740
DGEEDTAELQ GLRPGSEYTV SVVALHDDME SQPLIGTQST AIPAPTDLKF TQVTPTSLSA   1800
QWTPPNVQLT GYRVRVTPKE KTGPMKEINL APDSSSVVVS GLMVATKYEV SVYALKDTLT   1860
SRPAQGVVTL LENVSPPRRA RVTDATETTI TISWRTKTET ITGFQVDAVP ANGQTPIQRT   1920
IKPDVRSYTI TGLQPGTDYK IYLYTLNDNA RSSPVVIDAS TAIDAPSNLR FLATTPNSLL   1980
VSWQPPRARI TGYIIKYEKP GSPPREVVPR PRPGVTEATI TGLEPGTEYT IYVIALKNNQ   2040
KSEPLIGRKK TDELPQLVTL PHPNLHGPEI LDVPSTVQKT PFVTHPGYDT GNGIQLPGTS   2100
GQQPSVGQQM IFEEHGFRRT TPPTTATPIR HRPRPYPPNV GEEIQIGHIP REDVDYHLYP   2160
HGPGLNPNAS TGQEALSQTT ISWAPFQDTS EYIISCHPVG TDEEPLQFRV PGTSTSATLT   2220
GLTRGATYNV IVEALKDQQR HKVREEVVTV GNSVNEGLNQ PTDDSCFDPY TVSHYAVGDE   2280
WERMSESGFK LLCQCLGFGS GHFRCDSSRW CHDNGVNYKI GEKWDRQGEN GQMMSCTCLG   2340
NGKGEFKCDP HEATCYDDGK TYHVGEQWQK EYLGAICSCT CFGGQRGWRC DNCRRPGGEP   2400
SPEGTTGQSY NQYSQRYHQR TNTNVNCPIE CFMPLDVQAD REDSRE                  2446

SEQ ID NO: 140          moltype = AA  length = 577
FEATURE                 Location/Qualifiers
source                  1..577
                        mol_type = protein
                        organism = Homo sapiens
SEQUENCE: 140
QAQQMVPQS PVAVSQSKPG CYDNGKHYQI NQQWERTYLG NALVCTCYGG SRGFNCESKP       60
EAEETCFDKY TGNTYRVGDT YERPKDSMIW DCTCIGAGRG RISCTIANRC HEGGQSYKIG      120
DTWRRPHETG GYMLECVCLG NGKGEWTCKP IAEKCFDHAA GTSYVVGETW EKPYQGWMMV     180
DCTCLGEGSG RITCTSRNRC NDQDTRTSYR IGDTWSKKDN RGNLLQCICT GNRGEWKCE      240
RHTSVQTTSS GSGPFTDVRA AVYQPQPHPQ PPPYGHCVTD SGVVYSVGMQ WLKTQGNKQM    300
```

```
LCTCLGNGVS CQETAVTQTY GGNSNGEPCV LPFTYNGRTF YSCTTEGRQD GHLWCSTTSN    360
YEQDQKYSFC TDHTVLVQTR GGNSNGALCH FPFLYNNHNY TDCTSEGRRD NMKWCGTTQN    420
YDADQKFGFC PMAAHEEICT TNEGVMYRIG DQWDKQHDMG HMMRCTCVGN GRGEWTCIAY    480
SQLRDQCIVD DITYNVNDTF HKRHEEGHML NCTCFGQGRG RWKCDPVDQC QDSETGTFYQ    540
IGDSWEKYVH GVRYQCYCYG RGIGEWHCQP LQTYPSS                            577

SEQ ID NO: 141            moltype = AA   length = 241
FEATURE                   Location/Qualifiers
source                    1..241
                          mol_type = protein
                          organism = Homo sapiens
SEQUENCE: 141
QAQQMVQPQS PVAVSQSKPG CYDNGKHYQI NQQWERTYLG NALVCTCYGG SRGFNCESKP     60
EAEETCFDKY TGNTYRVGDT YERPKDSMIW DCTCIGAGRG RISCTIANRC HEGGQSYKIG    120
DTWRRPHETG GYMLECVCLG NGKGEWTCKP IAEKCFDHAA GTSYVVGETW EKPYQGWMMV    180
DCTCLGEGSG RITCTSRNRC NDQDTRTSYR IGDTWSKKDN RGNLLQCICT GNGRGEWKCE    240
R                                                                   241

SEQ ID NO: 142            moltype = AA   length = 336
FEATURE                   Location/Qualifiers
source                    1..336
                          mol_type = protein
                          organism = Homo sapiens
SEQUENCE: 142
HTSVQTTSSG SGPFTDVRAA VYQPQPHPQP PPYGHCVTDS GVVYSVGMQW LKTQGNKQML     60
CTCLGNGVSC QETAVTQTYG GNSNGEPCVL PFTYNGRTFY SCTTEGRQDG HLWCSTTSNY    120
EQDQKYSFCT DHTVLVQTRG GNSNGALCHF PFLYNNHNYT DCTSEGRRDN MKWCGTTQNY    180
DADQKFGFCP MAAHEEICTT NEGVMYRIGD QWDKQHDMGH MMRCTCVGNG RGEWTCIAYS    240
QLRDQCIVDD ITYNVNDTFH KRHEEGHMLN CTCFGQGRGR WKCDPVDQCQ DSETGTFYQI    300
GDSWEKYVHG VRYQCYCYGR GIGEWHCQPL QTYPSS                             336

SEQ ID NO: 143            moltype = AA   length = 44
FEATURE                   Location/Qualifiers
source                    1..44
                          mol_type = protein
                          organism = Homo sapiens
SEQUENCE: 143
PGCYDNGKHY QINQQWERTY LGNALVCTCY GGSRGFNCES KPEA                     44

SEQ ID NO: 144            moltype = AA   length = 44
FEATURE                   Location/Qualifiers
source                    1..44
                          mol_type = protein
                          organism = Homo sapiens
SEQUENCE: 144
ETCFDKYTGN TYRVGDTYER PKDSMIWDCT CIGAGRGRIS CTIA                     44

SEQ ID NO: 145            moltype = AA   length = 44
FEATURE                   Location/Qualifiers
source                    1..44
                          mol_type = protein
                          organism = Homo sapiens
SEQUENCE: 145
NRCHEGGQSY KIGDTWRRPH ETGGYMLECV CLGNGKGEWT CKPI                     44

SEQ ID NO: 146            moltype = AA   length = 46
FEATURE                   Location/Qualifiers
source                    1..46
                          mol_type = protein
                          organism = Homo sapiens
SEQUENCE: 146
AEKCFDHAAG TSYVVGETWE KPYQGWMMVD CTCLGEGSGR ITCTSR                   46

SEQ ID NO: 147            moltype = AA   length = 45
FEATURE                   Location/Qualifiers
source                    1..45
                          mol_type = protein
                          organism = Homo sapiens
SEQUENCE: 147
NRCNDQDTRT SYRIGDTWSK KDNRGNLLQC ICTGNGRGEW KCERH                    45

SEQ ID NO: 148            moltype = AA   length = 372
FEATURE                   Location/Qualifiers
source                    1..372
                          mol_type = protein
                          organism = Homo sapiens
SEQUENCE: 148
MAAPVPWACC AVLAAAAAVV YAQRHSPQEA PHVQYERLGS DVTLPCGTAN WDAAVTWRVN     60
GTDLAPDLLN GSQLVLHGLE LGHSGLYACF HRDSWHLRHQ VLLHVGLPPR EPVLSCRSNT    120
```

```
YPKGFYCSWH LPTPTYIPNT FNVTVLHGSK IMVCEKDPAL KNRCHIRYMH LFSTIKYKVS    180
ISVSNALGHN ATAITFDEFT IVKPDPPENV VARPVPSNPR RLEVTWQTPS TWPDPESFPL    240
KFFLRYRPLI LDQWQHVELS DGTAHTITDA YAGKEYIIQV AAKDNEIGTW SDWSVAAHAT    300
PWTEEPRHLT TEAQAAETTT STTSSLAPPP TTKICDPGEL GSGGGPSAPF LVSVPITLAL    360
AAAAATASSL LI                                                       372

SEQ ID NO: 149          moltype = AA   length = 350
FEATURE                 Location/Qualifiers
source                  1..350
                        mol_type = protein
                        organism = Homo sapiens
SEQUENCE: 149
QRHSPQEAPH VQYERLGSDV TLPCGTANWD AAVTWRVNGT DLAPDLLNGS QLVLHGLELG     60
HSGLYACFHR DSWHLRHQVL LHVGLPPREP VLSCRSNTYP KGFYCSWHLP TPTYIPNTFN    120
VTVLHGSKIM VCEKDPALKN RCHIRYMHLF STIKYKVSIS VSNALGHNAT AITFDEFTIV    180
KPDPPENVVA RPVPSNPRRL EVTWQTPSTW PDPESFPLKF FLRYRPLILD QWQHVELSDG    240
TAHTITDAYA GKEYIIQVAA KDNEIGTWSD WSVAAHATPW TEEPRHLTTE AQAAETTTST    300
TSSLAPPPTT KICDPGELGS GGGPSAPFLV SVPITLALAA AAATASSLLI               350

SEQ ID NO: 150          moltype = AA   length = 320
FEATURE                 Location/Qualifiers
source                  1..320
                        mol_type = protein
                        organism = Homo sapiens
SEQUENCE: 150
QRHSPQEAPH VQYERLGSDV TLPCGTANWD AAVTWRVNGT DLAPDLLNGS QLVLHGLELG     60
HSGLYACFHR DSWHLRHQVL LHVGLPPREP VLSCRSNTYP KGFYCSWHLP TPTYIPNTFN    120
VTVLHGSKIM VCEKDPALKN RCHIRYMHLF STIKYKVSIS VSNALGHNAT AITFDEFTIV    180
KPDPPENVVA RPVPSNPRRL EVTWQTPSTW PDPESFPLKF FLRYRPLILD QWQHVELSDG    240
TAHTITDAYA GKEYIIQVAA KDNEIGTWSD WSVAAHATPW TEEPRHLTTE AQAAETTTST    300
TSSLAPPPTT KICDPGELGS                                               320

SEQ ID NO: 151          moltype = AA   length = 82
FEATURE                 Location/Qualifiers
source                  1..82
                        mol_type = protein
                        organism = Homo sapiens
SEQUENCE: 151
QRHSPQEAPH VQYERLGSDV TLPCGTANWD AAVTWRVNGT DLAPDLLNGS QLVLHGLELG     60
HSGLYACFHR DSWHLRHQVL LH                                             82

SEQ ID NO: 152          moltype = AA   length = 118
FEATURE                 Location/Qualifiers
source                  1..118
                        mol_type = protein
                        organism = Homo sapiens
SEQUENCE: 152
PPREPVLSCR SNTYPKGFYC SWHLPTPTYI PNTFNVTVLH GSKIMVCEKD PALKNRCHIR     60
YMHLFSTIKY KVSISVSNAL GHNATAITFD EFTIVKPDPP ENVVARPVPS NPRRLEVT      118

SEQ ID NO: 153          moltype = AA   length = 81
FEATURE                 Location/Qualifiers
source                  1..81
                        mol_type = protein
                        organism = Homo sapiens
SEQUENCE: 153
WQTPSTWPDP ESFPLKFFLR YRPLILDQWQ HVELSDGTAH TITDAYAGKE YIIQVAAKDN     60
EIGTWSDWSV AAHATPWTEE P                                              81

SEQ ID NO: 154          moltype = AA   length = 6
FEATURE                 Location/Qualifiers
source                  1..6
                        mol_type = protein
                        note = Description of Artificial Sequence: Synthetic 6xHis
                          tag
                        organism = synthetic construct
SEQUENCE: 154
HHHHHH                                                                 6

SEQ ID NO: 155          moltype = AA   length = 136
FEATURE                 Location/Qualifiers
source                  1..136
                        mol_type = protein
                        organism = Homo sapiens
SEQUENCE: 155
PTLSALPSPL VTSGKSVTLL CQSRSPMDTF LLIKERAAHP LLHLRSEHGA QQHQAEFPMS     60
PVTSVHGGTY RCFSSHGFSH YLLSHPSDPL ELIVSGSLED PRPSPTRSVS TAAGPEDQPL    120
MPTGSVPHSG LRRHWE                                                   136
```

```
SEQ ID NO: 156          moltype = AA  length = 121
FEATURE                 Location/Qualifiers
source                  1..121
                        mol_type = protein
                        note = Description of Artificial Sequence: Synthetic
                          polypeptide
                        organism = synthetic construct
SEQUENCE: 156
EVQLVESGGG LVQPGGSLRL SCAASGFTFS SYGMSWVRQA PGKGLEWVAT ISSGGTYTFY    60
PDSVKGRFTI SRDNAKNSLY LQMNSLRAED TAVYYCARRG WLLHYYAMDY WGQGTSVTVS   120
S                                                                  121

SEQ ID NO: 157          moltype = AA  length = 121
FEATURE                 Location/Qualifiers
source                  1..121
                        mol_type = protein
                        note = Description of Artificial Sequence: Synthetic
                          polypeptide
                        organism = synthetic construct
SEQUENCE: 157
EVQLVESGGG LMQPGGSLRL SCAASGFTFS SYGMSWVRQA PGKGLEWVAT ISSGGTYTFY    60
PDSVKGRFTI SRDNAKNSLY LQMNSLRAED TAVYYCARRG WLLHYYAMDY WGQGTSVTVS   120
S                                                                  121

SEQ ID NO: 158          moltype = AA  length = 121
FEATURE                 Location/Qualifiers
source                  1..121
                        mol_type = protein
                        note = Description of Artificial Sequence: Synthetic
                          polypeptide
                        organism = synthetic construct
SEQUENCE: 158
EVQLVESGGG LVQPGGSLRL SCAASGFTFS SYGMSWVRQA PGKGLEWVGT ISSGGTYTFY    60
PDSVKGRFTI SRDNSKNTLY LQMNSLRAED TAVYYCARRG WLLHYYAMDY WGQGTLVTVS   120
S                                                                  121

SEQ ID NO: 159          moltype = AA  length = 121
FEATURE                 Location/Qualifiers
source                  1..121
                        mol_type = protein
                        note = Description of Artificial Sequence: Synthetic
                          polypeptide
                        organism = synthetic construct
SEQUENCE: 159
EVQLVESGGG LVQPGGSLRL SCAASGFTFS SYGMSWVRQA PGKGLEWVAT ISSGGTYTFY    60
PDSVKGRFTI SRDNSKNTLY LQMNSLRAED TAVYYCARRG WLLHYYAMDY WGQGTLVTVS   120
S                                                                  121

SEQ ID NO: 160          moltype = AA  length = 121
FEATURE                 Location/Qualifiers
source                  1..121
                        mol_type = protein
                        note = Description of Artificial Sequence: Synthetic
                          polypeptide
                        organism = synthetic construct
SEQUENCE: 160
EVQLVESGGG LMQPGGSLRL SCAASGFTFS SYGMSWVRQA PGKGLEWVAT ISSGGTYTFY    60
PDSVKGRFTI SRDNSKNTLY LQMNSLRAED TAVYYCARRG WLLHYYAMDY WGQGTLVTVS   120
S                                                                  121

SEQ ID NO: 161          moltype = AA  length = 111
FEATURE                 Location/Qualifiers
source                  1..111
                        mol_type = protein
                        note = Description of Artificial Sequence: Synthetic
                          polypeptide
                        organism = synthetic construct
SEQUENCE: 161
DIQLTQSPSF LSASVGDRVT ITCRPSESVD SFGNSFMHWF QQKPGKAPKL LIYLSSKLES    60
GVPSRFSGSG SGTEFTLTIS SLQPEDFATY YCQQHNEDPF TFGQGTKVEI K            111

SEQ ID NO: 162          moltype = AA  length = 118
FEATURE                 Location/Qualifiers
source                  1..118
                        mol_type = protein
                        note = Description of Artificial Sequence: Synthetic
                          polypeptide
                        organism = synthetic construct
SEQUENCE: 162
```

```
EVQLVESGGG LVQPGGSLRL SCAASGFTFS DYGMHWVRQA PGKGLEWVAY IFSGSSTIYY    60
ADTVKGRFTI SRDNAKNSLY LQMNSLRAED TAVYYCARAD GRGAMDYWGQ GTTVTVSS     118

SEQ ID NO: 163         moltype = AA  length = 118
FEATURE                Location/Qualifiers
source                 1..118
                       mol_type = protein
                       note = Description of Artificial Sequence: Synthetic
                         polypeptide
                       organism = synthetic construct
SEQUENCE: 163
EVQLVESGGG LVKPGGSLRL SCAASGFTFS DYGMHWVRQA PGKGLEWVSY IFSGSSTIYY    60
ADTVKGRFTI SRDNAKNSLY LQMNSLRAED TAVYYCARAD GRGAMDYWGQ GTLVTVSS     118

SEQ ID NO: 164         moltype = AA  length = 107
FEATURE                Location/Qualifiers
source                 1..107
                       mol_type = protein
                       note = Description of Artificial Sequence: Synthetic
                         polypeptide
                       organism = synthetic construct
SEQUENCE: 164
DIQMTQSPSS LSASVGDRVT ITCRASQDIS KFLNWYQQKP GKAPKLLIYY TSRLHSGVPS    60
RFSGSGSGTD FTFTISSLQP EDIATYFCQQ GNTLPWTFGG GTKLEIK                 107
```

ILT3-BINDING AGENTS AND METHODS OF USE THEREOF

CROSS-REFERENCE TO RELATED APPLICATIONS

This application is a Divisional application of U.S. application Ser. No. 17/125,734 filed Dec. 17, 2020, which claims the benefit of priority of U.S. Provisional Appl. No. 62/950,434, filed Dec. 19, 2019, the contents of each of which are incorporated by reference herein in their entireties.

SEQUENCE LISTING

This application contains a computer readable Sequence Listing which has been submitted in XML file format with this application, the entire content of which is incorporated by reference herein in its entirety. The Sequence Listing XML file submitted with this application is entitled "13370-184-999_SequenceListing.xml", was created on Jul. 28, 2023 and is 187,021 bytes in size.

FIELD OF THE DISCLOSURE

The present disclosure generally relates to agents that bind immunoglobulin-like transcript 3 (ILT3), particularly antibodies that bind human ILT3, as well as compositions comprising the ILT3-binding agents and methods of using the agents and compositions.

BACKGROUND

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances, immunotherapy is used to treat autoimmune diseases, which may arise from an abnormal immune response against proteins, molecules, and/or tissues normally present in the body. Immunotherapy may include methods to induce or enhance specific immune responses or to inhibit or reduce specific immune responses.

The immune system is a highly complex system made up of a great number of cell types, including but not limited to, T-cells, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases or a cytokine storm).

Some of the inhibitory mechanisms of the immune system use proteins from the leukocyte Ig-like receptor (LILR) family. The leukocyte Ig-like receptor subfamily B (LILRB) is a group of type I transmembrane glycoproteins with extracellular Ig-like domains and cytoplasmic immunoreceptor tyrosine-based inhibitory motifs (ITIMs). This group of ITIM-containing receptors includes 5 members: LILRB1 (also known as CD85J, LIR1, ILT2), LILRB2 (also known as CD85D, LIR2, ILT4), LILRB3 (also known as CD85A, LIR3, ILT5), LILRB4 (also known as CD85K, LIR5, ILT3), and LILRB5 (also known as CD85C, LIRE). The biological functions and clinical significance of many of these LILRBs (ILTs) are still being investigated.

The concept of cancer immunosurveillance is based on the theory that the immune system can recognize tumor cells, mount an immune response, and suppress the development and/or growth of a tumor. However, it is clear that many cancerous cells have developed mechanisms and/or hijacked normal inhibitory mechanisms to evade the immune system which can allow for uninhibited growth of tumors. Cancer/tumor immunotherapy (immuno-oncology) focuses on the development of new and novel agents that can activate and/or boost the immune system to achieve a more effective attack against cancer/tumor cells resulting in increased killing of cancer/tumor cells and/or inhibition of cancer/tumor growth.

BRIEF SUMMARY

The present disclosure provides agents that bind immunoglobulin-like transcript 3 (ILT3). Although the LILRB family members are referred to by many names in publications, the term "ILT3" (LILRB4) will be used herein. The agents include, but are not limited to, polypeptides such as antibodies that specifically bind ILT3. The agents may be referred to herein as "ILT3-binding agents". The disclosure provides methods of making and of using an ILT3-binding agent. In some embodiments, an ILT3-binding agent inhibits ILT3 activity. In some embodiments, an ILT3-binding agent enhances an immune response. In some embodiments, an ILT3-binding agent reverses suppression of an immune cell. In some embodiments, an ILT3-binding agent is used in a combination therapy. In some embodiments, an ILT3-binding agent is used in combination with at least one additional therapeutic agent.

The disclosure also provides compositions comprising the ILT3-binding agents described herein. In some embodiments, the disclosure provides pharmaceutical compositions comprising the ILT3-binding agents described herein. Polynucleotides and/or vectors encoding the ILT3-binding agents are provided. Cells comprising the polynucleotides and/or the vectors described herein are also provided. Cells comprising or producing the ILT3-binding agents described herein are provided. Methods of making the binding agents described herein are also provided.

In one aspect, this disclosure features an antibody that binds human ILT3 and inhibits binding of human ILT3 to fibronectin. In some instances, this antibody has one or more (e.g., 1, 2, 3, 4, 5, 6, 7, 8, 9, 10, 11, or 12) of the following properties in any combination or permutation: also binds cyno ILT3; does not bind, or only weakly binds (relative to ILT3), ILT2, ILT4, ILT5, and LILRB5; does not bind, or only weakly binds (relative to ILT3), LILRA1, LILRA2, LILRA4, LILRA5, and LILRA6; is an ILT3 antagonist; inhibits ILT3 activity; inhibits ILT3 signaling in cells that express ILT3; inhibits binding of ILT3 to APOE; inhibits binding of ILT3 to CNTFR; inhibits ILT3-induced suppression of myeloid cells; inhibits ILT3-induced suppression of myeloid cell activity; restores FcR activation in myeloid cells that express ILT3; and restores chemokine production in myeloid cells that express ILT3. In some instances, this antibody has a $K_D$ for human ILT3 of 1 μM to 1 pM, 1 nM to 1 pM, or 100 nM to 1 pM (e.g., as assessed by Biacore). In some instances, this antibody comprises a human IgG1 constant region. In some instances, this antibody comprises a human kappa light chain constant region. In some instances, this antibody comprises a human IgG1 constant region and a human kappa light chain constant region. In certain cases, the human IgG1 constant region comprises one or more mutations that reduce or eliminate Fc effector functions. In certain cases, the human IgG1 constant region comprises a N297G mutation that reduces effector function. In some instances, this antibody is an ILT3-binding antibody fragment.

In one aspect, the present disclosure provides agents that bind ILT3. In some embodiments, an agent binds human ILT3. In some embodiments, an agent binds cynomolgus monkey ("cyno") ILT3. In some embodiments, an agent binds human ILT3 and cyno ILT3. In some embodiments, an agent binds SEQ ID NO:2, SEQ ID NO:3, SEQ ID NO:4, and/or SEQ ID NO:5. In some embodiments, an agent binds SEQ ID NO:7, SEQ ID NO:8, SEQ ID NO:9, and/or SEQ ID NO:10. In some embodiments, an agent is an antibody. In some embodiments, an agent is an antibody that binds human ILT3. In some embodiments, an agent is an antibody that binds cyno ILT3. In some embodiments, an agent is an antibody that binds human ILT3 and cyno ILT3.

In some embodiments, an agent binds within the extracellular domain of ILT3. In some embodiments, an agent binds within amino acids 22-259 of SEQ ID NO:1. In some embodiments, an agent binds within amino acids 27-118 of SEQ ID NO:1. In some embodiments, an agent binds within amino acids 124-218 of SEQ ID NO:1. In some embodiments, an agent binds within amino acids 27-218 of SEQ ID NO:1 In some embodiments, an agent binds within amino acids 124-259 of SEQ ID NO:1 In some embodiments, an agent binds a conformational epitope within the extracellular domain of ILT3. In some embodiments, an agent binds a conformational epitope within one of the Ig-like C2-type domains of ILT3 (e.g., D1 or D2 domain). In some embodiments, an agent binds a conformational epitope within the two Ig-like C2-type domains of ILT3 (D1 and D2 domains). In some embodiments, an agent binds a conformational epitope within the D2-stem region of ILT3. In some embodiment, an agent binds to a conformational epitope located between D1 and D2 domain (e.g., the junction between D1 and D2 domain) of ILT3.

In one aspect, the present disclosure provides agents that bind human ILT3 and have at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi) inhibits ILT3-induced suppression of myeloid cells; (xii) inhibits ILT3-induced suppression of myeloid cell activity; (xiii) restores FcR activity in myeloid cells that express ILT3; and (xiv) restores or increases chemokine production in myeloid cells that express ILT3. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are antigen-presenting cells (APCs).

In one aspect, the present disclosure provides agents that specifically bind human ILT3. In some embodiments, the present disclosure provides an ILT3-binding agent (e.g., an antibody), wherein the binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or SEQ ID NO:29 with one substitution (e.g., of methionine at position 5 to another amino acid (e.g., tyrosine)), and (b) a light chain variable region comprising a light chain variable region CDR1 comprising the amino acid sequence RASESVDSYGNSFMH (SEQ ID NO:30) or SEQ ID NO:30 with one or two substitutions (e.g., of aspartic acid at position 7 to another amino acid (e.g., glutamic acid)) and/or asparagine at position 11 to another amino acid (e.g., serine), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises heavy and light chain variable region CDRs with amino acid sequences substantially identical to SEQ ID NOs:27-32. In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:105), and a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises heavy and light chain variable region CDRs with amino acid sequences substantially identical to SEQ ID NOs:27, 28, 105, 106, 31 and 32.

In some embodiments, an ILT3-binding agent (e.g., an antibody) comprises: (a) a heavy chain variable region having at least 80% sequence identity to SEQ ID NO:111 (5A7) or SEQ ID NO:123 (Hz5A7.v5); and/or (b) a light chain variable region having at least 80% sequence identity to SEQ ID NO:112 (5A7) or SEQ ID NO:124 (Hz5A7.v5). In some embodiments, an ILT3-binding agent comprises a heavy chain variable region having least 80%, at least 85%, at least 90%, at least 95%, at least 96%, at least 97%, at least 98%, or at least 99% sequence identity to SEQ ID NO:111 and/or a light chain variable region having least 80%, at least 85%, at least 90%, at least 95%, at least 96%, at least 97%, at least 98%, or at least 99% sequence identity to SEQ ID NO:112. In some embodiments, an ILT3-binding agent comprises a heavy chain variable region having least 80%, at least 85%, at least 90%, at least 95%, at least 96%, at least 97%, at least 98%, or at least 99% sequence identity to SEQ ID NO:123 and/or a light chain variable region having least 80%, at least 85%, at least 90%, at least 95%, at least 96%, at least 97%, at least 98%, or at least 99% sequence identity to SEQ ID NO:124. In some embodiments, an ILT3-binding agent comprises a heavy chain variable region of SEQ ID NO:111 and/or a light chain variable region of SEQ ID NO:112. In some embodiments, the ILT3-binding agent comprises a heavy chain variable region of SEQ ID NO:111 and a light chain variable region of SEQ ID NO:112. In some embodiments, an ILT3-binding agent comprises a heavy chain variable region of SEQ ID NO:123 and/or a light chain variable region of SEQ ID NO:124. In some embodiments, an ILT3-binding agent comprises a heavy chain variable region of SEQ ID NO:123 and a light chain variable region of SEQ ID NO:124.

In some embodiments, an ILT3-binding agent (e.g., an antibody) comprises a heavy chain variable region CDR1, CDR2, and CDR3 from the amino acid sequence of SEQ ID NO:111 and/or a light chain variable region CDR1, CDR2, and CDR3 from the amino acid sequence of SEQ ID NO:112. In some embodiments, an ILT3-binding agent comprises a heavy chain variable region CDR1, CDR2, and CDR3 from the amino acid sequence of SEQ ID NO:123 and/or a light chain variable region CDR1, CDR2, and CDR3 from the amino acid sequence of SEQ ID NO:124. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:111 and/or a light chain variable region CDR1, CDR2, and CDR3 with amino acid sequences substantially identical to CDR1, CDR2, and CDR3 from the amino acid sequence of SEQ ID NO:112. In some embodiments, an ILT3-binding agent comprises a heavy chain variable region CDR1, CDR2, and CDR3 with amino acid sequences substantially identical to CDR1, CDR2, and CDR3 from the amino acid sequence of SEQ ID NO:123 and/or a light chain variable region CDR1, CDR2, and CDR3 with amino acid sequences substantially identical to CDR1, CDR2, and CDR3 from the amino acid sequence of SEQ ID NO:124.

In some embodiments, an ILT3-binding agent (e.g., an antibody) comprises a heavy chain variable region comprising a heavy chain variable region CDR1, CDR2, and CDR3 from the amino acid sequence of SEQ ID NO:111 and/or a light chain variable region comprising a light chain variable region CDR1, CDR2, and CDR3 from the amino acid sequence of SEQ ID NO:112. In some embodiments, an ILT3-binding agent comprises a heavy chain variable region comprising a heavy chain variable region CDR1, CDR2, and CDR3 from the amino acid sequence of SEQ ID NO:123 and/or a light chain variable region comprising a light chain variable region CDR1, CDR2, and CDR3 from the amino acid sequence of SEQ ID NO:124. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:111 and/or a light chain variable region comprising a light chain variable region CDR1, CDR2, and CDR3 with amino acid sequences substantially identical to CDR1, CDR2, and CDR3 from the amino acid sequence of SEQ ID NO:112. In some embodiments, an ILT3-binding agent comprises a heavy chain variable region comprising a heavy chain variable region CDR1, CDR2, and CDR3 with amino acid sequences substantially identical to CDR1, CDR2, and CDR3 from the amino acid sequence of SEQ ID NO:123 and/or a light chain variable region comprising a light chain variable region CDR1, CDR2, and CDR3 with amino acid sequences substantially identical to CDR1, CDR2, and CDR3 from the amino acid sequence of SEQ ID NO:124.

In some embodiments, an ILT3-binding agent is an antibody that comprises a heavy chain of SEQ ID NO:126 and/or a light chain of SEQ ID NO:128. In some embodiments, an ILT3-binding agent is an antibody that comprises a heavy chain of SEQ ID NO:126 and a light chain of SEQ ID NO:128. In some embodiments, an ILT3-binding agent is a monoclonal antibody that comprises a heavy chain comprising the amino acid sequence of SEQ ID NO:126 and a light chain comprising the amino acid sequence of SEQ ID NO:128.

In some embodiments, an ILT3-binding agent is an antibody that comprises a heavy chain with the VH CDRs of Hz5A7.v5 and an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and/or a light chain with the VL CDRs of Hz5A7.v5 and an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128. In some embodiments, an ILT3-binding agent is an antibody that comprises a heavy chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and a light chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128. In some embodiments, an ILT3-binding agent is a monoclonal antibody that comprises a heavy chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and a light chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128.

In some embodiments, the heavy chain variable region of Hz48A6, as set forth in any one of SEQ ID NOS:156-160 or the heavy chain variable region of Hz45G10, as set forth in any one of SEQ ID NOS:162-163 is appended to SEQ ID NO:129. In certain embodiments, the heavy chain variable region of Hz48A6, as set forth in any one of SEQ ID NOS:156-160 or the heavy chain variable region of Hz45G10, as set forth in any one of SEQ ID NOS:162-163 is appended to SEQ ID NO:129, except that N297G mutation is introduced in SEQ ID NO:129 to eliminate effector functions.

In some embodiments, the light chain variable region of Hz48A6 as set forth in SEQ ID NO:161 or the light chain variable region of Hz45G10 set forth in SEQ ID NO:164 is appended to SEQ ID NO:135. In other embodiments, the light chain variable region of Hz48A6 as set forth in SEQ ID NO: 161 or the light chain variable region of Hz45G10 set forth in SEQ ID NO: 164 is appended to SEQ ID NO:136.

In some embodiments, an ILT3-binding agent (e.g., an antibody) comprises (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and/or (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, the ILT3-binding agent comprises heavy and light chain variable region CDRs with amino acid sequences substantially identical to SEQ ID NOs:11-16.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:109 and/or a light chain variable region having at least 80% (e.g., at least 85%, at least 90%, at least 95%, at least 96%, at least 97%, at least 98%, or at least 99%) identity to SEQ ID NO:110. In some embodiments, the ILT3-binding agent comprises a heavy chain variable region of SEQ ID NO:109 and/or a light chain variable region of SEQ ID NO:110. In some embodiments, an ILT3-binding agent comprises a heavy chain variable region of SEQ ID NO:109 and a light chain variable region of SEQ ID NO:110.

In some embodiments, an ILT3-binding agent comprises a heavy chain variable region CDR1, CDR2, and CDR3 from the amino acid sequence of SEQ ID NO:109 and/or a light chain variable region CDR1, CDR2, and CDR3 from the amino acid sequence of SEQ ID NO:110. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:109 and/or a light chain variable region CDR1, CDR2, and CDR3 with amino acid sequences substantially identical to CDR1, CDR2, and CDR3 from the amino acid sequence of SEQ ID NO:110.

In some embodiments, an ILT3-binding agent comprises a heavy chain variable region comprising a heavy chain variable region CDR1, CDR2, and CDR3 from the amino acid sequence of SEQ ID NO:109 and/or a light chain variable region comprising a light chain variable region CDR1, CDR2, and CDR3 from the amino acid sequence of SEQ ID NO:110. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:109 and/or a light chain variable region comprising a light chain variable region CDR1, CDR2, and CDR3 with amino acid sequences substantially identical to CDR1, CDR2, and CDR3 from the amino acid sequence of SEQ ID NO:110.

In some embodiments, an ILT3-binding agent (e.g., an antibody) comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and/or (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, the ILT3-binding agent comprises heavy and light chain variable region CDRs with amino acid sequences substantially identical to SEQ ID NOs:43-48.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:113 and/or a light chain variable region having at least 80% (e.g., at least 85%, at least 90%, at least 95%, at least 96%, at least 97%, at least 98%, or at least 99%) identity to SEQ ID NO:114. In some embodiments, the ILT3-binding agent comprises a heavy chain variable region of SEQ ID NO:113 and/or a light chain variable region of SEQ ID NO:114. In some embodiments, an ILT3-binding agent comprises a heavy chain variable region of SEQ ID NO:113 and a light chain variable region of SEQ ID NO:114.

In some embodiments, an ILT3-binding agent comprises a heavy chain variable region CDR1, CDR2, and CDR3 from the amino acid sequence of SEQ ID NO:113 and/or a light chain variable region CDR1, CDR2, and CDR3 from the amino acid sequence of SEQ ID NO:114. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:113 and/or a light chain variable region CDR1, CDR2, and CDR3 with amino acid sequences substantially identical to CDR1, CDR2, and CDR3 from the amino acid sequence of SEQ ID NO:114.

In some embodiments, an ILT3-binding agent comprises a heavy chain variable region comprising a heavy chain variable region CDR1, CDR2, and CDR3 from the amino acid sequence of SEQ ID NO:113 and/or a light chain variable region comprising a light chain variable region CDR1, CDR2, and CDR3 from the amino acid sequence of SEQ ID NO:114. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:113 and/or a light chain variable region comprising a light chain variable region CDR1, CDR2, and CDR3 with amino acid sequences substantially identical to CDR1, CDR2, and CDR3 from the amino acid sequence of SEQ ID NO:114.

In some embodiments, an ILT3-binding agent (e.g., an antibody) comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and/or (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, the ILT3-binding agent comprises heavy and light chain variable region CDRs with amino acid sequences substantially identical to SEQ ID NOs:43, 59, 60, 61, 62, and 63.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:115 and/or a light chain variable region having at least 80% (e.g., at least 85%, at least 90%, at least 95%, at least 96%, at least 97%, at least 98%, or at least 99%) identity to SEQ ID NO:116. In some embodiments, the ILT3-binding agent comprises a heavy chain variable region of SEQ ID NO:115 and/or a light chain variable region of SEQ ID NO:116. In some embodiments, an ILT3-binding agent comprises a heavy chain variable region of SEQ ID NO:115 and a light chain variable region of SEQ ID NO:116.

In some embodiments, an ILT3-binding agent comprises a heavy chain variable region CDR1, CDR2, and CDR3 from the amino acid sequence of SEQ ID NO:115 and/or a light chain variable region CDR1, CDR2, and CDR3 from the amino acid sequence of SEQ ID NO:116. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:115 and/or a light chain variable region CDR1, CDR2, and CDR3 with amino acid sequences substantially identical to CDR1, CDR2, and CDR3 from the amino acid sequence of SEQ ID NO:116.

In some embodiments, an ILT3-binding agent comprises a heavy chain variable region comprising a heavy chain variable region CDR1, CDR2, and CDR3 from the amino acid sequence of SEQ ID NO:115 and/or a light chain variable region comprising a light chain variable region CDR1, CDR2, and CDR3 from the amino acid sequence of SEQ ID NO:116. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:115 and/or a light chain variable region comprising a light chain variable region CDR1, CDR2, and CDR3 with amino acid sequences substantially identical to CDR1, CDR2, and CDR3 from the amino acid sequence of SEQ ID NO:116.

In some embodiments, an ILT3-binding agent (e.g., an antibody) comprises (a) a heavy chain variable region comprising a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and/or (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, the ILT3-binding agent comprises heavy and light chain variable region CDRs with amino acid sequences substantially identical to SEQ ID NOs:71-76.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:117 and/or a light chain variable region having at least 80% (e.g., at least 85%, at least 90%, at least 95%, at least 96%, at least 97%, at least 98%, or at least 99%) identity to SEQ ID NO:118. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:162 and/or a light chain variable region having at least 80% (e.g., at least 85%, at least 90%, at least 95%, at least 96%, at least 97%, at least 98%, or at least 99%) identity to SEQ ID NO:164. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:163 and/or a light chain variable region having at least 80% (e.g., at least 85%, at least 90%, at least 95%, at least 96%, at least 97%, at least 98%, or at least 99%) identity to SEQ ID NO:164. In some embodiments, the ILT3-binding agent comprises a heavy chain variable region of SEQ ID NO:117 and/or a light chain variable region of SEQ ID NO:118. In some embodiments, an ILT3-binding agent comprises a heavy chain variable region of SEQ ID NO:117 and a light chain variable region of SEQ ID NO:118. In some embodiments, the ILT3-binding agent comprises a heavy chain variable region of SEQ ID NO:162 and/or a light chain variable region of SEQ ID NO:164. In some embodiments, an ILT3-binding agent comprises a heavy chain variable region of SEQ ID NO:162 and a light chain variable region of SEQ ID NO:164. In some embodiments, the ILT3-binding agent comprises a heavy chain variable region of SEQ ID NO:163 and/or a light chain variable region of SEQ ID NO:164. In some embodiments, an ILT3-binding agent comprises a heavy chain variable region of SEQ ID NO:163 and a light chain variable region of SEQ ID NO:163.

In some embodiments, an ILT3-binding agent comprises a heavy chain variable region CDR1, CDR2, and CDR3 from the amino acid sequence of SEQ ID NO:117 and/or a light chain variable region CDR1, CDR2, and CDR3 from the amino acid sequence of SEQ ID NO:118. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:117 and/or a light chain variable region CDR1, CDR2, and CDR3 with amino acid sequences substantially identical to CDR1, CDR2, and CDR3 from the amino acid sequence of SEQ ID NO:118.

In some embodiments, an ILT3-binding agent comprises a heavy chain variable region comprising a heavy chain variable region CDR1, CDR2, and CDR3 from the amino acid sequence of SEQ ID NO:117 and/or a light chain variable region comprising a light chain variable region CDR1, CDR2, and CDR3 from the amino acid sequence of SEQ ID NO:118. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:117 and/or a light chain variable region comprising a light chain variable region CDR1, CDR2, and CDR3 with amino acid sequences substantially identical to CDR1, CDR2, and CDR3 from the amino acid sequence of SEQ ID NO:118.

In some embodiments, an ILT3-binding agent (e.g., an antibody) comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and/or (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).). In some embodiments, the ILT3-binding agent comprises heavy and light chain variable region CDRs with amino acid sequences substantially identical to SEQ ID NOs:27, 87, 88, 89, 90 and 91.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:119 and/or a light chain variable region having at least 80% (e.g., at least 85%, at least 90%, at least 95%, at least 96%, at least 97%, at least 98%, or at least 99%) identity to SEQ ID NO:120. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:156 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:157 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:158 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:159 and/or a light chain variable region having at least 80% (e.g., at least 85%, at least 90%, at least 95%, at least 96%, at least 97%, at least 98%, or at least 99%) identity to SEQ ID NO:161, In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:160 and/or a light chain variable region having at least 80% (e.g., at least 85%, at least 90%, at least 95%, at least 96%, at least 97%, at least 98%, or at least 99%) identity to SEQ ID NO:161. In some embodiments, the ILT3-binding agent comprises a heavy chain variable region of SEQ ID NO:119 and/or a light chain variable region of SEQ ID NO:120. In some embodiments, an ILT3-binding agent comprises a heavy chain variable region of SEQ ID NO:119 and a light chain variable region of SEQ ID NO:120. In some embodiments, the ILT3-binding agent comprises a heavy chain variable region of SEQ ID NO:156 and/or a light chain variable region of SEQ ID NO:161. In some embodiments, an ILT3-binding agent comprises a heavy chain variable region of SEQ ID NO:156 and a light chain variable region of SEQ ID NO:161. In some embodiments, the ILT3-binding agent comprises a heavy chain variable region of SEQ ID NO:157 and/or a light chain variable region of SEQ ID NO:161. In some embodiments, an ILT3-binding agent comprises a heavy chain variable region of SEQ ID NO:157 and a light chain variable region of SEQ ID NO:161. In some embodiments, the ILT3-binding agent comprises a heavy chain variable region of SEQ ID NO:158 and/or a light chain variable region of SEQ ID NO:161. In some embodiments, an ILT3-binding agent comprises a heavy chain variable region of SEQ ID NO:158 and a light chain variable region of SEQ ID NO:161. In some embodiments, the ILT3-binding agent comprises a heavy chain variable region of SEQ ID NO:159 and/or a light chain variable region of SEQ ID NO:161. In some embodiments, an ILT3-binding agent comprises a heavy chain variable region of SEQ ID NO:159 and a light chain variable region of SEQ ID NO:161. In some embodiments, the ILT3-binding agent comprises a heavy chain variable region of SEQ ID NO:160 and/or a light chain variable region of SEQ ID NO:161. In some embodiments, an ILT3-binding agent comprises a heavy chain variable region of SEQ ID NO:160 and a light chain variable region of SEQ ID NO:161.

In some embodiments, an ILT3-binding agent comprises a heavy chain variable region CDR1, CDR2, and CDR3 from the amino acid sequence of SEQ ID NO:119 and/or a light chain variable region CDR1, CDR2, and CDR3 from the amino acid sequence of SEQ ID NO:120. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:119 and/or a light chain variable region CDR1, CDR2, and CDR3 with amino acid sequences substantially identical to CDR1, CDR2, and CDR3 from the amino acid sequence of SEQ ID NO:120.

In some embodiments, an ILT3-binding agent comprises a heavy chain variable region comprising a heavy chain variable region CDR1, CDR2, and CDR3 from the amino acid sequence of SEQ ID NO:119 and/or a light chain variable region comprising a light chain variable region CDR1, CDR2, and CDR3 from the amino acid sequence of SEQ ID NO:120. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:119 and/or a light chain variable region comprising a light chain variable region CDR1, CDR2, and CDR3 with amino acid sequences substantially identical to CDR1, CDR2, and CDR3 from the amino acid sequence of SEQ ID NO:120.

In some embodiments, an ILT3-binding agent (e.g., an antibody) comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and/or (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, the ILT3-binding agent comprises heavy and light chain variable region CDRs with amino acid sequences substantially identical to SEQ ID NOs:71, 99, 73, 100, 75, and 76.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:121 and/or a light chain variable region having at least 80% (e.g., at least 85%, at least 90%, at least 95%, at least 96%, at least 97%, at least 98%, or at least 99%) identity to SEQ ID NO:122. In some embodiments, the ILT3-binding agent comprises a heavy chain variable region of SEQ ID NO:121 and/or a light chain variable region of SEQ ID NO:122. In some embodiments, an ILT3-binding agent comprises a heavy chain variable region of SEQ ID NO:121 and a light chain variable region of SEQ ID NO:122.

In some embodiments, an ILT3-binding agent comprises a heavy chain variable region CDR1, CDR2, and CDR3 from the amino acid sequence of SEQ ID NO:121 and/or a light chain variable region CDR1, CDR2, and CDR3 from the amino acid sequence of SEQ ID NO:122. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:121 and/or a light chain variable region CDR1, CDR2, and CDR3 with amino acid sequences substantially identical to CDR1, CDR2, and CDR3 from the amino acid sequence of SEQ ID NO:122.

In some embodiments, an ILT3-binding agent comprises a heavy chain variable region comprising a heavy chain variable region CDR1, CDR2, and CDR3 from the amino acid sequence of SEQ ID NO:121 and/or a light chain variable region comprising a light chain variable region CDR1, CDR2, and CDR3 from the amino acid sequence of SEQ ID NO:122. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:121 and/or a light chain variable region comprising a light chain variable region CDR1, CDR2, and CDR3 with amino acid sequences substantially identical to CDR1, CDR2, and CDR3 from the amino acid sequence of SEQ ID NO:122.

In another aspect of the disclosure, provided herein is a binding agent (e.g., an antibody) that competes for binding to ILT3 with any of the ILT3-binding agents described herein. In some embodiments, provided herein is an agent that competes for binding to ILT3 with a reference antibody, wherein the reference antibody comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRMTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, provided herein is an agent that competes for binding to ILT3 with a reference antibody, wherein the reference antibody comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVE-SYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32) and wherein the agent that competes with the reference antibody comprises: (a) a heavy chain variable region CDR1 comprising the amino acid sequence GFTFSSYGMS (SEQ ID NO:27), a heavy chain variable region CDR2 comprising the amino acid sequence TISGGTYTFYPDSVKG (SEQ ID NO:87), and a heavy chain variable region CDR3 comprising the amino acid sequence RGWLLHYYAMDY (SEQ ID NO:88), and (b) a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments of each of the aforementioned aspects and embodiments, as well as other aspects and embodiments described herein, an ILT3-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody (i.e., the variable regions of the antibody are from one species and the constant region of the antibody is from a different species). In some embodiments, the antibody is a whole or intact antibody. In some embodiments, the antibody is a bispecific antibody or a multispecific antibody. In some embodiments, the antibody is an antibody fragment comprising at least one antigen-binding site. In some embodiments, the antibody or antibody fragment is a Fab, Fab', F(ab')$_2$, Fv, scFv, (scFv)$_2$, single chain antibody, dual variable region antibody, single variable region antibody, linear antibody, diabody, nanobody, or a V region antibody. In some embodiments, the antibody is an IgG antibody. In some embodiments, the antibody is an IgG1 antibody, an IgG2 antibody, an IgG3 antibody, or an IgG4 antibody. In some embodiments, the antibody comprises a kappa light chain. In some embodiments, the antibody comprises a lambda light chain.

In some embodiments of each of the aforementioned aspects and embodiments, as well as other aspects and embodiments described herein, an ILT3-binding agent is attached (either directly or indirectly) to a half-life extending moiety.

In some embodiments of each of the aforementioned aspects and embodiments, as well as other aspects and embodiments described herein, an ILT3-binding agent described herein is an antagonist of ILT3. In some embodiments, an ILT3-binding agent inhibits ILT3 activity. In some embodiments, the ILT3-binding agent is an antagonistic antibody. In some embodiments, the ILT3-binding agent is an antibody that inhibits ILT3-induced immune cell suppression. In some embodiments, the ILT3-binding agent is an antibody that inhibits ILT3-induced myeloid cell suppression. In some embodiments, the ILT3-binding agent is an antibody that reactivates tolerogenic dendritic cells.

In another aspect, the disclosure provides compositions comprising an ILT3-binding agent described herein. In some embodiments, a composition comprises an anti-ILT3 antibody described herein. In some embodiments, a composition comprises a monoclonal anti-ILT3 antibody described herein. In some embodiments, a composition comprises an anti-ILT3 antibody selected from the group consisting of:

3A3, 5A7, Hz5A7.v5, 12A12, 16C5, 45G10, 48A6, Hz45G10, Hz48A6, and 53F10.

In another aspect, the disclosure provides pharmaceutical compositions comprising an ILT3-binding agent described herein and a pharmaceutically acceptable carrier. In some embodiments, a pharmaceutical composition comprises an anti-ILT3 antibody described herein and a pharmaceutically acceptable carrier. In some embodiments, a pharmaceutical composition comprises a monoclonal anti-ILT3 antibody described herein and a pharmaceutically acceptable carrier. In some embodiments, a pharmaceutical composition comprises an anti-ILT3 antibody selected from the group consisting of: 3A3, 5A7, Hz5A7.v5, 12A12, 16C5, 45G10, 48A6, Hz45G10, Hz48A6, and 53F10 and a pharmaceutically acceptable carrier. In some embodiments, a pharmaceutical composition comprises an anti-ILT3 antibody comprising a heavy chain variable region comprising a VHCDR1, a VHCDR2, and a VHCDR3 of an anti-ILT3 antibody selected from the group consisting of: 3A3, 5A7, Hz5A7.v5, 12A12, 16C5, 48A6, Hz45G10 (any of the 2 humanized Hz45G10 antibodies described in Example Hz48A6 (any of the 5 humanized Hz48A6 antibodies described in Example 15), and 53F10; and a light chain variable region comprising a VLCDR1, a VLCDR2, and a VLCDR3 of an anti-ILT3 antibody selected from the group consisting of: 3A3, 5A7, Hz5A7.v5, 12A12, 16C5, 48A6, Hz45G10 (any of the 2 humanized Hz45G10 antibodies described in Example Hz48A6 (any of the 5 humanized Hz48A6 antibodies described in Example 15), and 53F10; and a pharmaceutically acceptable carrier.

In some embodiments of each of the aforementioned aspects, as well as other aspects and/or embodiments described elsewhere herein, the ILT3-binding agent is isolated. In some embodiments, the ILT3-binding agent is substantially pure.

In another aspect, the disclosure provides polynucleotides comprising one or more polynucleotides that encode an ILT3-binding agent described herein. In some embodiments, the one or more polynucleotide(s) are isolated. In some embodiments, a vector comprises one or more polynucleotides that encode an ILT3-binding agent described herein. In some embodiments, an isolated cell comprises one or more polynucleotide that encode an ILT3-binding agent described herein. In some embodiments, an isolated cell comprises a vector comprising one or more polynucleotides that encode an ILT3-binding agent described herein. In some embodiments, a cell comprises an ILT3-binding agent described herein. In some embodiments, a cell produces an ILT3-binding agent described herein. In some embodiments, the cell is a monoclonal cell line. In some embodiments, the cell is a hybridoma.

In another aspect, the disclosure provides methods of using the ILT3-binding agents described herein. In some embodiments, a method comprises using a composition comprising an ILT3-binding agent described herein. In some embodiments, a method comprises using a pharmaceutical composition comprising an ILT3-binding agent described herein.

In some embodiments, methods of disrupting, inhibiting, or blocking the binding of ILT3 to a ligand and/or binding partner are provided. In some embodiments, a method of disrupting, inhibiting, or blocking the binding of ILT3 to fibronectin in a mixture of cells comprises contacting the cells with an ILT3-binding agent described herein. In some embodiments, a method of disrupting, inhibiting, or blocking the binding of ILT3 to APOE in a mixture of cells comprises contacting the cells with an ILT3-binding agent described herein. In some embodiments, a method of disrupting, inhibiting, or blocking the binding of ILT3 to CNTFR in a mixture of cells comprises contacting the cells with an ILT3-binding agent described herein.

In some embodiments, a method of disrupting, inhibiting, or blocking the binding of ILT3 to fibronectin in a subject comprises administering to the subject an effective amount of an ILT3-binding agent described herein. In some embodiments, a method of disrupting, inhibiting, or blocking the binding of ILT3 to APOE in a subject comprises administering to the subject an effective amount of an ILT3-binding agent described herein. In some embodiments, a method of disrupting, inhibiting, or blocking the binding of ILT3 to CNTFR in a subject comprises administering to the subject an effective amount of an ILT3-binding agent described herein.

In some embodiments, methods of disrupting, inhibiting, or blocking ILT3 activity are provided. In some embodiments, a method of disrupting, inhibiting, or blocking fibronectin-induced ILT3 activity in a mixture of cells comprises contacting the cells with an ILT3-binding agent described herein. In some embodiments, a method of disrupting, inhibiting, or blocking ILT3-induced suppression of myeloid cells comprises contacting the cells with an ILT3-binding agent described herein. In some embodiments, a method of disrupting, inhibiting, or blocking ILT3-induced suppression of myeloid cell activity comprises contacting the cells with an ILT3-binding agent described herein. In some embodiments, a method of disrupting, inhibiting, or blocking ILT3-induced suppression of myeloid cell activity restores FcR activity in the myeloid cells. In some embodiments, a method of disrupting, inhibiting, or blocking ILT3-induced suppression of myeloid activity restores chemokine/cytokine production in the myeloid cells. In some embodiments, a method of disrupting, inhibiting, or blocking ILT3-induced suppression of myeloid cell activity restores the cell proliferation activity. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are APCs.

In some embodiments, a method of disrupting, inhibiting, or blocking fibronectin-induced ILT3 activity in a subject comprises administering to the subject an effective amount of an ILT3-binding agent described herein. In some embodiments, a method of disrupting, inhibiting, or blocking ILT3-induced suppression of myeloid cells in a subject, comprising administering to the subject an effective amount of an ILT3-binding agent described herein. In some embodiments, a method of disrupting, inhibiting, or blocking ILT3-induced suppression of myeloid cell activity in a subject comprises administering to the subject an effective amount of an ILT3-binding agent described herein. In some embodiments, a method of disrupting, inhibiting, or blocking ILT3-induced suppression of myeloid cell activity in a subject restores FcR activity in myeloid cells, and/or restores chemokine/cytokine production in myeloid cells. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are antigen-presenting cells (APCs).

In some embodiments, a method of treating cancer in a subject comprises administering to the subject a therapeutically effective amount of an ILT3-binding agent described herein. In some embodiments, administration of an ILT3-binding agent described herein stimulates/activates tumor-associated suppressive myeloid cells, for example, by blocking the interaction between ILT3 and fibronectin, APOE or CNTFR, resulting in an increase of immune responses such as anti-tumor T cell responses, and thus activates immune response against the cancer/tumor in the subject. In some embodiments, administration of an ILT3-binding agent described herein blocks the interaction between ILT3 and fibronectin in a suppressive tumor microenvironment, and reprograms/stimulates myeloid cells such as tolerogenic dendritic cells. As a result, this increases the secretion of T cell-recruiting chemokines by the myeloid cells, and the ability of myeloid cells to induce proliferation and cytokine secretion of T cells in the tumor microenvironment. In some embodiments, the cancer is breast cancer, lung cancer, head and neck cancer, colorectal cancer, prostate cancer, skin cancer, melanoma, stomach cancer, gastric cancer, intestinal cancer, cervical cancer, uterine cancer, endometrial cancer, urinary bladder cancer, brain cancer, esophageal cancer, liver cancer, kidney cancer, or testicular cancer. In some embodiments, the cancer is a pancreatic cancer. In some embodiments, the cancer is an ovarian cancer. In some embodiments, the cancer is a sarcoma. In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia. In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML. In some embodiments, the cancer or the microenvironment where the cancer resides is fibronectin rich. In some embodiments, the cancer or the microenvironment where the cancer resides has higher expression of fibronectin than its non-cancerous counterpart. In some embodiments, the tumor microenvironment of the cancer has increased expression level of fibronectin. In some embodiments, the cancer expresses ILT3. In some embodiments, the cancer is a certain type of B cell leukemia or lymphoma which expresses ILT3.

In some embodiments, a method of inhibiting tumor growth in a subject comprises administering to the subject a therapeutically effective amount of an ILT3-binding agent described herein. In some embodiments, a method of increasing or enhancing an immune response to a tumor or tumor cells in a subject comprises administering to the subject a therapeutically effective amount of an ILT3-binding agent described herein. In some embodiments, a method of activating or enhancing a persistent or long-term immune response to a tumor or tumor cells in a subject comprises administering to the subject a therapeutically effective amount of an ILT3-binding agent described herein. In some embodiments, a method of inhibiting tumor relapse or tumor regrowth in a subject comprises administering to the subject a therapeutically effective amount of an ILT3-binding agent described herein. In some embodiments a method of inducing a persistent or long-term immunity that inhibits tumor relapse or tumor regrowth in a subject comprises administering to the subject a therapeutically effective amount of an ILT3-binding agent described herein. In some embodiments, the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a testicular tumor, a sarcoma, or a hematologic tumor. In some embodiments, the tumor arises from Myelodysplastic syndromes. In some embodiments, the tumor expresses ILT3. In some embodiments, the tumor is a certain type of B cell leukemia or lymphoma which expresses ILT3.

In some embodiments, a method of activating myeloid cells, for example, in the tumor microenvironment, in a subject with a tumor comprises administering to the subject a therapeutically effective amount of an ILT3-binding agent described herein. In some embodiments, the myeloid cells are primary dendritic cells or tolerogenic dendritic cells. In some embodiments, the myeloid cells are monocytes or macrophages. In some embodiments, a method of reactivating tolerogenic dendritic cells in a subject comprises administering to the subject a therapeutically effective amount of an ILT3-binding agent described herein. In some embodiments, the tolerogenic dendritic cells are found in the tumor microenvironment.

In yet another aspect, the disclosure provides a method of treating cancer in a human subject. The method comprises administering to the human subject a therapeutically effective amount of the antibody or the pharmaceutical composition described herein. In some cases, the cancer or the microenvironment where the cancer resides is fibronectin rich. In some embodiments, the cancer or the microenvironment where the cancer resides has higher expression of fibronectin than its non-cancerous counterpart. In some embodiments, the tumor microenvironment of the cancer has increased expression level of fibronectin. In some embodiments, the cancer expresses ILT3. In certain cases, the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, urinary bladder cancer, brain cancer, esophageal cancer, liver cancer, kidney cancer, sarcoma or testicular cancer, a hematologic cancer, myelogenous leukemia, acute myeloid leukemia (AML), chronic myeloid leukemia, or myelodysplastic syndrome.

In some embodiments of any of the methods described herein, the ILT3-binding agent is administered to a subject as part of a combination therapy. In some embodiments, the combination therapy comprises at least one additional therapeutic agent.

In another aspect, the disclosure provides a combination comprising a binding agent or antibody described herein and an anti-PD-1 antibody. In another aspect, the disclosure provides a combination comprising a means for inhibiting the interaction between human ILT-3 and fibronectin and an anti-PD-1 antibody. The means for inhibiting the interaction between ILT-3 and fibronectin is an antibody described herein.

In another aspect, the disclosure features a pharmaceutical composition comprising the antibody described herein, and a pharmaceutically acceptable carrier. Also disclosed is the use of an ILT3-binding agent (e.g., an antibody) described herein in the manufacture of a medicament for the treatment of cancer. In some embodiments, use of an ILT3-binding agent described herein is for treatment of cancer. In some embodiments, use of an ILT3-binding agent described herein is for inhibition of tumor growth.

In another aspect, the disclosure features a pharmaceutical composition comprising a means for inhibiting the interaction between human ILT3 and fibronectin; and a pharmaceutically acceptable carrier. In some instances, the means for inhibiting the interaction between human ILT3 and fibronectin is an anti-human ILT3 antibody. In certain cases, the antibody comprises the VH-CDR1, VH-CDR2, and VH-CDR3 of a heavy chain variable region and the VL-CDR1, VL-CDR2, and VL-CDR3 of a light chain variable region, wherein the heavy chain variable region and the light chain variable region comprises the amino acids sequences respectively in: SEQ ID NOs.:123 and 124; SEQ ID NOs.: 156 and 161; SEQ ID NOs.:157 and 161; SEQ ID NOs.:158 and 161; SEQ ID NOs.:159 and 161; SEQ ID NOs.:160 and 161; SEQ ID NOs.:162 and 164; or SEQ ID NOs.:163 and 164. In some cases, the antibody comprises the VH-CDR1, VH-CDR2, and VH-CDR3 of a heavy chain variable region and the VL-CDR1, VL-CDR2, and VL-CDR3 of a light chain variable region, wherein the heavy chain variable region and the light chain variable region comprises the amino acids sequences respectively in: SEQ ID NOs.:123 and 124; SEQ ID NOs.:156 and 161; SEQ ID NOs.:157 and 161; SEQ ID NOs.:158 and 161; SEQ ID NOs.:159 and 161; SEQ ID NOs.:160 and 161; SEQ ID NOs.:162 and 164; or SEQ ID NOs.:163 and 164.

In some embodiments of each of the aforementioned aspects and embodiments, as well as other aspects and embodiments described herein, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

DETAILED DESCRIPTION

Figure 1A:
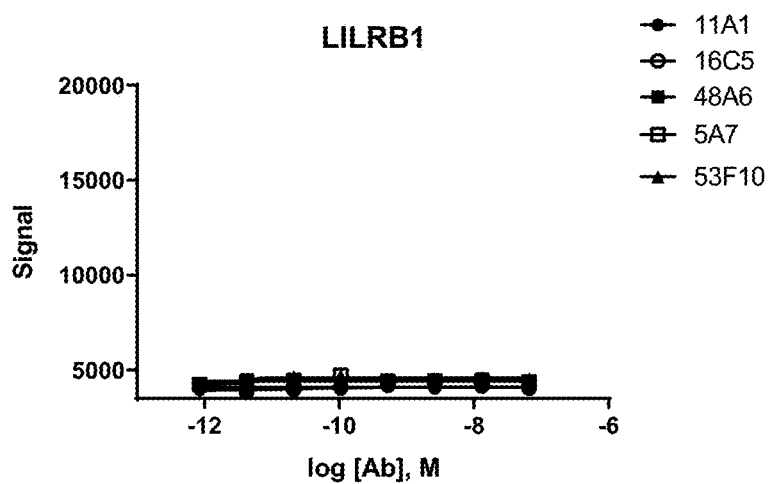
FIG. 1A-1F. Representative results of FACS screening with anti-ILT3 antibodies and LILRB-expressing cells.
Figure 1B:
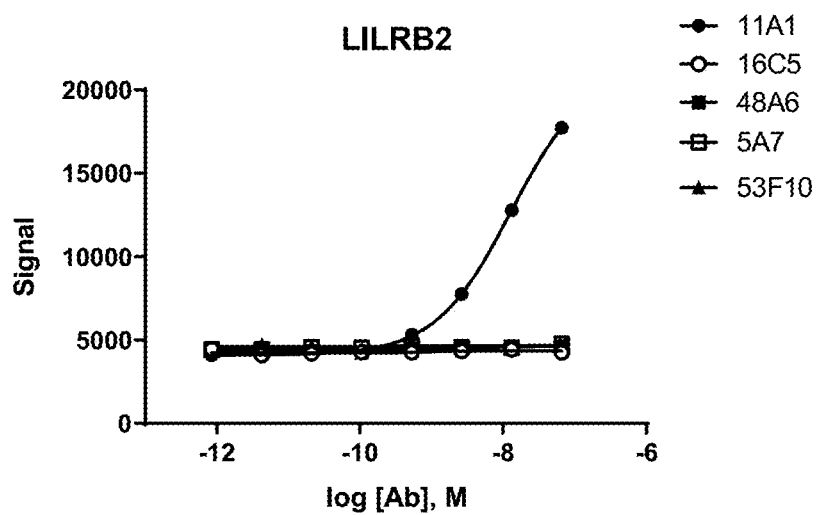
Figure 1C:
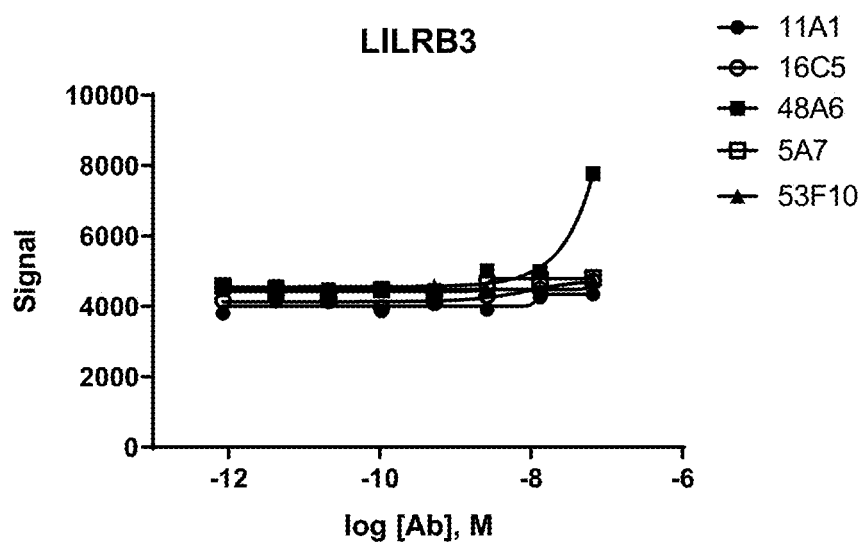
Figure 1D:
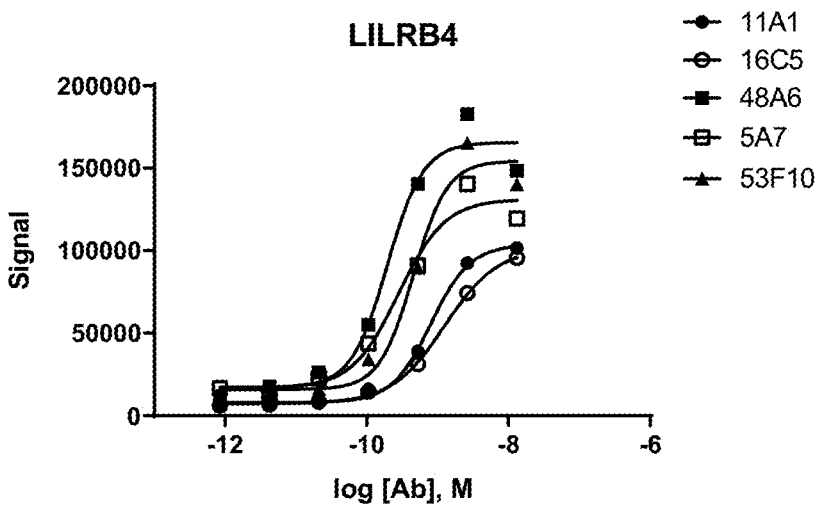
Figure 1E:
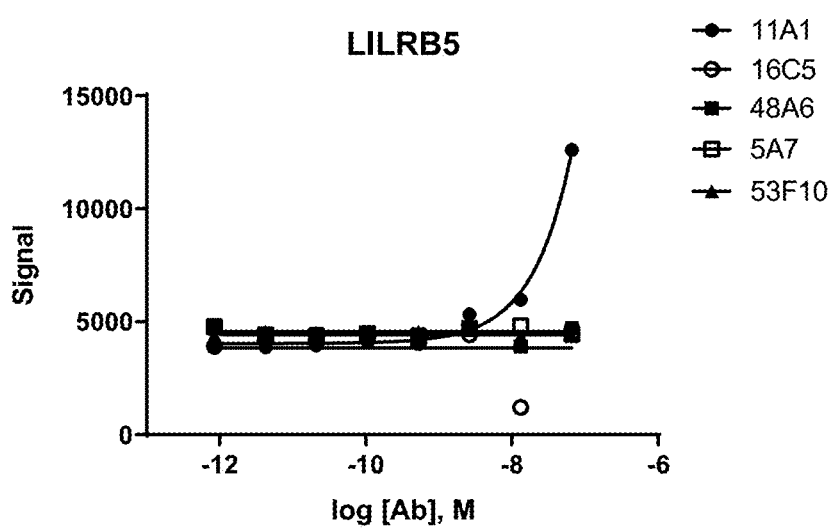
Figure 1F:
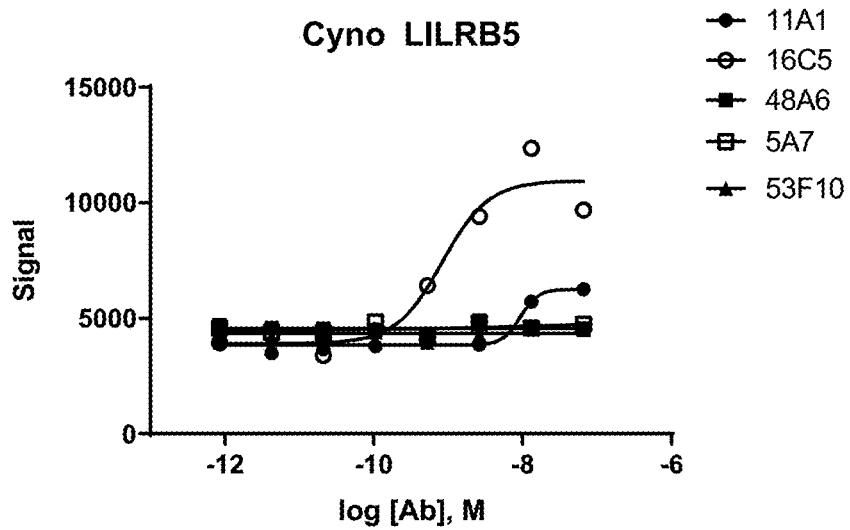
Figure 2A:
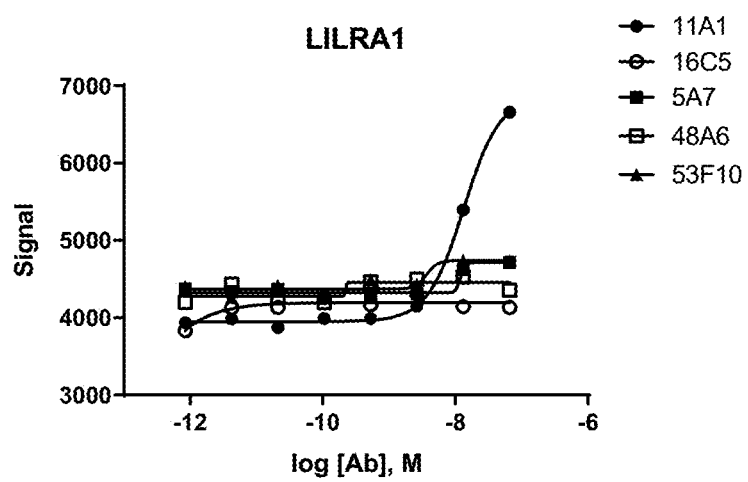
FIG. 2A-2E. Representative results of FACS screening with anti-ILT3 antibodies and LILRA-expressing cells.
Figure 2B:
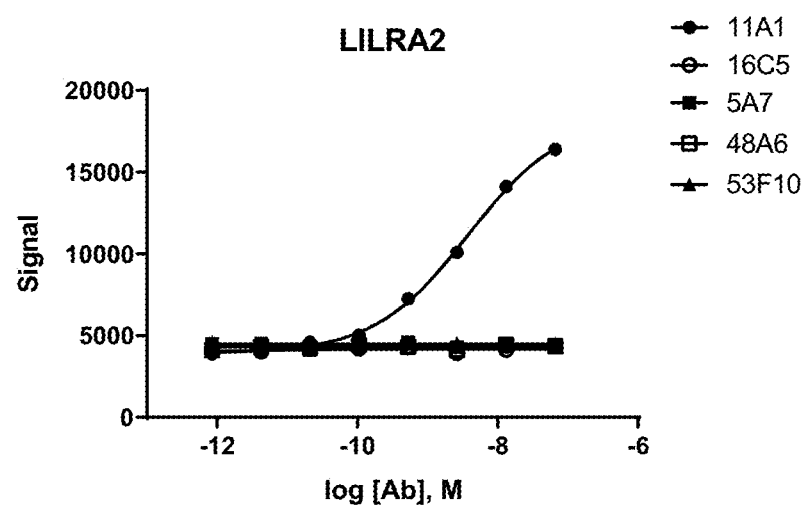
Figure 2C:
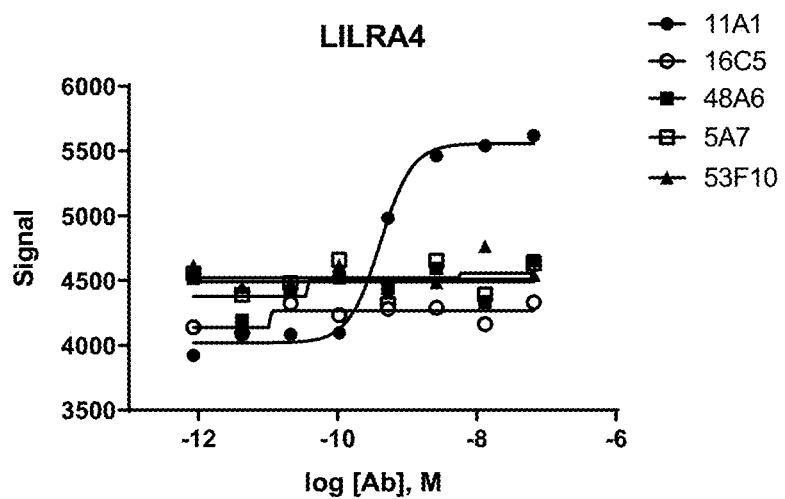
Figure 2D:
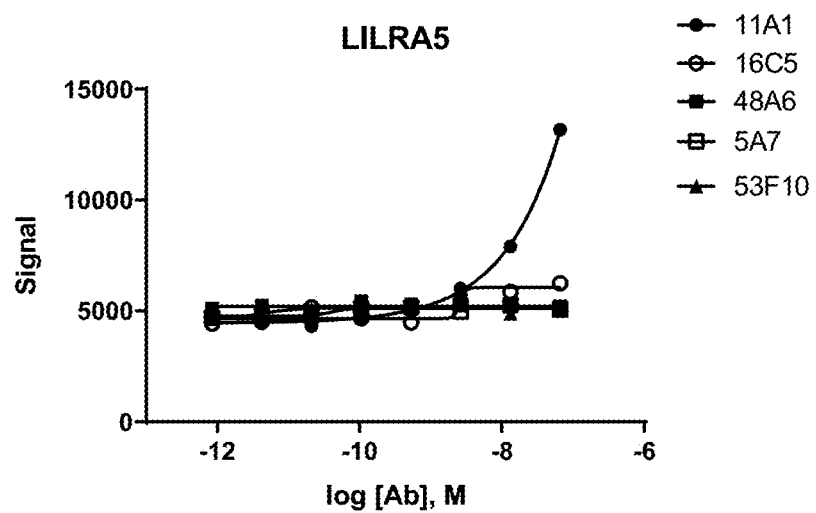
Figure 2E:
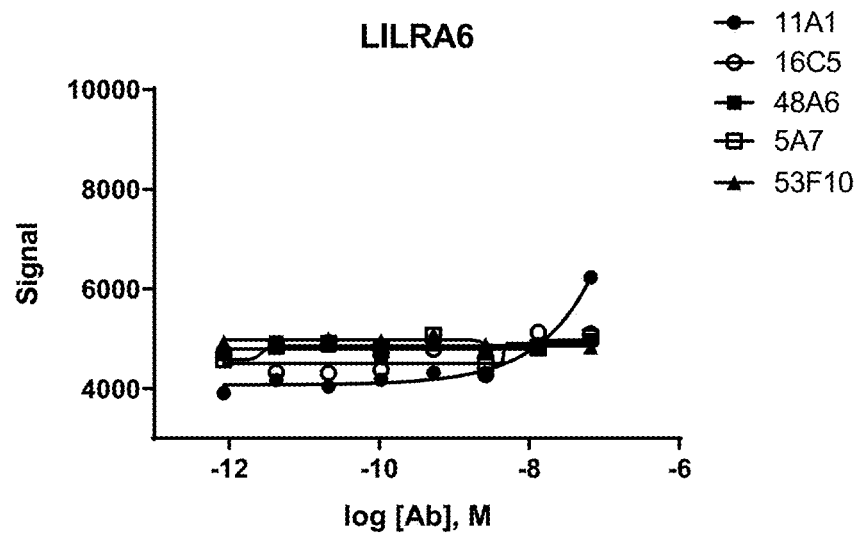

The present disclosure provides novel agents, including but not limited to polypeptides such as antibodies, that bind immunoglobulin-like transcript 3 (ILT3). The ILT3-binding agents include, but are not limited to, polypeptides, antibodies (including antigen-binding fragments thereof), scaffold proteins, and heterodimeric molecules. ILT3-binding agents include, but are not limited to, antagonists of ILT3 activity, inhibitors of ILT3 activity, and/or agents that inhibit ILT3 suppressive activity. Related polypeptides, polynucleotides, vectors, compositions comprising the agents, cells comprising the related polynucleotides or vectors, and methods of making the agents are also provided. Methods of using the novel ILT3-binding agents are also provided.

I. Definitions

In order that the application may be more completely understood, several definitions are set forth below. Such definitions are meant to encompass grammatical equivalents.

The term "antibody" is used in the broadest sense and includes, for example, an intact immunoglobulin, and an antibody fragment containing an antigen binding portion. Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies or antibody fragments (antibody monomers) that generally are based on the IgG class, which has several subclasses, including, but not limited to IgG1, IgG2, IgG3, and IgG4. In general, IgG1, IgG2 and IgG4 are used more frequently than IgG3. It should be noted that IgGs have different allotypes. All IgGs allotypes can be used for this invention. For example, IgG1 has polymorphisms at 356 (D or E) and 358 (L or M). The sequences depicted herein use the 356E/358M allotype, however, the other allotypes are included herein. As will be appreciated by those in the art, the exact numbering and placement of the Complementary Determining Regions (CDRs) can be different among different numbering systems. However, it should be understood that the disclosure of a variable heavy and/or variable light sequence includes the disclosure of the associated (inherent) CDRs. Accordingly, the disclosure of each variable heavy region (VH) is a disclosure of the VHCDRs (e.g. VHCDR1, VHCDR2 and VHCDR3) and the disclosure of each variable light region (VL) is a disclosure of the VLCDRs (e.g. VLCDR1, VLCDR2 and VLCDR3).

A useful comparison of CDR numbering is as below, see Lafranc et al., Dev. Comp. Immunol. 27(1):55-77 (2003):

|        | Kabat + Chothia | IMGT    | Kabat  | AbM    | Chothia | Contact |
|--------|-----------------|---------|--------|--------|---------|---------|
| vhCDR1 | 26-35           | 27-38   | 31-35  | 26-35  | 26-32   | 30-35   |
| vhCDR2 | 50-65           | 56-65   | 50-65  | 50-58  | 52-56   | 47-58   |
| vhCDR3 | 95-102          | 105-117 | 95-102 | 95-102 | 95-102  | 93-101  |
| vlCDR1 | 24-34           | 27-38   | 24-34  | 24-34  | 24-34   | 30-36   |
| vlCDR2 | 50-56           | 56-65   | 50-56  | 50-56  | 50-56   | 46-55   |
| vlCDR3 | 89-97           | 105-117 | 89-97  | 89-97  | 89-97   | 89-96   |

"Percent (%) amino acid sequence identity", "Percent (%) sequence identity" or "Percent (%) identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs to of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3). In some embodiments, as is more fully described below, amino acid modifications are made to the Fc region, for example to alter binding to one or more FcγR receptors or to the FcRn receptor.

By "myeloid cells" as used herein refer to any cells having myeloid origin, including but not limited to monocytes, macrophages, and dendritic cells.

By "substantially identical" as used herein with respect to a CDR amino acid sequence refers to at least 1 amino acid modification (e.g., 1, 2, 3, 4, 5, or 6 amino acid modifications) in the CDR sequence, wherein the modification of the CDR sequence in combination with the rest five CDRs (with or without further modifications in any one or more of the five CDRs) do not change the affinity ($K_D$ measured by e.g., SPR technology in a Biacore system) of the resulting antigen binding domain more than 50 folds in comparison to the antigen binding domain comprising the six original CDRs.

II. ILT3-Binding Agents

Amino acid (aa) sequences for human ILT3 (UniProtKB No. Q8NHJ6) and cynomolgus monkey ("cyno") ILT3 (NCBI Ref No. XP_015297198) are provided herein as SEQ ID NO:1 and SEQ ID NO:6, respectively. As used herein, reference to amino acid positions of ILT3 refer to the numbering of amino acid sequences including the signal sequence. ILT3 is a single pass type I transmembrane protein with a predicted molecular weight of approximately 47 kDa. ILT3 has been observed to be predominantly expressed on myeloid antigen presenting cells, such as normal monocytes, macrophages, and dendritic cells. ILT3 is characterized by an extracellular domain comprising two Ig-like C2 type domains, a transmembrane domain, and a long cytoplasmic domain containing 3 ITIM domains (see, e.g., Cella et al., 1997, J. Exp. Med., 185:1743-1751). The two Ig-like C2-type domains may be referred to herein as Domain 1 (D1) and Domain 2 (D2). D1 is situated at the N-terminal portion of the protein and D2 is situated closest to the transmembrane region. As characterized within UniProtKB, human ILT3 is a protein of 448 amino acids (aa)—the signal sequence is aa 1-21, the extracellular domain is aa 22-259, the transmembrane region is aa 260-280, and the cytoplasmic domain is aa 281-448. Within the extracellular domain, D1 is aa 27-188, D2 is aa 124-218, and the "stem region" is aa 219-259. With the cytoplasmic domain, ITIMs are aa 358-363, 410-415, and 440-445.

In some embodiments, an ILT3-binding agent binds ILT3 or a fragment of ILT3. In some embodiments, a fragment of ILT3 comprises the extracellular domain. In some embodiments, a fragment of ILT3 comprises one of the Ig-like C2 type domains (e.g., D1 or D2). In some embodiments, a fragment of ILT3 comprises both of the Ig-like C2 type domains (e.g., D1-D2). In some embodiments, a fragment of ILT3 comprises both of the Ig-like C2 type domains and the stem region (e.g., D1-D2-stem). In some embodiments, a fragment of ILT3 comprises one of the Ig-like C2 type domains and the stem region (e.g., D1-stem or D2-stem). In some embodiments, the extracellular domain of human ILT3 comprises amino acids 22-259 of SEQ ID NO:1. In some embodiments, D1 of human ILT3 comprises amino acids 27-118 of SEQ ID NO:1. In some embodiments, D2 of human ILT3 comprises amino acids 124-218 of SEQ ID NO:1. In some embodiments, D1-D2 of human ILT3 comprises amino acids 27-218 of SEQ ID NO:1. In some embodiments, D1-D2-stem of human ILT3 comprises amino acids 27-259 of SEQ ID NO:1. In some embodiments, D2-stem of human ILT3 comprises amino acids 124-259 of SEQ ID NO:1. In some embodiments, a fragment of human ILT3 comprises the amino acid sequence of SEQ ID NO:3. In some embodiments, a fragment of human ILT3 comprises the amino acid sequence of SEQ ID NO:4. In some embodiments, a fragment of human ILT3 comprises the amino acid sequence of SEQ ID NO:5. In some embodiments, a fragment of human ILT3 comprises the amino acid sequence of SEQ ID NO:4 and SEQ ID NO:5. In some embodiments, the extracellular domain of cyno ILT3 comprises amino acids 22-259 of SEQ ID NO:6. In some embodiments, D1 of cyno ILT3 comprises amino acids 27-118 of SEQ ID NO:6. In some embodiments, D2 of cyno ILT3 comprises amino acids 124-218 of SEQ ID NO:6. In some embodiments, D1-D2 of cyno ILT3 comprises amino acids 27-218 of SEQ ID NO:6. In some embodiments, D1-D2-stem of cyno ILT3 comprises amino acids 27-259 of SEQ ID NO:6. In some embodiments, D2-stem of cyno ILT3 comprises amino acids 124-259 of SEQ ID NO:6. In some embodiments, a fragment of cyno ILT3 comprises the amino acid sequence of SEQ ID NO:8. In some embodiments, a fragment of cyno ILT3 comprises the amino acid sequence of SEQ ID NO:9. In some embodiments, a fragment of cyno ILT3 comprises the amino acid sequence of SEQ ID NO:10. In some embodiments, a fragment of cyno ILT3 comprises the amino acid sequence of SEQ ID NO:9 and SEQ ID NO:10. It is understood that the domains of ILT3 (e.g., human ILT3 or cyno ILT3) may be defined differently by those of skill in the art, therefore the N-terminal amino acids and the C-terminal amino acids of any ILT3 domain or region may vary by 1, 2, 3, 4, 5, or more amino acid residues.

The present disclosure provides agents (e.g., antibodies) that bind ILT3. In some embodiments, an ILT3-binding agent binds a fragment of ILT3. In some embodiments, an ILT3-binding agent binds within a specific region of ILT3. In some embodiments, an ILT3-binding agent binds within the extracellular domain of ILT3. In some embodiments, an ILT3-binding agent binds within the D1 domain of ILT3. In some embodiments, an ILT3-binding agent binds within the D2 domain of ILT3. In some embodiments, an ILT3-binding agent binds within the D2-stem region of ILT3. In some embodiments, an ILT3-binding agent binds within the junction between D1 and D2 domains of ILT3. In some embodiments, an ILT3-binding agent binds an epitope on ILT3. In some embodiments, an ILT3-binding agent binds a conformational epitope on ILT3. In some embodiments, an ILT3-binding agent does not bind other human LILRB proteins (e.g., ILT2, ILT4, ILT5, or LILRB5). In some embodiments, an ILT3-binding agent does not bind human LILRA proteins (e.g., LILRA1, LILRA2, LILRA4, LILRA5, or LILRA6).

In some embodiments, an ILT3-binding agent binds human ILT3. In some embodiments, an ILT3-binding agent binds cyno ILT3. In some embodiments, an ILT3-binding agent binds human ILT3 and cyno ILT3. In some embodiments, an ILT3-binding agent binds SEQ ID NO:1. In some embodiments, an ILT3-binding agent binds SEQ ID NO:2. In some embodiments, an ILT3-binding agent binds within amino acids 22-259 of SEQ ID NO:1. In some embodiments, an ILT3-binding agent binds within amino acids 27-118 of SEQ ID NO:1. In some embodiments, an ILT3-binding agent binds within amino acids 124-218 of SEQ ID NO:1. In some embodiments, an ILT3-binding agent binds within amino acids 124-259 of SEQ ID NO:1. In some embodiments, an ILT3-binding agent binds within amino acids 27-218 of SEQ ID NO:1. In some embodiments, an ILT3-binding agent binds SEQ ID NO:3. In some embodiments, an ILT3-binding agent binds SEQ ID NO:4. In some embodiments, an ILT3-binding agent binds SEQ ID NO:5. In some embodiments, an ILT3-binding agent binds a fragment of ILT3 that comprises SEQ ID NO:4 and SEQ ID NO:5. In some embodiments, an ILT3-binding agent binds SEQ ID NO:6. In some embodiments, an ILT3-binding agent binds SEQ ID NO:7. In some embodiments, an ILT3-binding agent binds within amino acids 22-259 of SEQ ID NO:6. In some embodiments, an ILT3-binding agent binds within amino acids 27-118 of SEQ ID NO:6. In some embodiments, an ILT3-binding agent binds within amino acids 124-218 of SEQ ID NO:6. In some embodiments, an ILT3-binding agent binds within amino acids 27-218 of SEQ ID NO:6. In some embodiments, an ILT3-binding agent binds SEQ ID NO:8. In some embodiments, an ILT3-binding agent binds SEQ ID NO:9. In some embodiments, an ILT3-binding agent binds SEQ ID NO:10. In some embodiments, an ILT3-binding agent binds a fragment of ILT3 that comprises SEQ ID NO:9 and SEQ ID NO:10.

In some embodiments, an ILT3-binding agent binds a polypeptide comprising the amino acid sequence of SEQ ID NO:2. In some embodiments, an ILT3-binding agent binds a polypeptide comprising the amino acid sequence of SEQ ID NO:3. In some embodiments, an ILT3-binding agent binds a polypeptide comprising the amino acid sequence of SEQ ID NO:4. In some embodiments, an ILT3-binding agent binds a polypeptide comprising the amino acid sequence of SEQ ID NO:5. In some embodiments, an ILT3-binding agent binds a polypeptide comprising the amino acid sequence of SEQ ID NO:4 and the amino acid sequence of SEQ ID NO:5. In some embodiments, an ILT3-binding agent binds a polypeptide comprising the amino acid sequence of SEQ ID NO:7. In some embodiments, an ILT3-binding agent binds a polypeptide comprising the amino acid sequence of SEQ ID NO:8. In some embodiments, an ILT3-binding agent binds a polypeptide comprising the amino acid sequence of SEQ ID NO:9. In some embodiments, an ILT3-binding agent binds a polypeptide comprising the amino acid sequence of SEQ ID NO:10.

In some embodiments, an ILT3-binding agent binds a polypeptide comprising the amino acid sequence of SEQ ID NO:9 and the amino acid sequence of SEQ ID NO:10.

In some embodiments, an ILT3-binding agent binds an epitope comprising amino acids within SEQ ID NO:2. In some embodiments, an ILT3-binding agent binds an epitope comprising amino acids within SEQ ID NO:3. In some embodiments, an ILT3-binding agent binds an epitope comprising amino acids within SEQ ID NO:4. In some embodiments, an ILT3-binding agent binds an epitope comprising amino acids within SEQ ID NO:5. In some embodiments, an ILT3-binding agent binds an epitope comprising amino acids within SEQ ID NO:4 and SEQ ID NO:5. In some embodiments, an ILT3-binding agent binds an epitope comprising amino acids within SEQ ID NO:7. In some embodiments, an ILT3-binding agent binds an epitope comprising amino acids within SEQ ID NO:8. In some embodiments, an ILT3-binding agent binds an epitope comprising amino acids within SEQ ID NO:9. In some embodiments, an ILT3-binding agent binds an epitope comprising amino acids within SEQ ID NO:10. In some embodiments, an ILT3-binding agent binds an epitope comprising amino acids within SEQ ID NO:9 and SEQ ID NO:10.

In some embodiments, an ILT3-binding agent binds human ILT3 and has at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi) inhibits ILT3-induced suppression of myeloid cells; (xii) inhibits ILT3-induced suppression of myeloid cell activity; (xiii) restores FcR activity in myeloid cells that express ILT3; and (xiv) restores the ability of myeloid cells that express ILT3 to respond to chemokines.

In some embodiments, an ILT3-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody comprises an IgG heavy chain. In some embodiments, the antibody comprises an IgG1 heavy chain. In some embodiments, the antibody comprises an IgG2 heavy chain. In some embodiments, the antibody comprises an IgG4 heavy chain. In some embodiments, the antibody comprises a kappa light chain. In some embodiments, the antibody comprises a kappa light chain constant region. In some embodiments, the antibody comprises a lambda light chain. In some embodiments, the antibody comprises a lambda light chain constant region. In some embodiments, the antibody is an antibody fragment comprising an antigen-binding site. In some embodiments, the antibody is an scFv. In some embodiments, the antibody is a disulfide-linked scFv. In some embodiments, the antibody is a disulfide-linked sc(Fv)$_2$. In some embodiments, the antibody is a Fab, Fab', or a F(ab)$_2$ antibody. In some embodiments, the antibody is a diabody. In some embodiments, the antibody is a nanobody. In some embodiments, the antibody is a monospecific antibody. In some embodiments, the antibody is a bispecific antibody. In some embodiments, the antibody is a multispecific antibody. In some embodiments, the antibody is a monovalent antibody. In some embodiments, the antibody is a multivalent antibody. In some embodiments, the antibody is a bivalent antibody. In some embodiments, the antibody is a tetravalent antibody.

In some embodiments, the antibody is isolated. In some embodiments, the antibody is substantially pure.

In some embodiments, an ILT3-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, an ILT3-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof. In some embodiments, the immunizing antigen is a cyno protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. In some embodiments, high-throughput methods are used to distribute single cell hybridoma cells into plates. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, an ILT3-binding agent is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region to use for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, an ILT3-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized human donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, an ILT3-binding agent is an antibody fragment. As used herein, the term "antibody fragment" refers to a molecule other than an intact antibody that comprises a portion of an antibody and generally an antigen-binding site. Examples of antibody fragments include, but are not limited to, Fab, Fab', F(ab')2, Fv, single chain antibody molecules (e.g., scFv), disulfide-linked scFv (dsscFv), nanobodies, diabodies, tribodies, tetrabodies, minibodies, dual variable domain antibodies (DVD), single variable domain antibodies (e.g., camelid antibodies), and multispecific antibodies formed from antibody fragments In some embodiments, an ILT3-binding agent is an scFv antibody. In some embodiments, the scFv is a disulfide-linked scFv (dsscFv), which is an scFv comprising an engineered disulfide bond between the light chain variable region and heavy chain variable region of the scFv. In some embodiments, the disulfide bond increases stability of the scFv molecule. In some embodiments, the disulfide bond increases thermostability of the scFv molecule.

In some embodiments, an ILT3-binding agent is an Fv. In some embodiments, an ILT3-binding agent is an Fab. In some embodiments, an ILT3-binding agent is a F(ab')2. In some embodiments, an ILT3-binding agent is a F(ab').

Antibody fragments can be made by various techniques, including but not limited to proteolytic digestion of an intact antibody. The antibody fragments described herein can be produced using recombinant technologies known in the art (e.g., E. coli or phage expression).

In some embodiments, an ILT3-binding agent is a bispecific antibody. Bispecific antibodies are capable of recognizing and binding at least two different antigens or epitopes. In some embodiments, an ILT3-binding agent is a multispecific antibody. Multispecific antibodies are capable of recognizing and binding at least three different antigens or epitopes. The different epitopes can either be within the same molecule (e.g., two or more epitopes on ILT3) or on different molecules (e.g., one epitope on ILT3 and the rest of the epitope(s) on one or more target(s) other than ILT3). In some embodiments, a bispecific or multispecific antibody has enhanced potency as compared to an individual antibody or to a combination of more than one antibody. In some embodiments, a bispecific or multispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific or multispecific antibody has the ability to synchronize the PK of two or more active binding agents wherein the two or more individual binding agents have different PK profiles. In some embodiments, a bispecific or multispecific antibody has the ability to concentrate the actions of two or more agents in a common area (e.g., tissue) in a subject (e.g., a human). In some embodiments, a bispecific or multispecific antibody has the ability to concentrate the actions of two or more agents to a common target (e.g., a specific cell type). In some embodiments, a bispecific or multispecific antibody has the ability to target the actions of two or more agents to more than one biological pathway or function. In some embodiments, a bispecific or multispecific antibody has the ability to target two or more different cells and bring them closer together.

In some embodiments, a bispecific or multispecific antibody has decreased toxicity and/or side effects. In some embodiments, a bispecific or multispecific antibody has decreased toxicity and/or side effects as compared to a mixture of the two or more individual antibodies or the antibodies as single agents. In some embodiments, a bispecific or multispecific antibody has an increased therapeutic index. In some embodiments, a bispecific or multispecific antibody has an increased therapeutic index as compared to a mixture of the two or more individual antibodies or the antibodies as single agents.

Many techniques for making bispecific or multispecific antibodies are known to those skilled in the art. In some embodiments, a bispecific or multispecific antibody comprises heavy chain constant regions with modifications in the amino acids that are part of the interface between the two heavy chains. These modifications are made to enhance heterodimer formation and generally reduce or eliminate homodimer formation. In some embodiments, the bispecific or multispecific antibody is generated using a knobs-into-holes (KIH) strategy. In some embodiments, the bispecific or multispecific antibody comprises variant hinge regions incapable of forming disulfide linkages between identical heavy chains (e.g., reduce homodimer formation). In some embodiments, the bispecific or multispecific antibody comprises heavy chains with changes in amino acids that result in altered electrostatic interactions. In some embodiments, the bispecific or multispecific antibodies comprise heavy chains with changes in amino acids that result in altered hydrophobic/hydrophilic interactions.

In some embodiments, the Bispecific or multispecific antibodies can be intact antibodies or antibody fragments comprising antigen-binding sites.

In some embodiments, an ILT3-binding agent is an antibody that binds ILT3. In some embodiments, an anti-ILT3 antibody binds human ILT3. In some embodiments, an anti-ILT3 antibody binds cyno ILT3. In some embodiments, an anti-ILT3 antibody binds human ILT3 and cyno ILT3. In some embodiments, an anti-ILT3 antibody binds an ILT3 epitope. In some embodiments, an anti-ILT3 antibody binds an ILT3 epitope within the extracellular domain of human ILT3. In some embodiments, an anti-ILT3 antibody binds an ILT3 epitope within the extracellular domain of cyno ILT3. In some embodiments, an anti-ILT3 antibody binds an epitope comprising at least one amino acid within amino acids 22-259 of SEQ ID NO:1. In some embodiments, an anti-ILT3 antibody binds an epitope comprising at least one amino acid within amino acids 22-120 of SEQ ID NO:1. In some embodiments, an anti-ILT3 antibody binds an epitope comprising at least one amino acid within amino acids 27-118 of SEQ ID NO:1. In some embodiments, an anti-ILT3 antibody binds an epitope comprising at least one amino acid within amino acids 121-259 of SEQ ID NO:1. In some embodiments, an anti-ILT3 antibody binds an epitope comprising at least one amino acid within amino acids 124-218 of SEQ ID NO:1. In some embodiments, an anti-ILT3 antibody binds an epitope comprising at least one amino acid within amino acids 124-259 of SEQ ID NO:1. In some embodiments, an anti-ILT3 antibody binds an epitope comprising amino acids within SEQ ID NO:3. In some embodiments, an anti-ILT3 antibody binds an epitope comprising amino acids within SEQ ID NO:4. In some embodiments, an anti-ILT3 antibody binds an epitope comprising amino acids within SEQ ID NO:5. In some embodiments, an anti-ILT3 antibody binds an epitope comprising amino acids within SEQ ID NO:4 and SEQ ID NO:5. In some embodiments, the epitope is a conformational epitope. In some embodiments, the epitope is a linear epitope.

In some embodiments, an anti-ILT3 antibody competes with a second agent for binding within the extracellular domain of human ILT3. In some embodiments, an anti-ILT3 antibody competes with a second agent for binding within the extracellular domain of cyno ILT3. In some embodiments, an anti-ILT3 antibody competes with a second agent for binding within amino acids 22-259 of SEQ ID NO:1. In some embodiments, an anti-ILT3 antibody competes with a second agent for binding within amino acids 22-120 of SEQ ID NO:1. In some embodiments, an anti-ILT3 antibody competes with a second agent for binding within amino acids 27-118 of SEQ ID NO:1. In some embodiments, an anti-ILT3 antibody competes with a second agent for binding within amino acids 121-259 of SEQ ID NO:1. In some embodiments, an anti-ILT3 antibody competes with a second agent for binding within amino acids 124-218 of SEQ ID NO:1. In some embodiments, an anti-ILT3 antibody competes with a second agent for binding within amino acids 124-259 of SEQ ID NO:1. In some embodiments, an anti-ILT3 antibody competes with a second agent for binding within amino acid sequence SEQ ID NO:3. In some embodiments, an anti-ILT3 antibody competes with a second agent for binding within amino acid sequence SEQ ID NO:4. In some embodiments, an anti-ILT3 antibody competes with a second agent for binding within amino acid sequence SEQ ID NO:5. In some embodiments, an anti-ILT3 antibody competes with a second agent for binding within amino acid sequences SEQ ID NO:4 and SEQ ID NO:5.

In some embodiments, an ILT3-binding agent is an anti-ILT3 antibody described herein. In some embodiments, the ILT3-binding agent is a variant of an anti-ILT3 antibody described herein. In some embodiments, the variant of an ILT3 antibody retain one or more binding characteristics of the ILT3-binding agent described herein. In some embodiments, a variant of an anti-ILT3 antibody comprises one to thirty amino acid substitutions. In some embodiments, a variant of the anti-ILT3 antibody comprises one to twenty-five amino acid substitutions. In some embodiments, a variant of the anti-ILT3 antibody comprises one to twenty amino acid substitutions. In some embodiments, a variant of the anti-ILT3 antibody comprises one to fifteen amino acid substitutions. In some embodiments, a variant of the anti-ILT3 antibody comprises one to ten amino acid substitutions. In some embodiments, a variant of the anti-ILT3 antibody comprises one to five amino acid substitutions. In some embodiments, the variant of the anti-ILT3 antibody comprises one to three amino acid substitutions. In some embodiments, the amino acid substitution(s) is in a CDR of the antibody. In some embodiments, the amino acid substitution(s) is not in a CDR of the antibody. In some embodiments, the amino acid substitution(s) is in a framework region of the antibody. In some embodiments, the amino acid substitution(s) is a conservative amino acid substitution.

In some embodiments, an ILT3-binding agent comprises one or more (e.g., 1, 2, 3, 4, 5, or 6 etc.) amino acid substitutions in a CDR of an antibody described herein while retaining one or more binding characteristics of the ILT3-binding agent described herein. In some embodiments, the amino acid substitutions are conservative substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the CDR is a heavy chain variable region CDR1. In some embodiments, the CDR is a heavy chain variable region CDR2. In some embodiment, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, one or more of such six CDRs have no more than six amino acids substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

CDRs of an antibody are defined using a variety of methods/systems by those skilled in the art. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary definition). However, it will be understood that reference to a heavy chain variable region CDR or CDRs and/or a light chain variable region CDR or CDRs of a specific antibody will encompass all CDR definitions as known to those of skill in the art.

In some embodiments, an anti-ILT3 antibody described herein comprises the six CDRs of antibody 3A3, 5A7, Hz5A7, 12A12, 16C5, 45G10, 48A6, or 53F10 based on the Kabat definition. In some embodiments, an anti-ILT3 antibody described herein comprises the six CDRs of antibody 3A3, 5A7, Hz5A7, 12A12, 16C5, 45G10, 48A6, or 53F10 based on the Chothia definition. In some embodiments, an anti-ILT3 antibody described herein comprises the six CDRs of antibody 3A3, 5A7, Hz5A7, 12A12, 16C5, 45G10, 48A6, or 53F10 based on the AbM definition. In some embodiments, an anti-ILT3 antibody described herein comprises the six CDRs of antibody 3A3, 5A7, Hz5A7, 12A12, 16C5, 45G10, 48A6, or 53F10 based on the IMGT definition. In some embodiments, an anti-ILT3 antibody described herein comprises the six CDRs of antibody 3A3, 5A7, Hz5A7, 12A12, 16C5, 45G10, 48A6, or 53F10 based on the Contact definition. In some embodiments, an anti-ILT3 antibody described herein comprises the six CDRs of antibody 3A3, 5A7, Hz5A7, 12A12, 16C5, 45G10, 48A6, or 53F10 based on the Exemplary definition.

In some embodiments, an ILT3-binding agent is an anti-ILT3 antibody that comprises one, two, three, four, five, and/or six CDRs of any one of the antibodies described herein. In some embodiments, an anti-ILT3 antibody comprises (i) a heavy chain variable region comprising one, two, and/or three heavy chain variable region CDRs from Table 1, and/or (ii) a light chain variable region comprising one, two, and/or three light chain variable region CDRs from Table 1. In some embodiments, an anti-ILT3 antibody comprises (i) a heavy chain variable region comprising one, two, and/or three heavy chain variable region CDRs from Table 2, and/or (ii) a light chain variable region comprising one, two, and/or three light chain variable region CDRs from Table 2. In some embodiments, an anti-ILT3 antibody comprises (i) a heavy chain variable region comprising one, two, and/or three heavy chain variable region CDRs from Table 3, and/or (ii) a light chain variable region comprising one, two, and/or three light chain variable region CDRs from Table 3. In some embodiments, an anti-ILT3 antibody comprises (i) a heavy chain variable region comprising one, two, and/or three heavy chain variable region CDRs from Table 4, and/or (ii) a light chain variable region comprising one, two, and/or three light chain variable region CDRs from Table 4. In some embodiments, an anti-ILT3 antibody comprises (i) a heavy chain variable region comprising one, two, and/or three heavy chain variable region CDRs from Table 5, and/or (ii) a light chain variable region comprising one, two, and/or three light chain variable region CDRs from Table 5. In some embodiments, an anti-ILT3 antibody comprises (i) a heavy chain variable region comprising one, two, and/or three heavy chain variable region CDRs from Table 6, and/or (ii) a light chain variable region comprising one, two, and/or three light chain variable region CDRs from Table 6. In some embodiments, an anti-ILT3 antibody comprises (i) a heavy chain variable region comprising one, two, and/or three heavy chain variable region CDRs from Table 7, and/or (ii) a light chain variable region comprising one, two, and/or three light chain variable region CDRs from Table 7. In some embodiments, an anti-ILT3 antibody comprises (i) a heavy chain variable region comprising one, two, and/or three heavy chain variable region CDRs from Table 8, and/or (ii) a light chain variable region comprising one, two, and/or three light chain variable region CDRs from Table 8.

In some embodiments, an anti-ILT3 antibody comprises (i) a heavy chain variable region comprising three heavy chain variable region CDRs from Table 1, and (ii) a light chain variable region comprising three light chain variable region CDRs from Table 1. In some embodiments, an anti-ILT3 antibody comprises (i) a heavy chain variable region comprising three heavy chain variable region CDRs from Table 2, and (ii) a light chain variable region comprising three light chain variable region CDRs from Table 2. In some embodiments, an anti-ILT3 antibody comprises (i) a heavy chain variable region comprising three heavy chain variable region CDRs from Table 3, and (ii) a light chain variable region comprising three light chain variable region CDRs from Table 3. In some embodiments, an anti-ILT3 antibody comprises (i) a heavy chain variable region comprising three heavy chain variable region CDRs from Table 4, and (ii) a light chain variable region comprising three light chain variable region CDRs from Table 4. In some embodiments, an anti-ILT3 antibody comprises (i) a heavy chain variable region comprising three heavy chain variable region CDRs from Table 5, and (ii) a light chain variable region comprising three light chain variable region CDRs from Table 5. In some embodiments, an anti-ILT3 antibody comprises (i) a heavy chain variable region comprising three heavy chain variable region CDRs from Table 6, and (ii) a light chain variable region comprising three light chain variable region CDRs from Table 6. In some embodiments, an anti-ILT3 antibody comprises (i) a heavy chain variable region comprising three heavy chain variable region CDRs from Table 7, and (ii) a light chain variable region comprising three light chain variable region CDRs from Table 7. In some embodiments, an anti-ILT3 antibody comprises (i) a heavy chain variable region comprising three heavy chain variable region CDRs from Table 8, and (ii) a light chain variable region comprising three light chain variable region CDRs from Table 8.

TABLE 1

Antibody 3A3 Sequences

| | Exemplary | Chothia | AbM | Kabat | Contact |
|---|---|---|---|---|---|
| Heavy Chain variable region CDR1 | GFSLTSYGVH (SEQ ID NO: 11) | GFSLTSY (SEQ ID NO: 17) | GFSLTSYGVH (SEQ ID NO: 11) | SYGVH (SEQ ID NO: 20) | TSYGVH (SEQ ID NO: 21) |
| Heavy Chain variable region CDR2 | VIWPGGTINYNSALMS (SEQ ID NO: 12) | WPGGT (SEQ ID NO: 18) | VIWPGGTIN (SEQ ID NO: 19) | VIWPGGTINYNSALMS (SEQ ID NO: 12) | WLGVIWPGGTIN (SEQ ID NO: 22) |
| Heavy Chain variable region CDR3 | DKYDGGWFAY (SEQ ID NO: 13) | DKYDGGWFAY (SEQ ID NO: 13) | DKYDGGWFAY (SEQ ID NO: 13) | DKYDGGWFAY (SEQ ID NO: 13) | ASDKYDGGWFA (SEQ ID NO: 23) |
| Light Chain variable region CDR1 | KASQNVRTAVA (SEQ ID NO: 14) | KASQNVRTAVA (SEQ ID NO: 14) | KASQNVRTAVA (SEQ ID NO: 14) | KASQNVRTAVA (SEQ ID NO: 14) | RTAVAWY (SEQ ID NO: 24) |
| Light Chain variable region CDR2 | LASNRHT (SEQ ID NO: 15) | LASNRHT (SEQ ID NO: 15) | LASNRHT (SEQ ID NO: 15) | LASNRHT (SEQ ID NO: 15) | ALIYLASNRH (SEQ ID NO: 25) |
| Light Chain variable region CDR3 | LQHLNYPLT (SEQ ID NO: 16) | LQHLNYPLT (SEQ ID NO: 16) | LQHLNYPLT (SEQ ID NO: 16) | LQHLNYPLT (SEQ ID NO: 16) | LQHLNYPL (SEQ ID NO: 26) |

3A3 Heavy chain variable region (SEQ ID NO: 109)
QVQLKESGPGLVAPSQSLSITCTVSGFSLTSYGVHWVRQPPGKGLEWLGVIWPGGTINYN
SALMSRLSISKDNSKSQVFLKLNSLQTDDTAMYYCASDKYDGGWFAYWGQGTLVTVSA 3A3 Light chain variable region (SEQ ID NO: 110)
DIVMTQSQKFMSTSVGDRVSITCKASQNVRTAVAWYQQKPGQSPEALIYLASNRHTGVPD
RFTGSGSGTDFSLSISNVQSEDLADYFCLQHLNYPLTFGSGTKLEIK

TABLE 2

Antibody 5A7 Sequences

| | Exemplary | Chothia | AbM | Kabat | Contact |
|---|---|---|---|---|---|
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISGGGSYTNYPDSVKG (SEQ ID NO: 28) | SGGGSY (SEQ ID NO: 34) | TISGGGSYTN (SEQ ID NO: 35) | TISGGGSYTNYPDSVKG (SEQ ID NO: 28) | WVATISGGGSYTN (SEQ ID NO: 38) |
| Heavy Chain variable region CDR3 | REWRMTLYAMDY (SEQ ID NO: 29) | REWRMTLYAMDY (SEQ ID NO: 29) | REWRMTLYAMDY (SEQ ID NO: 29) | REWRMTLYAMDY (SEQ ID NO: 29) | ARREWRMTLYAMD (SEQ ID NO: 39) |
| Light Chain variable region CDR1 | RASESVDSYGNSFMH (SEQ ID NO: 30) | RASESVDSYGNSFMH (SEQ ID NO: 30) | RASESVDSYGNSFMH (SEQ ID NO: 30) | RASESVDSYGNSFMH (SEQ ID NO: 30) | DSYGNSFMHWY (SEQ ID NO: 40) |

TABLE 2-continued

Antibody 5A7 Sequences

| | Exemplary | Chothia | AbM | Kabat | Contact |
|---|---|---|---|---|---|
| Light Chain variable region CDR2 | LTSNLES (SEQ ID NO: 31) | LTSNLES (SEQ ID NO: 31) | LTSNLES (SEQ ID NO: 31) | LTSNLES (SEQ ID NO: 31) | LLIYLTSNLE (SEQ ID NO: 41) |
| Light Chain variable region CDR3 | QQNNEDPFT (SEQ ID NO: 32) | QQNNEDPFT (SEQ ID NO: 32) | QQNNEDPFT (SEQ ID NO: 32) | QQNNEDPFT (SEQ ID NO: 32) | QQNNEDPF (SEQ ID NO: 42) |

5A7 Heavy chain variable region (SEQ ID NO: 111)
EVKLVESGGGLVKPGGSLKLSCAASGFTFSSYGMSWVRQTPEKRLEWVATISGGGSYTNY
PDSVKGRLTISRDNAKKNLYLEMSSLRSEDTALYYCARREWRMTLYAMDYWGQGTSVTVSS 5A7 Light chain variable region (SEQ ID NO: 112)
NIVLTQSPASLAVSLGQRATISCRASESVDSYGNSFMHWYQQKPGQAPKLLIYLTSNLES
GVPARFSGSGSRTDFTLTIDPVEADDAATYYCQQNNEDPFTFGSGTKLEIK

TABLE 3

Antibody 12A12 Sequences

| | Exemplary | Chothia | AbM | Kabat | Contact |
|---|---|---|---|---|---|
| Heavy Chain variable region CDR1 | GYTFTDYNMD (SEQ ID NO: 43) | GYTFTDY (SEQ ID NO: 49) | GYTFTDYNMD (SEQ ID NO: 43) | DYNMD (SEQ ID NO: 52) | TDYNMD (SEQ ID NO: 53) |
| Heavy Chain variable region CDR2 | YIYPNNGGTGYNQKFNS (SEQ ID NO: 44) | YPNNGG (SEQ ID NO: 50) | YIYPNNGGTG (SEQ ID NO: 51) | YIYPNNGGTGYNQKFNS (SEQ ID NO: 44) | WIGYIYPNNGGTG (SEQ ID NO: 54) |
| Heavy Chain variable region CDR3 | SPYYDYVGSYAMDY (SEQ ID NO: 45) | SPYYDYVGSYAMDY (SEQ ID NO: 45) | SPYYDYVGSYAMDY (SEQ ID NO: 45) | SPYYDYVGSYAMDY (SEQ ID NO: 45) | ASSPYYDYVGSYAMD (SEQ ID NO: 55) |
| Light Chain variable region CDR1 | TASSSVSSSYLH (SEQ ID NO: 46) | TASSSVSSSYLH (SEQ ID NO: 46) | TASSSVSSSYLH (SEQ ID NO: 46) | TASSSVSSSYLH (SEQ ID NO: 46) | SSSYLHWY (SEQ ID NO: 56) |
| Light Chain variable region CDR2 | STSNLAS (SEQ ID NO: 47) | STSNLAS (SEQ ID NO: 47) | STSNLAS (SEQ ID NO: 47) | STSNLAS (SEQ ID NO: 47) | LWIYSTSNLA (SEQ ID NO: 57) |
| Light Chain variable region CDR3 | HQYHRSPRT (SEQ ID NO: 48) | HQYHRSPRT (SEQ ID NO: 48) | HQYHRSPRT (SEQ ID NO: 48) | HQYHRSPRT (SEQ ID NO: 48) | HQYHRSPR (SEQ ID NO: 58) |

12A12 Heavy chain variable region (SEQ ID NO: 113)
EVQLQQSGPELVKPGASVKISCKASGYTFTDYNMDWVKQSHGKSLEWIGYIYPNNGGTGY
NQKFNSKATLTVDKSSSTAYMELHSLTSEDSAVYYCASSPYYDYVGSYAMDYWGQGTSVTVSS 12A12 Light chain variable region (SEQ ID NO: 114)
QIVLTQSPAIMSASLGERVTMTCTASSSVSSSYLHWYQQKPGSSPKLWIYSTSNLASGVP
ARFSGSGSGTSYSLTISSMEAEDAATYYCHQYHRSPRTFGGGTKLEIK

TABLE 4

Antibody 16C5 Sequences

| | Exemplary | Chothia | AbM | Kabat | Contact |
|---|---|---|---|---|---|
| Heavy Chain variable region CDR1 | GYTFTDYNMD (SEQ ID NO: 43) | GYTFTDY (SEQ ID NO: 49) | GYTFTDYNMD (SEQ ID NO: 43) | DYNMD (SEQ ID NO: 52) | TDYNMD (SEQ ID NO: 53) |
| Heavy Chain variable region CDR2 | YIYPSNGGTGYNQKFKS (SEQ ID NO: 59) | YPSNGG (SEQ ID NO: 64) | YIYPSNGGTG (SEQ ID NO: 65) | YIYPSNGGTGYNQKFKS (SEQ ID NO: 59) | WIGYIYPSNGGTG (SEQ ID NO: 66) |

TABLE 4-continued

Antibody 16C5 Sequences

| | Exemplary | Chothia | AbM | Kabat | Contact |
|---|---|---|---|---|---|
| Heavy Chain variable region CDR3 | VPYYDYLYYYAMDY (SEQ ID NO: 60) | VPYYDYLYYYAMDY (SEQ ID NO: 60) | VPYYDYLYYYAMDY (SEQ ID NO: 60) | VPYYDYLYYYAMDY (SEQ ID NO: 60) | ARVPYYDYLYYYAMD (SEQ ID NO: 67) |
| Light Chain variable region CDR1 | RASSSVSFMH (SEQ ID NO: 61) | RASSSVSFMH (SEQ ID NO: 61) | RASSSVSFMH (SEQ ID NO: 61) | RASSSVSFMH (SEQ ID NO: 61) | SFMHWY (SEQ ID NO: 68) |
| Light Chain variable region CDR2 | ATSNLAS (SEQ ID NO: 62) | ATSNLAS (SEQ ID NO: 62) | ATSNLAS (SEQ ID NO: 62) | ATSNLAS (SEQ ID NO: 62) | PWIYATSNLA (SEQ ID NO: 69) |
| Light Chain variable region CDR3 | QQWSTNPYMYT (SEQ ID NO: 63) | QQWSTNPYMYT (SEQ ID NO: 63) | QQWSTNPYMYT (SEQ ID NO: 63) | QQWSTNPYMYT (SEQ ID NO: 63) | QQWSTNPYMY (SEQ ID NO: 70) |

16C5 Heavy chain variable region (SEQ ID NO: 115)
EVQLQQSGPELVKPGASVKISCKASGYTFTDYNMDWVKQSHGKSLEWIGYIYPSNGGTGY
NQKFKSKATLTVDKSSNTAYMELHSLTSEDSAVYYCARVPYYDYLYYYAMDYWGQGTSVTVSS 16C5 Light chain variable region (SEQ ID NO: 116)
QIVLSQSPAILSASPGEKVTMACRASSSVSFMHWYQQKPGSSPQPWIYATSNLASGVPAR
FSGSGSGTSYSLTISRVEAEDAATYYCQQWSTNPYMYTFGGGTKLEIK

TABLE 5

Antibody 45G10 Sequences

| | Exemplary | Chothia | AbM | Kabat | Contact |
|---|---|---|---|---|---|
| Heavy Chain variable region CDR1 | GFTFSDYGMH (SEQ ID NO: 71) | GFTFSDY (SEQ ID NO: 77) | GFTFSDYGMH (SEQ ID NO: 71) | DYGMH (SEQ ID NO: 80) | SDYGMH (SEQ ID NO: 81) |
| Heavy Chain variable region CDR2 | YIFSGSSTIYYADTVKG (SEQ ID NO: 72) | FSGSST (SEQ ID NO: 78) | YIFSGSSTIY (SEQ ID NO: 79) | YIFSGSSTIYYADTVKG (SEQ ID NO: 72) | WVAYIFSGSSTIY (SEQ ID NO: 82) |
| Heavy Chain variable region CDR3 | ADGRGAMDY (SEQ ID NO: 73) | ADGRGAMDY (SEQ ID NO: 73) | ADGRGAMDY (SEQ ID NO: 73) | ADGRGAMDY (SEQ ID NO: 73) | ARADGRGAMD (SEQ ID NO: 83) |
| Light Chain variable region CDR1 | RASQDISKFLN (SEQ ID NO: 74) | RASQDISKFLN (SEQ ID NO: 74) | RASQDISKFLN (SEQ ID NO: 74) | RASQDISKFLN (SEQ ID NO: 74) | SKFLNWY (SEQ ID NO: 84) |
| Light Chain variable region CDR2 | YTSRLHS (SEQ ID NO: 75) | YTSRLHS (SEQ ID NO: 75) | YTSRLHS (SEQ ID NO: 75) | YTSRLHS (SEQ ID NO: 75) | LLIYYTSRLH (SEQ ID NO: 85) |
| Light Chain variable region CDR3 | QQGNTLPWT (SEQ ID NO: 76) | QQGNTLPWT (SEQ ID NO: 76) | QQGNTLPWT (SEQ ID NO: 76) | QQGNTLPWT (SEQ ID NO: 76) | QQGNTLPW (SEQ ID NO: 86) |

45G10 Heavy chain variable region (SEQ ID NO: 117)
EVQLVESGGGLVKPGGSLKLSCAASGFTFSDYGMHWVRQAPEKGLEWVAYIFSGSSTIYY
ADTVKGRFTISRDNAKNTLFLQMTSLRSEDTAMYYCARADGRGAMDYWGQGTSVTVSS 45G10 Light chain variable region (SEQ ID NO: 118)
DVQMTQTTSSLSASLGDRVTISCRASQDISKFLNWYQQKPDGTVTLLIYYTSRLHSGVPS
RFSGSGSGTDYSLTISNLDQEDIATYFCQQGNTLPWTFGGGTKLEIK

TABLE 6

Antibody 48A6 Sequences

| | Exemplary | Chothia | AbM | Kabat | Contact |
|---|---|---|---|---|---|
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISSGGTYTFYPDSVKG (SEQ ID NO: 87) | SSGGTY (SEQ ID NO: 92) | TISSGGTYTF (SEQ ID NO: 93) | TISSGGTYTFYPDSVKG (SEQ ID NO: 87) | WVATISSGGTYTF (SEQ ID NO: 94) |
| Heavy Chain variable region CDR3 | RGWLLHYYAMDY (SEQ ID NO: 88) | RGWLLHYYAMDY (SEQ ID NO: 88) | RGWLLHYYAMDY (SEQ ID NO: 88) | RGWLLHYYAMDY (SEQ ID NO: 88) | ARRGWLLHYYAMD (SEQ ID NO: 95) |
| Light Chain variable region CDR1 | RPSESVDSFGNSFMH (SEQ ID NO: 89) | RPSESVDSFGNSFMH (SEQ ID NO: 89) | RPSESVDSFGNSFMH (SEQ ID NO: 89) | RPSESVDSFGNSFMH (SEQ ID NO: 89) | DSFGNSFMHWF (SEQ ID NO: 96) |
| Light Chain variable region CDR2 | LSSKLES (SEQ ID NO: 90) | LSSKLES (SEQ ID NO: 90) | LSSKLES (SEQ ID NO: 90) | LSSKLES (SEQ ID NO: 90) | LLIYLSSKLE (SEQ ID NO: 97) |
| Light Chain variable region CDR3 | QQHNEDPFT (SEQ ID NO: 91) | QQHNEDPFT (SEQ ID NO: 91) | QQHNEDPFT (SEQ ID NO: 91) | QQHNEDPFT (SEQ ID NO: 91) | QQHNEDPF (SEQ ID NO: 98) |

48A6 Heavy chain variable region (SEQ ID NO: 119)
EVQLVESGGDLMKPGGSLKLSCAASGFTFSSYGMSWVRQTPDKRLEWVATISSGGTYTFY
PDSVKGRFTISRDNAKNTLYLQMSSLKSEDTAMYYCARRGWLLHYYAMDYWGQGTSVTVSS 48A6 Light chain variable region (SEQ ID NO: 120)
NIVLTQSPASLAVSLGQRATISCRPSESVDSFGNSFMHWFQQKPGQPPKLLIYLSSKLES
GVPARFSGSGSRTDFTLTIDPVEADDAATYYCQQHNEDPFTFGSGTKLEIK

TABLE 7

Antibody 53F10 Sequences

| | Exemplary | Chothia | AbM | Kabat | Contact |
|---|---|---|---|---|---|
| Heavy Chain variable region CDR1 | GFTFSDYGMH (SEQ ID NO: 71) | GFTFSDY (SEQ ID NO: 77) | GFTFSDYGMH (SEQ ID NO: 71) | DYGMH (SEQ ID NO: 80) | SDYGMH (SEQ ID NO: 81) |
| Heavy Chain variable region CDR2 | YISTGIITVYYADTVKG (SEQ ID NO: 99) | STGIIT (SEQ ID NO: 101) | YISTGIITVY (SEQ ID NO: 102) | YISTGIITVYYADTVKG (SEQ ID NO: 99) | WVAYISTGIITVY (SEQ ID NO: 103) |
| Heavy Chain variable region CDR3 | ADGRGAMDY (SEQ ID NO: 73) | ADGRGAMDY (SEQ ID NO: 73) | ADGRGAMDY (SEQ ID NO: 73) | ADGRGAMDY (SEQ ID NO: 73) | ARADGRGAMD (SEQ ID NO: 83) |
| Light Chain variable region CDR1 | RASQDISNFLN (SEQ ID NO: 100) | RASQDISNFLN (SEQ ID NO: 100) | RASQDISNFLN (SEQ ID NO: 100) | RASQDISNFLN (SEQ ID NO: 100) | SNFLNWY (SEQ ID NO: 104) |
| Light Chain variable region CDR2 | YTSRLHS (SEQ ID NO: 75) | YTSRLHS (SEQ ID NO: 75) | YTSRLHS (SEQ ID NO: 75) | YTSRLHS (SEQ ID NO: 75) | LLIYYTSRLH (SEQ ID NO: 85) |
| Light Chain variable region CDR3 | QQGNTLPWT (SEQ ID NO: 76) | QQGNTLPWT (SEQ ID NO: 76) | QQGNTLPWT (SEQ ID NO: 76) | QQGNTLPWT (SEQ ID NO: 76) | QQGNTLPW (SEQ ID NO: 86) |

53F10 Heavy chain variable region (SEQ ID NO: 121)
EVQVVESGGGLVKPGGSLKLSCAASGFTFSDYGMHWVRQAPEKGLEWVAYISTGIITVYY
ADTVKGRFTMSRDNAKNTLFLQMTSLRSEDTAIYYCARADGRGAMDYWGQGTSVIVSS 53F10 Light chain variable region (SEQ ID NO: 122)
DIQMTQTTSSLSASLGDRVTISCRASQDISNFLNWYQQKPDGTVTLLIYYTSRLHSGVPS
RFSGSGSGTDYSLTISNLEQEDFATYFCQQGNTLPWTFGGGTKLEIK

TABLE 8

Antibody Hz5A7.v5 Sequences

| | Exemplary | Chothia | AbM | Kabat | Contact |
|---|---|---|---|---|---|
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISGGGSYTNYPDSVKG (SEQ ID NO: 28) | SGGGSY (SEQ ID NO: 34) | TISGGGSYTN (SEQ ID NO: 35) | TISGGGSYTNYPDSVKG (SEQ ID NO: 28) | WVATISGGGSYTN (SEQ ID NO: 38) |
| Heavy Chain variable region CDR3 | REWRYTLYAMDY (SEQ ID NO: 105) | REWRYTLYAMDY (SEQ ID NO: 105) | REWRYTLYAMDY (SEQ ID NO: 105) | REWRYTLYAMDY (SEQ ID NO: 105) | ARREWRYTLYAMD (SEQ ID NO: 107) |
| Light Chain variable region CDR1 | RASESVESYGSSFMH (SEQ ID NO: 106) | RASESVESYGSSFMH (SEQ ID NO: 106) | RASESVESYGSSFMH (SEQ ID NO: 106) | RASESVESYGSSFMH (SEQ ID NO: 106) | ESYGSSFMHWY (SEQ ID NO: 108) |
| Light Chain variable region CDR2 | LTSNLES (SEQ ID NO: 31) | LTSNLES (SEQ ID NO: 31) | LTSNLES (SEQ ID NO: 31) | LTSNLES (SEQ ID NO: 31) | LLIYLTSNLE (SEQ ID NO: 41) |
| Light Chain variable region CDR3 | QQNNEDPFT (SEQ ID NO: 32) | QQNNEDPFT (SEQ ID NO: 32) | QQNNEDPFT (SEQ ID NO: 32) | QQNNEDPFT (SEQ ID NO: 32) | QQNNEDPF (SEQ ID NO: 42) |

Hz5A7.v5 Heavy chain variable region (SEQ ID NO: 123)
EVQLVESGGGLVQPGGSLRLSCAASGFTFSSYGMSWVRQAPGKGLEWVATISGGGSYTNY
PDSVKGRFTISRDNAKNSLYLQMNSLRAEDTAVYYCARREWRYTLYAMDYWGQGTTVTSS Hz5A7.v5 Light chain variable region (SEQ ID NO: 124)
DIQLTQSPSFLSASVGDRVTITCRASESVESYGSSFMHWYQQKPGKAPKLLIYLTSNLES
GVPSRFSGSGSGTEFTLTISSLQPEDFATYYCQQNNEDPFTFGQGTKLEIK In some embodiments, an ILT3-binding agent comprises a heavy chain variable region CDR1, CDR2, and CDR3 and/or a light chain variable region CDR1, CDR2, and CDR3 from an antibody described herein. In some embodiments, an ILT3-binding agent comprises a heavy chain variable region CDR1, CDR2, and CDR3 and a light chain variable region CDR1, CDR2, and CDR3 from an antibody described herein. In some embodiments, an ILT3-binding agent comprises: (a) a heavy chain variable region comprising a heavy chain variable region CDR1, CDR2, and CDR3; and (b) a light chain variable region comprising a light chain variable region CDR1, CDR2, and CDR3 from an antibody described herein.

In some embodiments, an ILT3-binding agent comprises a heavy chain variable region CDR1, CDR2, and CDR3 and/or a light chain variable region CDR1, CDR2, and CDR3 from antibody 5A7, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 5A7. In other embodiments, an ILT3-binding agent comprises a light chain variable region comprising a light chain variable region CDR1, a light chain variable region CDR2, and a light chain variable region CDR3 from antibody 5A7. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 5A7. In some embodiments, an ILT3-binding agent is a humanized version of antibody 5A7 (e.g., Hz5A7). In some embodiments, an ILT3-binding agent is a variant of antibody 5A7 or humanized 5A7 (e.g., Hz5A7.v5). In some embodiments, an ILT3-binding agent comprises a heavy chain variable region comprising a heavy chain variable region CDR1, a heavy chain variable region CDR2, and a heavy chain variable region CDR3 from antibody Hz5A7.v5. In other embodiments, an ILT3-binding agent comprises a light chain variable region comprising a light chain variable region CDR1, a light chain variable region CDR2, and a light chain variable region CDR3 from antibody Hz5A7.v5. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody Hz5A7.v5.

In some embodiments, an ILT3-binding agent comprises a heavy chain variable region CDR1, CDR2, and CDR3 and/or a light chain variable region CDR1, CDR2, and CDR3 from antibody 3A3, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 3A3. In other embodiments, an ILT3-binding agent comprises a light chain variable region comprising a light chain variable region CDR1, a light chain variable region CDR2, and a light chain variable region CDR3 from antibody 3A3. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 3A3. In some embodiments, an ILT3-binding agent is a humanized version of antibody 3A3. In some embodiments, an ILT3-binding agent is a variant of antibody 3A3.

In some embodiments, an ILT3-binding agent comprises a heavy chain variable region CDR1, CDR2, and CDR3 and/or a light chain variable region CDR1, CDR2, and CDR3 from antibody 12A12, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 12A12. In other embodiments, an ILT3-binding agent comprises a light chain variable region comprising a light chain variable region CDR1, a light chain variable region CDR2, and a light chain variable region CDR3 from antibody 12A12. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 12A12. In some embodiments, an ILT3-binding agent is a humanized version of antibody 12A12. In some embodiments, an ILT3-binding agent is a variant of antibody 12A12.

In some embodiments, an ILT3-binding agent comprises a heavy chain variable region CDR1, CDR2, and CDR3 and/or a light chain variable region CDR1, CDR2, and CDR3 from antibody 16C5, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 16C5. In other embodiments, an ILT3-binding agent comprises a light chain variable region comprising a light chain variable region CDR1, a light chain variable region CDR2, and a light chain variable region CDR3 from antibody 16C5. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 16C5. In some embodiments, an ILT3-binding agent is a humanized version of antibody 16C5. In some embodiments, an ILT3-binding agent is a variant of antibody 16C5.

In some embodiments, an ILT3-binding agent comprises a heavy chain variable region CDR1, CDR2, and CDR3 and/or a light chain variable region CDR1, CDR2, and CDR3 from antibody 45G10, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 45G10. In other embodiments, an ILT3-binding agent comprises a light chain variable region comprising a light chain variable region CDR1, a light chain variable region CDR2, and a light chain variable region CDR3 from antibody 45G10. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 45G10. In some embodiments, an ILT3-binding agent is a humanized version of antibody 45G10. In some embodiments, an ILT3-binding agent is a variant of antibody 45G10.

In some embodiments, an ILT3-binding agent comprises a heavy chain variable region CDR1, CDR2, and CDR3 and/or a light chain variable region CDR1, CDR2, and CDR3 from antibody 48A6, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 48A6. In other embodiments, an ILT3-binding agent comprises a light chain variable region comprising a light chain variable region CDR1, a light chain variable region CDR2, and a light chain variable region CDR3 from antibody 48A6. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 48A6. In some embodiments, an ILT3-binding agent is a humanized version of antibody 48A6. In some embodiments, an ILT3-binding agent is a variant of antibody 48A6.

In some embodiments, an ILT3-binding agent comprises a heavy chain variable region CDR1, CDR2, and CDR3 and/or a light chain variable region CDR1, CDR2, and CDR3 from antibody 53F10, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 53F10. In other embodiments, an ILT3-binding agent comprises a light chain variable region comprising a light chain variable region CDR1, a light chain variable region CDR2, and a light chain variable region CDR3 from antibody 53F10. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 53F10. In some embodiments, an ILT3-binding agent is a humanized version of antibody 53F10. In some embodiments, an ILT3-binding agent is a variant of antibody 53F10.

In some embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (b) a heavy chain variable region comprising a heavy chain variable region CDR1 comprising the amino acid sequence GFTFSSY (SEQ ID NO:33), a heavy chain variable region CDR2 comprising the amino acid sequence SGGGSY (SEQ ID NO:34), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (c) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTN (SEQ ID NO:35), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (d) a heavy chain variable region comprising a heavy chain variable region CDR1 comprising the amino acid sequence SYGMS (SEQ ID NO:36), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); or (e) a heavy chain variable region comprising a heavy chain variable region CDR1 comprising the amino acid sequence SSYGMS (SEQ ID NO:37), a heavy chain variable region CDR2 comprising the amino acid sequence WVATISGGGSYTN (SEQ ID NO:38), and a heavy chain variable region CDR3 comprising the amino acid sequence ARREWRMTLYAMD (SEQ ID NO:39) or ARREWRMTLYAMD (SEQ ID NO:107), and a light chain variable region comprising a light chain variable region CDR1 comprising the amino acid sequence DSYGNSFVIEIWY (SEQ ID NO:40) or ESYGSSFMHWY (SEQ ID NO:108), a light chain variable region CDR2 comprising the amino acid sequence LLIYLTSNLE (SEQ ID NO:41), and a light chain variable region CDR3 comprising the amino acid sequence QQNNEDPF (SEQ ID NO:42).

In some embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRMTLYAMDY (SEQ ID NO:105), and/or (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29). In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:105). In some embodiments, the ILT3-binding agent comprises a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29), and (b) a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRYTLYAMDY (SEQ ID NO:105), and (b) a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32).

In certain embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), or a variant thereof comprising 1, 2, 3, 4, or 6 amino acid substitutions; a heavy chain variable region CDR2 comprising the amino acid sequence TISGGGSYTNYPDSVKG (SEQ ID NO:28), or a variant thereof comprising 1, 2, 3, 4, or 6 amino acid substitutions; and a heavy chain variable region CDR3 comprising the amino acid sequence REWRMTLYAMDY (SEQ ID NO:29), REWRYTLYAMDY (SEQ ID NO:105), or a variant thereof comprising 1, 2, 3, 4, 5 or 6 amino acid substitutions; and (b) a light chain variable region comprising a light chain variable region CDR1 comprising the amino acid sequence RASESVDSYGNSFMH (SEQ ID NO:30), RASESVESYGSSFMH (SEQ ID NO:106), or a variant thereof comprising 1, 2, 3, 4, 5 or 6 amino acid substitutions; a light chain variable region CDR2 comprising the amino acid sequence LTSNLES (SEQ ID NO:31), or a variant thereof comprising 1, 2, 3, 4, 5 or 6 amino acid substitutions; and a light chain variable region CDR3 comprising the amino acid sequence QQNNEDPFT (SEQ ID NO:32), or a variant thereof comprising 1, 2, 3, 4, 5 or 6 amino acid substitutions.

In some embodiments, an ILT3-binding agent (e.g., an antibody) comprises one or more heavy chain variable region CDRs or light chain variable region CDRs that have been modified to reduce deamidation within the CDR sequence. Deamidation is a chemical reaction in which an amide functional group in the side chain of the amino acids asparagine (Asn or N) or glutamine (Gln or Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity. In some embodiments, the light chain variable region CDR1, CDR2, and/or CDR3 of an antibody described herein is modified to reduce deamidation. In some embodiments, the light chain variable region CDR1, CDR2, and/or CDR3 of an antibody described herein is modified to reduce deamidation. Any one of the heavy chain variable region CDRs and light chain variable region CDRs of antibody 5A7, 3A3, Hz5A7, 12A12, 16C5, 45G10, 48A6, or 53F10 can be modified to reduce deamidation.

In some embodiments, an ILT3-binding agent (e.g., an antibody) comprises one or more heavy chain variable region CDRs or light chain variable region CDRs that have been modified to reduce isomerization. Isomerization is a chemical process by which a compound is transformed into any of its isomeric forms, i.e., forms with the same chemical composition but with different structure or configuration and, potentially with different physical and chemical properties. Studies have shown that asparatate (Asp or D) isomerization within a CDR can impact antibody binding and/or stability. In some embodiments, the heavy chain variable region CDR1, CDR2, and/or CDR3 of an antibody described herein is modified to reduce isomerization. In some embodiments, the light chain variable region CDR1, CDR2, and/or CDR3 is modified to reduce isomerization. Any one of the heavy chain variable region CDRs and light chain variable region CDRs of antibody 5A7, 3A3, Hz5A7, 12A12, 16C5, 45G10, 48A6, or 53F10 can be modified to reduce isomerization.

In some embodiments, an ILT3-binding agent (e.g., an antibody) comprises one or more heavy chain variable region CDRs or light chain variable region CDRs that have been modified to reduce oxidation. Oxidation is a chemical process by which an oxygen is added to an atom, for example, methionine is converted to methionine sulfoxide by addition of an oxygen to the sulfur atom. Oxidation of one or more amino acids can potentially affect the physical and chemical properties of a protein. Studies have shown that oxidation of methionine (Met or M) within a CDR has the potential to impact antibody binding and/or stability. In some embodiments, the heavy chain variable region CDR1, CDR2, and/or CDR3 of an antibody described herein is modified to reduce oxidation (e.g., methionine oxidation). In some embodiments, the light chain variable region CDR1, CDR2, and/or CDR3 of an antibody described herein is modified to reduce oxidation (e.g., methionine oxidation). Any one of the heavy chain variable region CDRs and light chain variable region CDRs of antibody 5A7, 3A3, Hz5A7, 12A12, 16C5, 45G10, 48A6, or 53F10 can be modified to reduce methionine oxidation.

In some embodiments, an anti-ILT3 binding agent (e.g., antibody) comprises a heavy chain variable region comprising the amino acid sequence of heavy chain variable region CDR1, CDR2, and CDR3 of antibody 5A7 and which has at least 75%, at least 80%, at least 85%, at least 90%, at least 95%, at least 96%, at least 97%, at least 98%, at least 99%, or 100% identity to the sequence of SEQ ID NO:111 and a light chain variable region comprising the amino acid sequence of light chain variable region CDR1, CDR2, and CDR3 of antibody 5A7 and which has at least 75%, at least 80%, at least 85%, at least 90%, at least 95%, at least 96%, at least 97%, at least 98%, at least 99%, or 100% identity to the sequence of SEQ ID NO:112. In some embodiments, an anti-ILT3 binding agent comprises a heavy chain variable region comprising the amino acid sequence of heavy chain variable region CDR1, CDR2, and CDR3 of antibody Hz5A7.v5 and which has at least 75%, at least 80%, at least 85%, at least 90%, at least 95%, at least 96%, at least 97%, at least 98%, at least 99%, or 100% identity to the sequence of SEQ ID NO:123 and a light chain variable region comprising the amino acid sequence of light chain variable region CDR1, CDR2, and CDR3s of antibody Hz5A7.v5 and which has at least 75%, at least 80%, at least 85%, at least 90%, at least 95%, at least 96%, at least 97%, at least 98%, at least 99%, or 100% identity to the sequence of SEQ ID NO:124.

In some embodiments, an ILT3-binding agent (e.g., an antibody) comprises a heavy chain variable region having at least 80%, at least 85%, at least 90%, at least 95%, at least 97%, or at least 99% identity to the sequence of SEQ ID NO:111. In some embodiments, an ILT3-binding agent comprises a light chain variable region having at least 80%, at least 85%, at least 90%, at least 95%, at least 97%, or at least 99% identity to the sequence of SEQ ID NO:112. In some embodiments, an ILT3-binding agent comprises a heavy chain variable region having at least 80%, at least 85%, at least 90%, at least 95%, at least 97%, or at least 99% identity to the sequence of SEQ ID NO:123. In some embodiments, an ILT3-binding agent comprises a light chain variable region having at least 80%, at least 85%, at least 90%, at least 95%, at least 97%, or at least 99% identity to the sequence of SEQ ID NO:124.

In some embodiments, an ILT3-binding agent (e.g., an antibody) comprises a heavy chain variable region comprising an amino acid sequence of SEQ ID NO:111. In some embodiments, an ILT3-binding agent comprises a light chain variable region comprising an amino acid sequence of SEQ ID NO:112. In some embodiments, an ILT3-binding agent comprises a heavy chain variable region comprising an amino acid sequence of SEQ ID NO:123. In some embodiments, an ILT3-binding agent comprises a light chain variable region comprising an amino acid sequence of SEQ ID NO:124.

In some embodiments, an ILT3-binding agent (e.g., an antibody) comprises a heavy chain variable region having at least 80% sequence identity to SEQ ID NO:111 and a light chain variable region having at least 80% sequence identity to SEQ ID NO:112. In some embodiments, an ILT3-binding agent comprises a heavy chain variable region having at least 90% sequence identity to SEQ ID NO:111 and a light chain variable region having at least 90% sequence identity to SEQ ID NO:112. In some embodiments, an ILT3-binding agent comprises a heavy chain variable region having at least 95% sequence identity to SEQ ID NO:111 and a light chain variable region having at least 95% sequence identity to SEQ ID NO:112. In some embodiments, an ILT3-binding agent comprises a heavy chain variable region comprising an amino acid sequence of SEQ ID NO:111 and a light chain variable region comprising an amino acid sequence of SEQ ID NO:112.

In some embodiments, an ILT3-binding agent (e.g., an antibody) comprises a heavy chain variable region having at least 80% sequence identity to SEQ ID NO:123 and a light chain variable region having at least 80% sequence identity to SEQ ID NO:124. In some embodiments, an ILT3-binding agent comprises a heavy chain variable region having at least 90% sequence identity to SEQ ID NO:123 and a light chain variable region having at least 90% sequence identity to SEQ ID NO:124. In some embodiments, an ILT3-binding agent comprises a heavy chain variable region having at least 95% sequence identity to SEQ ID NO:123 and a light chain variable region having at least 95% sequence identity to SEQ ID NO:124. In some embodiments, an ILT3-binding agent comprises a heavy chain variable region comprising an amino acid sequence of SEQ ID NO:123 and a light chain variable region comprising an amino acid sequence of SEQ ID NO:124.

In certain embodiments, an ILT3-binding agent (e.g., an antibody) comprises a heavy chain variable region comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain variable region comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain variable region comprises at least 80%, at least 85%, at least 90%, at least 95%, at least 97% identity to the sequence of SEQ ID NO:123, and wherein the light chain variable region comprises at least 80%, at least 85%, at least 90%, at least 95%, at least 97% identity to the sequence of SEQ ID NO:124.

In certain embodiments, an ILT3-binding agent (e.g., an antibody) comprises a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain comprises at least 80%, at least 85%, at least 90%, at least 95%, at least 97%, or 100% identity to the sequence of SEQ ID NO:126, and wherein the light chain comprises at least 80%, at least 85%, at least 90%, at least 95%, at least 97%, or 100% identity to the sequence of SEQ ID NO:128. In certain embodiments, an ILT3-binding agent comprises a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain comprises at least 95% identity to the sequence of SEQ ID NO:126, and wherein the light chain comprises at least 95% identity to the sequence of SEQ ID NO:128. In certain embodiments, an ILT3-binding agent comprises (a) a heavy chain comprising the amino acids of SEQ ID NO:126 and (b) a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the light chain comprises at least 80%, at least 85%, at least 90%, at least 95%, at least 97%, or 100% identity to the sequence of SEQ ID NO:128. In certain embodiments, an ILT3-binding agent comprises (a) a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), wherein the heavy chain comprises at least 80%, at least 85%, at least 90%, at least 95%, at least 97%, or 100% identity to the sequence of SEQ ID NO:126, and (b) a light chain comprising the amino acid sequence of SEQ ID NO:128. In some embodiments, an ILT3-binding agent is an antibody comprising a heavy chain comprising the amino acid sequence of SEQ ID NO:126 and a light chain comprising the amino acid sequence of SEQ ID NO:128.

In some embodiments, the ILT3-binding agent is antibody 5A7. In some embodiments, the ILT3-binding agent is antibody Hz5A7.v5.

In some embodiments, an ILT3-binding agent (e.g., an antibody) comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (b) a heavy chain variable region comprising a heavy chain variable region CDR1 comprising the amino acid sequence GFSLTSY (SEQ ID NO:17), a heavy chain variable region CDR2 comprising the amino acid sequence WPGGT (SEQ ID NO:18), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (c) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTIN (SEQ ID NO:19), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (d) a heavy chain variable region comprising a heavy chain variable region CDR1 comprising the amino acid sequence SYGVH (SEQ ID NO:20), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); or (e) a heavy chain variable region comprising a heavy chain variable region CDR1 comprising the amino acid sequence TSYGVH (SEQ ID NO:21), a heavy chain variable region CDR2 comprising the amino acid sequence WLGVIWPGGTIN (SEQ ID NO:22), and a heavy chain variable region CDR3 comprising the amino acid sequence ASDKYDGGWFA (SEQ ID NO:23), and a light chain variable region comprising a light chain variable region CDR1 comprising the amino acid sequence RTAVAWY (SEQ ID NO:24), a light chain variable region CDR2 comprising the amino acid sequence ALIYLASNRH (SEQ ID NO:25), and a light chain variable region CDR3 comprising the amino acid sequence LQHLNYPL (SEQ ID NO:26).

In some embodiments, an ILT3-binding agent comprises a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13). In some embodiments, an ILT3-binding agent comprises a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an ILT3-binding agent comprises (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16).

In some embodiments, an ILT3-binding agent comprises a heavy chain variable region having at least 80%, at least 85%, at least 90%, at least 95%, at least 97%, or at least 99% identity to the sequence of SEQ ID NO:109. In some embodiments, an ILT3-binding agent comprises a light chain variable region having at least 80%, at least 85%, at least 90%, at least 95%, at least 97%, or at least 99% identity to the sequence of SEQ ID NO:110. In some embodiments, an ILT3-binding agent comprises a heavy chain variable region comprising an amino acid sequence of SEQ ID NO:109. In some embodiments, an ILT3-binding agent comprises a light chain variable region comprising an amino acid sequence of SEQ ID NO:110.

In some embodiments, an ILT3-binding agent comprises a heavy chain variable region having at least 80% sequence identity to SEQ ID NO:109 and a light chain variable region having at least 80% sequence identity to SEQ ID NO:110. In some embodiments, an ILT3-binding agent comprises a heavy chain variable region having at least 90% sequence identity to SEQ ID NO:109 and a light chain variable region having at least 90% sequence identity to SEQ ID NO:110. In some embodiments, an ILT3-binding agent comprises a heavy chain variable region having at least 95% sequence identity to SEQ ID NO:109 and a light chain variable region having at least 95% sequence identity to SEQ ID NO:110. In some embodiments, an ILT3-binding agent comprises a heavy chain variable region comprising an amino acid sequence of SEQ ID NO:109 and a light chain variable region comprising an amino acid sequence of SEQ ID NO:110.

In some embodiments, the ILT3-binding agent is antibody 3A3. In some embodiments, the ILT3-binding agent is a humanized version of antibody 3A3. In some embodiments, the ILT3-binding agent is a variant of antibody 3A3 or humanized antibody 3A3.

In certain embodiments, an ILT3-binding agent (e.g., an antibody) comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (b) a heavy chain variable region comprising a heavy chain variable region CDR1 comprising the amino acid sequence GYTFTDY (SEQ ID NO:49), a heavy chain variable region CDR2 comprising the amino acid sequence YPNNGG (SEQ ID NO:50), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (c) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTG (SEQ ID NO:51), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (d) a heavy chain variable region comprising a heavy chain variable region CDR1 comprising the amino acid sequence DYNMD (SEQ ID NO:52), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); or (e) a heavy chain variable region comprising a heavy chain variable region CDR1 comprising the amino acid sequence TDYNMD (SEQ ID NO:53), a heavy chain variable region CDR2 comprising the amino acid sequence WIGYIYPNNGGTG (SEQ ID NO:54), and a heavy chain variable region CDR3 comprising the amino acid sequence ASSPYYDYVGSYAMD (SEQ ID NO:55), and a light chain variable region comprising a light chain variable region CDR1 comprising the amino acid sequence SSSYLHWY (SEQ ID NO:56), a light chain variable region CDR2 comprising the amino acid sequence LWIYSTSNLA (SEQ ID NO:57), and a light chain variable region CDR3 comprising the amino acid sequence HQYHRSPR (SEQ ID NO:58).

In some embodiments, an ILT3-binding agent comprises a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45). In some embodiments, an ILT3-binding agent comprises a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an ILT3-binding agent comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48).

In some embodiments, an ILT3-binding agent comprises a heavy chain variable region having at least 80%, at least 85%, at least 90%, at least 95%, at least 97%, or at least 99% identity to the sequence of SEQ ID NO:113. In some embodiments, an ILT3-binding agent comprises a light chain variable region having at least 80%, at least 85%, at least 90%, at least 95%, at least 97%, or at least 99% identity to the sequence of SEQ ID NO:114. In some embodiments, an ILT3-binding agent comprises a heavy chain variable region comprising an amino acid sequence of SEQ ID NO:113. In some embodiments, an ILT3-binding agent comprises a light chain variable region comprising an amino acid sequence of SEQ ID NO:114.

In some embodiments, an ILT3-binding agent comprises a heavy chain variable region having at least 80% sequence identity to SEQ ID NO:113 and a light chain variable region having at least 80% sequence identity to SEQ ID NO:114. In some embodiments, an ILT3-binding agent comprises a heavy chain variable region having at least 90% sequence identity to SEQ ID NO:113 and a light chain variable region having at least 90% sequence identity to SEQ ID NO:114. In some embodiments, an ILT3-binding agent comprises a heavy chain variable region having at least 95% sequence identity to SEQ ID NO:113 and a light chain variable region having at least 95% sequence identity to SEQ ID NO:114. In some embodiments, an ILT3-binding agent comprises a heavy chain variable region comprising an amino acid sequence of SEQ ID NO:113 and a light chain variable region comprising an amino acid sequence of SEQ ID NO:114.

In some embodiments, the ILT3-binding agent is antibody 12A12. In some embodiments, the ILT3-binding agent is a humanized version of antibody 12A12. In some embodiments, the ILT3-binding agent is a variant of antibody 12A12 or humanized antibody 12A12.

In certain embodiments, an ILT3-binding agent (e.g., an antibody) comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (b) a heavy chain variable region comprising a heavy chain variable region CDR1 comprising the amino acid sequence GYTFTDY (SEQ ID NO:49), a heavy chain variable region CDR2 comprising the amino acid sequence YPSNGG (SEQ ID NO:64), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (c) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTG (SEQ ID NO:65), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (d) a heavy chain variable region comprising a heavy chain variable region CDR1 comprising the amino acid sequence DYNMD (SEQ ID NO:52), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); or (e) a heavy chain variable region comprising a heavy chain variable region CDR1 comprising the amino acid sequence TDYNMD (SEQ ID NO:53), a heavy chain variable region CDR2 comprising the amino acid sequence WIGYIYPSNGGTG (SEQ ID NO:66), and a heavy chain variable region CDR3 comprising the amino acid sequence ARVPYYDYLYYYAMD (SEQ ID NO:67), and a light chain variable region comprising a light chain variable region CDR1 comprising the amino acid sequence SFMHWY (SEQ ID NO:68), a light chain variable region CDR2 comprising the amino acid sequence PWIYATSNLA (SEQ ID NO:69), and a light chain variable region CDR3 comprising the amino acid sequence QQWSTNPYMY (SEQ ID NO:70).

In some embodiments, an ILT3-binding agent comprises a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60). In some embodiments, an ILT3-binding agent comprises a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an ILT3-binding agent comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63).

In some embodiments, an ILT3-binding agent comprises a heavy chain variable region having at least 80%, at least 85%, at least 90%, at least 95%, at least 97%, or at least 99% identity to the sequence of SEQ ID NO:115. In some embodiments, an ILT3-binding agent comprises a light chain variable region having at least 80%, at least 85%, at least 90%, at least 95%, at least 97%, or at least 99% identity to the sequence of SEQ ID NO:116. In some embodiments, an ILT3-binding agent comprises a heavy chain variable region comprising an amino acid sequence of SEQ ID NO:115. In some embodiments, an ILT3-binding agent comprises a light chain variable region comprising an amino acid sequence of SEQ ID NO:116.

In some embodiments, an ILT3-binding agent comprises a heavy chain variable region having at least 80% sequence identity to SEQ ID NO:115 and a light chain variable region having at least 80% sequence identity to SEQ ID NO:116. In some embodiments, an ILT3-binding agent comprises a heavy chain variable region having at least 90% sequence identity to SEQ ID NO:115 and a light chain variable region having at least 90% sequence identity to SEQ ID NO:116. In some embodiments, an ILT3-binding agent comprises a heavy chain variable region having at least 95% sequence identity to SEQ ID NO:115 and a light chain variable region having at least 95% sequence identity to SEQ ID NO:116. In some embodiments, an ILT3-binding agent comprises a heavy chain variable region comprising an amino acid sequence of SEQ ID NO:115 and a light chain variable region comprising an amino acid sequence of SEQ ID NO:116.

In some embodiments, the ILT3-binding agent is antibody 16C5. In some embodiments, the ILT3-binding agent is a humanized version of antibody 16C5. In some embodiments, the ILT3-binding agent is a variant of antibody 16C5 or humanized antibody 16C5.

In certain embodiments, an ILT3-binding agent (e.g., an antibody) comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (b) a heavy chain variable region comprising a heavy chain variable region CDR1 comprising the amino acid sequence GFTFSDY (SEQ ID NO:77), a heavy chain variable region CDR2 comprising the amino acid sequence FSGSST (SEQ ID NO:78), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (c) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIY (SEQ ID NO:79), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (d) a heavy chain variable region comprising a heavy chain variable region CDR1 comprising the amino acid sequence DYGMH (SEQ ID NO:80), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); or (e) a heavy chain variable region comprising a heavy chain variable region CDR1 comprising the amino acid sequence SDYGMH (SEQ ID NO:81), a heavy chain variable region CDR2 comprising the amino acid sequence WVAYIFSGSSTIY (SEQ ID NO:82), and a heavy chain variable region CDR3 comprising the amino acid sequence ARADGRGAMD (SEQ ID NO:83), and a light chain variable region comprising a light chain variable region CDR1 comprising the amino acid sequence SKFLNWY (SEQ ID NO:84), a light chain variable region CDR2 comprising the amino acid sequence LLIYYTSRLH (SEQ ID NO:85), and a light chain variable region CDR3 comprising the amino acid sequence QQGNTLPW (SEQ ID NO:86).

In some embodiments, an ILT3-binding agent comprises a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73). In some embodiments, an ILT3-binding agent comprises a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent comprises a heavy chain variable region having at least 80%, at least 85%, at least 90%, at least 95%, at least 97%, or at least 99% identity to the sequence of SEQ ID NO:117. In some embodiments, an ILT3-binding agent comprises a light chain variable region having at least 80%, at least 85%, at least 90%, at least 95%, at least 97%, or at least 99% identity to the sequence of SEQ ID NO:118. In some embodiments, an ILT3-binding agent comprises a heavy chain variable region comprising an amino acid sequence of SEQ ID NO:117. In some embodiments, an ILT3-binding agent comprises a light chain variable region comprising an amino acid sequence of SEQ ID NO:118.

In some embodiments, an ILT3-binding agent comprises a heavy chain variable region having at least 80% sequence identity to SEQ ID NO:117 and a light chain variable region having at least 80% sequence identity to SEQ ID NO:118. In some embodiments, an ILT3-binding agent comprises a heavy chain variable region having at least 90% sequence identity to SEQ ID NO:117 and a light chain variable region having at least 90% sequence identity to SEQ ID NO:118. In some embodiments, an ILT3-binding agent comprises a heavy chain variable region having at least 95% sequence identity to SEQ ID NO:117 and a light chain variable region having at least 95% sequence identity to SEQ ID NO:118. In some embodiments, an ILT3-binding agent comprises a heavy chain variable region comprising an amino acid sequence of SEQ ID NO:117 and a light chain variable region comprising an amino acid sequence of SEQ ID NO:118.

In some embodiments, an ILT3-binding agent comprises a heavy chain variable region having at least 80%, at least 85%, at least 90%, at least 95%, at least 97%, or at least 99% identity to the sequence selected from SEQ ID NOs:162-163. In some embodiments, an ILT3-binding agent comprises a light chain variable region having at least 80%, at least 85%, at least 90%, at least 95%, at least 97%, or at least 99% identity to the sequence of SEQ ID NO:164. In some embodiments, an ILT3-binding agent comprises a heavy chain variable region comprising an amino acid sequence selected from SEQ ID NOs:162-163. In some embodiments, an ILT3-binding agent comprises a light chain variable region comprising an amino acid sequence of SEQ ID NO:164.

In some embodiments, an ILT3-binding agent comprises a heavy chain variable region having at least 80% (e.g., at least 85%, at least 90%, at least 95%, at least 97%, or at least 99%) sequence identity to an amino acid sequence selected from SEQ ID Nos:162-163, and a light chain variable region having at least 80% (e.g., at least 85%, at least 90%, at least 95%, at least 97%, or at least 99%) sequence identity to SEQ ID NO:164. In some embodiments, an ILT3-binding agent comprises a heavy chain variable region comprising an amino acid sequence of SEQ ID NO:162 and a light chain variable region comprising an amino acid sequence of SEQ ID NO:164. In some embodiments, an ILT3-binding agent comprises a heavy chain variable region comprising an amino acid sequence of SEQ ID NO:163 and a light chain variable region comprising an amino acid sequence of SEQ ID NO:164.

In some embodiments, the ILT3-binding agent is antibody 45G10. In some embodiments, the ILT3-binding agent is a humanized version of antibody 45G10. In some embodiments, the ILT3-binding agent is a variant of antibody 45G10 or humanized antibody 45G10.

In certain embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (b) a heavy chain variable region comprising a heavy chain variable region CDR1 comprising the amino acid sequence GFTFSSY (SEQ ID NO:33), a heavy chain variable region CDR2 comprising the amino acid sequence SSGGTY (SEQ ID NO:92), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (c) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTF (SEQ ID NO:93), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (d) a heavy chain variable region comprising a heavy chain variable region CDR1 comprising the amino acid sequence SYGMS (SEQ ID NO:36), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); or (e) a heavy chain variable region comprising a heavy chain variable region CDR1 comprising the amino acid sequence SSYGMS (SEQ ID NO:37), a heavy chain variable region CDR2 comprising the amino acid sequence WVATISSGGTYTF (SEQ ID NO:94), and a heavy chain variable region CDR3 comprising the amino acid sequence ARRGWLLHYYAMD (SEQ ID NO:95), and a light chain variable region comprising a light chain variable region CDR1 comprising the amino acid sequence DSFGNSFMHWF (SEQ ID NO:96), a light chain variable region CDR2 comprising the amino acid sequence LLIYLSSKLE (SEQ ID NO:97), and a light chain variable region CDR3 comprising the amino acid sequence QQHNEDPF (SEQ ID NO:98).

In some embodiments, an ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88). In some embodiments, an ILT3-binding agent comprises a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an ILT3-binding agent comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments, an ILT3-binding agent comprises a heavy chain variable region having at least 80%, at least 85%, at least 90%, at least 95%, at least 97%, or at least 99% identity to the sequence of SEQ ID NO:119. In some embodiments, an ILT3-binding agent comprises a light chain variable region having at least 80%, at least 85%, at least 90%, at least 95%, at least 97%, or at least 99% identity to the sequence of SEQ ID NO:120. In some embodiments, an ILT3-binding agent comprises a heavy chain variable region comprising an amino acid sequence of SEQ ID NO:119. In some embodiments, an ILT3-binding agent comprises a light chain variable region comprising an amino acid sequence of SEQ ID NO:120.

In some embodiments, an ILT3-binding agent comprises a heavy chain variable region having at least 80% sequence identity to SEQ ID NO:119 and a light chain variable region having at least 80% sequence identity to SEQ ID NO:120. In some embodiments, an ILT3-binding agent comprises a heavy chain variable region having at least 90% sequence identity to SEQ ID NO:119 and a light chain variable region having at least 90% sequence identity to SEQ ID NO:120. In some embodiments, an ILT3-binding agent comprises a heavy chain variable region having at least 95% sequence identity to SEQ ID NO:119 and a light chain variable region having at least 95% sequence identity to SEQ ID NO:120. In some embodiments, an ILT3-binding agent comprises a heavy chain variable region comprising an amino acid sequence of SEQ ID NO:119 and a light chain variable region comprising an amino acid sequence of SEQ ID NO:120.

In some embodiments, an ILT3-binding agent comprises a heavy chain variable region having at least 80%, at least 85%, at least 90%, at least 95%, at least 97%, or at least 99% identity to the sequence selected from SEQ ID NOs:156-160. In some embodiments, an ILT3-binding agent comprises a light chain variable region having at least 80%, at least 85%, at least 90%, at least 95%, at least 97%, or at least 99% identity to the sequence of SEQ ID NO:161. In some embodiments, an ILT3-binding agent comprises a heavy chain variable region comprising an amino acid sequence selected from SEQ ID NOs:156-160. In some embodiments, an ILT3-binding agent comprises a light chain variable region comprising an amino acid sequence of SEQ ID NO:161.

In some embodiments, an ILT3-binding agent comprises a heavy chain variable region having at least 80% (e.g., at least 85%, at least 90%, at least 95%, at least 97%, or at least 99%) sequence identity to an amino acid sequence selected from SEQ ID Nos:156-160, and a light chain variable region having at least 80% (e.g., at least 85%, at least 90%, at least 95%, at least 97%, or at least 99%) sequence identity to SEQ ID NO:161. In some embodiments, an ILT3-binding agent comprises a heavy chain variable region comprising an amino acid sequence of SEQ ID NO:156 and a light chain variable region comprising an amino acid sequence of SEQ ID NO:161. In some embodiments, an ILT3-binding agent comprises a heavy chain variable region comprising an amino acid sequence of SEQ ID NO:157 and a light chain variable region comprising an amino acid sequence of SEQ ID NO:161. In some embodiments, an ILT3-binding agent comprises a heavy chain variable region comprising an amino acid sequence of SEQ ID NO:158 and a light chain variable region comprising an amino acid sequence of SEQ ID NO:161. In some embodiments, an ILT3-binding agent comprises a heavy chain variable region comprising an amino acid sequence of SEQ ID NO:159 and a light chain variable region comprising an amino acid sequence of SEQ ID NO:161. In some embodiments, an ILT3-binding agent comprises a heavy chain variable region comprising an amino acid sequence of SEQ ID NO:160 and a light chain variable region comprising an amino acid sequence of SEQ ID NO:161.

In some embodiments, the ILT3-binding agent is antibody 48A6. In some embodiments, the ILT3-binding agent is a humanized version of antibody 48A6. In some embodiments, the ILT3-binding agent is a variant of antibody 48A6 or humanized antibody 48A6.

In certain embodiments, an ILT3-binding agent (e.g., an antibody) comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (b) a heavy chain variable region comprising a heavy chain variable region CDR1 comprising the amino acid sequence GFTFSDY (SEQ ID NO:77), a heavy chain variable region CDR2 comprising the amino acid sequence STGIIT (SEQ ID NO:101), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (c) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVY (SEQ ID NO:102), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (d) a heavy chain variable region comprising a heavy chain variable region CDR1 comprising the amino acid sequence DYGMH (SEQ ID NO:80), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); or (e) a heavy chain variable region comprising a heavy chain variable region CDR1 comprising the amino acid sequence SDYGMH (SEQ ID NO:81), a heavy chain variable region CDR2 comprising the amino acid sequence WVAYISTGIITVY (SEQ ID NO:103), and a heavy chain variable region CDR3 comprising the amino acid sequence ARADGRGAMD (SEQ ID NO:83), and a light chain variable region comprising a light chain variable region CDR1 comprising the amino acid sequence SNFLNWY (SEQ ID NO:104), a light chain variable region CDR2 comprising the amino acid sequence LLIYYTSRLH (SEQ ID NO:85), and a light chain variable region CDR3 comprising the amino acid sequence QQGNTLPW (SEQ ID NO:86).

In some embodiments, an ILT3-binding agent comprises a heavy chain variable region comprising a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73). In some embodiments, an ILT3-binding agent comprises a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent comprises a heavy chain variable region having at least 80%, at least 85%, at least 90%, at least 95%, at least 97%, or at least 99% identity to the sequence of SEQ ID NO:121. In some embodiments, an ILT3-binding agent comprises a light chain variable region having at least 80%, at least 85%, at least 90%, at least 95%, at least 97%, or at least 99% identity to the sequence of SEQ ID NO:122. In some embodiments, an ILT3-binding agent comprises a heavy chain variable region comprising an amino acid sequence of SEQ ID NO:121. In some embodiments, an ILT3-binding agent comprises a light chain variable region comprising an amino acid sequence of SEQ ID NO:122.

In some embodiments, an ILT3-binding agent comprises a heavy chain variable region having at least 80% sequence identity to SEQ ID NO:121 and a light chain variable region having at least 80% sequence identity to SEQ ID NO:122. In some embodiments, an ILT3-binding agent comprises a heavy chain variable region having at least 90% sequence identity to SEQ ID NO:121 and a light chain variable region having at least 90% sequence identity to SEQ ID NO:122. In some embodiments, an ILT3-binding agent comprises a heavy chain variable region having at least 95% sequence identity to SEQ ID NO:121 and a light chain variable region having at least 95% sequence identity to SEQ ID NO:122. In some embodiments, an ILT3-binding agent comprises a heavy chain variable region comprising an amino acid sequence of SEQ ID NO:121 and a light chain variable region comprising an amino acid sequence of SEQ ID NO:122.

In some embodiments, the ILT3-binding agent is antibody 53F10. In some embodiments, the ILT3-binding agent is a humanized version of antibody 53F10. In some embodiments, the ILT3-binding agent is a variant of antibody 53F10 or humanized antibody 53F10.

Provided herein are agents that compete with one or more of the binding agents (e.g., antibodies) described herein for binding to ILT3. In some embodiments, an agent competes with one of more of the antibodies described herein for binding to ILT3. In some embodiments, an agent that competes with one of more of the antibodies described herein is an antibody. In some embodiments, an agent binds the same epitope as one of the antibodies described herein. In some embodiments, an agent binds an epitope overlapping with an epitope bound by one of the antibodies described herein. Antibodies and antigen-binding fragments that compete with or bind the same epitope as the antibodies described herein are expected to show similar functional properties.

In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRMTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRMTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); and wherein the competing agent comprises a heavy chain variable region comprising a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent described herein comprises an antibody in which at least one or more of the constant regions of the antibody has been modified or deleted. In some embodiments, an antibody comprises one or more modifications to one or more of the three heavy chain constant regions (CH1, CH2 or CH3) and/or to the light chain constant region (CL). In some embodiments, an antibody comprises one or more modifications to the hinge region. In some embodiments, the heavy chain constant region of the modified antibody comprises at least one human constant region. In some embodiments, the heavy chain constant region of the modified antibody comprises more than one human constant region. In some embodiments, modifications to the constant region comprise additions, deletions, or substitutions of one or more amino acids in one or more regions. In some embodiments, one or more regions are partially or entirely deleted from the constant regions of a modified antibody. In some embodiments, the entire CH2 domain has been removed from an antibody (ΔCH2 constructs). In some embodiments, one or more regions are partially or entirely deleted from the hinge region of a modified antibody. In some embodiments, a deleted constant region is replaced by a short amino acid spacer that provides some of the molecular flexibility typically imparted by the absent constant region. In some embodiments, a deleted hinge region is replaced by a short amino acid spacer that provides some of the molecular flexibility typically imparted by the absent hinge region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an ILT3-binding agent (e.g., an antibody) comprises a variant Fc region. The amino acid sequences of the Fc region of human IgG1, IgG2, IgG3, and IgG4 are known to those of ordinary skill in the art (e.g., a representative human IgG1 region is SEQ ID NO:129). In some cases, Fc regions with amino acid variations have been identified in native antibodies. In some embodiments, a variant Fc region is engineered with substitutions at specific amino acid positions as compared to a native Fc region. Variant Fc regions are well-known in the art and include, but are not limited to, SEQ ID NO:130, SEQ ID NO:131, SEQ ID NO:132, SEQ ID NO:133, and SEQ ID NO:134.

In some embodiments, a modified antibody (e.g., comprising a modified Fc region) provides for altered effector functions that, in turn, affect the biological profile of the antibody. For example, in some embodiments, the deletion or inactivation (through point mutations or other means) of a constant region reduces Fc receptor binding of a modified antibody as it circulates. In some embodiments, constant region modifications increase the serum half-life of an antibody. In some embodiments, constant region modifications reduce the serum half-life of an antibody. In some embodiments, constant region modifications decrease or remove ADCC and/or complement-dependent cytotoxicity (CDC) of an antibody. In some embodiments, specific amino acid substitutions in a human IgG1 Fc region with corresponding IgG2 or IgG4 residues reduce effector functions (e.g., ADCC and CDC) in a modified antibody. In some embodiments, a modified antibody does not have one or more effector functions. In some embodiments, a modified antibody does not have any detectable effector functions (e.g., "effectorless" antibodies). In some embodiments, a modified antibody has no ADCC activity and/or no CDC activity. In some embodiments, a modified antibody does not bind an Fc receptor and/or complement factors. In some embodiments, a modified antibody has no effector function(s). In some embodiments, constant region modifications increase or enhance ADCC and/or CDC of an antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

In some embodiments, an ILT3-binding agent (e.g., an antibody) comprises a heavy chain having at least 80%, at least 85%, at least 90%, or at least 95% identity to the amino acid sequence of SEQ ID NO:126. In some embodiments, an ILT3-binding agent (e.g., an antibody) comprises a light chain having at least 80%, at least 85%, at least 90%, or at least 95% identity to the amino acid sequence of SEQ ID NO:128. In some embodiments, an ILT3-binding agent comprises a heavy chain having at least 80%, at least 85%, at least 90%, or at least 95% identity to the amino acid sequence of SEQ ID NO:126 and a light chain having at least 80%, at least 85%, at least 90%, or at least 95% identity to the amino acid sequence of SEQ ID NO:128. In some embodiments, an ILT3-binding agent comprises a heavy chain having at least 90% identity to the amino acid sequence of SEQ ID NO:126. In some embodiments, an ILT3-binding agent comprises a light chain having at least 90% identity to the amino acid sequence of SEQ ID NO:128. In some embodiments, an ILT3-binding agent comprises a heavy chain having at least 90% identity to the amino acid sequence of SEQ ID NO:126 and a light chain having at least 90% identity to the amino acid sequence of SEQ ID NO:128. In some embodiments, an ILT3-binding agent comprises a heavy chain comprising the amino acid sequence of SEQ ID NO:126. In some embodiments, an ILT3-binding agent comprises a light chain comprising the amino acid sequence of SEQ ID NO:128. In some embodiments, an ILT3-binding agent comprises a heavy chain comprising the amino acid sequence of SEQ ID NO:126 and a light chain comprising the amino acid sequence of SEQ ID NO:128. In some embodiments, an ILT3-binding agent is an antibody that comprises a heavy chain of SEQ ID NO:126 and/or a light chain of SEQ ID NO:128. In some embodiments, an ILT3-binding agent is an antibody that comprises a heavy chain of SEQ ID NO:126. In some embodiments, an ILT3-binding agent is an antibody that comprises a light chain of SEQ ID NO:128. In some embodiments, an ILT3-binding agent is an antibody that comprises a heavy chain of SEQ ID NO:126 and a light chain of SEQ ID NO:128.

Modifications to the constant region of antibodies described herein may be made using well-known biochemical or molecular engineering techniques. In some embodiments, antibody variants are prepared by introducing appropriate nucleotide changes into the encoding DNA, and/or by synthesis of the desired antibody or polypeptide. Using these engineering techniques to modify an antibody it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine (i.e., conservative amino acid replacements). In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein to create a fusion protein. In some embodiments, a variant is engineered to be detectable and may comprise a detectable label and/or protein (e.g., a fluorescent tag, a fluorescent protein, or an enzyme).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell epitopes (known or predicted) without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, an ILT3-binding agent described herein is chemically modified. In some embodiments, an ILT3-binding agent is an anti-ILT3 antibody that is chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques. In some embodiments, an ILT3-binding agent is an antibody fragment (e.g., scFv, Fv, Fab, F(ab')$_2$, or F(ab')), wherein the antibody fragment is attached (either directly or indirectly) to a half-life extending moiety including, but not limited to, a Fc region or its variants, a human serum albumin, a CH3 domain of an immunoglobulin, polyethylene glycol (PEG), a PEG mimetic, XTEN®, serum albumin, polysialic acid, N-(2-hydroxypropyl)methacrylamide, or dextran.

The present disclosure encompasses ILT3-binding agents built upon non-immunoglobulin backbones, wherein the agents bind the same epitope or essentially the same epitope as an anti-ILT3 antibody disclosed herein. In some embodiments, a non-immunoglobulin-based binding agent is an agent that competes with an anti-ILT3 antibody described herein in a competitive binding assay. In some embodiments, alternative ILT3-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the 10$^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid antiparallel β-strand protein fold; and Kunitz domain inhibitor scaffolds, which are based upon a structure that contains three disulfide bonds and three loops.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 1. In some embodiments, an ILT3-binding agent comprises an engineered scaffold protein comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), a heavy chain variable region CDR3 comprising the amino acid sequence DKYDGGWFAY (SEQ ID NO:13), a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an ILT3-binding agent comprises an engineered scaffold protein comprising a heavy chain variable region CDR1, CDR2, and CDR3 and a light chain variable region CDR1, CDR2, and CDR3 from antibody 3A3.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 2. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), a heavy chain variable region CDR3 comprising the amino acid sequence REWRMTLYAMDY (SEQ ID NO:29), a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an ILT3-binding agent comprises an engineered scaffold protein comprising a heavy chain variable region CDR1, CDR2, and CDR3 and a light chain variable region CDR1, CDR2, and CDR3 from antibody 5A7. In some embodiments, an ILT3-binding agent comprises an engineered scaffold protein comprising a heavy chain variable region CDR1, CDR2, and CDR3 and a light chain variable region CDR1, CDR2, and CDR3 shown in Table 8. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), a heavy chain variable region CDR3 comprising the amino acid sequence REWRYTLYAMDY (SEQ ID NO:105), a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an ILT3-binding agent comprises an engineered scaffold protein comprising a heavy chain variable region CDR1, CDR2, and CDR3 and a light chain variable region CDR1, CDR2, and CDR3 from antibody Hz5A7.v5.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 3. In some embodiments, an ILT3-binding agent comprises an engineered scaffold protein comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), a heavy chain variable region CDR3 comprising the amino acid sequence SPYYDYVGSYAMDY (SEQ ID NO:45), a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an ILT3-binding agent comprises an engineered scaffold protein comprising a heavy chain variable region CDR1, CDR2, and CDR3 and a light chain variable region CDR1, CDR2, and CDR3 from antibody 12A12.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 4. In some embodiments, an ILT3-binding agent comprises an engineered scaffold protein comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), a heavy chain variable region CDR3 comprising the amino acid sequence VPYYDYLYYYAMDY (SEQ ID NO:60), a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an ILT3-binding agent comprises an engineered scaffold protein comprising a heavy chain variable region CDR1, CDR2, and CDR3 and a light chain variable region CDR1, CDR2, and CDR3 from antibody 16C5.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 5. In some embodiments, an ILT3-binding agent comprises an engineered scaffold protein comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), a heavy chain variable region CDR3 comprising the amino acid sequence ADGRGAMDY (SEQ ID NO:73), a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises an engineered scaffold protein comprising a heavy chain variable region CDR1, CDR2, and CDR3 and a light chain variable region CDR1, CDR2, and CDR3 from antibody 45G10.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 6. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), a heavy chain variable region CDR3 comprising the amino acid sequence RGWLLHYYAMDY (SEQ ID NO:88), a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an ILT3-binding agent comprises an engineered scaffold protein comprising a heavy chain variable region CDR1, CDR2, and CDR3 and a light chain variable region CDR1, CDR2, and CDR3 from antibody 48A6.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 7. In some embodiments, an ILT3-binding agent comprises an engineered scaffold protein comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), a heavy chain variable region CDR3 comprising the amino acid sequence ADGRGAMDY (SEQ ID NO:73), a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises an engineered scaffold protein comprising a heavy chain variable region CDR1, CDR2, and CDR3 and a light chain variable region CDR1, CDR2, and CDR3 from antibody 53F10.

In some embodiments, a composition comprises an ILT3-binding agent described herein. In some embodiments, a composition comprises an anti-ILT3 antibody described herein. In some embodiments, a composition comprises a monoclonal anti-ILT3 antibody described herein.

In some embodiments, a pharmaceutical composition comprises an ILT3-binding agent described herein and a pharmaceutically acceptable carrier. In some embodiments, a pharmaceutical composition comprises an anti-ILT3 antibody described herein and a pharmaceutically acceptable carrier. In some embodiments, a composition comprises a monoclonal anti-ILT3 antibody described herein and a pharmaceutically acceptable carrier.

In some embodiments, an ILT3-binding agent is isolated. In some embodiments, an ILT3-binding agent is substantially pure.

Generally speaking, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are commonly used. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, an ILT3-binding agent (e.g., an antibody) binds ILT3 with a dissociation constant ($K_D$) of 1 µM or less, 100 nM or less, 40 nM or less, 20 nM or less, 10 nM or less, 1 nM or less, 0.1 nM or less, 50 pM or less, 10 pM or less, or 1 pM or less. In some embodiments, an ILT3-binding agent binds ILT3 with a $K_D$ of about 20 nM or less. In some embodiments, an ILT3-binding agent binds ILT3 with a $K_D$ of 10 nM or less. In some embodiments, an ILT3-binding agent binds ILT3 with a $K_D$ of 5 nM or less. In some embodiments, an ILT3-binding agent binds ILT3 with a $K_D$ of 3 nM or less. In some embodiments, an ILT3-binding agent binds ILT3 with a $K_D$ of 2 nM or less. In some embodiments, an ILT3-binding agent binds ILT3 with a $K_D$ of 1 nM or less. In some embodiments, an ILT3-binding agent binds ILT3 with a $K_D$ of 0.5 nM or less. In some embodiments, an ILT3-binding agent binds ILT3 with a $K_D$ of 0.1 nM or less. In some embodiments, an ILT3-binding agent binds ILT3 with a $K_D$ of 50 pM or less. In some embodiments, an ILT3-binding agent binds ILT3 with a $K_D$ of 25 pM or less. In some embodiments, an ILT3-binding agent binds ILT3 with a $K_D$ of 10 pM or less. In some embodiments, an ILT3-binding agent binds ILT3 with a $K_D$ of 1 pM or less. In some embodiments, an ILT3-binding agent binds ILT3 with a $K_D$ of 0.01 nM to 2.5 nM. In some embodiments, an ILT3-binding agent binds ILT3 with a $K_D$ of 0.1 nM to 5 nM. In some embodiments, an ILT3-binding agent binds ILT3 with a $K_D$ of 1 nM to 5 nM. In some embodiments, the dissociation constant of the binding agent for ILT3 is the dissociation constant determined using an ILT3 protein immobilized on a Biacore chip and the binding agent flowed over the chip. In some embodiments, the dissociation constant of the binding agent for ILT3 is the dissociation constant determined using the binding agent captured by an anti-human IgG antibody on a Biacore chip and soluble ILT3 flowed over the chip.

In some embodiments, an ILT3-binding agent (e.g., an antibody) binds ILT3 with a half maximal effective concentration (EC50) of 1 µM or less, 100 nM or less, 40 nM or less, 20 nM or less, 10 nM or less, 1 nM or less, or 0.1 nM or less. In some embodiments, an ILT3-binding agent binds human ILT3 with an EC50 of 1 µM or less, 100 nM or less, 40 nM or less, 20 nM or less, 10 nM or less, 1 nM or less, or 0.1 nM or less. In some embodiments, an ILT3-binding agent binds cyno ILT3 and/or human ILT3 with an EC50 of 40 nM or less, 20 nM or less, 10 nM or less, 1 nM or less or 0.1 nM or less. In some embodiments, an ILT3-binding agent binds ILT3 with an EC50 of 0.1 nM to about 3 nM, 0.1 nM to 2 nM, 0.1 nM to 1 nM, 0.5 nM to 3 nM, 0.5 nM to 2 nM, or 0.5 nM to 1 nM.

In some embodiments, an ILT3-binding agent binds human ILT3 and has at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi) inhibits ILT3-induced suppression of myeloid cells; (xii) inhibits ILT3-induced suppression of myeloid cell activity; (xiii) restores FcR activity in myeloid cells that express ILT3; and (xiv) restores the ability of myeloid cells that express ILT3 to respond to chemokines and/or produce chemokines.

The ILT3-binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host.

In some embodiments, recombinant expression vectors are used to amplify and express DNA encoding the ILT3-binding agents described herein. For example, recombinant expression vectors can be replicable DNA constructs which have synthetic or cDNA-derived DNA fragments encoding one or more polypeptide chain(s) of an ILT3-binding agent, such as an anti-ILT3 antibody, or antigen-binding fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

In some embodiments, an ILT3-binding agent (e.g., an antibody) of the present disclosure is expressed from one or more vectors. In some embodiments, a heavy chain variable region is expressed by one vector and a light chain variable region is expressed by a second vector. In some embodiments, a heavy chain variable region and a light chain variable region are expressed by one vector. In some embodiments, a vector encodes a heavy chain variable region of an ILT3-binding agent described herein. In some embodiments, a vector encodes a light chain variable region of an ILT3-binding agent described herein. In some embodiments, a vector encodes a heavy chain variable region and a light chain variable region of an ILT3-binding agent described herein. In some embodiments, a heavy chain polypeptide is expressed by one vector and a light chain polypeptide is expressed by a second vector. In some embodiments, a heavy chain polypeptide and a light chain polypeptide are expressed by one vector. In some embodiments, a vector encodes a heavy chain polypeptide of an ILT3-binding agent described herein. In some embodiments, a vector encodes a light chain polypeptide of an ILT3-binding agent described herein. In some embodiments, a vector encodes a heavy chain polypeptide and a light chain polypeptide of an ILT3-binding agent described herein.

Suitable host cells for expression of an ILT3-binding agent (e.g., an antibody) or a ILT3 protein or fragment thereof to use as an antigen or immunogen include prokaryotes, yeast cells, insect cells, or higher eukaryotic cells under the control of appropriate promoters. Prokaryotes include gram-negative or gram-positive organisms, for example E. coli or Bacillus. Higher eukaryotic cells include established cell lines of mammalian origin as described herein. Cell-free translation systems may also be employed. Appropriate cloning vectors and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the ILT3-binding agents described herein. In some embodiments, the cells produce the ILT3-binding agents described herein. In some embodiments, the cells produce an antibody. In some embodiments, the cells produce an antibody that binds human ILT3. In some embodiments, the cells produce an antibody that binds cyno ILT3. In some embodiments, the cells produce an antibody that binds human ILT3 and cyno ILT3. In some embodiments, the cells produce an antibody designated 45G10. In some embodiments, the cells produce a humanized version of antibody 5A7, referred to as Hz5A7. In some embodiments, the cells produce a variant of Hz5A7, for example, Hz5A7.v5. In some embodiments, the cells produce an antibody designated 3A3. In some embodiments, the cells produce an antibody designated 12A12. In some embodiments, the cells produce an antibody designated 16C5. In some embodiments, the cells produce an antibody designated 45G10. In some embodiments, the cells produce a humanized version of antibody 45G10, referred to as Hz45G10. In some embodiments, the cells produce an antibody designated 48A6. In some embodiments, the cells produce a humanized version of antibody 48A6, referred to as Hz48A6. In some embodiments, the cells produce an antibody designated 53F10. In some embodiments, the cell is a prokaryotic cell (e.g., E. coli). In some embodiments, the cell is an eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexahistidine (His6; SEQ ID NO:154), maltose binding domain, influenza coat sequence, and glutathione-S-transferase can be attached to the protein to allow easy purification by passage over an appropriate affinity column. Affinity chromatography methods used for purifying immunoglobulins can include, but are not limited to, Protein A, Protein G, and Protein L chromatography. Isolated proteins can be physically characterized using techniques that include, but are not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

ILT3-binding agents (e.g., antibodies) of the present disclosure may be analyzed for their physical/chemical properties and/or biological activities by various assays known in the art. In some embodiments, an anti-ILT3 antibody is tested for its ability to bind ILT3 (e.g., human ILT3 and/or cyno ILT3). Binding assays include, but are not limited to, SPR (e.g., Biacore), ELISA, and FACS. In some embodiments, an anti-ILT3 antibody is tested for its ability to inhibit, reduce, or block binding to fibronectin, APOE, and/or CNTFR. In addition, antibodies may be evaluated for solubility, stability, thermostability, viscosity, expression levels, expression quality, and/or purification efficiency.

In some embodiments, monoclonal antibodies generated against ILT3 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of a second antibody and antigen is flowed over the immobilized first antibody. In tandem, the antigen is immobilized on a surface and the two antibodies are flowed over the immobilized antigen and compete to bind. Using these techniques, antibodies that block one another can be identified. A competitive blocking profile is created for each antibody relative to the other antibodies. The blocking results determine which bin each antibody is placed in. High-throughput methods of epitope binning are known in the art and allow for screening and characterization of large numbers of antibodies within a short period of time. Antibodies that bind similar epitopes often share similar functions and/or capabilities. Conversely, antibodies that bind different epitopes may have different functional activities.

In some embodiments, an epitope bin comprises at least one antibody from the group consisting of: 3A3, 5A7, 12A12, 16C5, 45G10, 48A6, and 53F10. In some embodiments, an epitope bin comprises at least antibodies 5A7 and 48A6. In some embodiments, an epitope bin comprises at least antibodies 12A12 and 16C5. In some embodiments, an epitope bin comprises at least antibodies 45G10 and 53F10. In some embodiments, an epitope bin comprises at least antibodies 12A12 and 16C5.

Epitope mapping is the process of identifying the binding site, or epitope on a target protein/antigen where an antibody (or other binding agent) binds. A variety of methods are known in the art for mapping epitopes on target proteins. These methods include (i) mutagenesis, including but not limited to, shotgun mutagenesis, site-directed mutagenesis, and alanine scanning; (ii) domain or fragment scanning; (iii) peptide scanning (e.g., Pepscan technology); (iv) display methods, including but not limited to, phage display, microbial display, and ribosome/mRNA display; (v) methods involving proteolysis and mass spectroscopy; (vi) methods involving amide hydrogen/deuterium exchange; and (vii) structural determination, including but not limited to, x-ray crystallography and NMR.

In some embodiments, purified anti-ILT3 antibodies are characterized by assays including, but not limited to, N-terminal sequencing, amino acid analysis, HPLC, mass spectrometry, differential scanning fluorimetry (DSF), nanoDSF, capillary isoelectric focusing (cIEF), ion exchange chromatography, and papain digestion.

In vitro assays that characterize immune cells function include, but are not limited to, cell activation assays (e.g., cell proliferation assays), cytotoxic T-cell (CTL) assays, mixed lymphocyte reaction (MLR) assays, cytokine/chemokine production assays, FcR binding assays, and cell migration assays. In some embodiments, assays are provided for identifying anti-ILT3 antibodies that affect ILT3 activity. "Affect or affecting ILT3 activity" may include, for example, inhibiting, reducing, blocking, antagonizing, suppressing, and/or interfering with ILT3 activity. As ILT3 generally acts a negative regulator/inhibitory molecule, in some embodiments, inhibiting, reducing, blocking, antagonizing, suppressing, and/or interfering with ILT3 activity results in a release of ILT3-induced suppression of a biological function (e.g., an activation signal). As described herein, ILT3 is expressed on myeloid cells, such as monocytes, macrophages, dendritic cells (DCs), and myeloid APCs. ILT3 is highly expressed on suppressive myeloid cells such as tolerogenic dendritic cells (tolDCs) and myeloid-derived suppressor cells (MDSCs). ILT3 activity or ILT3 signaling activity includes, but is not limited to, suppression of myeloid cells, suppression of myeloid cell activity, and suppression of tumor-associated myeloid cells. In some embodiments, inhibiting, reducing, blocking, antagonizing, suppressing, and/or interfering with ILT3 activity results in a release of ILT3-induced suppression of an activation signal. In some embodiments, an anti-ILT3 antibody inhibits ILT3 signaling. In some embodiments, an anti-ILT3 antibody inhibits ILT3 signaling thereby reversing an ILT3-induced suppressive effect. In some embodiments, an anti-ILT3 antibody inhibits an ILT3-induced extinction signal.

In some embodiments, an anti-ILT3 antibody disrupts the ILT3 signaling pathway. In some embodiments, an anti-ILT3 antibody disrupts the ILT3 signaling pathway and activates myeloid cells. In some embodiments, an anti-ILT3 antibody disrupts the ILT3 signaling pathway and activates myeloid APCs. In some embodiments, an anti-ILT3 antibody disrupts the ILT3 signaling pathway and activates dendritic cells. In some embodiments, an anti-ILT3 antibody disrupts the ILT3 signaling pathway and activates or reactivates tolDCs. In some embodiments, an anti-ILT3 antibody disrupts the ILT3 signaling pathway and restores the ability of tolDCs to respond to stimuli (e.g., LPS). In some embodiments, an anti-ILT3 antibody disrupts the ILT3 signaling pathway and activates primary dendritic cells.

In some embodiments, the terms "inhibiting", "reducing", "blocking", "antagonizing", "suppressing", and "interfering" are relative to levels and/or activity in the absence of treatment with the ILT3-binding agent. In some embodiments, the terms "inhibiting", "reducing", "blocking", "antagonizing", "suppressing", and "interfering" are relative to levels and/or activity prior to treatment with the ILT3-binding agent.

In some embodiments, an anti-ILT3 antibody that inhibits ILT3 activity is antibody 3A3. In some embodiments, an anti-ILT3 antibody that inhibits ILT3 activity is antibody 5A7. In some embodiments, an anti-ILT3 antibody that inhibits ILT3 activity is antibody Hz5A7.v5. In some embodiments, an anti-ILT3 antibody that inhibits ILT3 activity is antibody 12A12. In some embodiments, an anti-ILT3 antibody that inhibits ILT3 activity is antibody 16C5. In some embodiments, an anti-ILT3 antibody that inhibits ILT3 activity is antibody 45G10. In some embodiments, an anti-ILT3 antibody that inhibits ILT3 activity is antibody 48A6. In some embodiments, an anti-ILT3 antibody that inhibits ILT3 activity is antibody 53F10. In some embodiments, an anti-ILT3 antibody that inhibits ILT3 activity is antibody Hz45G10. In some embodiments, an anti-ILT3 antibody that inhibits ILT3 activity is antibody Hz48A6.

The present disclosure also provides conjugates comprising an anti-ILT3 antibody described herein. In some embodiments, the antibody is attached to a second molecule. In some embodiments, the antibody is conjugated to a cytotoxic agent or moiety. In some embodiments, the antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065. A derivative of any one of these toxins may be used as long as the derivative retains the cytotoxic activity of the parent molecule.

Conjugates comprising an anti-ILT3 antibody described herein may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-ILT3 antibody described herein is conjugated to a detectable substance or molecule that allows the antibody to be used for diagnosis and/or detection. In some embodiments, a labeled anti-ILT3 antibody is used to monitor immune cells in a tumor or in the microenvironment of a tumor. In some embodiments, a labeled anti-ILT3 antibody is used to monitor immune cells in a tumor or in the microenvironment of a tumor after treatment. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin;

, bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$SC, $^{75}$Se, $^{153}$Sm, $^{113}$Sn, $^{117}$Sn, $^{85}$Sr, $^{99}$mTc, $^{201}$Ti, $^{133}$Xe, $^{90}$Y, $^{69}$Yb, $^{175}$Yb, $^{65}$Zn; positron emitting metals; and magnetic metal ions.

In some embodiments, an anti-ILT3 antibody described herein is used in an immunoassay. Immunoassays are known to those of skill in the art and include, but are not limited to, ELISA, SPR (e.g., Biacore), FACS, and immunohistochemistry (IHC). In some embodiments, an anti-ILT3 antibody described herein is used on a tissue sample or a tumor sample.

An anti-ILT3 antibody described herein can also be conjugated to a second antibody to form an antibody heteroconjugate.

An anti-ILT3 antibody as described herein may be attached to a solid support. Such solid supports include, but are not limited to, glass, cellulose, polyacrylamide, nylon, polystyrene, polyvinyl chloride, or polypropylene. In some embodiments, immobilized anti-ILT3 antibodies are used in immunoassays. In some embodiments, immobilized anti-ILT3 antibodies are used in purification of the target antigen.

III Polynucleotides

In some embodiments, the disclosure encompasses polynucleotides comprising polynucleotides that encode a polypeptide (e.g., an ILT3-binding agent) described herein. The term "polynucleotides that encode a polypeptide" encompasses a polynucleotide that includes only coding sequences for the polypeptide as well as a polynucleotide that includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, a polynucleotide comprises a polynucleotide encoding a heavy chain variable region and/or a light chain variable region of an ILT3-binding agent (e.g., antibody) described herein. In some embodiments, a polynucleotide comprises a polynucleotide encoding a heavy chain variable region of an ILT3-binding agent described herein. In some embodiments, a polynucleotide comprises a polynucleotide encoding a light chain variable region of an ILT3-binding agent described herein. In some embodiments, a polynucleotide comprises a polynucleotide encoding a heavy chain variable region of an ILT3-binding agent described herein and a polynucleotide encoding a light chain variable region of the ILT3-binding agent.

In some embodiments, a polynucleotide comprises a polynucleotide encoding a heavy chain and/or a light chain of an ILT3-binding agent (e.g., antibody) described herein. In some embodiments, a polynucleotide comprises a polynucleotide encoding a heavy chain of an ILT3-binding agent described herein. In some embodiments, a polynucleotide comprises a polynucleotide encoding a light chain of an ILT3-binding agent described herein. In some embodiments, a polynucleotide comprises a polynucleotide encoding a heavy chain of an ILT3-binding agent described herein and a polynucleotide encoding a light chain of the ILT3-binding agent.

In some embodiments, the polynucleotide comprises a polynucleotide encoding a polypeptide comprising an amino acid sequence selected from the group consisting of: SEQ ID NOs:109-128. In some embodiments, the polynucleotide comprises a polynucleotide encoding a polypeptide comprising an amino acid sequence of SEQ ID NO:109. In some embodiments, the polynucleotide comprises a polynucleotide encoding a polypeptide comprising an amino acid sequence of SEQ ID NO:110. In some embodiments, the polynucleotide comprises a polynucleotide encoding a polypeptide comprising an amino acid sequence of SEQ ID NO:111. In some embodiments, the polynucleotide comprises a polynucleotide encoding a polypeptide comprising an amino acid sequence of SEQ ID NO:112. In some embodiments, the polynucleotide comprises a polynucleotide encoding a polypeptide comprising an amino acid sequence of SEQ ID NO:113. In some embodiments, the polynucleotide comprises a polynucleotide encoding a polypeptide comprising an amino acid sequence of SEQ ID NO:114. In some embodiments, the polynucleotide comprises a polynucleotide encoding a polypeptide comprising an amino acid sequence of SEQ ID NO:115. In some embodiments, the polynucleotide comprises a polynucleotide encoding a polypeptide comprising an amino acid sequence of SEQ ID NO:116. In some embodiments, the polynucleotide comprises a polynucleotide encoding a polypeptide comprising an amino acid sequence of SEQ ID NO:117. In some embodiments, the polynucleotide comprises a polynucleotide encoding a polypeptide comprising an amino acid sequence of SEQ ID NO:118. In some embodiments, the polynucleotide comprises a polynucleotide encoding a polypeptide comprising an amino acid sequence of SEQ ID NO:119. In some embodiments, the polynucleotide comprises a polynucleotide encoding a polypeptide comprising an amino acid sequence of SEQ ID NO:120. In some embodiments, the polynucleotide comprises a polynucleotide encoding a polypeptide comprising an amino acid sequence of SEQ ID NO:121. In some embodiments, the polynucleotide comprises a polynucleotide encoding a polypeptide comprising an amino acid sequence of SEQ ID NO:122. In some embodiments, the polynucleotide comprises a polynucleotide encoding a polypeptide comprising an amino acid sequence of SEQ ID NO:123. In some embodiments, the polynucleotide comprises a polynucleotide encoding a polypeptide comprising an amino acid sequence of SEQ ID NO:124. In some embodiments, the polynucleotide comprises a polynucleotide encoding a polypeptide comprising an amino acid sequence of SEQ ID NO:125. In some embodiments, the polynucleotide comprises a polynucleotide encoding a polypeptide comprising an amino acid sequence of SEQ ID NO:126. In some embodiments, the polynucleotide comprises a polynucleotide encoding a polypeptide comprising an amino acid sequence of SEQ ID NO:127. In some embodiments, the polynucleotide comprises a polynucleotide encoding a polypeptide comprising an amino acid sequence of SEQ ID NO:128.

In some embodiments, the polynucleotide comprises a polynucleotide encoding a polypeptide comprising more than one amino acid sequence selected from the group consisting of: SEQ ID NOs:109-128. In some embodiments, the polynucleotide comprises a polynucleotide encoding (i) a polypeptide comprising an amino acid sequence of SEQ ID NO:109 and (ii) a polypeptide comprising an amino acid sequence of SEQ ID NO:110. In some embodiments, the polynucleotide comprises a polynucleotide encoding (i) a polypeptide comprising an amino acid sequence of SEQ ID NO:111 and (ii) a polypeptide comprising an amino acid sequence of SEQ ID NO:112. In some embodiments, the polynucleotide comprises a polynucleotide encoding (i) a polypeptide comprising an amino acid sequence of SEQ ID NO:113 and (ii) a polypeptide comprising an amino acid sequence of SEQ ID NO:114. In some embodiments, the polynucleotide comprises a polynucleotide encoding (i) a polypeptide comprising an amino acid sequence of SEQ ID NO:115 and (ii) a polypeptide comprising an amino acid sequence of SEQ ID NO:116. In some embodiments, the polynucleotide comprises a polynucleotide encoding (i) a polypeptide comprising an amino acid sequence of SEQ ID NO:117 and (ii) a polypeptide comprising an amino acid sequence of SEQ ID NO:118. In some embodiments, the polynucleotide comprises a polynucleotide encoding (i) a polypeptide comprising an amino acid sequence of SEQ ID NO:119 and (ii) a polypeptide comprising an amino acid sequence of SEQ ID NO:120. In some embodiments, the polynucleotide comprises a polynucleotide encoding (i) a polypeptide comprising an amino acid sequence of SEQ ID NO:121 and (ii) a polypeptide comprising an amino acid sequence of SEQ ID NO:122. In some embodiments, the polynucleotide comprises a polynucleotide encoding (i) a polypeptide comprising an amino acid sequence of SEQ ID NO:123 and (ii) a polypeptide comprising an amino acid sequence of SEQ ID NO:124. In some embodiments, the polynucleotide comprises a polynucleotide encoding (i) a polypeptide comprising an amino acid sequence of SEQ ID NO:125 and (ii) a polypeptide comprising an amino acid sequence of SEQ ID NO:127. In some embodiments, the polynucleotide comprises a polynucleotide encoding (i) a polypeptide comprising an amino acid sequence of SEQ ID NO:126 and (ii) a polypeptide comprising an amino acid sequence of SEQ ID NO:128.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding a polypeptide described herein.

In some embodiments, a polynucleotide comprises a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding an amino acid sequence selected from the group consisting of: SEQ ID NOs:109-128. Also provided is a polynucleotide that comprises a polynucleotide that hybridizes to a polynucleotide encoding an amino acid sequence selected from the group consisting of: SEQ ID NOs:109-128. In some embodiments, the hybridization is under conditions of high stringency as is known to those skilled in the art.

As used herein, the phrase "a polynucleotide having a nucleotide sequence at least 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. It is understood by those of skill in the art that an appropriate calculation would be made for other "% identical" statements, for example, 90% identical or 85% identical. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, including by not limited to, PCR mutagenesis and site-directed mutagenesis. Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide (e.g., an antibody) fused in the same reading frame to a polynucleotide that aids in expression and secretion of a polypeptide from a host cell. In some embodiments, the polynucleotide that aids in expression and secretion is a leader sequence that functions as a secretory sequence for controlling transport of a polypeptide. In some embodiments, the polypeptide has a leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag (HIS-tag; SEQ ID NO:154) that allows for efficient purification of the polypeptide fused to the marker. In some embodiments, a marker sequence is a hemagglutinin (HA) tag derived from the influenza hemagglutinin protein when a mammalian host is used. In some embodiments, the marker sequence is a FLAG™ tag. In some embodiments, a marker may be used in conjunction with other markers or tags.

In some embodiments, a polynucleotide is isolated. In some embodiments, a polynucleotide is substantially pure.

Vectors and cells comprising each and every one of the polynucleotides described herein are also provided. In some embodiments, a vector (e.g., an expression vector) comprises a polynucleotide molecule encoding an ILT3-binding agent (e.g., an antibody) described herein. In some embodiments, a vector comprises a polynucleotide molecule encoding a polypeptide that is part of an ILT3-binding agent described herein. In some embodiments, a cell comprises a vector comprising a polynucleotide molecule encoding an ILT3-binding agent described herein. In some embodiments, a cell comprises a vector comprising a polynucleotide molecule encoding a polypeptide that is part of an ILT3-binding agent described herein. In some embodiments, a cell comprises a polynucleotide molecule encoding an ILT3-binding agent described herein. In some embodiments, a cell comprises one or more polynucleotides encoding an ILT3-binding agent described herein. In some embodiments, a cell comprises a single polynucleotide encoding an ILT3-binding agent described herein. In some embodiments, a cell comprises a first polynucleotide encoding a heavy chain variable region of an ILT3-binding agent described herein and a second polynucleotide encoding a light chain variable region of an ILT3-binding agent described herein. In some embodiments, a cell comprises a polynucleotide encoding a heavy chain variable region and a light chain variable region of an ILT3-binding agent described herein. In some embodiments, a cell comprises a first polynucleotide encoding a heavy chain of an ILT3-binding agent described herein and a second polynucleotide encoding a light chain of an ILT3-binding agent described herein. In some embodiments, a cell comprises a polynucleotide encoding a heavy chain and a light chain of an ILT3-binding agent described herein. In some embodiments, a cell comprises one or more vectors encoding an ILT3-binding agent described herein. In some embodiments, a cell comprises a vector encoding an ILT3-binding agent described herein. In some embodiments, a cell comprises a first vector encoding a heavy chain variable region of an ILT3-binding agent described herein and a second vector encoding a light chain variable region of an ILT3-binding agent described herein. In some embodiments, a cell comprises a single vector encoding a heavy chain variable region and a light chain variable region of an ILT3-binding agent described herein. In some embodiments, a cell comprises a first vector encoding a heavy chain of an ILT3-binding agent described herein and a second vector encoding a light chain of an ILT3-binding agent described herein. In some embodiments, a cell comprises a single vector encoding a heavy chain and a light chain of an ILT3-binding agent described herein.

IV. Methods of Making Binding Agents

The disclosure provides methods for making the ILT3-binding agents (e.g., antibodies) described herein. In some embodiments, a method comprises providing a cell comprising a heavy chain and/or light chain of an ILT3-binding agent, culturing the cell under conditions that permit the expression of the binding agent, and isolating the binding agent. In some embodiments, a method further comprises purifying the binding agent. In some embodiments, a method further comprises formulating the binding gent as a pharmaceutical composition. In some embodiments, a cell comprises one or more vectors encoding the heavy chain variable region and the light chain variable region of an ILT3-binding agent described herein. In some embodiments, a cell comprises a first vector encoding the heavy chain variable region of an ILT3-binding agent and a second vector encoding the light chain variable region of an ILT3-binding agent. In other embodiments, a cell comprises a vector encoding the heavy chain variable region and the light chain variable region of an ILT3-binding agent. In some embodiments, a cell comprises one or more vectors encoding the heavy chain and the light chain of an ILT3-binding agent described herein. In some embodiments, a cell comprises a first vector encoding the heavy chain of an ILT3-binding agent and a second vector encoding the light chain of an ILT3-binding agent. In other embodiments, a cell comprises a vector encoding the heavy chain and the light chain of an ILT3-binding agent. In some embodiments, a cell comprises one or more polynucleotides encoding the heavy chain and the light chain of an ILT3-binding agent. In some embodiments, a cell comprises a first polynucleotide encoding the heavy chain of an ILT3-binding agent and a second polynucleotide encoding the light chain of an ILT3-binding agent. In other embodiments, a cell comprises a polynucleotide encoding the heavy chain and the light chain of an ILT3-binding agent. In some embodiments, a polynucleotide encoding an ILT3-binding agent described herein is transiently transfected into a cell. In some embodiments, a polynucleotide encoding an ILT3-binding agent described herein is stably transfected into a cell.

In some embodiments, the ILT3-binding agent is an antibody fragment comprising at least one antigen-binding site and the method involves providing a cell comprising the fragment of an anti-ILT3 antibody, incubating the cell under conditions that permit the expression of the antibody fragment, and isolating the antibody fragment. In certain embodiments, the cell comprises a vector encoding an antibody fragment described herein. In certain embodiments, the cell comprises a polynucleotide encoding an antibody fragment described herein. In some embodiments, the method comprises purifying the antibody fragment. In certain embodiments, the antibody fragment is a Fab, Fab', F(ab')$_2$, Fv, scFv, (scFv)$_2$, single chain antibody, dual variable region antibody, diabody, or nanobody.

In some embodiments, the ILT3-binding agent is a scFv and the method involves providing a cell comprising the scFv, incubating the cell under conditions that permit the expression of the scFv, and isolating the scFv. In certain embodiments, the cell comprises a vector described herein encoding the scFv. In certain embodiments, the cell comprises a polynucleotide described herein encoding the scFv. In some embodiments, the method comprises purifying the scFv.

In some embodiments, the cell used to make an ILT3-binding agent is a bacterial cell (e.g., *E. coli*). In some embodiments, the cell used to make an ILT3-binding agent is a yeast cell (e.g., *Pichia pastoris*). In some embodiments, the cell used to make an ILT3-binding agent is a mammalian cells, such as a CHO cell or a HEK-293 cell.

In some embodiments, a signal sequence is used (e.g., by fusing a signal sequence to the peptide to be expressed) for expression of an ILT3-binding agent described herein from a cell. Any suitable signal sequence can be used for this purpose. For example, for expressing an antibody heavy and light chain, an IgG kappa light chain signal peptide sequence or a native antibody signal peptide can be fused to the heavy chain and light chain sequence.

V. ILT3 Ligands

The present disclosure provides fibronectin as a newly identified ligand for human ILT3. Ciliary neurotrophic factor receptor (CNTFR) was also found to be a binding partner of ILT3. Recently, several ligands for ILT3 have been identified and include CD166 (also known as activated leukocyte cell adhesion molecule; ALCAM), apolipoprotein E (APOE), and peptidase inhibitor 16 (PI16) (Xu et al., 2018, *J. Immunol.*, 200:1207-1219; Deng et al., 2018, Nature, 562: 605-609; Intl. Pub. No. WO 2018/089300). Currently, there appears to be no agreement on whether all of these proteins are biologically functional as ILT3 ligands and research is ongoing to further understand the relevance of each of these different interactions.

Amino acid (aa) sequences for human fibronectin (UniProtKB No. P02751) and human CNTFR-alpha (UniProKB No. P26992) are provided herein as SEQ ID NO:138 and SEQ ID NO:148, respectively. There are at least 17 different isoforms of human fibronectin, UniProtKB lists SEQ ID NO:138 as its canonical sequence. As used herein, reference to amino acid positions of these proteins refer to the numbering of amino acid sequences including the signal sequence.

Fibronectin (FN) usually exists as a dimer composed of two nearly identical approximately 250 kDa subunits linked covalently near their C-termini by a pair of disulfide bonds. Each monomer comprises three types of repeating units (termed FN repeats): type I, type II and type III. FN contains 12 type I repeats, two type II repeats, and 15-17 type III repeats, which together account for approximately 90% of the fibronectin sequence. See FIG. 8 for a representation of the fibronectin structure. The type I and type II repeats are stabilized by the presence of intra-domain disulfide bonds, while the type III domains are structurally more labile and subject to mechanical unfolding. Fibronectin can exist in multiple forms that arise from alternative splicing of a single pre-mRNA that can generate as many as 20 variants.

Fibronectin is a plasma protein synthesized by the liver which undergoes a cell-dependent polymerization into a fibrillar extracellular matrix in most tissues. Both plasma-derived and local synthesis by resident stromal cells contribute to the fibronectin which makes up the tissue matrix.

Fibronectin is a ligand for at least a dozen members of the integrin receptor family. Fibronectin has a wide variety of functional activities in addition to binding to cell surfaces through integrins. It binds a number of other proteins, including heparin, collagen/gelatin, and fibrin. These interactions are mediated by several distinct structural and functional domains within fibronectin and groups of the fibronectin repeats. The biological role of many of the other fibronectin domains is not characterized and/or well understood.

As disclosed herein, fibronectin was identified as a ligand for ILT3. In some embodiments, an ILT3-binding agent (e.g., an antibody) described herein inhibits, disrupts, or blocks binding of ILT3 to fibronectin. In some embodiments, an ILT3-binding agent described herein blocks the interaction of ILT3 with fibronectin. In some embodiments, an ILT3-binding agent described herein inhibits binding of ILT3 to fibronectin. In some embodiments, an ILT3-binding agent described herein blocks or inhibits a functional interaction between ILT3 and fibronectin.

In some embodiments, an ILT3 binding agent (e.g., an antibody) described herein inhibits, disrupts, or blocks binding of ILT3 to SEQ ID NO:138 or 139. In some embodiments, an ILT3 binding agent (e.g., an antibody) described herein inhibits, disrupts, or blocks binding of ILT3 to the N-terminal region of fibronectin (without the signal sequence/peptide). In some embodiments, an ILT3 binding agent (e.g., an antibody) described herein inhibits, disrupts, or blocks binding of ILT3 to the heparin-binding and collagen-binding domains of fibronectin. In some embodiments, an ILT3 binding agent (e.g., an antibody) described herein inhibits, disrupts, or blocks binding of ILT3 to the heparin-binding domain of fibronectin. In some embodiments, an ILT3 binding agent (e.g., an antibody) described herein inhibits, disrupts, or blocks binding of ILT3 to type I repeats 1-5 of fibronectin. In some embodiments, an ILT3 binding agent (e.g., an antibody) described herein inhibits, disrupts, or blocks binding of ILT3 to type I repeats 1-4 of fibronectin. In some embodiments, an ILT3 binding agent (e.g., an antibody) described herein inhibits, disrupts, or blocks binding of ILT3 to type I repeats 1-3 of fibronectin. In some embodiments, an ILT3 binding agent (e.g., an antibody) described herein inhibits, disrupts, or blocks binding of ILT3 to type I repeats 1-2 of fibronectin. The boundaries of any domain are not exactly known and the amino acids used herein to define domains and/or the repeats of FN are based on information from UniProtKB. Therefore, the boundaries of any domain and/or repeat may vary from those recited herein.

In some embodiments, an ILT3 binding agent (e.g., an antibody) described herein inhibits, disrupts, or blocks binding of ILT3 to amino acids 32-608 of SEQ ID NO:138. In some embodiments, an ILT3 binding agent (e.g., an antibody) described herein inhibits, disrupts, or blocks binding of ILT3 to amino acids 32-280 of SEQ ID NO:138. In some embodiments, an ILT3 binding agent (e.g., an antibody) described herein inhibits, disrupts, or blocks binding of ILT3 to amino acids 32-300 of SEQ ID NO:138. In some embodiments, an ILT3 binding agent (e.g., an antibody) described herein inhibits, disrupts, or blocks binding of ILT3 to amino acids 32-228 of SEQ ID NO:138. In some embodiments, an ILT3 binding agent (e.g., an antibody) described herein inhibits, disrupts, or blocks binding of ILT3 to amino acids 32-182 of SEQ ID NO:138. In some embodiments, an ILT3 binding agent (e.g., an antibody) described herein inhibits, disrupts, or blocks binding of ILT3 to amino acids 32-138 of SEQ ID NO:138. In some embodiments, an ILT3 binding agent (e.g., an antibody) described herein inhibits, disrupts, or blocks binding of ILT3 to amino acids 32-290 of SEQ ID NO:138.

In some embodiments, an ILT3-binding agent (e.g., an antibody) described herein inhibits fibronectin-induced ILT3 activity. In some embodiments, an ILT3-binding agent described herein inhibits fibronectin-induced ILT3 suppressive activity. In some embodiments, an ILT3-binding agent described herein inhibits fibronectin-induced ILT3 suppression of myeloid cells. In some embodiments, an ILT3-binding agent described herein inhibits fibronectin-induced ILT3 suppression of myeloid cell activity. In some embodiments, an ILT3-binding agent described herein inhibits fibronectin-induced ILT3 suppression of APCs. In some embodiments, an ILT3-binding agent described herein inhibits fibronectin-induced ILT3 suppression of APC activity. In some embodiments, an ILT3-binding agent described herein inhibits fibronectin-induced ILT3 suppression of dendritic cells. In some embodiments, an ILT3-binding agent described herein inhibits fibronectin-induced ILT3 suppression of dendritic cell activity. In some embodiments, an ILT3-binding agent described herein inhibits fibronectin-induced ILT3 suppression of macrophages. In some embodiments, an ILT3-binding agent described herein inhibits fibronectin-induced ILT3 suppression of macrophage activity. In some embodiments, the myeloid cells, including but not limited to dendritic cells, APCs, monocytes, and macrophages are tumor-associated cells. In some embodiments, the myeloid cells, including but not limited to dendritic cells, APCs, monocytes and macrophages are residing in the tumor microenvironment. In some embodiments, the myeloid cells, including but not limited to dendritic cells, APCs, monocytes and macrophages are residing within a tumor.

As disclosed herein, CNTFR-alpha was identified as a ligand for ILT3. CNTFR-alpha is part of a tripartite CNTFR complex that is known to bind ciliary neurotrophic factor. CNTFR-alpha subunit is a membrane bound protein and is anchored to the cell membrane by a glycosyl-phosphatidylinositol (GPI) linkage. This receptor has no signal transducing capabilities without the co-receptor components of the complex. The two other components are gp130 and leukemia inhibitory factor receptor (LIFR) beta, that provide the signal transducing capabilities of the complex (Stahl et al., 1994, *J. Neurobiol.*, 25:1454-1466). The biological relevance of ILT3 binding to CNTFR is still being investigated.

In some embodiments, an ILT3-binding agent described herein inhibits, disrupts, or blocks binding of ILT3 to CNTFR-alpha. In some embodiments, an ILT3-binding agent described herein blocks the interaction of ILT3 with CNTFR-alpha. In some embodiments, an ILT3-binding agent described herein inhibits binding of ILT3 to CNTFR-alpha. In some embodiments, an ILT3-binding agent described herein inhibits, disrupts, or blocks binding of ILT3 to CNTFR-alpha and modulates the CNTFR complex signaling.

In some embodiments, an ILT3-binding agent described herein inhibits, disrupts, or blocks binding of ILT3 to the mature form of CNTFR-alpha. In some embodiments, an ILT3-binding agent described herein inhibits, disrupts, or blocks binding of ILT3 to the Ig-like C2 type domain of CNTFR-alpha. In some embodiments, an ILT3-binding agent described herein inhibits, disrupts, or blocks binding of ILT3 to one or both of the FN type III domains (i.e., FN type III domain 1, FN type III domain 2, or FN type III domains 1 and 2) of CNTFR-alpha.

In some embodiments, an ILT3-binding agent described herein inhibits, disrupts, or blocks binding of ILT3 to SEQ ID NO:149 or SEQ ID NO:150. In some embodiments, an ILT3-binding agent described herein inhibits, disrupts, or blocks binding of ILT3 to amino acids 23-342 of SEQ ID NO:148. In some embodiments, an ILT3-binding agent described herein inhibits, disrupts, or blocks binding of ILT3 to amino acids 23-104 of SEQ ID NO:148. In some embodiments, an ILT3-binding agent described herein inhibits, disrupts, or blocks binding of ILT3 to amino acids 105-205 of SEQ ID NO:148. In some embodiments, an ILT3-binding agent described herein inhibits, disrupts, or blocks binding of ILT3 to amino acids 206-306 of SEQ ID NO:148. In some embodiments, an ILT3-binding agent described herein inhibits, disrupts, or blocks binding of ILT3 to amino acids 23-306 of SEQ ID NO:148.

VI. Methods of Use and Pharmaceutical Compositions

The ILT3-binding agents (e.g., antibodies) of the disclosure are useful in a variety of applications including, but not limited to, therapeutic treatment methods, such as treatment of cancer. In some embodiments, the therapeutic treatment methods comprise immunotherapy for cancer. In some embodiments, an ILT3-binding agent is useful for activating, promoting, increasing, and/or enhancing an immune response to cancer or cancer cells. In some embodiments, an ILT3-binding agent is useful for activating, promoting, increasing, and/or enhancing an immune response to a tumor or tumor cells. The methods of use may be in vitro, ex vivo, or in vivo methods.

The present disclosure provides methods of disrupting, inhibiting, or blocking the binding of ILT3 to fibronectin. In some embodiments, a method of disrupting, inhibiting, or blocking the binding of ILT3 to fibronectin comprises contacting cells with an ILT3-binding agent described herein. In some embodiments, a method of disrupting, inhibiting, or blocking the binding of ILT3 to fibronectin comprises contacting cells with an ILT3-binding agent described herein, wherein the method results in disrupting, inhibiting, or blocking fibronectin-induced ILT3 activity. In some embodiments, a method of disrupting, inhibiting, or blocking the binding of ILT3 to fibronectin comprises contacting cells with an ILT3-binding agent described herein, wherein the method results in disrupting, inhibiting, or blocking ILT3-induced suppression of myeloid cells. In some embodiments, a method of disrupting, inhibiting, or blocking the binding of ILT3 to fibronectin comprises contacting cells with an ILT3-binding agent described herein, wherein the method results in disrupting, inhibiting, or blocking of ILT3-induced suppression of myeloid cell activity. In some embodiments, a method of disrupting, inhibiting, or blocking the binding of ILT3 to fibronectin: (i) restores FcR signaling activity in myeloid cells; (ii) restores chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an APC.

The present disclosure provides methods of disrupting, inhibiting, or blocking the binding of ILT3 to fibronectin in a subject. In some embodiments, a method of disrupting, inhibiting, or blocking the binding of ILT3 to fibronectin in a subject, comprises administering to the subject an effective amount of an ILT3-binding agent (e.g., an antibody) described herein. In some embodiments, a method of disrupting, inhibiting, or blocking fibronectin-induced ILT3 activity in a subject comprises administering to the subject an effective amount of an ILT3-binding agent described herein. In some embodiments, a method of disrupting, inhibiting, or blocking ILT3-induced suppression of myeloid cells in a subject comprises administering to the subject an effective amount of an ILT3-binding agent described herein. In some embodiments, a method of disrupting, inhibiting, or blocking ILT3-induced suppression of myeloid cell activity in a subject comprises administering to the subject an effective amount of an ILT3-binding agent described herein. In some embodiments, a method of disrupting, inhibiting, or blocking ILT3-induced suppression of antigen-presenting cell activity in a subject (i) restores FcR activity in myeloid cells; (ii) restores chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an APC.

The present disclosure provides methods for activating an immune response in a subject using an ILT3-binding agent (e.g., an antibody) described herein. In some embodiments, the disclosure provides methods for promoting an immune response in a subject using an ILT3-binding agent described herein. In some embodiments, the disclosure provides methods for increasing an immune response in a subject using an ILT3-binding agent described herein. In some embodiments, the disclosure provides methods for enhancing an immune response in a subject using an ILT3-binding agent described herein. In some embodiments, the activating, promoting, increasing, and/or enhancing of an immune response comprises stimulating myeloid cells. In some embodiments, the activating, promoting, increasing, and/or enhancing of an immune response comprises stimulating monocytes. In some embodiments, the activating, promoting, increasing, and/or enhancing of an immune response comprises stimulating macrophages. In some embodiments, the activating, promoting, increasing, and/or enhancing of an immune response comprises stimulating dendritic cells. In some embodiments, the activating, promoting, increasing, and/or enhancing of an immune response comprises stimulating APCs. In some embodiments, the activating, promoting, increasing, and/or enhancing of an immune response comprises stimulating tolDCs. In some embodiments, the activating, promoting, increasing, and/or enhancing of an immune response comprises reactivating tolDCs. In some embodiments, the activating, promoting, increasing, and/or enhancing of an immune response comprises increasing cell-mediated immunity. In some embodiments, the activating, promoting, increasing, and/or enhancing of an immune response comprises increasing effector T-cell activity. In some embodiments, the activating, promoting, increasing, and/or enhancing of an immune response comprises increasing CTL activity. In some embodiments, the activating, promoting, increasing, and/or enhancing of an immune response comprises inhibiting or decreasing the suppressive activity of Tregs. In some embodiments, the activating, promoting, increasing, and/or enhancing of an immune response comprises inhibiting or decreasing the suppressive activity of MDSCs. In some embodiments, the immune response is a result of antigenic stimulation. In some embodiments, the antigenic stimulation is a tumor cell. In some embodiments, the antigenic stimulation is cancer.

The disclosure also provides methods of disrupting and/or inhibiting ILT3 signaling in a cell comprising contacting the cell with an effective amount of an ILT3-binding agent described herein. In some embodiments, the method of disrupting and/or inhibiting ILT3 signaling in a cell comprises contacting the cell with an effective amount of antibody 3A3, antibody 5A7, antibody 12A12, antibody 16C5, antibody 45G10, antibody 48A6, or antibody 53F10, or humanized versions thereof. In some embodiments, the method of disrupting and/or inhibiting ILT3 signaling in a cell comprises contacting the cell with an effective amount of antibody Hz5A7.v5. In some embodiments, the method of disrupting and/or inhibiting ILT3 signaling in a cell comprises contacting the cell with an effective amount of antibody Hz45G10. In some embodiments, the method of disrupting and/or inhibiting ILT3 signaling in a cell comprises contacting the cell with an effective amount of antibody Hz48A6. In some embodiments, the disclosure provides use of an ILT3-binding agent described herein in the manufacture or preparation of a medicament for disrupting and/or inhibiting ILT3 signaling in a cell. In certain embodiments, the cell is a myeloid cell. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an antigen-presenting cell. In certain embodiments, the method is an in vivo method wherein the step of contacting the cell with the agent comprises administering a therapeutically effective amount of an ILT3-binding agent to a subject. In some embodiments, the method is an in vitro or ex vivo method.

The present disclosure also provides methods for inhibiting growth of a tumor using an ILT3-binding agent described herein. In some embodiments, the method of inhibiting growth of a tumor comprises using antibody 3A3, antibody 5A7, antibody 12A12, antibody 16C5, antibody antibody 48A6, or antibody 53F10, or humanized versions thereof. In some embodiments, the method of inhibiting growth of a tumor comprises using antibody Hz5A7.v5. In some embodiments, the method of inhibiting growth of a tumor comprises using antibody Hz45G10. In some embodiments, the method of inhibiting growth of a tumor comprises using antibody Hz48A6. In certain embodiments, the method of inhibiting growth of a tumor comprises contacting a cell mixture with an ILT3-binding agent in vitro. For example, an immortalized cell line or a cancer cell line mixed with immune cells (e.g., tolerogenic dendritic cells) is cultured in medium to which is added a test agent that binds ILT3. In some embodiments, tumor cells are isolated from a patient sample such as, for example, a tissue biopsy, pleural effusion, or blood sample, mixed with immune cells (e.g., tolDCs), and cultured in medium to which is added a test agent that binds ILT3. In some embodiments, the disclosure provides use of an ILT3-binding agent described herein in the manufacture or preparation of a medicament for inhibiting growth of a tumor or a tumor cell. In some embodiments, an ILT3-binding agent increases, promotes, and/or enhances the activity of effector immune cells. In some embodiments, an ILT3-binding agent inhibits tumor cell growth.

In some embodiments, a method of inhibiting tumor growth comprises contacting the tumor and/or tumor microenvironment with an ILT3-binding agent described herein in vivo. In certain embodiments, contacting a tumor and/or tumor microenvironment with an ILT3-binding agent is undertaken in an animal model. For example, a test agent may be administered to mice that have tumors. In some embodiments, an ILT3-binding agent increases, promotes, and/or enhances the activity of immune cells in the mice. In some embodiments, an ILT3-binding agent inhibits tumor growth. In some embodiments, an ILT3-binding agent causes a tumor to regress. In some embodiments, an ILT3-binding agent is administered at the same time or shortly after introduction of tumor cells into the animal to prevent tumor growth ("preventative model"). In some embodiments, an ILT3-binding agent is administered after tumors have grown to a specified size or have become "established" for treatment ("therapeutic model"). In some embodiments, an ILT3-binding agent is administered to a transgenic animal (e.g., a transgenic mouse) that expresses human ILT3, wherein the transgenic animal has a tumor derived from human cells.

In certain embodiments, a method of inhibiting tumor growth comprises administering to a subject a therapeutically effective amount of an ILT3-binding agent (e.g., an antibody) described herein. In certain embodiments, the subject is a human. In some embodiments, a method of increasing or enhancing an immune response to a tumor or tumor cells in a subject comprises administering to the subject a therapeutically effective amount of an ILT3-binding agent described herein. In some embodiments, a method of activating or enhancing a persistent or long-term immune response to a tumor or tumor cells in a subject comprises administering to the subject a therapeutically effective amount of an ILT3-binding agent described herein. In some embodiments, a method of inhibiting tumor relapse or tumor regrowth in a subject comprises administering to the subject a therapeutically effective amount of an ILT3-binding agent described herein. In some embodiments, a method of inducing a persistent or long-term immunity that inhibits tumor relapse or tumor regrowth in a subject comprises administering to the subject a therapeutically effective amount of an ILT3-binding agent described herein. In some embodiments of the methods described herein, the tumor is a solid tumor. In some embodiments, the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, or a testicular tumor. In some embodiments, the tumor is a pancreatic tumor. In some embodiments, the tumor is an ovarian tumor. In some embodiments, the tumor is a breast tumor. In some embodiments, the tumor is an uterine tumor. In certain embodiments, the subject has a tumor or the subject had a tumor that was at least partially removed.

In some embodiments, the disclosure provides use of an ILT3-binding agent described herein in the manufacture or preparation of a medicament for inhibiting growth of a tumor or tumor cell. In some embodiments, the method of inhibiting growth of a tumor comprises administering to a subject a therapeutically effective amount of antibody 3A3, antibody 5A7, antibody 12A12, antibody 16C5, antibody 45G10, antibody 48A6, or antibody 53F10, or humanized versions thereof. In some embodiments, the method of inhibiting growth of a tumor comprises administering to a subject a therapeutically effective amount of antibody Hz5A7.v5. In some embodiments, the method of inhibiting growth of a tumor comprises administering to a subject a therapeutically effective amount of antibody Hz48A6. In some embodiments, the method of inhibiting growth of a tumor comprises administering to a subject a therapeutically effective amount of antibody Hz45G10.

The present disclosure provides methods of treating cancer. In some embodiments, a method of treating cancer comprises administering to a subject a therapeutically effective amount of an ILT3-binding agent described herein. In some embodiments, an ILT3-binding agent binds ILT3 and inhibits or reduces growth of the cancer. In some embodiments, an ILT3-binding agent binds human ILT3-expressing cells, enhances an immune response to a cancer, and inhibits or reduces growth of the cancer. In some embodiments, an ILT3-binding agent binds human ILT3-expressing cells, reactivates tolDCs, enhances an immune response to a cancer, and inhibits or reduces growth of the cancer. In certain embodiments, the subject is a human. In certain embodiments, the subject has a cancerous tumor. In certain embodiments, the subject has had a tumor at least partially removed.

In some embodiments, the disclosure provides use of an ILT3-binding agent described herein in the manufacture or preparation of a medicament for the treatment of cancer.

In some embodiments of the methods described herein, the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, bladder cancer, brain cancer, esophageal cancer, liver cancer, kidney cancer, or testicular cancer. In some embodiments, the cancer is a sarcoma. In some embodiments, the cancer expresses ILT3.

In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia. In some embodiments, the cancer is a certain type of B cell leukemia or lymphoma which expresses ILT3. In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML.

In some embodiments, a method for treating cancer in a subject comprises administering to the subject a therapeutically effective amount of antibody 3A3, antibody 5A7, antibody 12A12, antibody 16C5, antibody 45G10, antibody 48A6, or antibody 53F10, or humanized versions thereof. In some embodiments, a method for treating cancer in a subject comprises administering to the subject a therapeutically effective amount of antibody Hz5A7.v5. In some embodiments, a method for treating cancer in a subject comprises administering to the subject a therapeutically effective amount of antibody Hz48A6. In some embodiments, a method for treating cancer in a subject comprises administering to the subject a therapeutically effective amount of antibody Hz45G10.

In some embodiments, the disclosure provides methods of activating myeloid cells in the tumor microenvironment. In some embodiments, a method of activating myeloid cells in the tumor microenvironment in a subject with a tumor comprises administering to the subject a therapeutically effective amount of an ILT3-binding agent described herein. In some embodiments, the myeloid cells are primary dendritic cells or tolDCs. In some embodiments, the myeloid cells are monocytes. In some embodiments, the myeloid cells are macrophages. In some embodiments, the myeloid cells are APCs. In some embodiments, the disclosure provides a method of reactivating tolDCs in a subject, the method comprising administering to the subject a therapeutically effective amount of an ILT3-binding agent described herein. In some embodiments, the tolDCs are found in the tumor microenvironment.

In some embodiments of the methods described herein, the ILT3-binding agent (e.g., an antibody) comprises a heavy chain variable region CDR1, CDR2, and CDR3 and a light chain variable region CDR1, CDR2, and CDR3 of antibody 5A7. In some embodiments of the methods described herein, the ILT3-binding agent comprises a heavy chain variable region CDR1, CDR2, and CDR3 and a light chain variable region CDR1, CDR2, and CDR3 of antibody Hz5A7.v5.

In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29), and (b) a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRYTLYAMDY (SEQ ID NO:105), and (b) a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32).

In some embodiments of the methods described herein, the anti-ILT3 antibody comprises: (a) a heavy chain variable region of SEQ ID NO:111 and (b) a light chain variable region of SEQ ID NO:112. In some embodiments of the methods described herein, the anti-ILT3 antibody comprises: (a) a heavy chain variable region of SEQ ID NO:123 and (b) a light chain variable region of SEQ ID NO:124.

In some embodiments of the methods described herein, the anti-ILT3 antibody comprises a heavy chain of SEQ ID NO:126. In some embodiments of the methods described herein, the anti-ILT3 antibody comprises a light chain of SEQ ID NO:128. In some embodiments of the methods described herein, the anti-ILT3 antibody comprises a heavy chain of SEQ ID NO:126 and a light chain of SEQ ID NO:128. In some embodiments of the methods described herein, the anti-ILT3 antibody is a humanized version of 5A7. In some embodiments of the methods described herein, the anti-ILT3 antibody is Hz5A7.v5.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 3A3 or a humanized version of 3A3.

In some embodiments of the methods described herein, the anti-ILT3 antibody comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16).

In some embodiments of the methods described herein, the anti-ILT3 antibody comprises a heavy chain variable region of SEQ ID NO:109 and a light chain variable region of SEQ ID NO:110. In some embodiments of the methods described herein, the anti-ILT3 antibody comprises a polypeptide of SEQ ID NO:109. In some embodiments of the methods described herein, the anti-ILT3 antibody comprises a polypeptide of SEQ ID NO:110. In some embodiments of the methods described herein, the anti-ILT3 antibody comprises a polypeptide of SEQ ID NO:109 and a polypeptide of SEQ ID NO:110.

In some embodiments of the methods described herein, the anti-ILT3 antibody is antibody 3A3. In some embodiments of the methods described herein, the anti-ILT3 antibody is a humanized version of antibody 3A3. In some embodiments of the methods described herein, the anti-ILT3 antibody is a variant of antibody 3A3 or a variant of humanized 3A3.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 12A12 or a humanized version of 12A12.

In some embodiments of the methods described herein, the anti-ILT3 antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48);

In some embodiments of the methods described herein, the anti-ILT3 antibody comprises a heavy chain variable region of SEQ ID NO:113 and a light chain variable region of SEQ ID NO:114. In some embodiments of the methods described herein, the anti-ILT3 antibody comprises a polypeptide of SEQ ID NO:113. In some embodiments of the methods described herein, the anti-ILT3 antibody comprises a polypeptide of SEQ ID NO:114. In some embodiments of the methods described herein, the anti-ILT3 antibody comprises a polypeptide of SEQ ID NO:113 and a polypeptide of SEQ ID NO:114.

In some embodiments of the methods described herein, the anti-ILT3 antibody is antibody 12A12. In some embodiments of the methods described herein, the anti-ILT3 antibody is a humanized version of antibody 12A12. In some embodiments of the methods described herein, the anti-ILT3 antibody is a variant of antibody 12A12 or variant of humanized 12A12.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 16C5 or a humanized version of 16C5.

In some embodiments of the methods described herein, the anti-ILT3 antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63).

In some embodiments of the methods described herein, the anti-ILT3 antibody comprises a heavy chain variable region of SEQ ID NO:115 and a light chain variable region of SEQ ID NO:116. In some embodiments of the methods described herein, the anti-ILT3 antibody comprises a polypeptide of SEQ ID NO:115. In some embodiments of the methods described herein, the anti-ILT3 antibody comprises a polypeptide of SEQ ID NO:116. In some embodiments of the methods described herein, the anti-ILT3 antibody comprises a polypeptide of SEQ ID NO:115 and a polypeptide of SEQ ID NO:116.

In some embodiments of the methods described herein, the anti-ILT3 antibody is antibody 16C5. In some embodiments of the methods described herein, the anti-ILT3 antibody is a humanized version of antibody 16C5. In some embodiments of the methods described herein, the anti-ILT3 antibody is a variant of antibody 16C5 or a variant of a humanized 16C5.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 45G10 or a humanized version of 45G10.

In some embodiments of the methods described herein, the anti-ILT3 antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments of the methods described herein, the anti-ILT3 antibody comprises a heavy chain variable region of SEQ ID NO:117 and a light chain variable region of SEQ ID NO:118. In some embodiments of the methods described herein, the anti-ILT3 antibody comprises a polypeptide of SEQ ID NO:117. In some embodiments of the methods described herein, the anti-ILT3 antibody comprises a polypeptide of SEQ ID NO:118. In some embodiments of the methods described herein, the anti-ILT3 antibody comprises a polypeptide of SEQ ID NO:117 and a polypeptide of SEQ ID NO:118.

In some embodiments of the methods described herein, the anti-ILT3 antibody is antibody 45G10. In some embodiments of the methods described herein, the anti-ILT3 antibody is a humanized version of antibody 45G10. In some embodiments of the methods described herein, the anti-ILT3 antibody is a variant of antibody 45G10 or a variant of a humanized 45G10.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 48A6 or a humanized version of 48A6.

In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments of the methods described herein, the anti-ILT3 antibody comprises a heavy chain variable region of SEQ ID NO:119 and a light chain variable region of SEQ ID NO:120. In some embodiments of the methods described herein, the anti-ILT3 antibody comprises a polypeptide of SEQ ID NO:119. In some embodiments of the methods described herein, the anti-ILT3 antibody comprises a polypeptide of SEQ ID NO:120. In some embodiments of the methods described herein, the anti-ILT3 antibody comprises a polypeptide of SEQ ID NO:119 and a polypeptide of SEQ ID NO:120.

In some embodiments of the methods described herein, the anti-ILT3 antibody is antibody 48A6. In some embodiments of the methods described herein, the anti-ILT3 antibody is a humanized version of antibody 48A6. In some embodiments of the methods described herein, the anti-ILT3 antibody is a variant of antibody 48A6 or a variant of a humanized 48A6.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 53F10 or a humanized version of 53F10.

In some embodiments of the methods described herein, the anti-ILT3 antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments of the methods described herein, the anti-ILT3 antibody comprises a heavy chain variable region of SEQ ID NO:121 and a light chain variable region of SEQ ID NO:122. In some embodiments of the methods described herein, the anti-ILT3 antibody comprises a polypeptide of SEQ ID NO:121. In some embodiments of the methods described herein, the anti-ILT3 antibody comprises a polypeptide of SEQ ID NO:122. In some embodiments of the methods described herein, the anti-ILT3 antibody comprises a polypeptide of SEQ ID NO:121 and a polypeptide of SEQ ID NO:122.

In some embodiments of the methods described herein, the anti-ILT3 antibody is antibody 53F10. In some embodiments of the methods described herein, the anti-ILT3 antibody is a humanized version of antibody 53F10. In some embodiments of the methods described herein, the anti-ILT3 antibody is a variant of antibody 53F10 or a variant of a humanized 53F10.

In some embodiments of the methods described herein, a method comprises administering an ILT3-binding agent (e.g., an antibody) described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments of the methods described, the combination of an ILT3-binding agent (e.g., an antibody) described herein and at least one additional therapeutic agent results in additive or synergistic results. In some embodiments, the combination therapy results in an increase in the therapeutic index of the ILT3-binding agent. In some embodiments, the combination therapy results in an increase in the therapeutic index of the additional therapeutic agent(s). In some embodiments, the combination therapy results in a decrease in the toxicity and/or side effects of the ILT3-binding agent. In some embodiments, the combination therapy results in a decrease in the toxicity and/or side effects of the additional therapeutic agent(s). In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, a combination treatment comprises one additional therapeutic agent or two or more additional therapeutic agents.

Useful classes of therapeutic agents include, but are not limited to, anti-tubulin agents, auristatins, DNA minor groove binders, DNA replication inhibitors, alkylating agents (e.g., platinum complexes such as cisplatin, mono (platinum), bis(platinum) and tri-nuclear platinum complexes and carboplatin), anthracyclines, antibiotics, antifolates, anti-metabolites, chemotherapy sensitizers, duocarmycins, etoposides, fhiorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent is an alkylating agent, an antimetabolite, an antimitotic, a topoisomerase inhibitor, or an angiogenesis inhibitor.

Therapeutic agents that may be administered in combination with the ILT3-binding agents described herein include chemotherapeutic agents. Thus, in some embodiments, the method or treatment involves the administration of an ILT3-binding agent of the present disclosure in combination with a chemotherapeutic agent or in combination with a cocktail of chemotherapeutic agents.

Chemotherapeutic agents useful in the present disclosure include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2''-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT 11; topoisomerase inhibitor RFS 2000; difluoromethylornithine (DMF0); retinoic acid; esperamicins; capecitabine (XELODA); and pharmaceutically acceptable salts, acids or derivatives of any of the above.

Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

In certain embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments of the methods described herein, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plkl. In certain embodiments, the additional therapeutic agent is paclitaxel. In certain embodiments, the additional therapeutic agent is nab-paclitaxel.

In some embodiments of the methods described herein, an additional therapeutic agent comprises an agent such as a small molecule. For example, treatment can involve the combined administration of an ILT3-binding agent of the present disclosure with a small molecule that acts as an inhibitor against tumor-associated antigens including, but not limited to, EGFR, HER2 (ErbB2), and/or VEGF. In some embodiments, an ILT3-binding agent of the present disclosure is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In some embodiments of the methods described herein, an additional therapeutic agent comprises a biological molecule, such as an antibody. For example, treatment can involve the combined administration of an ILT3-binding agent of the present disclosure with antibodies against tumor-associated antigens including, but not limited to, antibodies that bind EGFR, HER2/ErbB2, and/or VEGF.

In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an antibody that modulates the immune response. In some embodiments, the additional therapeutic agent is an anti-PD-1 antibody, an anti-PD-L1 antibody, an anti-PD-L2 antibody, an anti-CTLA-4 antibody, or an anti-TIGIT antibody.

Furthermore, treatment with an ILT3-binding agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immunotherapeutic agent.

In some embodiments of the methods described herein, an ILT3-binding agent is combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-a, TGF-β, TNF-α, VEGF, PIGF, IL-1, IL-2, IL-3, IL-4, IL-5, IL-6, IL-7, IL-12, IL-15, and IL-18.

In some embodiments of the methods described herein, the additional therapeutic agent is an immunotherapeutic agent. In some embodiments, the immunotherapeutic agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD-1 antibody, anti-PD-L1 antibody, anti-LAG-3 antibody, and anti-TIM-3 antibody.

In some embodiments of the methods described herein, an immunotherapeutic agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments of the methods described herein, an immunotherapeutic agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the PD-1 antagonist is an antibody that specifically binds PD-1. In some embodiments, the antibody that binds PD-1 is pembrolizumab (KEYTRUDA, MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AU P-12.

In some embodiments, the PD-L1 antagonist is an antibody that specifically binds PD-L1. In some embodiments, the antibody that binds PD-L1 is atezolizumab (TECENTRIQ, RG7446, MPDL3280A), MEDI4736, BMS-936559 (MDX-1105), avelumab (BAVENCIO, MSB0010718C), durvalumab (IMFINZI), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies.

In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is lirilumab.

In some embodiments, an immunotherapeutic agent is selected from the group consisting of: a CD28 agonist, a 4-1BB agonist, an OX40 agonist, a CD27 agonist, a CD80 agonist, a CD86 agonist, a CD40 agonist, and a GITR agonist.

In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RG-DOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises a GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments, immunotherapeutic agents include, but are not limited to, cytokines such as chemokines, interferons, interleukins, lymphokines, and members of the tumor necrosis factor (TNF) family. In some embodiments, immunotherapeutic agents include immunostimulatory oligonucleotides, such as CpG dinucleotides.

In some embodiments, an immunotherapeutic agent includes, but is not limited to, anti-PD-1 antibodies, anti-PD-L1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, or anti-IDO1 antibodies.

In some embodiments, treatment with an ILT3-binding agent can occur prior to, concurrently with, or subsequent to administration of the additional therapeutic agents. In some embodiments, combined administration includes co-administration, either in a single pharmaceutical formulation or using separate formulations, or consecutive administration in either order but generally within a time period such that all active agents can exert their biological activities. In some embodiments, preparation of agents and/or dosing schedules for additional therapeutic agents are according to manufacturers' instructions or as determined empirically by the skilled practitioner.

In some embodiments of the methods described herein, an ILT3-binding agent (e.g., an antibody) is administered to a subject (e.g., a human) as part of a combination therapy.

It will be appreciated that the combination of an ILT3-binding agent (e.g., an antibody) described herein and at least one additional therapeutic agent may be administered in any order or concurrently. In some embodiments, an ILT3-binding agent is administered to subjects that have previously undergone treatment with a therapeutic agent. In some embodiments, an ILT3-binding agent and a second therapeutic agent are administered substantially simultaneously or concurrently. For example, a subject may be given an ILT3-binding agent while undergoing a course of treatment with a second therapeutic agent (e.g., a chemotherapeutic agent). In some embodiments, an ILT3-binding agent is administered within 1 year of the treatment with a second therapeutic agent. In some embodiments, an ILT3-binding agent is administered within 10, 8, 6, 4, or 2 months of any treatment with a second therapeutic agent. In some embodiments, an ILT3-binding agent is administered within 4, 3, 2, or 1 weeks of any treatment with a second therapeutic agent. In some embodiments, an ILT3-binding agent is administered within 5, 4, 3, 2, or 1 days of any treatment with a second therapeutic agent. It will further be appreciated that the two (or more) agents or treatments can be administered to the subject within a matter of hours or minutes (i.e., substantially simultaneously).

For the treatment of a disease, the appropriate dosage of an ILT3-binding agent (e.g., an antibody) of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. An ILT3-binding agent can be administered one time or over a series of treatments lasting from several days to several months, or until a cure is effected or a diminution of the disease state is achieved.

The present disclosure provides compositions comprising an ILT3-binding agent described herein. The present disclosure also provides pharmaceutical compositions comprising an ILT3-binding agent described herein and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol. (*Remington: The Science and Practice of Pharmacy*, $22^{nd}$ Edition, 2012, Pharmaceutical Press, London.). In some embodiments, the formulation is in the form of an aqueous solution. In some embodiments, the formulation is stored in a lyophilized or in an alternative dried form.

The binding agents of the present disclosure can be formulated in any suitable form for delivery to a target cell/tissue. In some embodiments, an ILT3-binding agent (e.g., an antibody) can be formulated as a liposome, microparticle, microcapsule, albumin microsphere, microemulsion, nanoparticle, nanocapsule, or macroemulsion.

In some embodiments, an ILT3-binding agent (e.g., an antibody) is formulated with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, an ILT3-binding agent (e.g., an antibody) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

EXAMPLES

Example 1

Generation of Antibodies

Anti-ILT3 antibodies were generated using the extracellular domain of human ILT3 (huILT3-ECD) and/or cyno ILT3 (cynoILT3-ECD) as the immunogen. Recombinant constructs comprising the extracellular region of human ILT3 (aa 22-259 of SEQ ID NO:1) or the extracellular region of cyno ILT3 (aa 22-259 of SEQ ID NO:6) were generated and expressed in mammalian cells. Mice were immunized with the huILT3-ECD and/or cynoILT3-ECD protein and were boosted several times to induce high titers. Blood was drawn from the immunized mice and antibody titers were determined by ELISA and FACS. Single cell suspensions of lymphocytes were obtained from the spleens and lymph nodes of immunized mice that had been determined to have suitably high antibody titers. Lymphocytes were fused with murine myeloma cells by standard methods (e.g., electrofusion). Cells were dispersed into 96-well plates in HAT-containing selection media.

Example 2

Screening of Antibodies

ELISA assays were used to screen antibodies against human ILT3 and human LILRA1,2,4-6. The antibodies that bound to human ILT3 but did not bind to human LILRA1, 2,4-6proteins were selected. These antibodies were rescreened by FACS for binding to human ILT3 and cyno ILT3 expressed on HEK-293T cells. The antibodies that bound to both human and cyno ILT3 were selected. This subset of antibodies were screened by FACS against human LILRB1-5 (ILT2, ILT4, ILT5, ILT3, and LILRB5, respectively), cyno LILRB5, and human LILRA1,2,4-6. For FACS screening, each antibody was incubated with cells expressing human ILT3, cyno ILT3, one of the LILRA proteins, or one of the LILRB proteins for 30 minutes at 4° C. After washing, the cells were incubated with labeled anti-mouse Fc antibody for 30 minutes at 4° C. After washing, cells were analyzed on a flow cytometer. Results from representative antibodies are shown in FIGS. 1A-1F and 2A-2E. Antibodies were selected on the criteria of binding to human ILT3, cyno ILT3, no or limited binding to other LILRB proteins, and no or limited binding to LILRA proteins. For example, antibody 11A1 was observed to bind human LILRB2, LILRA1, LILRA2, LILRA4 and LILRA5 and therefore was not selected for additional studies.

Example 3

Binding Characteristics of Anti-Human ILT3 Antibodies

The binding affinities of anti-ILT3 antibodies to human ILT3 and cyno ILT3 were measured using a Biacore system (GE Healthcare LifeSciences). Briefly, anti-Fc antibody (Sigma-Aldrich) was immobilized on all four flow cells of a CM5 chip using amine coupling reagents (GE Healthcare LifeSciences). Antibodies were captured on flow cells 2, 3, and 4 using flow cell 1 as a reference. Concentrations ranging from 3.3-10 nM of human or cyno ILT3-ECD were injected at a flow rate of 50 μL/min at 37° C. Kinetic data were collected over time and fit using the simultaneous global fit equation to yield affinity constants ($K_D$ values) for each antibody.

Binding data is shown in Table 9.

TABLE 9

| Antibody | Human ILT3 | | | Cyno ILT3 | | |
|---|---|---|---|---|---|---|
| | $K_{on}$ [1/Ms] | $K_{off}$ [s$^{-1}$] | $K_D$ M | $K_{on}$ [1/Ms] | $K_{off}$ [s$^{-1}$] | $K_D$ M |
| 3A3 | $3.3 \times 10^5$ | $6.5 \times 10^{-4}$ | $2.0 \times 10^{-9}$ | $3.4 \times 10^6$ | $2.1 \times 10^{-2}$ | $6.3 \times 10^{-9}$ |
| 5A7 | $3.8 \times 10^6$ | $1.1 \times 10^{-4}$ | $2.8 \times 10^{-11}$ | $3.3 \times 10^6$ | $2.2 \times 10^{-3}$ | $6.6 \times 10^{-10}$ |
| 12A12 | $1.1 \times 10^5$ | $9.4 \times 10^{-4}$ | $8.5 \times 10^{-9}$ | $1.5 \times 10^5$ | $2.8 \times 10^{-4}$ | $1.9 \times 10^{-9}$ |
| 16C5 | $1.1 \times 10^5$ | $2.0 \times 10^{-4}$ | $1.8 \times 10^{-9}$ | $2.9 \times 10^5$ | $9.0 \times 10^{-5}$ | $3.1 \times 10^{-10}$ |
| 45G10 | $3.9 \times 10^5$ | $5.1 \times 10^{-5}$ | $1.3 \times 10^{-10}$ | $1.5 \times 10^5$ | $7.6 \times 10^{-4}$ | $5.0 \times 10^{-9}$ |
| 48A6 | $7.0 \times 10^6$ | $1.8 \times 10^{-7}$ | <100 pM | $1.4 \times 10^7$ | $2.4 \times 10^{-2}$ | $1.7 \times 10^{-9}$ |
| 53F10 | $3.3 \times 10^5$ | $8.0 \times 10^{-5}$ | $2.4 \times 10^{-10}$ | $5.9 \times 10^5$ | $5.5 \times 10^{-3}$ | $9.4 \times 10^{-9}$ |

The binding sites of the anti-ILT3 antibodies on the extracellular domain of human ILT3 were also assessed (data not shown). 3A3 binds to a conformational epitope within the D2 domain or within the junction between the D1 and D2 domains of ILT3. 16C5 binds to a conformational epitope within the D1 domain of ILT3. 12A12 binds to a conformational epitope within the D2 domain or within the junction between the D1 and D2 domains of ILT3. 5A7 binds to a conformational epitope within the D2 domain or within the junction between the D1 and D2 domains of ILT3. 48A6 binds to a conformational epitope within the D2 domain or within the junction between the D1 and D2 domains of ILT3. 45G10 binds to a conformational epitope within the D2 domain or within the junction between the D1 and D2 domains of ILT3. 53F10 binds to a conformational epitope within the D2 domain or within the junction between the D1 and D2 domains of ILT3.

Competitive binding among the anti-ILT3 antibodies on the extracellular domain of human ILT3 were also carried out. Table 10 shows that some anti-ILT3 antibodies bind to overlapping or partially overlapping epitopes on ILT3, and some anti-ILT3 antibodies bind to different epitopes on ILT3. "Yes" indicates competitive binding to the extracellular domain of ILT3 between two antibodies. "Partial" indicates partially competitive binding to the extracellular domain of ILT3 between two antibodies. "No" indicates no competitive binding to the extracellular domain of ILT3 between two antibodies. "ND" indicates no data available.

TABLE 10

|       | 5A7 | 3A3 | 12A12 | 16C5 | 45G10 | 48A6 | 53F10 |
|-------|-----|-----|-------|------|-------|------|-------|
| 5A7   | yes |     |       |      |       |      |       |
| 3A3   | No  | yes |       |      |       |      |       |
| 12A12 | No  | No  | yes   |      |       |      |       |
| 16C5  | No  | No  | partial | yes |       |      |       |
| 45G10 | No  | ND  | ND    | No   | yes   |      |       |
| 48A6  | Yes | ND  | ND    | No   | No    | yes  |       |
| 53F10 | No  | ND  | ND    | No   | yes   | No   | yes   |

Example 4

Sequence Analyses of Anti-ILT3 Antibodies

Representative antibodies 3A3, 5A7, 12A12, 16C5, 45G10, 48A6, and 53F10 were sequenced and the heavy chain variable region and light chain variable region amino acid sequences are disclosed herein and summarized in Table 11.

TABLE 11

| Antibody | Heavy Chain Variable Region | Light Chain Variable Region |
|----------|----------------------------|----------------------------|
| 3A3      | SEQ ID NO: 109             | SEQ ID NO: 110             |
| 5A7      | SEQ ID NO: 111             | SEQ ID NO: 112             |
| 12A12    | SEQ ID NO: 113             | SEQ ID NO: 114             |
| 16C5     | SEQ ID NO: 115             | SEQ ID NO: 116             |
| 45G10    | SEQ ID NO: 117             | SEQ ID NO: 118             |
| 48A6     | SEQ ID NO: 119             | SEQ ID NO: 120             |
| 53F10    | SEQ ID NO: 121             | SEQ ID NO: 122             |

The heavy chain and light chain variable region CDRs for the individual antibodies are disclosed in Tables 1-7 and as SEQ ID NOs:11-104.

Example 5

Screening for ILT3 Ligand

Approximately 100 cell lines were screened in the process of identifying a ligand or ligands for ILT3. A construct comprising ILT3 extracellular domain (amino acids 22-259 of SEQ ID NO:1) fused to an immunoglobulin Fc region was generated (ILT3ECD-Fc). The ILT3ECD-Fc construct was used to evaluate binding to the cell lines. Previous in-house studies had suggested that CNTFR was a binding partner for ILT3 and LX-2 was included in the cell line panel to follow up on this earlier observation. LX-2 is an adherent human hepatic stellate cell line that retains key biological features. Following is a brief description of the screening assay using LX-2 as an exemplary cell line. LX-2 cells were seeded into 384-well poly-D-lysine-coated plates (Grenier) in DMEM containing 10% FBS and 1% penicillin/streptomycin. TGF-β (Peprotech) was added at 10 ng/mL to a portion of the wells to activate the LX-2 cells. After two days, the cells were washed three times with Hank's buffered saline solution (HBSS) containing $Mg^{2+}$ and $Ca^{2+}$, leaving approximately 10 µL of buffer per well. Next, cells (untreated and TGF-β-treated) were incubated with ILT3ECD-Fc (10 µL per well at a concentration of 10 µg/mL) in DMEM for 30 minutes at room temperature. An AlexaFluor 647-conjugated goat anti-human Fc antibody (1:500 dilution; Jackson ImmunoResearch Laboratories) and Hoechst stain (2.5 ThermoFisher Scientific) were added to the wells. After a 30 minute incubation, cells were washed and fixed with 3.7% formalin, then washed again, and imaged at 10× on a CellInsight instrument (ThermoFisher Scientific).

The results showed that ILT3ECD-Fc bound to activated LX-2 cells and did not bind to basal/untreated LX-2 cells. Viability of the cells was equivalent in the basal and activated cells. These results suggested that activated LX-2 cells expressed a ligand for ILT3.

Example 6

Activation of Reporter Cells by Interaction with LX-2 Cells

To investigate whether binding of ILT3 to LX-2 cells was a functional interaction, LX-2 cells were co-cultured with cells expressing a stable reporter system and a cell surface receptor of interest ("reporter cells"). In this chimeric receptor system, the extracellular domain of the receptor of interest, e.g., ILT3, is fused with the transmembrane/intracellular domain of PILRβ that associates with the adaptor protein DAP12. When the chimeric receptor is activated by binding to a ligand, DAP12 becomes phosphorylated and activates an NFAT-responsive promoter which drives GFP expression (see, e.g., Deng et al., 2014, *Blood*, 124:924-935). Bulk cultures of LX-2 cells were cultured in basal media (DMEM as described above) or in activation media (DMEM plus TGF-β as described above) for three days. Treated and untreated LX-2 cells were harvested and washed. $2\times10^5$ of LX-2 cells were co-cultured with $4\times10^5$ reporter cells containing (i) no receptor; (ii) B7-H4 extracellular domain; or (iii) ILT3 extracellular domain. Cells were incubated overnight at 37° C. in RPMI 1640 containing 10% FBS. The reporter cells were pre-stained with CellTracker Deep Red (ThermoFisher) to distinguish them from LX-2 cells upon analysis. The next day, reporter cells were assayed for GFP expression by FACS.

Figure 3:
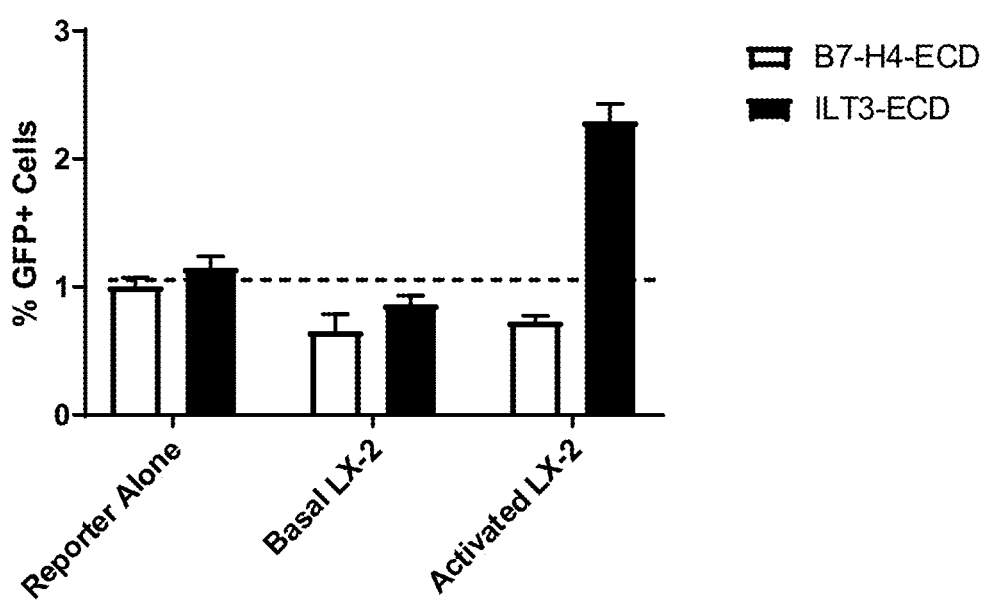
FIG. 3. Reporter cell assay—ILT3 and LX-2 cell interaction. Bulk cultures of LX-2 cells were cultured in basal media or in activation media for three days. Treated and untreated LX-2 cells were harvested and washed. $2 \times 10^5$ of LX-2 cells were co-cultured with $4 \times 10^5$ reporter cells containing (i) reporter cells with no receptor; (ii) reporter cells with B7-H4 extracellular domain; or (iii) reporter cells with ILT3 extracellular domain. Cells were incubated overnight at 37° C. in RPMI 1640 containing 10% FBS. The reporter cells were pre-stained with CellTracker Deep Red to distinguish them from LX-2 cells upon analysis. The next day, reporter cells were assayed for GFP expression by FACS.

As shown in FIG. 3, expression of GFP was induced only when ILT3 was expressed on the surface of the reporter cells and only in the presence of activated LX-2 cells. These results suggest that not only did ILT3 bind to a potential ligand on the cell surface of activated LX-2 cells but that the interaction was biologically functional.

Example 7

Identification of Fibronectin as ILT3 Ligand

Immunoprecipitation and mass spectrometry methods were used to identify the binding partner of ILT3. Briefly, LX-2 cells were seeded in basal media or activation media with $2.5\times10^6$ cells in a 150 mm³ tissue culture dish and incubated for 3 days. Media was removed and the cells were lysed in 100 µl of cell lysis buffer (Cell Signaling Technologies) supplemented with HALT™ protease and inhibitor cocktail (ThermoFisher). Lysates were cleared by centrifugation at >16,000 RCF at 4° C. for 10 minutes, and supernatants were transferred to new microfuge tubes. Protein concentrations of the cleared lysates were quantified using a bicinchoninic acid (BCA) assay (Pierce Biotechnology).

Immunoprecipitation was performed using Protein G dynabeads (Invitrogen/ThermoFisher Scientific) according to the manufacturer's instructions. Briefly, 10 µg of ILT3ECD-Fc or control human Fc was bound to 50 µl of magnetic Dynabeads for 30 minutes at 4° C. Supernatant was removed and protein lysate from the untreated or activated LX-2 cells was added. For each treatment condition, lysate containing approximately 615 µg of protein was added to the Dynabead complexes (either ILT3ECD-Fc Dynabeads or Fc Dynabeads) and incubated overnight at 4° C. with gentle rotation. Protein lysates were removed and Dynabeads were washed three times with 200 µl of lysis buffer for 5 minutes per wash. 50 µl of elution buffer comprised of protein loading buffer, reducing agent, and lysis buffer in a ratio of 15:4:1 was added to Dynabeads. Proteins were eluted at 95° C. for 5 minutes and samples (10 µl of each protein elute) were run on polyacrylamide electrophoresis gels. To identify bands of interest, silver stain analysis was performed using a PlusOne Silver Staining kit (GE Healthcare) according to the manufacturer's instructions. Gels were imaged using a Gel Doc™ EZ system (Bio-Rad).

Figure 4:
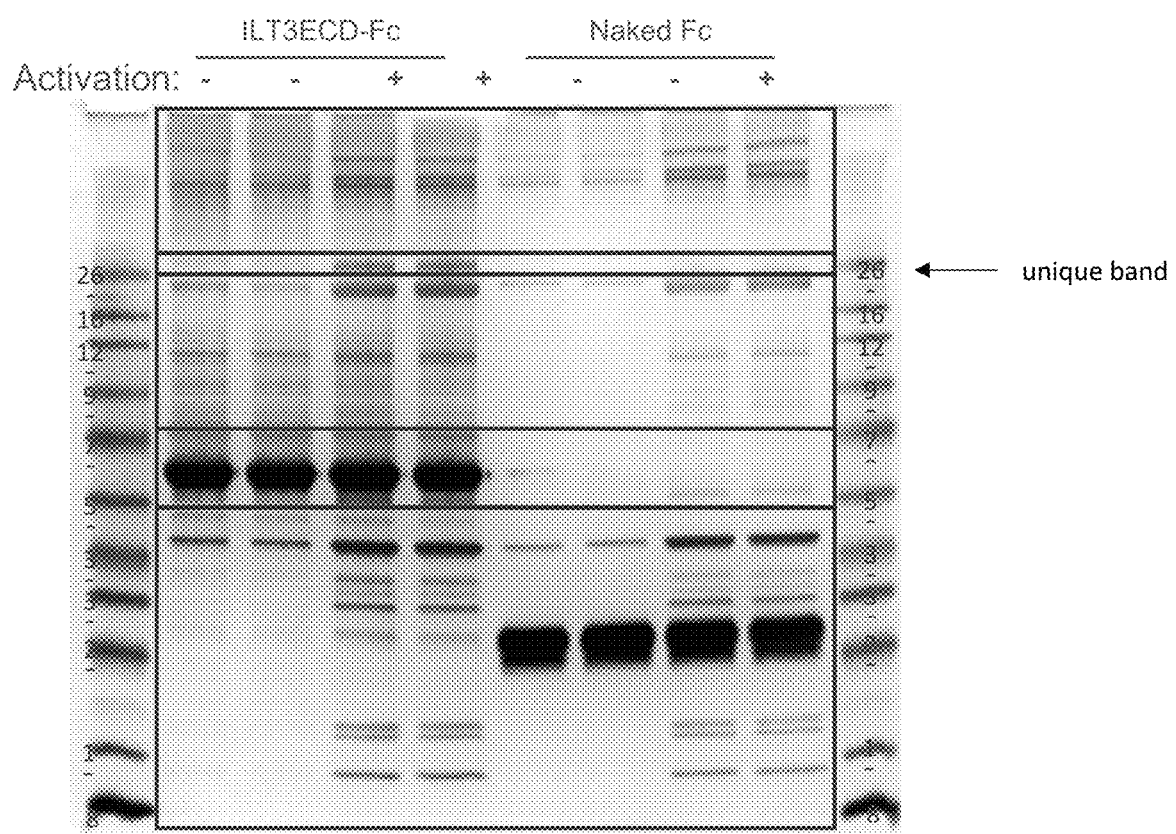
FIG. 4. Identification of ILT3 ligand using immunoprecipitation and gel electrophoresis. Immunoprecipitation was performed using Protein G dynabeads according to the manufacturer's instructions. 10 µg of ILT3ECD-Fc or control human Fc was bound to 50 µl of magnetic Dynabeads for 30 minutes at 4° C. Supernatant was removed and protein lysate from the untreated or activated LX-2 cells was added. For each treatment condition, lysate containing approximately 615 µg of protein was added to the Dynabead complexes and incubated overnight at 4° C. with gentle rotation. Protein lysates were removed and Dynabeads were washed three times with 200 µl of lysis buffer for 5 minutes per wash. 50 µl of elution buffer comprised of protein loading buffer, reducing agent, and lysis buffer in a ratio of 15:4:1 was added to Dynabeads. Proteins were eluted at 95° C. for 5 minutes and samples (10 µl of each protein elute) were run on polyacrylamide electrophoresis gels. To identify bands of interest, silver stain analysis was performed using a PlusOne Silver Staining kit (GE Healthcare) according to the manufacturer's instructions. Gels were imaged using a Gel Doc™ EZ system (Bio-Rad).

As shown in FIG. 4, a unique band was observed in the protein sample eluted from the Dynabead complex of ILT3ECD-Fc and activated LX-2 cell lysate (within box near 260 MW marker).

Gel electrophoresis was performed on the remaining 40 µl of eluate and the gel was stained with Bio-Safe Coomassie Stain (Bio-Rad). Gel bands corresponding to the unique band and control bands from other samples at the same size were excised in a biological safety cabinet and gel pieces were sliced into small fragments. Gel pieces were washed in 50% acetonitrile and 200 mM ammonium bicarbonate, incubated in 100% acetonitrile for 10 minutes, and dried in a SpeedVac vacuum concentrator. Proteins in the gel pieces were reduced and alkylated by sequential incubation with 25 mM tris(2-carboxyethyl)phosphine (TCEP) and 50 mM iodoacetamide. Gel pieces were washed and incubated with acetonitrile again and digested with trypsin (20 µg/ml in 50 mM ammonium bicarbonate, pH 8.0) overnight at 37° C.

The digested samples were analyzed by mass spectrometry. Briefly, peptides were separated over an EASY-Spray™ PepMap C18 column connected to an UltiMate™ RSLCnano LC system (ThermoFisher Scientific). Peptides were eluted from the column with a gradient of 2% to 32% acetonitrile over 135 minutes and injected into an Orbitrap Velos Pro™ mass spectrometer. Liquid chromatography with tandem mass spectrometry (LC-MS/MS) data was collected using a top 10 method, with MS data collected at 60,000 resolution from 200-2000 m/z. MS/MS data was collected with dynamic exclusion, monoisotopic precursor selection, and charge state screening enabled on the ion trap. Singly charged peptides were excluded. Raw files were analyzed with PEAKS X proteomics software (Bioinformatics Solutions) searching against a database of human proteins. In the PEAKS program, proteins were identified with a −10 log p setting of 20 and a false discovery rate (FDR) of no higher than 1.5%. Hits were ranked by total peptide count and screened for hits that were found in experimental samples but not controls. Hits were additionally screened for extracellular and transmembrane proteins. Surprisingly, the unique band was identified as fibronectin. The number of identified peptides for fibronectin in the sample from ILT3ECD-Fc and activated LX-2 cells was 306, as compared to peptides for fibronectin in the sample from (1) ILT3ECD-Fc and basal LX-2 cells which was 111; (2) control-Fc and activated LX-2 cells which was 15; and (3) control-Fc and basal LX-2 cells which was 1. This clearly demonstrated the enrichment of fibronectin peptides in the ILT3ECD-Fc plus activated LX-2 cells sample.

Additional studies showed that ILT3ECD-Fc binding was undetectable in a fibronectin knock-out LX-2 cell line, whether the cells were activated or not. These results further supported the conclusion that fibronectin is a ligand for ILT3.

The binding of ILT3 to fibronectin was evaluated by Biacore. Human plasma fibronectin was immobilized onto a CM5 sensor chip surface (flow cell 2) using standard amine coupling chemistry. Collagen type IV was immobilized onto flow cell 3 and used as a control. Human ILT3ECD-Fc or human LAIR1ECD-Fc were injected over both surfaces at different concentrations (125-4000 nM) at a flow rate of 50 µL/min at 37° C. Kinetic data were collected over time and fit using the simultaneous global fit equation to yield affinity constants ($K_D$ values) for each antibody.

ILT3 bound to fibronectin with a $K_D$ of at least 5 µM and did not bind collagen IV at a detectable level. In contrast, LAIR1 bound to collagen IV with a $K_D$ of at least 5 µM and did not bind fibronectin.

Example 8

Activation of Reporter Cells by Interaction of ILT3 and Fibronectin

To investigate whether binding of ILT3 to fibronectin was a functional interaction, reporter cells expressing ILT3 ECD were incubated with fibronectin. 96-well Maxisorp (Nunc) plates were coated with 5 µg/mL of human Fc protein (R&D Systems), plasma-derived fibronectin (Millipore), or recombinant fibronectin (R&D Systems) in PBS at room temperature for 2 hrs. Plates were washed twice with PBS and then blocked with RPMI 1640 containing 10% FBS. NFAT-GFP reporter cells (as described herein in Example 5) expressing B7-H4 extracellular domain, LAIR1 extracellular domain, or ILT3 extracellular domain ($1 \times 10^5$ cells/well) were added to the coated wells and the plates were incubated overnight at 37° C. Cells were assayed for GFP expression by FACS and compared with non-activated reporter cells.

Figure 5:
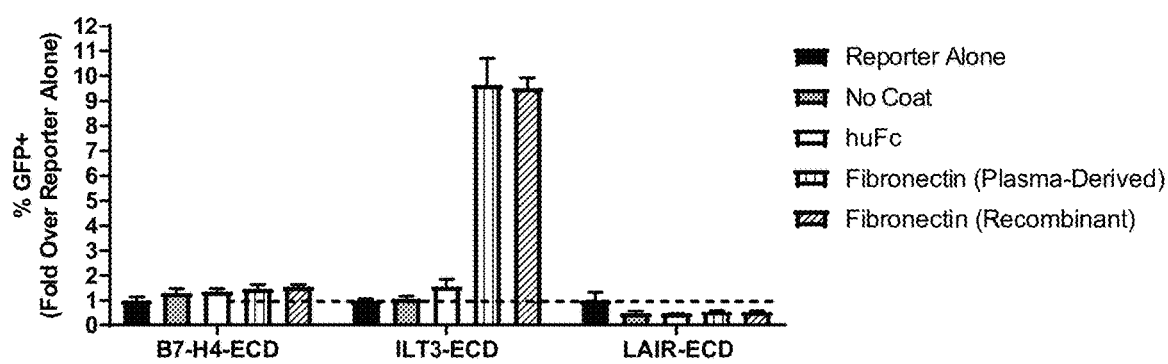
FIG. 5. Reporter cell assay—ILT3 and fibronectin interaction. 96-well Maxisorp (Nunc) plates were coated with 5 µg/mL of human Fc protein (R&D Systems), plasma-derived fibronectin (Millipore), or recombinant fibronectin (R&D Systems) in PBS at room temperature for 2 hrs. Plates were washed twice with PBS and then blocked with RPMI 1640 containing 10% FBS. NFAT-GFP reporter cells (as described herein in Example 5) expressing B7-H4 extracellular domain, LAIR1 extracellular domain, or ILT3 extracellular domain ($1 \times 10^5$ cells/well) were added to the coated wells and the plates were incubated overnight at 37° C. Cells were assayed for GFP expression by FACS and compared with non-activated reporter cells.

As shown in FIG. 5, only cells expressing ILT3 cultured with fibronectin (either plasma-derived or recombinant) were able to activate the reporter system as demonstrated by GFP expression. These results showed that the interaction with fibronectin was specific for ILT3 as there was no GFP expression in response to B7-H4 or LAIR1-expressing cells cultured with fibronectin.

In follow-up studies, 96-well Maxisorp (Nunc) plates were coated with 5 µg/mL plasma-derived fibronectin (Millipore) in PBS at room temperature for 1 hr. After coating, an isotype control antibody, anti-ILT3 antibody 16C5, anti-fibronectin antibody F14 (rabbit monoclonal antibody from Abcam), or anti-fibronectin antibody PA5 (rabbit polyclonal antibody from ThermoFisher Scientific) were added to the wells at a final concentration of 5 or 20 µg/mL. Next, NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

Figure 6:
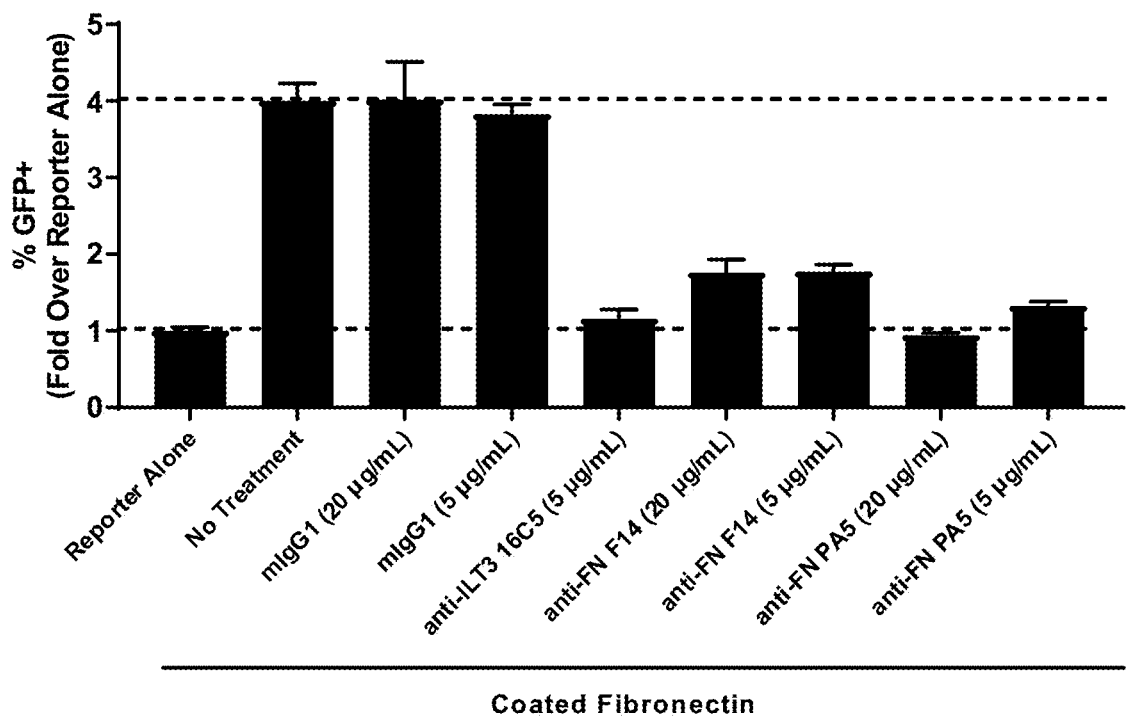
FIG. 6. Antibody inhibition of ILT3 and fibronectin interaction. 96-well Maxisorp plates were coated with 5 µg/mL plasma-derived fibronectin in PBS at room temperature for 1 hr. After coating, an isotype control antibody, anti-ILT3 antibody 16C5, anti-fibronectin antibody F14 (a rabbit monoclonal antibody), or anti-fibronectin antibody PA5 (a rabbit polyclonal antibody) were added to the wells at a final concentration of 5 or 20 µg/mL. NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

As shown in FIG. 6, anti-ILT3 antibody 16C5 as well as anti-fibronectin antibodies F14 and PA5, reduced the expression of GFP in the reporter cells. A control antibody at two different concentrations did not inhibit the expression of GFP resulting from the interaction between ILT3 and fibronectin.

Another study was performed using anti-ILT3 antibodies 16C5 and ch5A7 (chimeric comprising mouse heavy chain variable region and light chain variable region, and human Fc domain). As described above, 96-well Maxisorp plates were coated with 5 µg/mL plasma-derived fibronectin at room temperature for 1 hour. After coating, an isotype control antibody, anti-ILT3 antibody 16C5, or anti-ILT3 antibody ch5A7 were added to the wells in 6-fold dilutions ranging from 66 nM to 0.0002 nM. Next, NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

Figure 7:
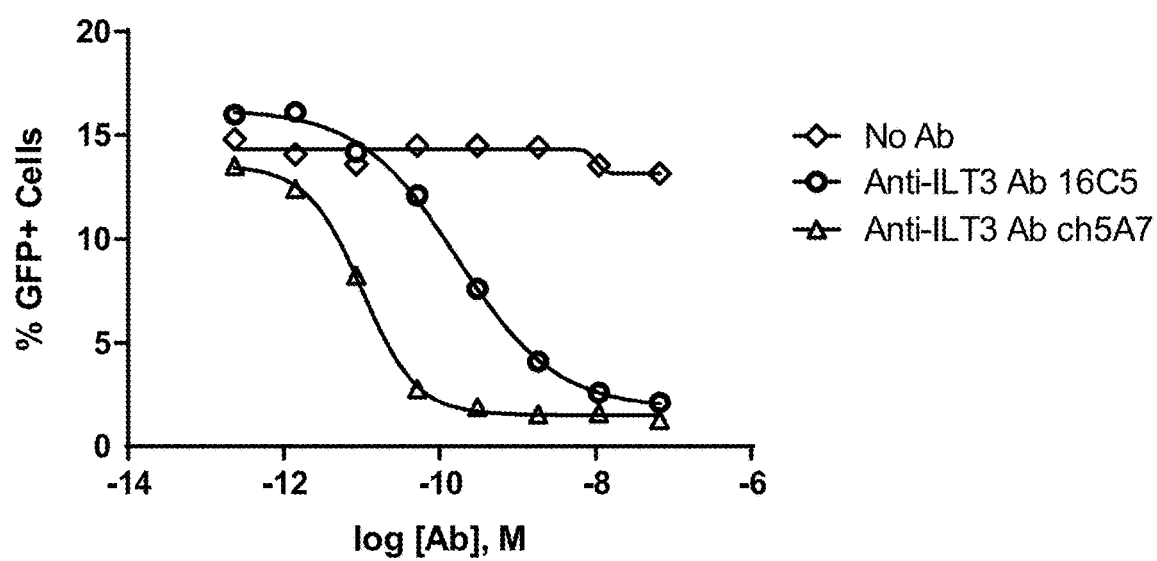
FIG. 7. Antibody inhibition of ILT3 and fibronectin interaction. 96-well Maxisorp plates were coated with 5 µg/mL plasma-derived fibronectin at room temperature for 1 hour. After coating, an isotype control antibody, anti-ILT3 antibody 16C5, or anti-ILT3 antibody ch5A7 were added to the wells in 6-fold dilutions ranging from 66 nM to 0.0002 nM. Next, NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

As shown in FIG. 7, anti-ILT3 antibodies 16C5 and ch5A7 inhibited the interaction of ILT3 and fibronectin as assessed by the reduction of GFP expression. In contrast, the control antibody had no effect on GFP expression.

These results demonstrate that an anti-ILT3 antibody can block the interaction between ILT3 and fibronectin and importantly, block biological activities resulting from that interaction.

Example 9

Identification of ILT3 Binding Site on Fibronectin

Figure 8:
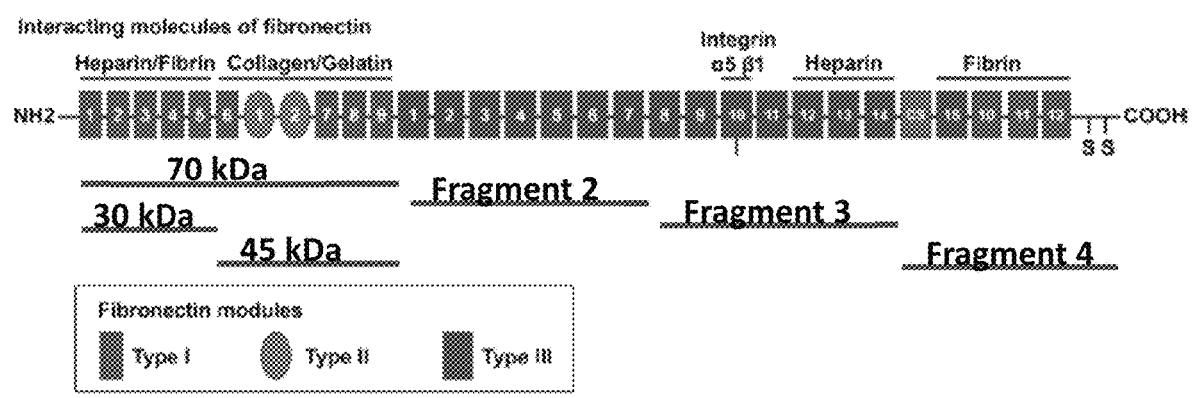
FIG. 8. Representative diagram of fibronectin structure.

A representative diagram of human fibronectin is shown in FIG. 8. Studies were performed to identify where ILT3 bound to fibronectin. 96-well Maxisorp (Nunc) plates were coated with 5 µg/mL of human Fc protein (R&D Systems), plasma-derived fibronectin (Millipore), recombinant fibronectin (R&D Systems), or the following fibronectin fragments: 70 kDa fibronectin fragment (Sigma-Aldrich), 30 kDa fibronectin fragment (Sigma-Aldrich), 45 kDa fibronectin fragment (Sigma-Aldrich), Fragment 2 (aa 607-1265 of SEQ ID NO:138; R&D Systems), Fragment 3 (aa 1266-1908 of SEQ ID NO:138; R&D Systems), or Fragment 4 (aa 1913-2477 of SEQ ID NO:138; R&D Systems). The plates were incubated at room temperature for 2 hours. Plates were washed twice with PBS and then blocked with RPMI 1640 containing 10% FBS. NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

Figure 9:
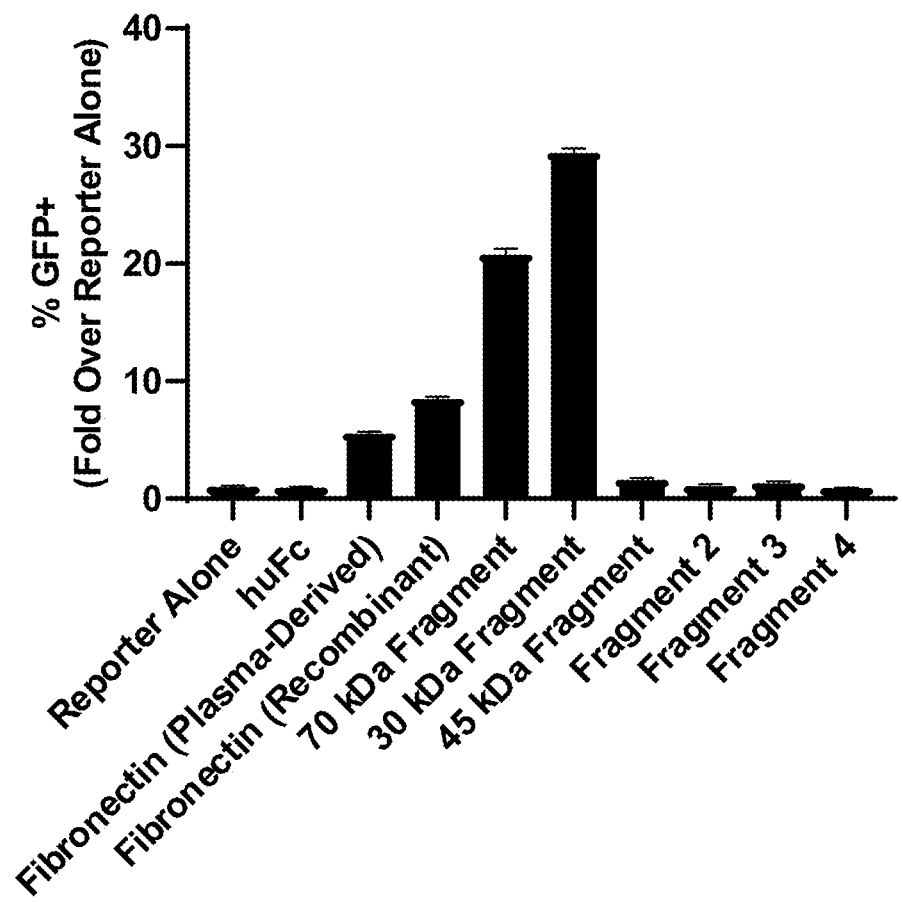
FIG. 9. Reporter cell assay to identify ILT3 binding site on fibronectin. 96-well Maxisorp plates were coated with full-length fibronectin or fibronectin fragments. The plates were incubated at room temperature for 2 hours. Plates were washed twice with PBS and then blocked with RPMI 1640 containing 10% FBS. NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

As shown in FIG. 9, only 70 kDa and 30 kDa fibronectin fragments (as well as full-length fibronectin) were able to activate the reporter system in ILT3-expressing cells as demonstrated by GFP expression. The level of activation was higher with the fragments than with full length fibronectin at equimolar concentrations. The N-terminal region (30 kDa fragment; Type I FN modules 1-5) which encompasses the heparin/fibrin binding domain elicited the highest level of GFP activity.

Additional studies were undertaken to see if the ILT3 binding site on fibronectin could be defined in greater detail. Fibronectin fragments were prepared that consisted of (i) Type I FN modules 1-4 (aa 32-228 of SEQ ID NO:138), (ii) Type I FN modules 2-5 (aa 93-290 of SEQ ID NO:138), (iii) Type IFN modules 1-3 (aa 32-182 of SEQ ID NO:138), (iv) Type IFN modules 2-4 (aa 93-228 of SEQ ID NO:138), (v) Type I FN modules 3-5 (aa 139-290 of SEQ ID NO:138), (vi) Type IFN modules 1-2 (aa 32-138 of SEQ ID NO:138), (vii) Type IFN modules 2-3 (aa 93-182 of SEQ ID NO:138), (viii) Type IFN modules 3-4 (aa 139-228 of SEQ ID NO:138), (ix) Type I FN modules 4-5 (aa 183-290 of SEQ ID NO:138), 70 kDa fragment (aa 32-608 of SEQ ID NO:138), 30 kDa fragment (aa 32-290 of SEQ ID NO:138), and 45 kDa fragment (aa 291-608 of SEQ ID NO:138). As described above, 96-well Maxisorp (Nunc) plates were coated with 40 nM of the fibronectin fragments, as well as full-length fibronectin. The plates were incubated at room temperature for 2 hours. Plates were washed twice with PBS and then blocked with RPMI 1640 containing 10% FBS. NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

Figure 10:
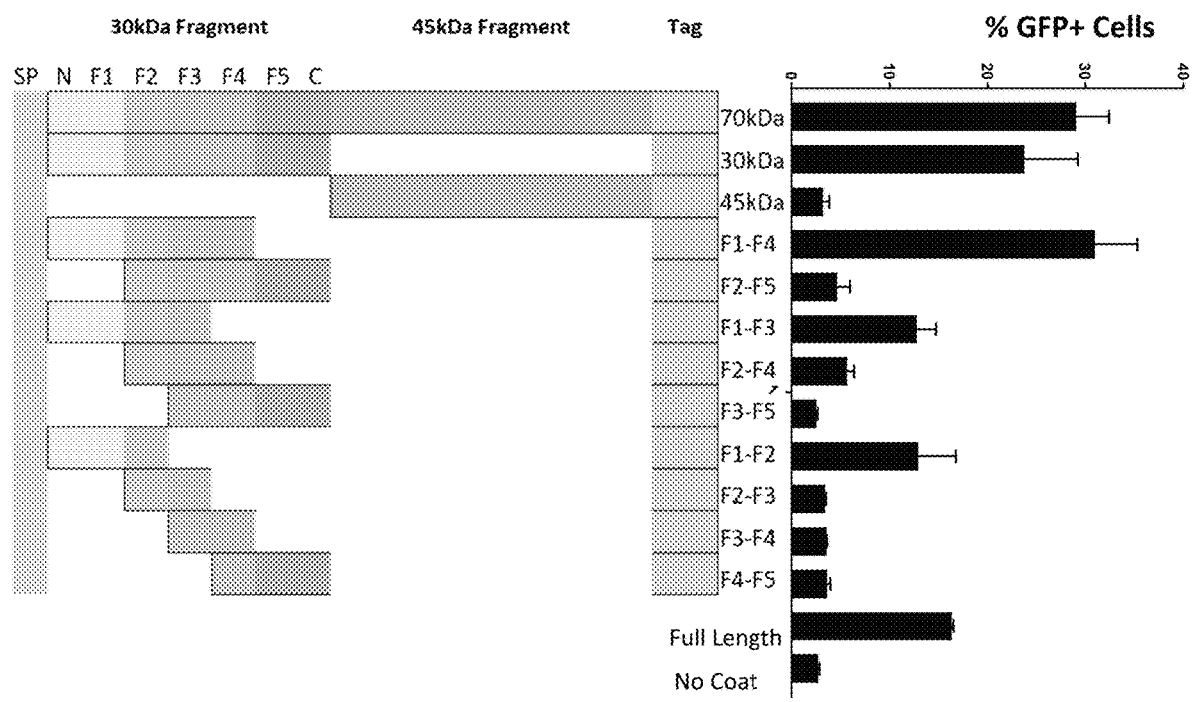
FIG. 10. Reporter cell assay to identify ILT3 binding site on fibronectin. Fibronectin fragments were prepared and coated onto 96-well Maxisorp plates, as well as full-length fibronectin. The plates were incubated at room temperature for 2 hours. Plates were washed twice with PBS and then blocked with RPMI 1640 containing 10% FBS. NFAT-GFP reporter cells expressing ILT3 extracellular domain ($1 \times 10^5$ cells/well) were added to the wells and the plates were incubated overnight at 37° C. Cells were assayed for GFP expression by FACS and compared with non-activated reporter cells.

These studies showed that Type I FN module 1 was necessary for activity in this reporter assay (FIG. 10). We believe that Type I FN module 1 is required for binding of ILT3 to fibronectin and resulting activity, but that other modules also play a part in the ILT3/fibronectin interaction.

Example 10

In Vitro Assays of ILT3 and Fibronectin Interaction

THP-1 is a human monocytic cell line established from acute monocytic leukemia cells and was obtained from ATCC. These cells have been used to study signaling pathways modulated by ILT3 in monocytes activated through Fc receptors (Lu et al., 2009, *JBC*, 284:34839-34848). Activation of monocytes can be achieved by cross-linking of FcR on the cell surface and the crosslinking results in cytokine production, for example, TNF-α and/or IL-8. Studies have shown that ILT3 is a potent inhibitor of FcR-mediated cytokine production in monocytes. THP-1 cells were used as part of an assay to study the interaction of ILT3 and fibronectin in a myeloid cell. In addition to the wild-type THP-1 cells (THP-1), an ILT3 knock-out THP-1 cell line was generated (THP-1 ILT3-KO).

96-well Maxisorp (Nunc) plates were co-coated with fibronectin at 5 µg/mL (Millipore) and an effectorless anti-KLH antibody at 0, 1, 5, and 10 µg/mL. Plates were incubated at room temperature for 2 hours, washed twice with PBS, and blocked with RPMI 1640 containing 10% FBS. THP-1 or THP-1 ILT3-KO cells ($2 \times 10^5$ cells/well) were added to the wells and the plates were incubated overnight at 37° C. The anti-KLH antibody will bind to the FcR and activate the THP-1 and THP-1 ILT3-KO cells to produce cytokines. The presence or absence of fibronectin and its interaction with ILT3 is able to be evaluated in this assay. Cell-free culture supernatants were collected and IL-8 was measured by Luminex assay (ProcartaPlex system; ThermoFisher Scientific). In some instances, IL-8 was normalized to that of THP-1 cells without FcR stimulation.

Figure 11:
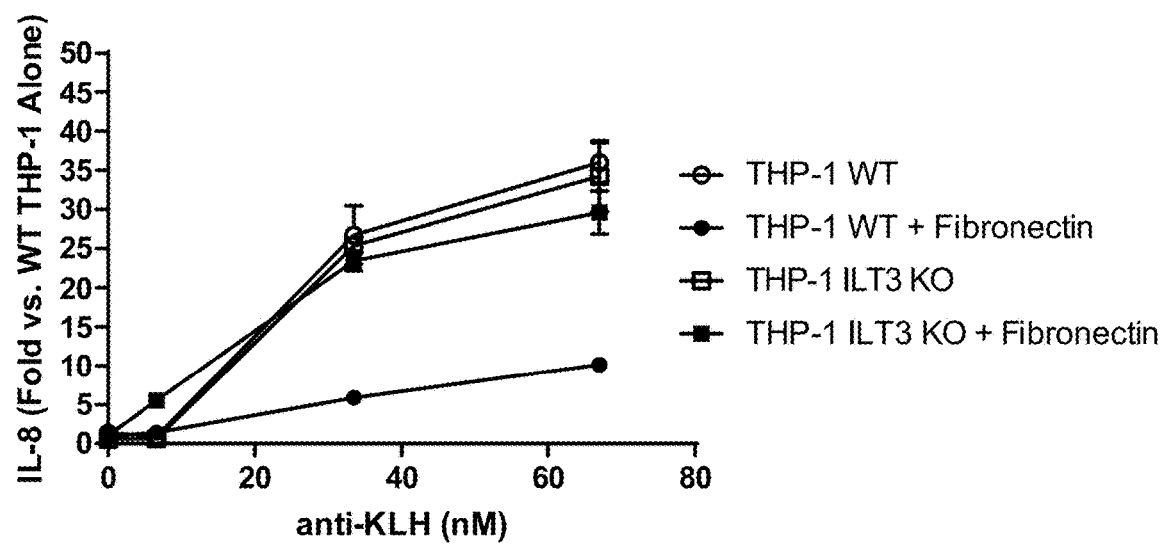
FIG. 11. FcR-induced activation in THP-1 cells. 96-well Maxisorp plates were co-coated with fibronectin at 5 μg/mL and an anti-KLH antibody at 0, 1, 5, and 10 μg/mL. Plates were incubated at room temperature for 2 hours, washed twice with PBS, and blocked with RPMI 1640 containing 10% FBS. THP-1 or THP-1 ILT3-KO cells ($2\times10^5$ cells/well) were added to the wells and the plates were incubated overnight at 37° C. Cell-free culture supernatants were collected and IL-8 was measured by Luminex assay. IL-8 was normalized to that of THP-1 cells without FcR stimulation.

As shown in FIG. 11, in both THP-1 cells and THP-1 cells lacking ILT3 (THP-1 ILT3-KO cells), anti-KLH antibody is able to activate the monocytes in a dose-dependent manner. In contrast, activation of THP-1 cells by anti-KLH antibody as assessed by IL-8 production is inhibited by the interaction of fibronectin and ILT3 on the cell surface. Activation of THP-1 cells by anti-KLH antibody as assessed by IL-8 production is inhibited only when fibronectin and ILT3 are both present and able to interact (i.e., no inhibition with THP-1 ILT3-KO cells and fibronectin).

These results demonstrate that ILT3 in the presence of fibronectin induces inhibition of FcR activation in myeloid cells.

A follow-up study was performed in the presence of an anti-ILT3 antibody. 96-well Maxisorp (Nunc) plates were co-coated with fibronectin at 5 µg/mL (Millipore) and an effectorless anti-KLH antibody at 5 µg/mL. Plates were incubated at room temperature for 2 hours, washed twice with PBS, and blocked with RPMI 1640 containing 10% FBS. THP-1 or THP-1 ILT3KO cells ($2 \times 10^5$ cells/well) were added to the wells in the presence of anti-ILT3 antibody 16C5 (effectorless; 5 µg/mL) or an anti-KLH antibody (effectorless; 5 µg/mL). The plates were incubated overnight at 37° C. and cell-free culture supernatants were collected and IL-8 was measured by Luminex assay.

Figure 12A:
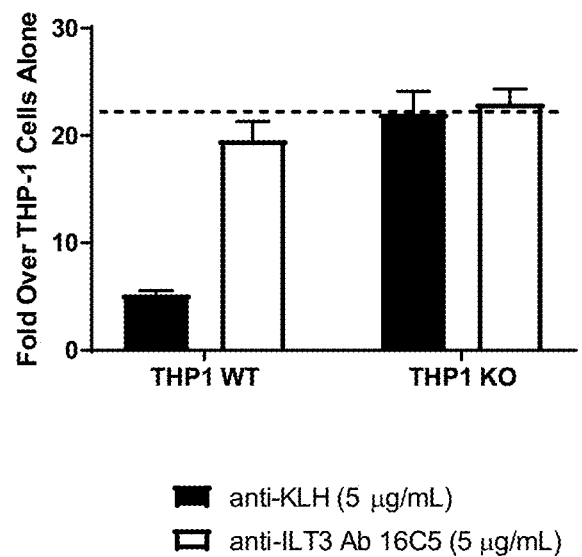
FIG. 12A-12C. FcR-induced activation in THP-1 cells. 12A. 96-well Maxisorp plates were co-coated with fibronectin and an anti-KLH antibody. Plates were incubated at room temperature for 2 hours, washed, and blocked with RPMI 1640 containing 10% FBS. THP-1 or THP-1 ILT3-KO cells ($2\times10^5$ cells/well) were added to the wells in the presence of anti-ILT3 antibody 16C5 (5 μg/mL) or an anti-KLH antibody. The plates were incubated overnight at 37° C., cell-free culture supernatants were collected, and IL-8 was measured by Luminex assay. 12B. Human monocytes were isolated from cryopreserved peripheral blood mononuclear cells. To generate dendritic cells, monocytes were plated at $2\times10^6$ cells/mL in X-VIVO™ 15 media containing human GM-CSF and human IL-4 and cultured for 5-7 days. 96-well Maxisorp plates were co-coated with fibronectin and an anti-KLH antibody. Plates were incubated at room temperature for 2 hours, washed, and blocked with RPMI 1640 containing 10% FBS. Dendritic cells ($2\times10^5$ cells/well) were added to the wells in the presence of anti-ILT3 antibody 16C5 or an anti-KLH antibody. The plates were incubated overnight at 37° C. and cell-free culture supernatants were collected and TNF-α was measured by Luminex assay. 12C. 96-well Maxisorp plates were coated with fibronectin and an anti-KLH antibody. Plates were incubated at room temperature for 1 hour, washed with PBS, and blocked with X-VIVO™ 15 media for 30 minutes. Dendritic cells were washed, resuspended in X-VIVO™ 15 media, and incubated with anti-ILT3 antibody 16C5, anti-ILT3 antibody ch5A7, or control anti-KLH antibody at room temperature for 20 minutes. Cells were plated into coated wells ($7\times10^4$ cells/well) and incubated overnight. Media was harvested for determination of TNFα production by Luminex assay after 24 hours.

As shown in FIG. 12A, the ILT3/fibronectin-induced inhibition of FcR activation of THP-1 cells is suppressed or blocked by anti-ILT3 antibody 16C5. In other words, an anti-ILT3 antibody was able to reverse the inhibition of the ILT3 and fibronectin interaction.

A similar experiment was set up with primary human dendritic cells. Human monocytes were isolated from cryopreserved peripheral blood mononuclear cells by negative selection using a Miltenyi Monocyte Isolation Kit, according to the manufacturer's instructions. To generate dendritic cells, monocytes were plated at $2 \times 10^6$ cells/mL in X-VIVO™ 15 media (Lonza) containing 50 ng/mL recombinant human GM-CSF and 50 ng/mL recombinant human IL-4 (both from Peprotech) and cultured for 5-7 days. As described above, 96-well Maxisorp (Nunc) plates were co-coated with fibronectin at 5 µg/mL (Millipore) and an effectorless anti-KLH antibody at 5 µg/mL. Plates were incubated at room temperature for 2 hours, washed twice with PBS, and blocked with RPMI 1640 containing 10% FBS. Dendritic cells ($2 \times 10^5$ cells/well) were added to the wells in the presence of anti-ILT3 antibody 16C5 (effectorless; 5 pg/mL) or an anti-KLH antibody (effectorless; 5 µg/mL). The plates were incubated overnight at 37° C. and cell-free culture supernatants were collected and TNF-α was measured by Luminex assay.

Figure 12B:
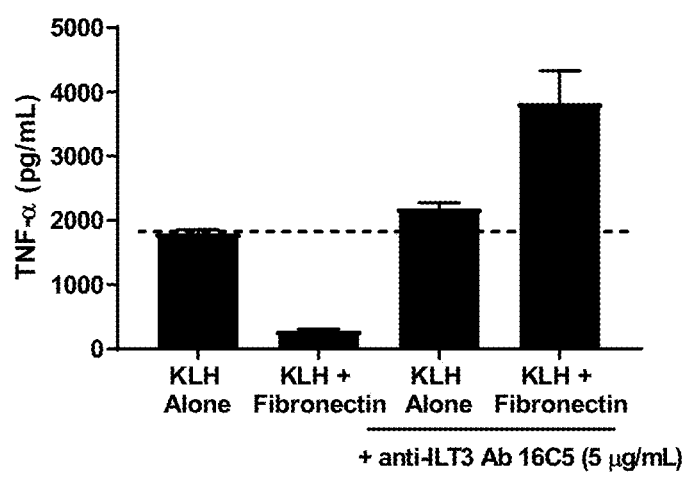

FIG. 12B shows that ILT3/fibronectin-induced suppression of FcR activation is observed in primary dendritic cells. Importantly, these results show that an exemplary anti-ILT3 antibody (e.g., antibody 16C5) is capable of inhibiting the suppression.

Figure 12C:
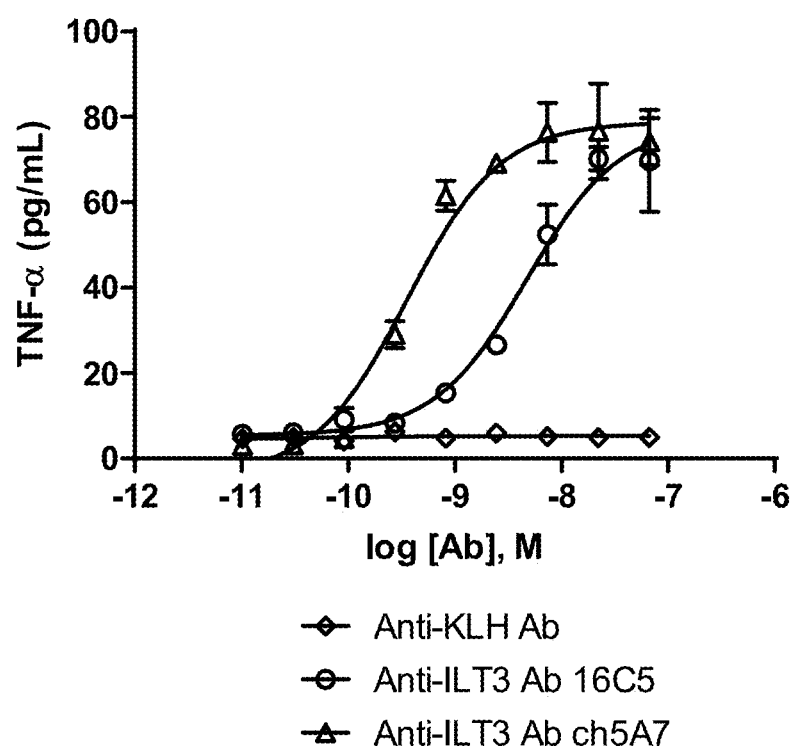

An additional study was done with anti-ILT3 antibodies 16C5 and ch5A7. As observed with previous assay, anti-ILT3 antibodies 16C5 and ch5A7 reversed the fibronectin-mediated suppression of TNF-α production by dendritic cells activated by FcR signaling (FIG. 12C).

Similar studies were undertaken in THP-1 Dual™ KI-mSTING cells that contain a NFκB-SEAP reporter (InvivoGen). Nunc Maxisorp plates were co-coated with human fibronectin and an effectorless anti-KLH antibody (each at 5 µg/mL) for 2 hr at room temperature. Plates were blocked with X-VIVO™ 15 media (Lonza) for 30 minutes prior to the addition of cells and test antibodies. THP-1 reporter cells in X-VIVO™ 15 media ($2 \times 10^6$ cells/mL) were mixed at a 1:1 ratio with a control antibody, anti-ILT3 antibody 16C5, or anti-ILT3 antibody ch5A7. The mixtures were incubated for 30 minutes, seeded onto plates at 100 µL/well, and the plates were incubated overnight. Reporter activity was measured by combining 25 µL of culture supernatant with 100 µL of Quanti-Blue SEAP substrate (InvivoGen), incubating the samples at 37° C. for 2 hours, and reading the absorbance at 620 nm.

Figure 13:
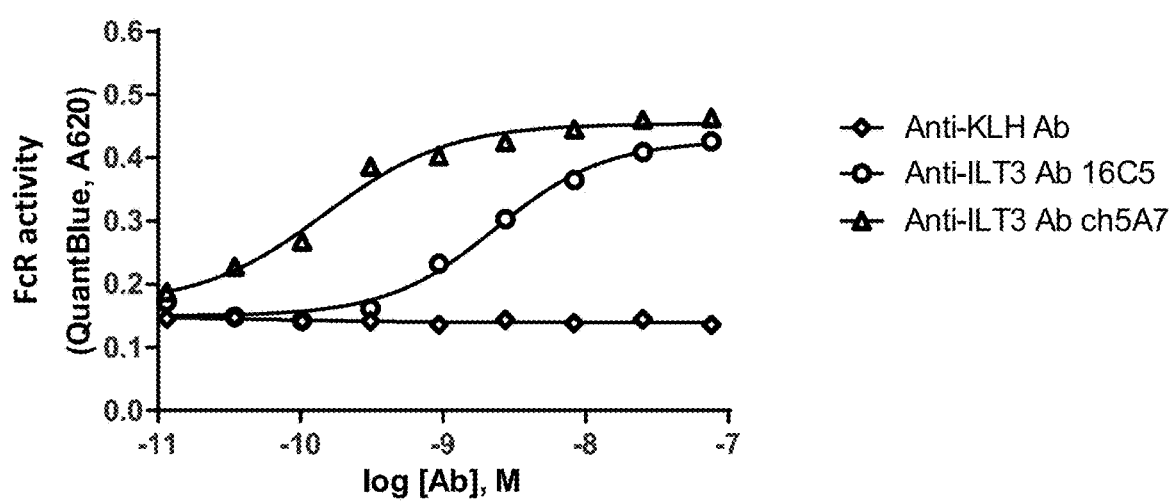
FIG. 13. FcR-induced activation in THP-1 cells. Nunc Maxisorp plates were co-coated with human fibronectin and an anti-KLH antibody for 2 hr at room temperature. Plates were blocked with X-VIVO™ 15 media for 30 minutes prior to the addition of cells and test antibodies. THP-1 Dual™ KI-mSTING reporter cells in X-VIVO™ 15 media ($2\times10^6$ cells/mL) were mixed at a 1:1 ratio with a control antibody, anti-ILT3 antibody 16C5, or anti-ILT3 antibody ch5A7. The mixtures were incubated for 30 minutes, seeded onto plates at 100 μL/well, and the plates were incubated overnight. Reporter activity was measured by combining 25 μL of culture supernatant with 100 μL of Quanti-Blue SEAP substrate, incubating the samples at 37° C. for 2 hours, and reading the absorbance at 620 nm.

The reporter is activated by interaction of the anti-KLH antibody and FcR on the surface of THP-1 cells resulting in activation of the FcR signaling pathway and production of secreted embryonic alkaline phosphate (SEAP). When ILT3 on the surface of THP-1 cells interacts with fibronectin, FcR signaling is suppressed and SEAP production is decreased. Anti-ILT3 antibodies 16C5 and ch5A7 blocked the ILT3/fibronectin interaction and reversed the suppression (FIG. 13).

The Detroit 551 cell line is composed of human skin fibroblasts established from normal fetal tissue. These cells have endogenously produced fibronectin bound to receptors on their surface. Detroit 551 cells allow for in vitro assays where fibronectin is naturally on the cell surface and not attached to assay plates. Detroit 551 cells were plated onto poly-D-lysine-coated 384-well plates at $6 \times 10^3$ cells/well (Greiner) and incubated for two days. Monolayers were rinsed with HBSS containing $Mg^{2+}$ and $Ca^{2+}$, leaving approximately 10 µL/well. ILT3-ECD-Fc was added to the wells (final concentration of 1 µg/mL) in the presence of ant-ILT3 antibody 16C5, anti-ILT3 antibody ch5A7, or control anti-KLH antibody. The antibodies were serially diluted 3-fold in media containing the ILT3-ECD-Fc (range of 66 nM to 0.27 nM). Cells were incubated for 1 hr at room temperature and then washed three times with HBSS and fixed with 3.7% formalin for 10 min. Monolayers were rinsed with PBS and blocked with 1% BSA in PBS before staining with Hoechst stain (2.5 µM) and a commercially available polyclonal anti-ILT3 antibody (R&D Systems). An AlexaFluor 647-conjugated rabbit anti-goat Fc secondary antibody (Jackson ImmunoResearch Labs) was added, cells were imaged, and the level of fluorescence was quantified using a CellInsight imaging system.

Figure 14:
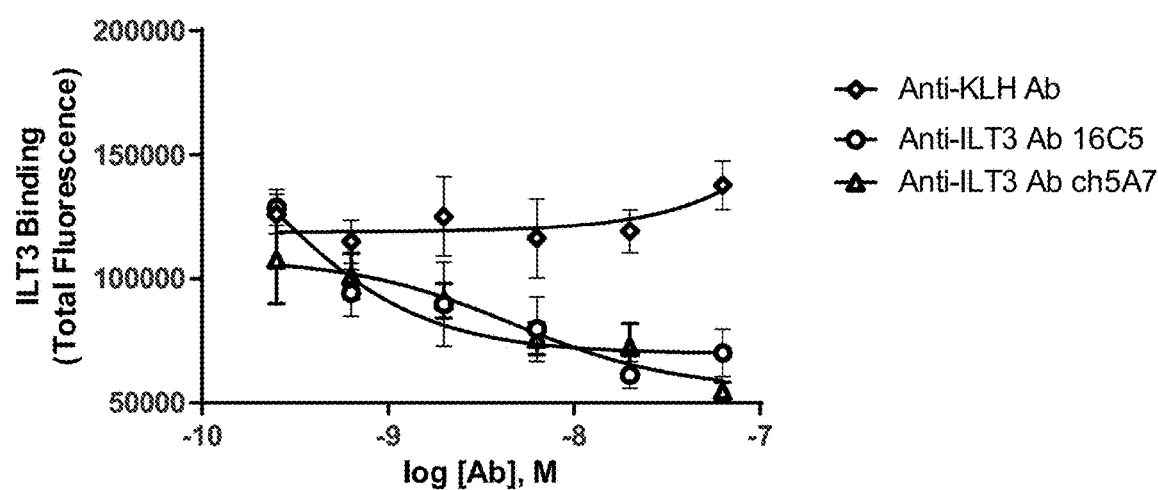
FIG. 14. ILT3 binding to endogenously expressed fibronectin. Detroit 551 cells were plated onto poly-D-lysine-coated 384-well plates at $6\times10^3$ cells/well and incubated for two days. Monolayers were rinsed with HBSS containing $Mg^{2+}$ and $Ca^{2+}$. ILT3-ECD-Fc was added to the wells in the presence of ant-ILT3 antibody 16C5, anti-ILT3 antibody ch5A7, or control anti-KLH antibody. The antibodies were serially diluted 3-fold in media containing the ILT3-ECD-Fc (range of 66 nM to 0.27 nM). Cells were incubated for 1 hr at room temperature and then washed three times with HBSS and fixed with 3.7% formalin for 10 min. Monolayers were rinsed with PBS and blocked with 1% BSA in PBS before staining with Hoechst stain and a commercially available polyclonal anti-ILT3 antibody. An AlexaFluor 647-conjugated rabbit anti-goat Fc secondary antibody was added, cells were imaged, and the level of fluorescence was quantified using a CellInsight imaging system.

As shown in FIG. 14, anti-ILT3 antibodies blocked the binding of ILT3-ECD to fibronectin-expressing cells.

Example 11

Effect of Anti-ILT3 Antibody on Chemokine Production by Dendritic Cells

Primary human monocytes were isolated from cryopreserved peripheral blood mononuclear cells by negative selection using a Miltenyi Monocyte Isolation Kit, according to the manufacturer's instructions. For differentiation of macrophages, monocytes were plated at $2 \times 10^6$ cells/mL in X-VIVO™ 15 media (Lonza) containing 100 ng/mL recombinant human M-CSF (Peprotech). After 2-3 days, fresh M-CSF was added to the media. After another 2-3 days, the macrophage cells are washed and harvested by scraping.

Dendritic cell conditioned media (used as the chemoattractant) was produced as follows. To generate dendritic cells, human monocytes were plated at $2 \times 10^6$ cells/mL in X-VIVO™ 15 media (Lonza) containing 50 ng/mL recombinant human GM-CSF and 50 ng/mL recombinant human IL-4 (both from Peprotech) and cultured for 5-7 days. These monocyte-derived dendritic cells were harvested and plated at $1 \times 10^6$ cells/mL onto fibronectin-coated Maxisorp plates (10 µg/mL) in the presence of anti-KLH antibody or anti-ILT3 antibody (10 µg/mL) and incubated for 2 days. The conditioned media was harvested and used in the migration assays described herein.

The macrophage migration assays were performed using an Incucyte® Zoom Live-Cell Analysis system (Sartorius). Membranes of Incucyte Clear-View 96-well chemotaxis plates (Sartorius) were pre-coated with 50 µg/mL of Matrigel® (diluted in X-VIVO™ 15 media with 10% FBS) for 30 minutes at 37° C., followed by 30 minutes at room temperature. Macrophages ($5 \times 10^3$ cells/well) were added to the top chambers of the chemotaxis plates, and the bottom chambers were filled with conditioned media derived from dendritic cells (as described herein). Phase-contrast images were captured every hour for 24 hours and data was analyzed using Incucyte analysis software.

Figure 15:
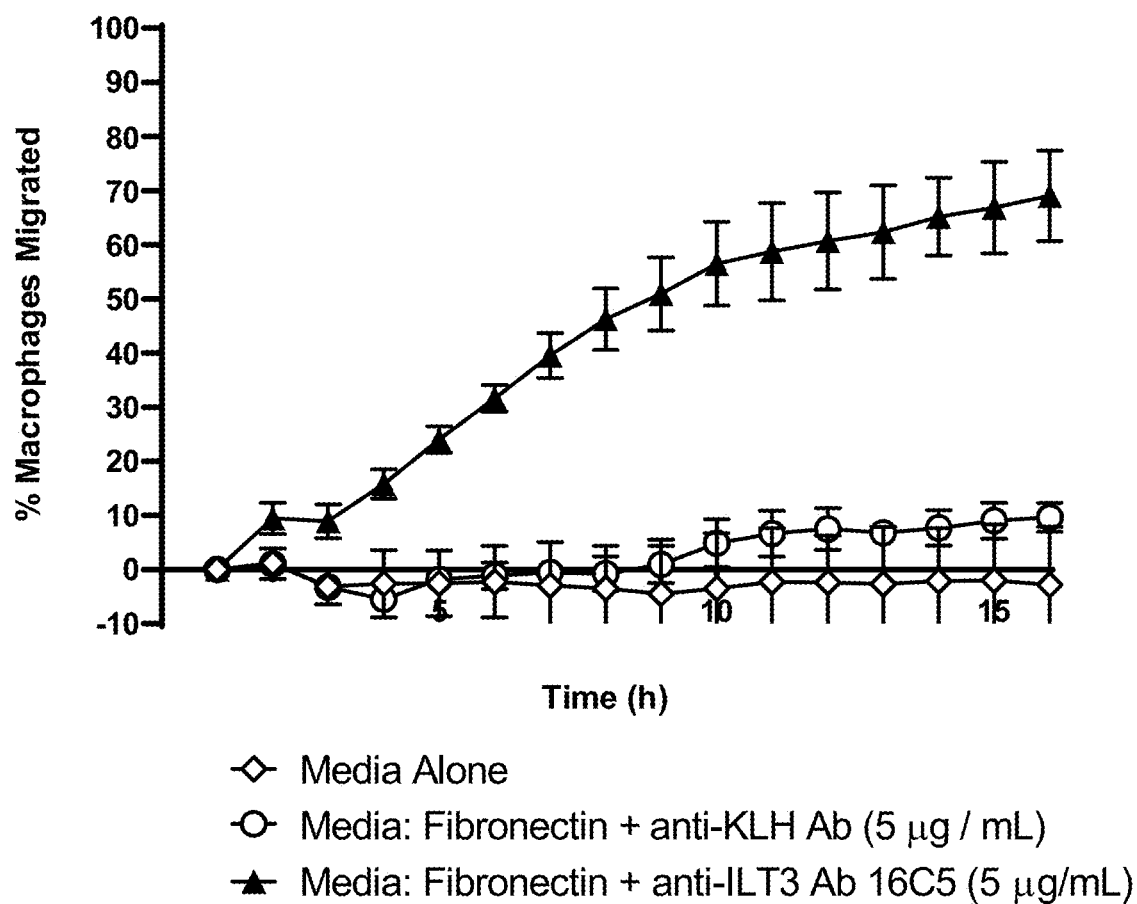
FIG. 15. Effect of anti-ILT3 antibody on chemokine production by dendritic cells. The macrophage migration assays were performed using an Incucyte® Zoom Live-Cell Analysis system. Membranes of Incucyte Clear-View 96-well chemotaxis plates (Sartorius) were pre-coated with 50 μg/mL of Matrigel® (diluted in X-VIVO™ 15 media with 10% FBS) for 30 minutes at 37° C., followed by 30 minutes at room temperature. Macrophages ($5\times10^3$ cells/well) were added to the top chambers of the chemotaxis plates, and the bottom chambers were filled with conditioned media derived from dendritic cells. Phase-contrast images were captured every hour for 24 hours and data was analyzed using Incucyte analysis software.

As shown in FIG. 15, macrophages did not migrate in response to conditioned media from fibronectin-treated dendritic cells. In contrast, a high percentage of macrophages migrated in response to conditioned media from dendritic cells treated with fibronectin in the presence of an anti-ILT3 antibody.

These results show that inhibition or blockade of the fibronectin/ILT3 interaction on dendritic cells by anti-ILT3 antibodies increases chemokine/chemoattractant production by the dendritic cells. The increased chemokine production results in an increase in macrophage migration. This suggests that anti-ILT3 antibodies could be effective in enhancing immune responses by helping to increase the recruitment of macrophages and other immune cells to the site of an immune response.

Example 12

Allogeneic Mixed Lymphocyte Reaction (MLR) Assays

Tolerogenic DCs were generated as described herein and resuspended at $4 \times 10^5$ cells/mL. Briefly, to generate tolerogenic DCs (tolDCs), monocytes were treated with GM-CSF and IL-4 for 5 days and then tolerized by treatment with 10 nM dexamethasone and 100 nM vitamin D3 (1α,25-dihydroxyvitamin D3) (both from Sigma-Aldrich) for 2 additional days. LX-2 cells (wild-type or a fibronectin knockout) were treated with 25 µg/mL mitomycin C (Sigma-Aldrich) for 1 hour at 37° C., washed, and resuspended at $1 \times 10^5$ cells/mL. Allogeneic T-cells were purified from peripheral blood monocytes by negative selection using a Miltenyi T-Cell Isolation kit and resuspended at $2 \times 10^6$ cells/mL. Anti-ILT3 antibody 16C5, anti-ILT3 antibody ch5A7, or a control antibody (50 µL) were added to wells of a 96-well, round-bottom plate. Mixed lymphocyte reaction (MLR) assays were set up by adding 50 µL of each cell type (T-cells, tolDCs, and LX-2 cells) for a final T-cell:tolDC:LX-2 cell ratio of 20:2:1. Plates were incubated for 5 days and then cell-free culture supernatants were harvested. Cytokine levels were determined using a Luminex assay (ProcartaPlex system; ThermoFisher Scientific). The media was replaced with fresh media containing tritiated thymidine ($^3$H-thymidine; Perkin-Elmer) at a concentration of 1 µCi/mL. After an additional 18 hrs of incubation, cells were harvested onto filters using a Tomtec cell harvester and $^3$H-thymidine incorporation was counted on a MicroBeta2 microplate reader.

In this assay, the mitomycin C-treated LX-2 cells serve as the source of fibronectin and are not capable of proliferating. In the absence of LX-2 cells (i.e., no fibronectin), the T-cells are activated by the dendritic cells and proliferate. In the presence of LX-2 cells, the activation of T-cells is suppressed and proliferation is reduced or eliminated.

Figure 16A:
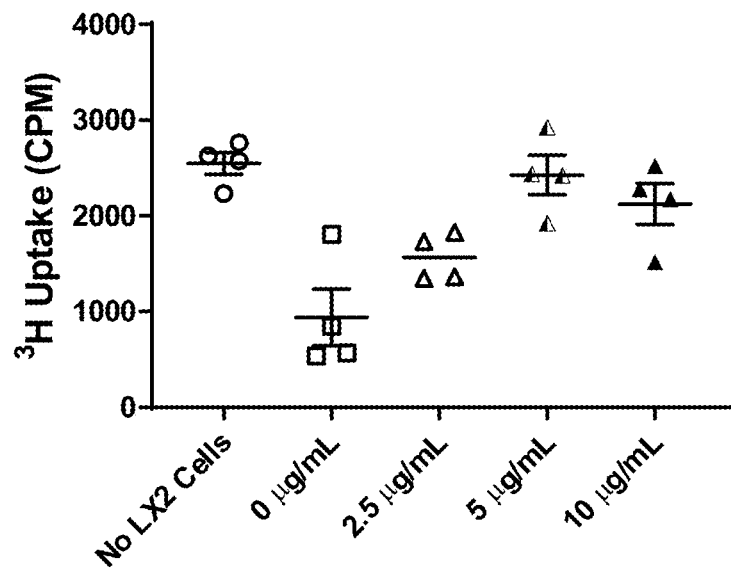
FIG. 16A-16B. Allogeneic MLR assay.
Figure 16B:
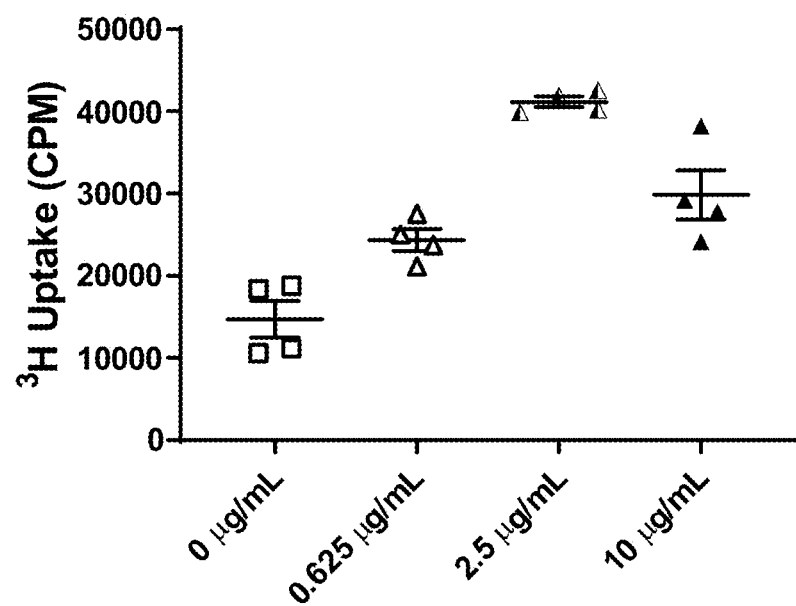

As shown in FIGS. 16A and 16B, anti-ILT3 antibodies 16C5 and ch5A7 reverse the fibronectin-mediated suppression of an allogeneic MLR in a dose-dependent manner. Activity of the anti-ILT3 antibodies is dependent on the presence of fibronectin, i.e., the suppression of MLR activity is not reversed in the presence of the anti-ILT3 antibodies if fibronectin is not present (data not shown).

Example 13

Effect of Anti-ILT3 Antibodies on Dendritic Cells

Dendritic cells were generated as described herein. 96-well Maxisorp plates (Nunc) were coated with fibronectin (5 µg/mL), incubated at room temperature for 1 hour, washed with PBS, and blocked with X-VIVO™ 15 media (Lonza) for 30 minutes. Dendritic cells were plated at $2 \times 10^5$ cells/well in the presence of anti-ILT3 antibody ch5A7, anti-ILT3 antibody Hz5A7.v5, anti-ILT3 antibody 45G10, or control antibody and incubated overnight. Antibody concentrations were 5-fold dilutions from 10 µg/mL to 0.128 ng/mL. Media was harvested for determination of MIP-la by Luminex assay (ProcartaPlex system; ThermoFisher Scientific) after 48 hours.

Figure 17A:
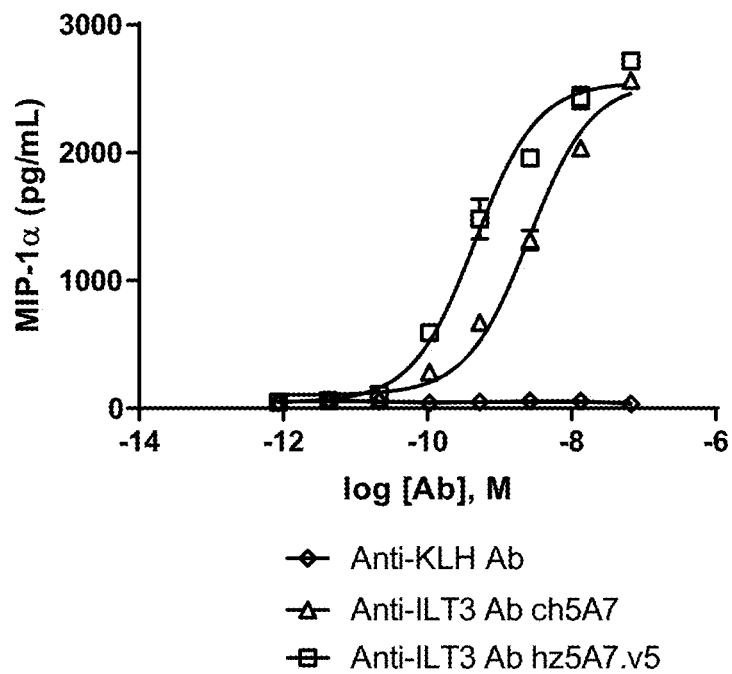
FIG. 17A-17B. Effect of anti-ILT3 antibodies on cytokine production from dendritic cells.
Figure 17B:
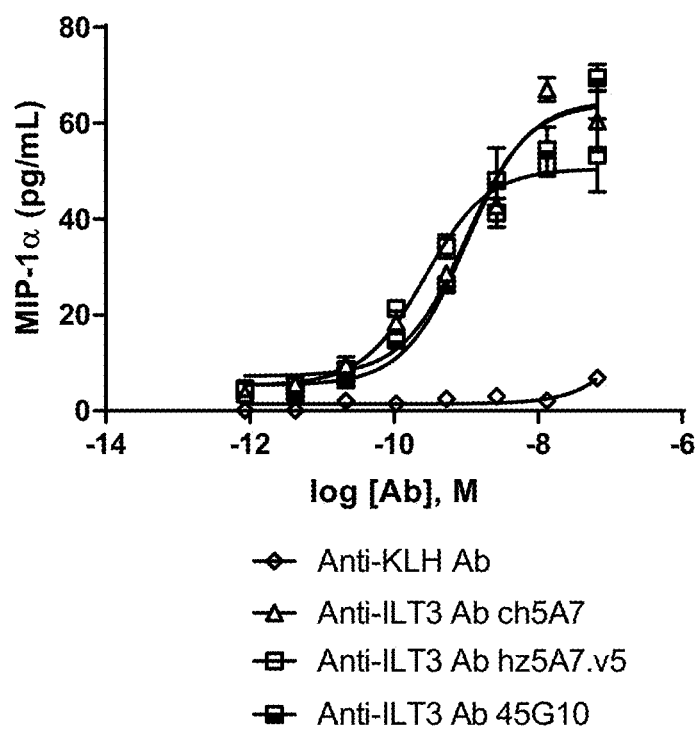

As shown in FIG. 17A, anti-ILT3 antibodies ch5A7 and Hz5A7.v5 increased levels of MIP-la produced by dendritic cells. FIG. 17B shows similar results with the inclusion of antibody 45G10.

Dendritic cells were generated as described herein. The dendritic cells were tolerized by treatment with 20 ng/mL recombinant human IL-10 (Peprotech). The cells were plated into 96-well, flat-bottom plates at $2 \times 10^5$ cells/well in media containing IL-10 and LPS (2 µg/mL; Sigma-Aldrich) and also in the presence of anti-ILT3 antibody 16C5, anti-ILT3 antibody ch5A7, anti-ILT3 antibody 45G10, or control anti-KLH antibody and incubated for 48 hours. Antibody concentrations were 5-fold dilutions from 5 µg/mL to 1.6 ng/mL. Media was harvested for measurement of TNF-α by Luminex assay (ProcartaPlex system; ThermoFisher Scientific).

Figure 18A:
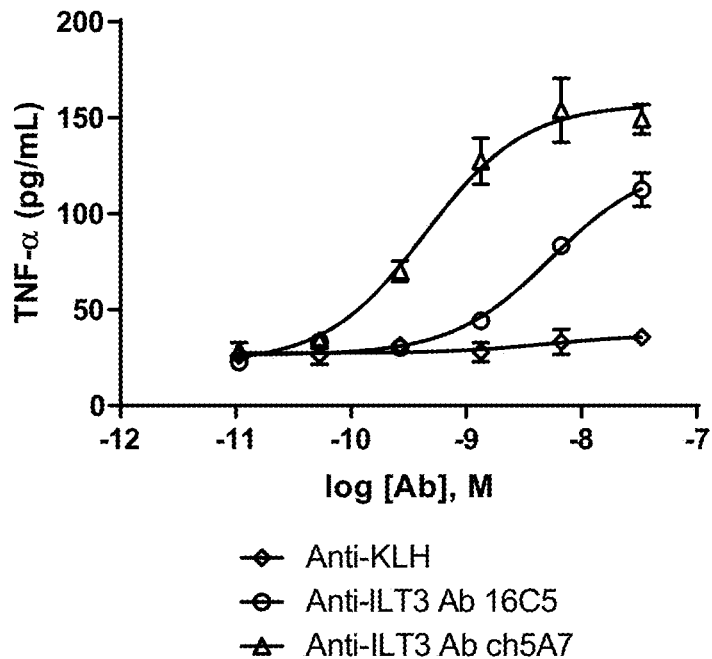
FIG. 18A-18B. Effect of anti-ILT3 antibodies on tolerized dendritic cells.
Figure 18B:
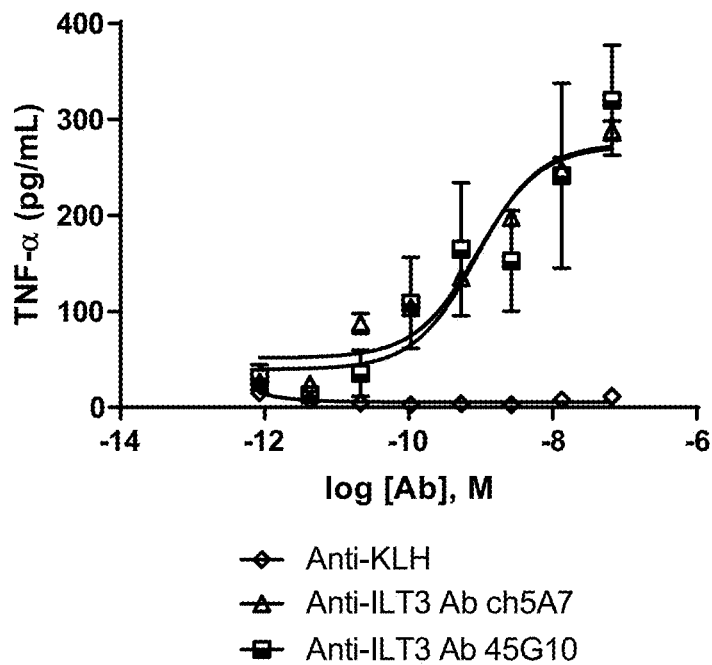

As shown in FIG. 18A, anti-ILT3 antibodies 16C5 and ch5A7 were able to restore the ability of IL-10-tolerized dendritic cells to respond to LPS as evaluated by the production of TNF-α. These results suggest that antibody ch5A7 may be a more potent antibody than 16C5. FIG. 18B shows results from a similar study with anti-ILT3 antibodies ch5A7 and 45G10. Other studies showed that anti-ILT3 antibody ch5A7 was also able to restore the ability of IL-10-tolerized dendritic cells to respond to a second stimulatory molecule, CD40L (data not shown).

Example 14

Allogeneic MLR in the Presence of Anti-ILT3 Antibody in Combination with an Anti-PD-1 Antibody Monocyte-derived dendritic cells were generated from peripheral blood monocytes as described herein. These cells were harvested and tolerized for 48 hours with recombinant human IL-10 (50 ng/mL) in the presence of an anti-KLH antibody or anti-ILT3 antibodies. Allogeneic T-cells were purified from peripheral blood monocytes by negative selection using the Miltenyi T Cell Isolation kit. For the MLR assays, T-cells and tolerized dendritic cells were mixed at a T-cell to 1DC ratio of 5:1 in the presence of anti-KLH antibody, anti-ILT3 antibody ch5A7, anti-PD-1 antibody (pembrolizumab), or anti-ILT3 antibody ch5A7 in combination with anti-PD-1 (all antibodies at 1 µg/mL each). Media was harvested for measurement of IFN-γ by Luminex assay (ProcartaPlex system; ThermoFisher Scientific) after 5 days.

Figure 19:
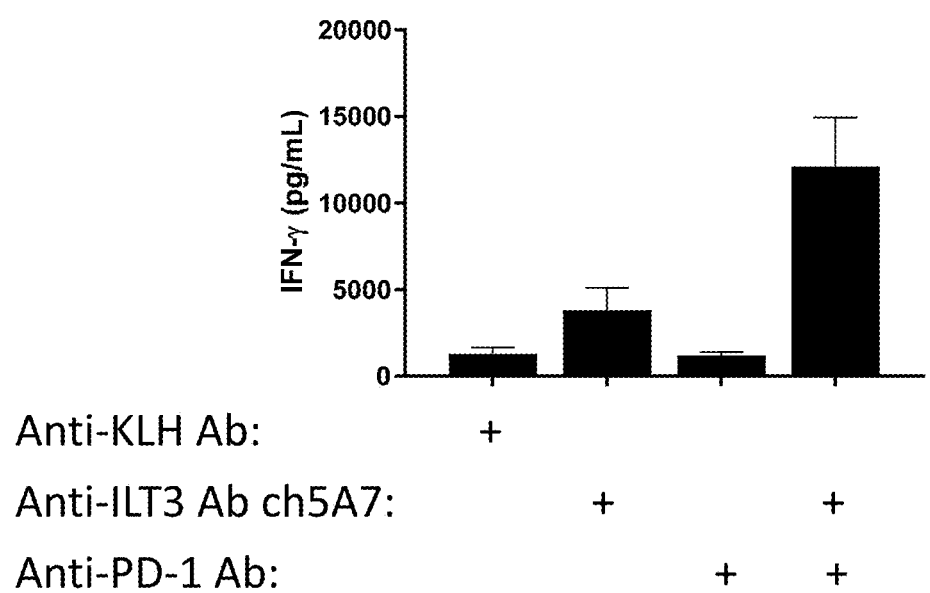
FIG. 19. Allogeneic MLR assay with anti-ILT3 antibody in combination with anti-PD-1 antibody.

As shown in FIG. 19, anti-ILT3 antibody ch5A7 reversed the suppression of response in IL-10-tolerized dendritic cells as demonstrated by an increase in IFN-γ production in T cells. This effect was increased more than 2-fold when the anti-ILT3 antibody was used in combination with an anti-PD-1 antibody.

Example 15

Generation of Humanized Antibody

Based on the antibody characterization data described herein as well as additional studies, antibody 5A7, 48A6, 45G10 were selected for humanization. Antibodies were humanized by methods known to those skilled in the art and humanized antibodies were referred to herein as Hz5A7, Hz48A6 and Hz45G10.

Antibody 5A7 had an undesirable methionine in the heavy chain variable region CDR3, REWR<u>M</u>TLYAMDY (SEQ ID NO:29). During the humanization process, the heavy chain variable region CDR3 was reengineered to remove the methionine and insert a tyrosine resulting in a heavy chain variable region CDR3 comprising REWR<u>Y</u>TLYAMDY (SEQ ID NO:105). In addition, antibody 5A7 was found to have a potential isomerization site in CDR1 of the light chain variable region, RASESV<u>D</u>SYGNSFMH (SEQ ID NO:30) as well as a potential deamidation site in CDR1 of the light chain variable region, RASESVDSYG<u>N</u>SFMH (SEQ ID NO:30). During the humanization process, the light chain variable region CDR1 was reengineered to remove the isomerization site and the deamidation site resulting in a light chain variable region CDR1 comprising RASESVE-<u>S</u>YG<u>SS</u>FMH (SEQ ID NO:106). This Hz5A7 variant that comprises all of these modifications is referred to as Hz5A7.v5. The heavy chain variable sequence of Hz5A7.v5 comprises the amino acid sequence SEQ ID NO:123 and the light chain variable sequence of Hz5A7.v5 comprises the amino acid sequence SEQ ID NO:124; CDRs are disclosed in Table 8.

The heavy chain sequence of antibody Hz5A7.v5 comprises an N297G mutation in the constant region that eliminates Fc effector functions. The heavy chain sequence of antibody Hz5A7.v5 is set forth as SEQ ID NO:125 and SEQ ID NO:126 (with and without signal sequence, respectively) and the light chain sequence of antibody Hz5A7.v5 is set forth as SEQ ID NO:127 and SEQ ID NO:128 (with and without signal sequence, respectively).

Several humanized variants of the 48A6 were generated. These include the B0/C2, B1/C2, C0/C2, C1/C2, and C2/C2 Hz48A6 antibodies. Antibody Hz48A6 B0/C2 comprises a heavy chain variable region (B0) with an amino acid sequence SEQ ID NO:156, and a light chain variable region (C2) with an amino acid sequence SEQ ID NO:161; antibody Hz48A6 B1/C2 comprises a heavy chain variable region (B1) with an amino acid sequence SEQ ID NO:157, and a light chain variable region (C2) with an amino acid sequence SEQ ID NO:161; antibody Hz48A6 C0/C2 comprises a heavy chain variable region (C0) with an amino acid sequence SEQ ID NO:158, and a light chain variable region (C2) with an amino acid sequence SEQ ID NO:161; antibody Hz48A6 C1/C2 comprises a heavy chain variable region (C1) with an amino acid sequence SEQ ID NO:159, and a light chain variable region (C2) with an amino acid sequence SEQ ID NO:161; and antibody Hz48A6 C2/C2 comprises a heavy chain variable region (C2) with an amino acid sequence SEQ ID NO:160, and a light chain variable region (C2) with an amino acid sequence SEQ ID NO:161. CDRs of antibody Hz48A6 are the same as the six CDRs of 48A6 and they are shown in Table 6.

Two humanized variants of 45G10 were generated. These include the A2/A4 and B1/A4 Hz45G10 antibodies. Antibody Hz45G10 A2/A4 comprises a heavy chain variable region (A2) with an amino acid sequence SEQ ID NO:162, and a light chain variable region (A4) with an amino acid sequence SEQ ID NO:164; and antibody Hz45G10 B1/A4 comprises a heavy chain variable region (B1) with an amino acid sequence SEQ ID NO:163, and a light chain variable region (A4) with an amino acid sequence SEQ ID NO:164. CDRs of antibody Hz45G10 are the same as the six CDRs of 45G10 and they are shown in Table 5.

Example 16

Characterization of Humanized Antibodies

The binding affinity of Hz5A7.v5 to human ILT3 and cyno ILT3 was determined using a Biacore system as described herein and compared with the binding affinity of the parental chimeric 5A7 (ch5A7) antibody and humanized 5A7 without any CDR modifications (Hz5A7.v1) (see Table 12).

TABLE 12

| | Human ILT3 | | | Cyno ILT3 | | |
|---|---|---|---|---|---|---|
| Antibody | $K_{on}$ [1/Ms] | $K_{off}$ [$s^{-1}$] | $K_D$ M | $K_{on}$ [1/Ms] | $K_{off}$ [$s^{-1}$] | $K_D$ M |
| ch5A7 | $2.9 \times 10^6$ | $1.7 \times 10^{-3}$ | $5.7 \times 10^{-10}$ | $7.5 \times 10^6$ | $1.8 \times 10^{-2}$ | $2.4 \times 10^{-9}$ |
| Hz5A7.v1 | $2.5 \times 10^6$ | $1.2 \times 10^{-3}$ | $4.8 \times 10^{-10}$ | $1.2 \times 10^7$ | $7.7 \times 10^{-3}$ | $6.5 \times 10^{-10}$ |
| Hz5A7.v5 | $2.8 \times 10^6$ | $8.1 \times 10^{-4}$ | $2.8 \times 10^{-10}$ | $1.1 \times 10^7$ | $7.1 \times 10^{-3}$ | $7.0 \times 10^{-10}$ |

Antibody Hz5A7.v5 had a binding affinity to human ILT3 of $2.8 \times 10^{-10}$ M at 37° C. as compared to the parental antibody ch5A7 binding affinity of $5.7 \times 10^{-10}$ M. In addition, antibody Hz5A7.v5 had a binding affinity to cyno ILT3 of $7.0 \times 10^{-10}$ M at 37° C. as compared to the parental antibody ch5A7 binding affinity of $2.4 \times 10^{-9}$ M.

These results demonstrated that the humanization process for antibody 5A7, as well as the removal of a methionine within CDR3 of the heavy chain variable region, a potential isomerization site within CDR1 of the light chain variable region, and a potential deamidation site within CDR1 of the light chain variable region, did not have a significant effect on the binding affinities to human ILT3 or cyno ILT3.

The binding affinities of various Hz48A6 and Hz45G10 antibodies to human ILT3 and cyno ILT3 were also determined using a Biacore system as described herein. Humanized antibodies comprising various combinations of a heavy chain variable region and a light chain variable region and a human Fc domain were tested, and compared with the binding affinity of the parental chimeric antibody (48A6 chimera comprising mouse 48A6 heavy and light variable regions and a human Fc domain, or 45G10 chimera comprising mouse 45G10 heavy and light variable regions and a human Fc domain).

Binding affinities of humanized 48A6 (Hz48A6) antibodies comprising a heavy chain variable region selected from B0 (SEQ ID NO:156), B1 (SEQ ID NO:157), C0 (SEQ ID NO:158), C1 (SEQ ID NO:159) and C2 (SEQ ID NO:160) and a light chain variable region C2 (SEQ ID NO:161) are shown in Table 13.

TABLE 13

| Antibody | Human ILT3 | | | Cyno ILT3 | | |
|---|---|---|---|---|---|---|
| | $K_{on}$ [1/Ms] | $K_{off}$ [$s^{-1}$] | $K_D$ M | $K_{on}$ [1/Ms] | $K_{off}$ [$s^{-1}$] | $K_D$ M |
| 48A6 chimera | $1.31 \times 10^7$ | $8.68 \times 10^{-4}$ | $0.66 \times 10^{-10}$ | $1.99 \times 10^6$ | $11 \times 10^{-2}$ | $54 \times 10^{-9}$ |
| B0-C2 | $2.80 \times 10^6$ | $7.84 \times 10^{-4}$ | $2.8 \times 10^{-10}$ | $2.13 \times 10^5$ | $9.7 \times 10^{-2}$ | $455 \times 10^{-9}$ |
| B1-C2 | $3.05 \times 10^6$ | $7.64 \times 10^{-4}$ | $2.5 \times 10^{-10}$ | $1.74 \times 10^5$ | $9.2 \times 10^{-2}$ | $531 \times 10^{-9}$ |
| C0-C2 | $3.45 \times 10^6$ | $5.41 \times 10^{-4}$ | $1.6 \times 10^{-10}$ | $3.27 \times 10^5$ | $5.8 \times 10^{-2}$ | $177 \times 10^{-9}$ |
| C1-C2 | $2.72 \times 10^6$ | $7.05 \times 10^{-4}$ | $2.6 \times 10^{-10}$ | $1.14 \times 10^5$ | $8.8 \times 10^{-2}$ | $770 \times 10^{-9}$ |
| C2-C2 | $3.06 \times 10^6$ | $7.52 \times 10^{-4}$ | $2.4 \times 10^{-10}$ | $2.17 \times 10^5$ | $8.2 \times 10^{-2}$ | $377 \times 10^{-9}$ |

Binding affinities of humanized 45G10 (Hz45G10) antibodies comprising a heavy chain variable region selected from A2 (SEQ ID NO: 162) and B1 (SEQ ID NO: 163) and a light chain variable region A4 (SEQ ID NO: 164) are shown in Table 14.

TABLE 14

| Antibody | Human ILT3 | | | Cyno ILT3 | | |
|---|---|---|---|---|---|---|
| | $K_{on}$ [1/Ms] | $K_{off}$ [$s^{-1}$] | $K_D$ M | $K_{on}$ [1/Ms] | $K_{off}$ [$s^{-1}$] | $K_D$ M |
| 45G10 chimera | $2.3 \times 10^6$ | $3.4 \times 10^{-4}$ | $1.4 \times 10^{-10}$ | $4.1 \times 10^5$ | $1.5 \times 10^{-2}$ | $37 \times 10^{-9}$ |
| A2-A4 | $1.4 \times 10^6$ | $2.8 \times 10^{-4}$ | $2 \times 10^{-10}$ | $1.9 \times 10^5$ | $2 \times 10^{-2}$ | $113 \times 10^{-9}$ |
| B1-A4 | $1.3 \times 10^6$ | $2.6 \times 10^{-4}$ | $2 \times 10^{-10}$ | $1.2 \times 10^6$ | $9 \times 10^{-2}$ | $76 \times 10^{-9}$ |

Example 17

Effects of Anti-ILT3 Antibodies on Macrophages

Macrophages were generated from primary human monocytes and polarized as described. Maxisorp plates (Nunc) were coated with anti-KLH and human fibronectin (FC0101, Millipore) (each at 5 µg/mL) at room temperature for 1 hour, then washed with PBS and blocked with X-Vivo 15 media for 30 minutes. For assaying anti-ILT3 antibody effects on macrophages, cells were washed, resuspended in X-Vivo 15 media, and incubated with the designated antibodies at room temperature for 20 minutes, then plated on coated wells ($7 \times 10^4$ cells/well in a 100 µL volume) and incubated overnight. Media was harvested for evaluation of cytokine secretion by Luminex assay (ProcartaPlex system; ThermoFisher Scientific) after 24 hours.

Figure 20A:
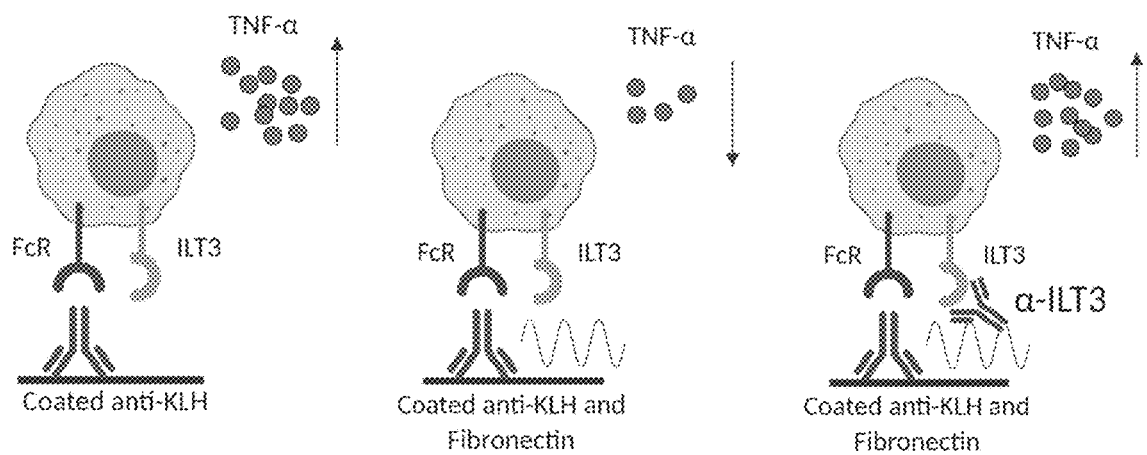
FIG. 20A-20B show that anti-ILT3 antibodies reversed fibronectin-mediated inhibition of FcR signaling and TNF-α production in primary macrophages.
Figure 20B:
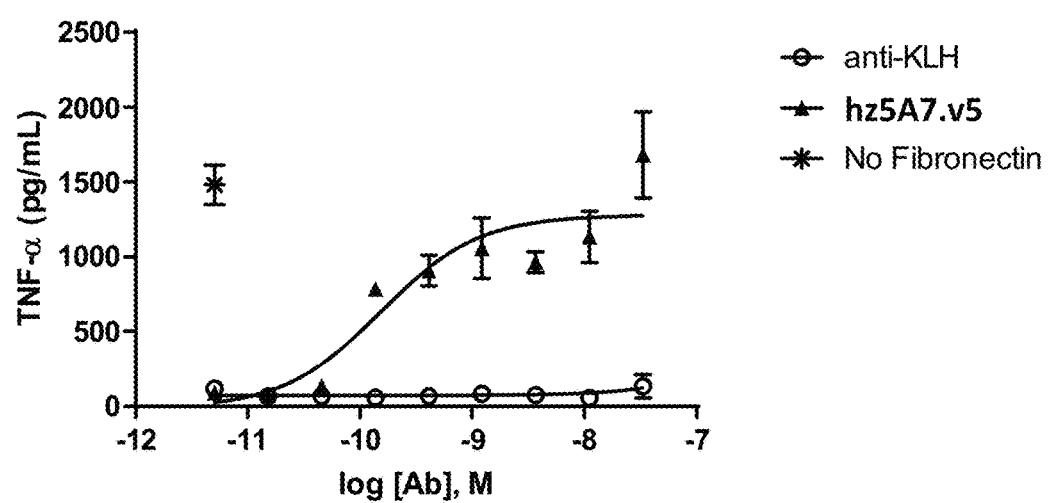

As shown in FIGS. 20A and 20B, unpolarized (MO) macrophages were stimulated with anti-KLH via the Fc receptor (FcR) and secreted TNF-α. In the presence of fibronectin, TNF-α secretion by the macrophages were inhibited. The inhibition of fibronectin induced TNF-α production in macrophages were blocked by an anti-ILT3 antibody (e.g., hz5A7.v5), which blocked interaction between ILT3 and fibronectin, and restored TNF-α secretion. Thus, an anti-ILT3 antibody described herein blocks fibronectin-mediated inhibition of FcR signaling in macrophages and increases FcR-driven cytokine production by macrophages in the presence of fibronectin.

Figure 21A:
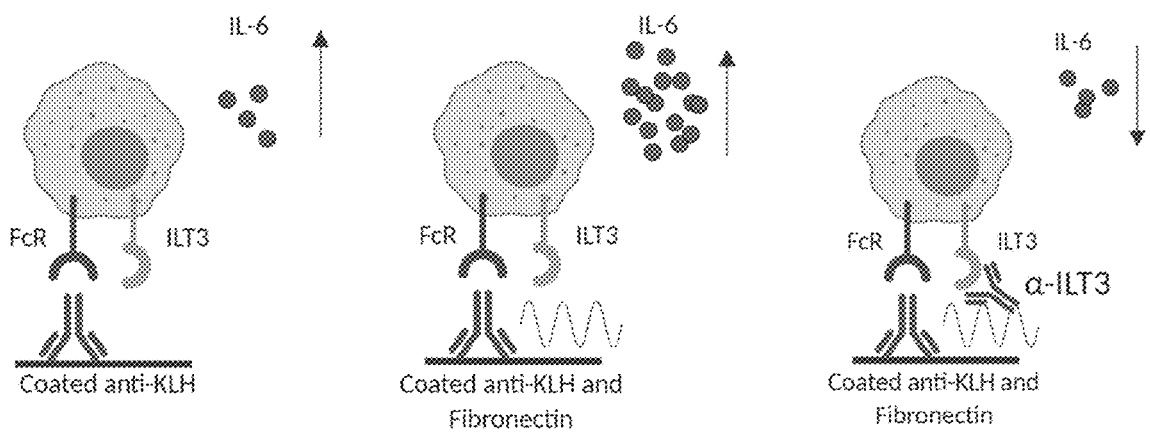
FIG. 21A-21B show that anti-ILT3 antibodies reversed fibronectin-mediated inhibition of FcR signaling and IL-6 production in IL-10 polarized macrophages.
Figure 21B:
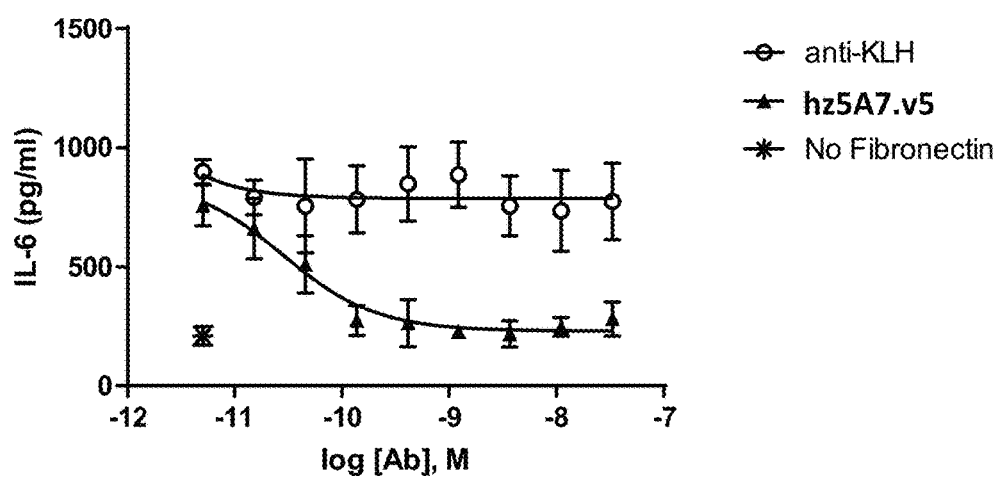

As shown in FIGS. 21A and 21B, IL-10-polarized (M2c) macrophages were stimulated with anti-KLH via the Fc receptor (FcR) and secreted little IL-6. In the presence of fibronectin, IL-6 secretion by the macrophages was increased. The increase of fibronectin induced IL-6 production in macrophages were blocked by an anti-ILT3 antibody (e.g., hz5A7.v5), which blocked interaction between ILT3 and fibronectin, and inhibited IL-6 production. Thus, an anti-ILT3 antibody described herein blocks fibronectin-mediated inhibition of FcR signaling in macrophages.

Example 18

Effects of Anti-ILT3 Antibodies on Cells Expressing Cynomolgus ILT3

A reporter cell line was generated to express cynomolgus ILT3. THP-1 Dual KI-mSTING reporter cells (Invivogen) were used, from which human ILT3 was deleted via CRISPR/Cas9-based gene editing. The cells were then stably infected with retrovirus containing cynomolgus ILT3 in the pBABEpuro vector. Nunc Maxisorp plates were co-coated with human fibronectin and an anti-KLH antibody for 2 hours at room temperature, then blocked with X-Vivo 15 media for 30 minutes at room temperature. The cynomolgus ILT3-expressing reporter cells were resuspended in X-Vivo 15 media ($1.5 \times 10^6$ cells/mL) and mixed at a 1:1 ratio with media containing serial dilutions of a control antibody or the anti-ILT3 antibody ch5A7. The mixtures were incubated for 30 minutes before being seeded onto the plates at 100 µL/well. The mixture was then incubated on the plates overnight before the NF-kB reporter activity from the cells was measured. To measure the reporter activity, 25 µL of culture supernatant was combined with 100 µL of Quanti-Blue SEAP substrate and incubated at 37° C. for 2 hours. Absorbance was read at 620 nm.

Figure 22:
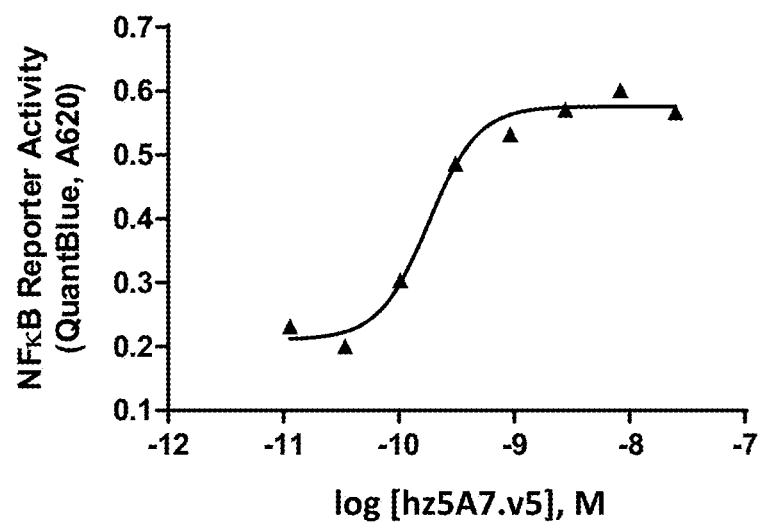
FIG. 22 shows that anti-ILT3 antibodies reversed fibronectin-mediated inhibition of FcR signaling (NF-kB reporter activity) in THP-1 cells expressing cynomolgus ILT3.

As shown in FIG. 22, an anti-ILT3 antibody (e.g., hz5A7.v5) reversed fibronectin-mediated inhibition of NF-kB reporter activity in THP-1 by blocking the interaction between cyno ILT3 and fibronectin.

Example 19

Effects of Anti-ILT3 Antibodies on Primary Cynomolgus Dendritic Cells

Figure 23:
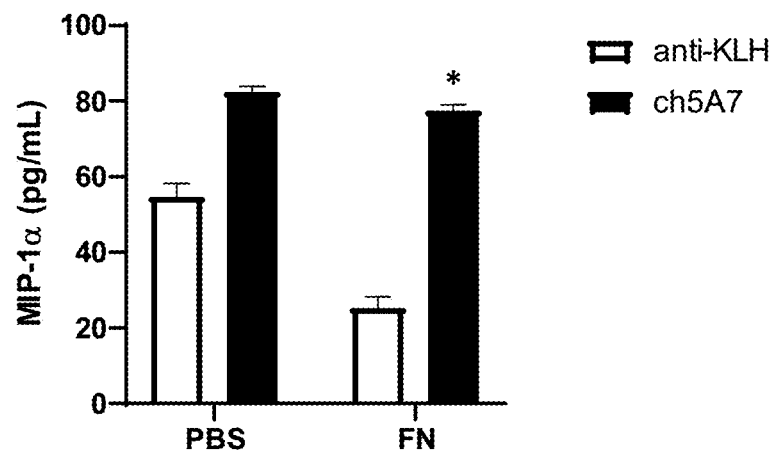
FIG. 23 shows that anti-ILT3 antibodies reversed fibronectin (FN)-mediated inhibition of MIP-1α production in cynomolgus monocyte derived dendritic cells. * indicates $P<0.001$.

Monocytes were isolated from cryopreserved cynomolgus PBMCs by positive selection using non-human primate CD14 microbeads (Miltenyi Biotec), and differentiated into monocyte-derived dendritic cells (DCs) by 5-day treatment with human GM-CSF and IL-4, as described for human monocyte-derived DCs. Maxisorp plates (Nunc) were coated with PBS or fibronectin (5 pg/mL) for 1 hour at room temperature, then washed with PBS and blocked with X-Vivo 15 media (Lonza) for 30 minutes at room temperature. The dendritic cells were plated at $2\times10^5$ cells/well in the presence of 2 µg/mL anti-KLH (control antibody) or anti-ILT3 antibody ch5A7 and cultured overnight. Cell culture media was harvested after 24 hours, and the MIP-la concentration was determined by Luminex assay using the ProcartaPlex system (ThermoFisher Scientific). As shown in FIG. 23, fibronectin reduced MIP-la secretion in the cynomolgus monocyte-derived DCs, and this reduction was rescued by ch5A7 which blocked interaction between cyno ILT3 and fibronectin.

Figure 24:
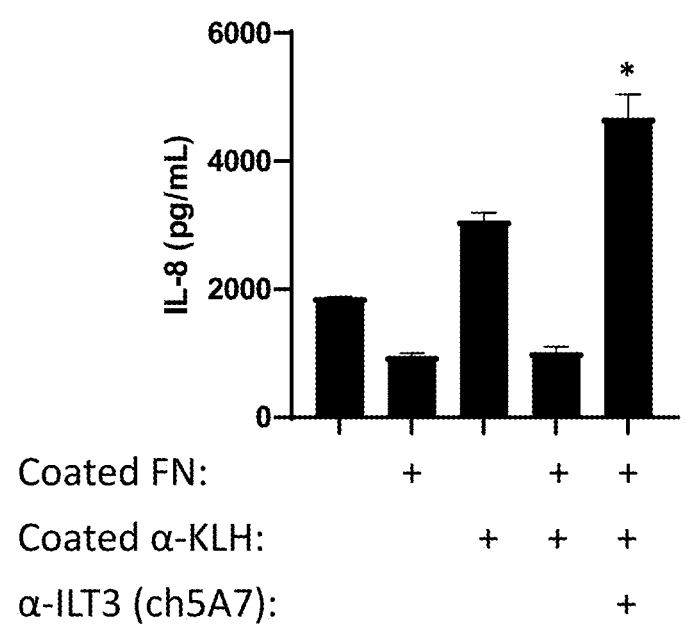
FIG. 24 shows that anti-ILT3 antibodies reversed fibronectin (FN)-mediated inhibition of FcR signaling and IL-8 production in cynomolgus monocyte derived dendritic cells. * indicates $P<0.01$.

In a separate experiment, DCs were generated from primary cynomolgus monocytes as described herein. Maxisorp plates (Nunc) were coated with anti-KLH and human fibronectin (FC0101, Millipore) (each at 5 µg/mL) at room temperature for 1 hour, then washed with PBS and blocked with X-Vivo 15 media for 30 minutes. The DCs were resuspended in X-Vivo 15 media, incubated with anti-KLH or anti-ILT3 ch5A7 at room temperature for 20 minutes, and then plated on coated wells ($7\times10^4$ cells/well in a 100 µL volume) for culturing overnight. After 24 hours of culturing, the culture supernatant was harvested for evaluation of IL-8 secretion by DCs using Luminex assay (ProcartaPlex system; ThermoFisher Scientific). As shown in FIG. 24, fibronectin reduced IL-8 secretion from the cynomolgus monocyte-derived DCs, and this reduction was rescued by ch5A7 which blocked interaction between cyno ILT3 and fibronectin.

Example 20

Anti-Tumor Activity of Anti-ILT3 Antibodies in Humanized Mouse Model

All animal procedures were performed under an Institutional Animal Care and Use Committee (IACUC)-approved animal use protocol (NGM-27-2017). NCI-H2009 lung adenocarcinoma cells (ATCC) were grown in RPMI 1640 containing 10% FBS and 1% penicillin/streptomycin. NSG mice were injected subcutaneously on the left flank with $3\times10^6$ NCI-H2009 tumor cells. Seven to 10 days after the implantation of tumor cells, each mouse was injected with $4\times10^6$ primary human PBMCs via the tail vein. Tumor growth was measured twice weekly using calipers. Once the tumors reached a volume of approximately 50 mm³, mice were treated twice weekly with 10 mg/kg control anti-KLH antibody or anti-ILT3 antibody 48A6 by intraperitoneal injection (3 doses total). Tumors was monitored and measured twice weekly. Once tumors reached a volume of approximately 2000 mm³, mice were sacrificed.

Figure 25:
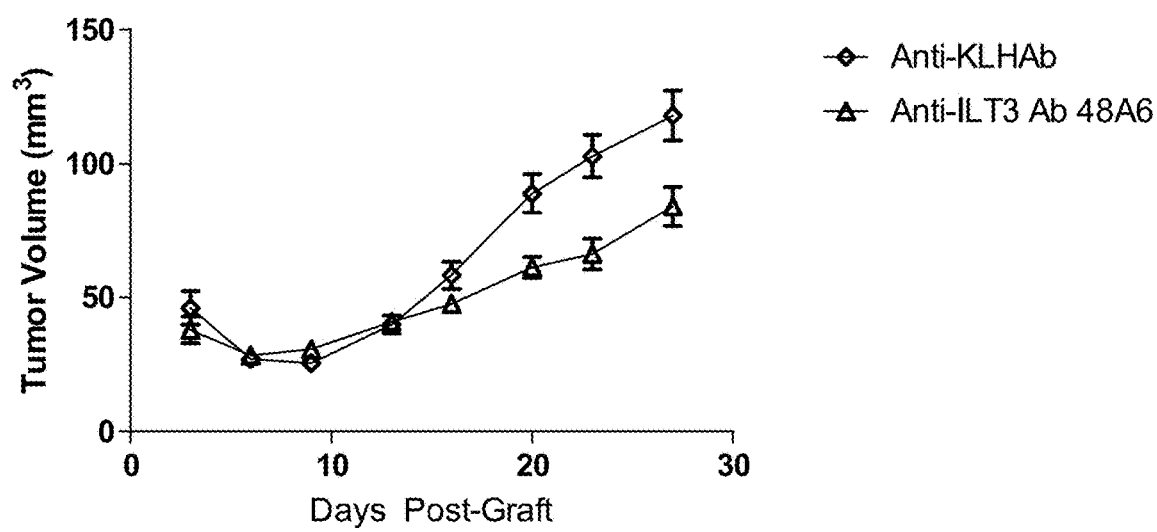
FIG. 25. Anti-tumor activity of anti-ILT3 antibodies in humanized mouse model.

As shown in FIG. 25, the anti-ILT3 antibody 48A6 significantly inhibited tumor growth in this mouse model.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application. CDR sequences are listed in Tables 1-4.

```
Human ILT3 amino acid sequence with predicted signal sequence underlined
                                                                    (SEQ ID NO: 1)
MIPTFTALLCLGLSLGPRTHMQAGPLPKPTLWAEPGSVISWGNSVTIWCQGTLEAREYR

LDKEESPAPWDRQNPLEPKNKARFSIPSMTEDYAGRYRCYYRSPVGWSQPSDPLELVMT

GAYSKPTLSALPSPLVTSGKSVTLLCQSRSPMDTFLLIKERAAHPLLHLRSEHGAQQHQA

EFPMSPVTSVHGGTYRCFSSHGFSHYLLSHPSDPLELIVSGSLEDPRPSPTRSVSTAAGPE

DQPLMPTGSVPHSGLRRHWEVLIGVLVVSILLLSLLLFLLLQHWRQGKHRTLAQRQADF

QRPPGAAEPEPKDGGLQRRSSPAADVQGENFCAAVKNTQPEDGVEMDTRQSPHDEDPQ

AVTYAKVKHSRPRREMASPPSPLSGEFLDTKDRQAEEDRQMDTEAAASEAPQDVTYAQ

LHSFTLRQKATEPPPSQEGASPAEPSVYATLAIH

Human ILT3 amino acid sequence without predicted signal sequence
                                                                    (SEQ ID NO: 2)
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVSGSLEDPRPSPTRSVSTAAGPEDQPLMPTGSVPHSGLRRHWE

VLIGVLVVSILLLSLLLFLLLQHWRQGKHRTLAQRQADFQRPPGAAEPEPKDGGLQRRS
```

```
SPAADVQGENFCAAVKNTQPEDGVEMDTRQSPHDEDPQAVTYAKVKHSRPRREMASP

PSPLSGEFLDTKDRQAEEDRQMDTEAAASEAPQDVTYAQLHSFTLRQKATEPPPSQEGA

SPAEPSVYATLAIH
```

Human ILT3 Extracellular domain (aa 22-259) (SEQ ID NO: 3)
```
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVSGSLEDPRPSPTRSVSTAAGPEDQPLMPTGSVPHSGLRRHWE
```

Human ILT3 Ig-like C2-type Domain 1 amino acid sequence without N-terminal domain (aa 27-118) (SEQ ID NO: 4)
```
PKPTLWAEPGSVISWGNSVTIWCQGTLEAREYRLDKEESPAPWDRQNPLEPKNKARFSI

PSMTEDYAGRYRCYYRSPVGWSQPSDPLELVMT
```

Human ILT3 Ig-like C2-type Domain 2 amino acid sequence (aa 124-218) (SEQ ID NO: 5)
```
PTLSALPSPLVTSGKSVTLLCQSRSPMDTFLLIKERAAHPLLHLRSEHGAQQHQAEFPMS

PVTSVHGGTYRCFSSHGFSHYLLSHPSDPLELIVS
```

Cyno ILT3 amino acid sequence with predicted signal sequence underlined (SEQ ID NO: 6)
```
MTPPLTVLFCLGLSLGPRTCVQAGPLPKPTVWAEPGSVISWGSPVTIWCQGTLDAQEYH

LDKEGSPAPWDTQNPLEPRNKAKFSIPSMTQHYAGRYRCYYHSHPDWSEDSDPLDLVM

TGAYSKPILSVLPSPLVTSGESVTLLCQSQSPMDTFLLFKEGAAHPLRLRSQHGAQLHW

AEFPMGPVTSVHGGTYRCISSRSFSHYLLSRPSDPVELTVLGSLESPSPSPTRSISAAAGPE

DQSLMPTGSDPQSGLRRHWEVLIGVLVVSILLLSLVFFLLLQHWRQGKHRTSAQRQADF

QRPPGAAEPEPKDGGLQRRSRPAADVQGENPNAAMKDTQPEDGVELDSRQRPHDEDPQ

AVTYARVKHSGPRREMASPPSPLSEEFLDTKDTQAEEDRQMDTQAATSEAPQDVTYAQ

LQSLTLRREATEPPPPQKREPSAEPSVYATLAIH
```

Cyno ILT3 amino acid sequence without predicted signal sequence (SEQ ID NO: 7)
```
QAGPLPKPTVWAEPGSVISWGSPVTIWCQGTLDAQEYHLDKEGSPAPWDTQNPLEPRN

KAKFSIPSMTQHYAGRYRCYYHSHPDWSEDSDPLDLVMTGAYSKPILSVLPSPLVTSGE

SVTLLCQSQSPMDTFLLFKEGAAHPLRLRSQHGAQLHWAEFPMGPVTSVHGGTYRCIS

SRSFSHYLLSRPSDPVELTVLGSLESPSPSPTRSISAAAGPEDQSLMPTGSDPQSGLRRHW

EVLIGVLVVSILLLSLVFFLLLQHWRQGKHRTSAQRQADFQRPPGAAEPEPKDGGLQRR

SRPAADVQGENPNAAMKDTQPEDGVELDSRQRPHDEDPQAVTYARVKHSGPRREMAS

PPSPLSEEFLDTKDTQAEEDRQMDTQAATSEAPQDVTYAQLQSLTLRREATEPPPPQKRE

PSAEPSVYATLAIH
```

Cyno ILT3 Extracellular domain (aa 22-259) (SEQ ID NO: 8)
```
QAGPLPKPTVWAEPGSVISWGSPVTIWCQGTLDAQEYHLDKEGSPAPWDTQNPLEPRN

KAKFSIPSMTQHYAGRYRCYYHSHPDWSEDSDPLDLVMTGAYSKPILSVLPSPLVTSGE

SVTLLCQSQSPMDTFLLFKEGAAHPLRLRSQHGAQLHWAEFPMGPVTSVHGGTYRCIS

SRSFSHYLLSRPSDPVELTVLGSLESPSPSPTRSISAAAGPEDQSLMPTGSDPQSGLRRHW

E
```

-continued

Cyno ILT3 Ig-like C2-type Domain 1 amino acid sequence without N-terminal domain
(aa 27-118)
(SEQ ID NO: 9)
PKPTVWAEPGSVISWGSPVTIWCQGTLDAQEYHLDKEGSPAPWDTQNPLEPRNKAKFSI

PSMTQHYAGRYRCYYHSHPDWSEDSDPLDLVMT

Cyno ILT3 Ig-like C2-type Domain 2 amino acid sequence without N-terminal domain
(aa 124-218)
(SEQ ID NO: 10)
PILSVLPSPLVTSGESVTLLCQSQSPMDTFLLFKEGAAHPLPRLRSQHGAQLHWAEFPMG

PVTSVHGGTYRCISSRSFSHYLLSRPSDPVELTVL

3A3 Heavy chain variable region amino acid sequence
(SEQ ID NO: 109)
QVQLKESGPGLVAPSQSLSITCTVSGFSLTSYGVHWVRQPPGKGLEWLGVIWPGGTINY

NSALMSRLSISKDNSKSQVFLKLNSLQTDDTAMYYCASDKYDGGWFAYWGQGTLVTV

SA

3A3 Light chain variable region amino acid sequence
(SEQ ID NO: 110)
DIVMTQSQKFMSTSVGDRVSITCKASQNVRTAVAWYQQKPGQSPEALIYLASNRHTGV

PDRFTGSGSGTDFSLSISNVQSEDLADYFCLQHLNYPLTFGSGTKLEIK

5A7 Heavy chain variable region amino acid sequence
(SEQ ID NO: 111)
EVKLVESGGGLVKPGGSLKLSCAASGFTFSSYGMSWVRQTPEKRLEWVATISGGGSYT

NYPDSVKGRLTISRDNAKKNLYLEMSSLRSEDTALYYCARREWRMTLYAMDYWGQGT

SVTVSS

5A7 Light chain variable region amino acid sequence
(SEQ ID NO: 112)
NIVLTQSPASLAVSLGQRATISCRASESVDSYGNSFMHWYQQKPGQAPKLLIYLTSNLES

GVPARFSGSGSRTDFTLTIDPVEADDAATYYCQQNNEDPFTFGSGTKLEIK

12A12 Heavy chain variable region amino acid sequence
(SEQ ID NO: 113)
EVQLQQSGPELVKPGASVKISCKASGYTFTDYNMDWVKQSHGKSLEWIGYIYPNNGGT

GYNQKFNSKATLTVDKSSSTAYMELHSLTSEDSAVYYCASSPYYDYVGSYAMDYWGQ

GTSVTVSS

12A12 Light chain variable region amino acid sequence
(SEQ ID NO: 114)
QIVLTQSPAIMSASLGERVTMTCTASSSVSSSYLHWYQQKPGSSPKLWIYSTSNLASGVP

ARFSGSGSGTSYSLTISSMEAEDAATYYCHQYHRSPRTFGGGTKLEIK

16C5 Heavy chain variable region amino acid sequence
(SEQ ID NO: 115)
EVQLQQSGPELVKPGASVKISCKASGYTFTDYNMDWVKQSHGKSLEWIGYIYPSNGGT

GYNQKFKSKATLTVDKSSNTAYMELHSLTSEDSAVYYCARVPYYDYLYYYAMDYWG

QGTSVTVSS

16C5 Light chain variable region amino acid sequence
(SEQ ID NO: 116)
QIVLSQSPAILSASPGEKVTMACRASSSVSFMHWYQQKPGSSPQPWIYATSNLASGVPAR

FSGSGSGTSYSLTISRVEAEDAATYYCQQWSTNPYMYTFGGGTKLEIK

45G10 Heavy chain variable region amino acid sequence
(SEQ ID NO: 117)
EVQLVESGGGLVKPGGSLKLSCAASGFTFSDYGMHWVRQAPEKGLEWVAYIFSGSSTIY

YADTVKGRFTISRDNAKNTLFLQMTSLRSEDTAMYYCARADGRGAMDYWGQGTSVTV

SS

45G10 Light chain variable region amino acid sequence
(SEQ ID NO: 118)
DVQMTQTTSSLSASLGDRVTISCRASQDISKFLNWYQQKPDGTVTLLIYYTSRLHSGVPS

RFSGSGSGTDYSLTISNLDQEDIATYFCQQGNTLPWTFGGGTKLEIK

48A6 Heavy chain variable region amino acid sequence
(SEQ ID NO: 119)
EVQLVESGGDLMKPGGSLKLSCAASGFTFSSYGMSWVRQTPDKRLEWVATISSGGTYT

FYPDSVKGRFTISRDNAKNTLYLQMSSLKSEDTAMYYCARRGWLLHYYAMDYWGQG

TSVTVSS

48A6 Light chain variable region amino acid sequence
(SEQ ID NO: 120)
NIVLTQSPASLAVSLGQRATISCRPSESVDSFGNSFMHWFQQKPGQPPKLLIYLSSKLESG

VPARFSGSGSRTDFTLTIDPVEADDAATYYCQQHNEDPFTFGSGTKLEIK

53F10 Heavy chain variable region amino acid sequence
(SEQ ID NO: 121)
EVQVVESGGGLVKPGGSLKLSCAASGFTFSDYGMHWVRQAPEKGLEWVAYISTGIITV

YYADTVKGRFTMSRDNAKNTLFLQMTSLRSEDTAIYYCARADGRGAMDYWGQGTSVI

VSS

53F10 Light chain variable region amino acid sequence
(SEQ ID NO: 122)
DIQMTQTTSSLSASLGDRVTISCRASQDISNFLNWYQQKPDGTVTLLIYYTSRLHSGVPS

RFSGSGSGTDYSLTISNLEQEDFATYFCQQGNTLPWTFGGGTKLEIK

Hz5A7.v5 Heavy chain variable region amino acid sequence
(SEQ ID NO: 123)
EVQLVESGGGLVQPGGSLRLSCAASGFTFSSYGMSWVRQAPGKGLEWVATISGGGSYT

NYPDSVKGRFTISRDNAKNSLYLQMNSLRAEDTAVYYCARREWRYTLYAMDYWGQG

TTVTVSS

Hz5A7.v5 Light chain variable region amino acid sequence
(SEQ ID NO: 124)
DIQLTQSPSFLSASVGDRVTITCRASESVESYGSSFMHWYQQKPGKAPKLLIYLTSNLES

GVPSRFSGSGSGTEFTLTISSLQPEDFATYYCQQNNEDPFTFGQGTKLEIK

Hz5A7.v5 Heavy chain amino acid sequence with signal sequence underlined
(SEQ ID NO: 125)
<u>MDMRVPAQLLGLLLLWLRGARC</u>EVQLVESGGGLVQPGGSLRLSCAASGFTFSSYGMS

WVRQAPGKGLEWVATISGGGSYTNYPDSVKGRFTISRDNAKNSLYLQMNSLRAEDTAV

YYCARREWRYTLYAMDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVDVS

HEDPEVKFNWYVDGVEVHNAKTKPREEQYGSTYRVVSVLTVLHQDWLNGKEYKCKV

SNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSL

SLSPGK

Hz5A7.v5 Heavy chain amino acid sequence without signal sequence
(SEQ ID NO: 126)
EVQLVESGGGLVQPGGSLRLSCAASGFTFSSYGMSWVRQAPGKGLEWVATISGGGSYT

NYPDSVKGRFTISRDNAKNSLYLQMNSLRAEDTAVYYCARREWRYTLYAMDYWGQG

TTVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAKT

KPREEQYGSTYRVVSVLTVLHQDWLNGKEYKCKVSNKALPAPIEKTISKAKGQPREPQ

VYTLPPSREEMTKNQVSLTCLVKGFYPSDIA VEWESNGQPENNYKTTPPVLDSDGSFFL

YSKLTVDKSRWQQGNVFSCSVMHEALHNHYTQKSLSLSPGK

Hz5A7.v5 Light chain amino acid sequence with signal sequence underlined (SEQ ID NO: 127)

<u>MDMRVPAQLLGLLLLWLRGARC</u>DIQLTQSPSFLSASVGDRVTITCRASESVESYGSSFM

HWYQQKPGKAPKLLIYLTSNLESGVPSRFSGSGSGTEFTLTISSLQPEDFATYYCQQNNE

DPFTFGQGTKLEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNR

GEC

Hz5A7.v5 Light chain amino acid sequence without signal sequence (SEQ ID NO: 128)

DIQLTQSPSFLSASVGDRVTITCRASESVESYGSSFMHWYQQKPGKAPKLLIYLTSNLES

GVPSRFSGSGSGTEFTLTISSLQPEDFATYYCQQNNEDPFTFGQGTKLEIKRTVAAPSVFIF

PPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC

Human IgG1 constant region (SEQ ID NO: 129)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG1 constant region E233A/L235A (SEQ ID NO: 130)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPALAG

GPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVD

KSRWQQGNVFSCSVMHEALHNHYTQKSLSLSPGK

Human IgG1 constant region L234A/L235A (SEQ ID NO: 131)

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSL

SPGK

Human IgG1 constant region L234A/L235A/P329G (SEQ ID NO: 132)

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEK

```
TISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSL

SPGK
```

Human IgG1 constant region N297G (SEQ ID NO: 133)

```
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

GSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK
```

Human IgG1 constant region N297G/H310A (SEQ ID NO: 134)

```
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

GSTYRVVSVLTVLAQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK
```

Human Kappa light chain constant region (SEQ ID NO: 135)

```
RTVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC
```

Human Lambda light chain constant region (SEQ ID NO: 136)

```
GQPKAAPSVTLFPPSSEELQANKATLVCLISDFYPGAVTVAWKADSSPVKAGVETTTPS

KQSNNKYAASSYLSLTPEQWKSHRSYSCQVTHEGSTVEKTVAPTECS
```

Human ILT3 Ig-like C2-type D1 and D2 amino acid sequence without N-terminal domain (aa 27-218) (SEQ ID NO: 137)

```
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVS
```

Human Fibronectin with predicted signal sequence underlined (SEQ ID NO: 138)

```
MLRGPGPGLLLLAVQCLGTAVPSTGASKSKRQAQQMVQPQSPVAVSQSKPGCYDNGK

HYQINQQWERTYLGNALVCTCYGGSRGFNCESKPEAEETCFDKYTGNTYRVGDTYERP

KDSMIWDCTCIGAGRGRISCTIANRCHEGGQSYKIGDTWRRPHETGGYMLECVCLGNG

KGEWTCKPIAEKCFDHAAGTSYVVGETWEKPYQGWMMVDCTCLGEGSGRITCTSRNR

CNDQDTRTSYRIGDTWSKKDNRGNLLQCICTGNRGEWKCERHTSVQTTSSGSGPFTD

VRAAVYQPQPHPQPPPYGHCVTDSGVVYSVGMQWLKTQGNKQMLCTCLGNGVSCQE

TAVTQTYGGNSNGEPCVLPFTYNGRTFYSCTTEGRQDGHLWCSTTSNYEQDQKYSFCT

DHTVLVQTRGGNSNGALCHFPFLYNNHNYTDCTSEGRRDNMKWCGTTQNYDADQKF

GFCPMAAHEEICTTNEGVMYRIGDQWDKQHDMGHMMRCTCVGNGRGEWTCIAYSQL

RDQCIVDDITYNVNDTFHKRHEEGHMLNCTCFGQGRGRWKCDPVDQCQDSETGTFYQI

GDSWEKYVHGVRYQCYCYGRGIGEWHCQPLQTYPSSSGPVEVFITETPSQPNSHPIQWN
```

-continued

```
APQPSHISKYILRWRPKNSVGRWKEATIPGHLNSYTIKGLKPGVVYEGQLISIQQYGHQE
VTRFDFTTTSTSTPVTSNTVTGETTPFSPLVATSESVTEITASSFVVSWVSASDTVSGFRVE
YELSEEGDEPQYLDLPSTATSVNIPDLLPGRKYIVNVYQISEDGEQSLILSTSQTTAPDAPP
DTTVDQVDDTSIVVRWSRPQAPITGYRIVYSPSVEGSSTELNLPETANSVTLSDLQPGVQ
YNITIYAVEENQESTPVVIQQETTGTPRSDTVPSPRDLQFVEVTDVKVTIMWTPPESAVT
GYRVDVIPVNLPGEHGQRLPISRNTFAEVTGLSPGVTYYFKVFAVSHGRESKPLTAQQTT
KLDAPTNLQFVNETDSTVLVRWTPPRAQITGYRLTVGLTRRGQPRQYNVGPSVSKYPLR
NLQPASEYTVSLVAIKGNQESPKATGVFTTLQPGSSIPPYNTEVTETTIVITWTPAPRIGFK
LGVRPSQGGEAPREVTSDSGSIVVSGLTPGVEYVYTIQVLRDGQERDAPIVNKVVTPLSP
PTNLHLEANPDTGVLTVSWERSTTPDITGYRITTTPTNGQQGNSLEEVVHADQSSCTFDN
LSPGLEYNVSVYTVKDDKESVPISDTIIPEVPQLTDLSFVDITDSSIGLRWTPLNSSTIIGYR
ITVVAAGEGIPIFEDFVDSSVGYYTVTGLEPGIDYDISVITLINGGESAPTTLTQQTAVPPPT
DLRFTNIGPDTMRVTWAPPPSIDLTNFLVRYSPVKNEEDVAELSISPSDNAVVLTNLLPG
TEYVVSVSSVYEQHESTPLRGRQKTGLDSPTGIDFSDITANSFTVHWIAPRATITGYRIRH
HPEHFSGRPREDRVPHSRNSITLTNLTPGTEYVVSIVALNGREESPLLIGQQSTVSDVPRD
LEVVAATPTSLLISWDAPAVTVRYYRITYGETGGNSPVQEFTVPGSKSTATISGLKPGVD
YTITVYAVTGRGDSPASSKPISINYRTEIDKPSQMQVTDVQDNSISVKWLPSSSPVTGYRV
TTTPKNGPGPTKTKTAGPDQTEMTIEGLQPTVEYVVSVYAQNPSGESQPLVQTAVTNID
RPKGLAFTDVDVDSIKIAWESPQGQVSRYRVTYSSPEDGIHELFPAPDGEEDTAELQGLR
PGSEYTVSVVALHDDMESQPLIGTQSTAIPAPTDLKFTQVTPTSLSAQWTPPNVQLTGYR
VRVTPKEKTGPMKEINLAPDSSSVVVSGLMVATKYEVSVYALKDTLTSRPAQGVVTTL
ENVSPPRRARVTDATETTITISWRTKTETITGFQVDAVPANGQTPIQRTIKPDVRSYTITGL
QPGTDYKIYLYTLNDNARSSPVVIDASTAIDAPSNLRFLATTPNSLLVSWQPPRARITGYII
KYEKPGSPPREVVPRPRPGVTEATITGLEPGTEYTIYVIALKNNQKSEPLIGRKKTDELPQ
LVTLPHPNLHGPEILDVPSTVQKTPFVTHPGYDTGNGIQLPGTSGQQPSVGQQMIFEEHG
FRRTTPPTTATPIRHRPRPYPPNVGEEIQIGHIPREDVDYHLYPHGPGLNPNASTGQEALS
QTTISWAPFQDTSEYIISCHPVGTDEEPLQFRVPGTSTSATLTGLTRGATYNVIVEALKDQ
QRHKVREEVVTVGNSVNEGLNQPTDDSCFDPYTVSHYAVGDEWERMSESGFKLLCQC
LGFGSGHFRCDSSRWCHDNGVNYKIGEKWDRQGENGQMMSCTCLGNGKGEFKCDPH
EATCYDDGKTYHVGEQWQKEYLGAICSCTCFGGQRGWRCDNCRRPGGEPSPEGTTGQ
SYNQYSQRYHQRTNTNVNCPIECFMPLDVQADREDSRE
```

Human Fibronectin with predicted signal sequence (SEQ ID NO: 139)

```
QAQQMVQPQSPVAVSQSKPGCYDNGKHYQINQQWERTYLGNALVCTCYGGSRGENCE
SKPEAEETCFDKYTGNTYRVGDTYERPKDSMIWDCTCIGAGRGRISCTIANRCHEGGQS
YKIGDTWRRPHETGGYMLECVCLGNGKGEWTCKPIAEKCFDHAAGTSYVVGETWEKP
YQGWMMVDCTCLGEGSGRITCTSRNRCNDQDTRTSYRIGDTWSKKDNRGNLLQCICTG
NGRGEWKCERHTSVQTTSSGSGPFTDVRAAVYQPQPHPQPPPYGHCVTDSGVVYSVGM
QWLKTQGNKQMLCTCLGNGVSCQETAVTQTYGGNSNGEPCVLPFTYNGRTFYSCTTEG
RQDGHLWCSTTSNYEQDQKYSFCTDHTVLVQTRGGNSNGALCHFPFLYNNHNYTDCTS
EGRRDNMKWCGTTQNYDADQKFGFCPMAAHEEICTTNEGVMYRIGDQWDKQHDMG
```

```
HMMRCTCVGNGRGEWTCIAYSQLRDQCIVDDITYNVNDTFHKRHEEGHMLNCTCFGQ

GRGRWKCDPVDQCQDSETGTFYQIGDSWEKYVHGVRYQCYCYGRGIGEWHCQPLQTY

PSSSGPVEVFITETPSQPNSHPIQWNAPQPSHISKYILRWRPKNSVGRWKEATIPGHLNSY

TIKGLKPGVVYEGQLISIQQYGHQEVTRFDFTTTSTSTPVTSNTVTGETTPFSPLVATSES

VTEITASSFVVSWVSASDTVSGFRVEYELSEEGDEPQYLDLPSTATSVNIPDLLPGRKYIV

NVYQISEDGEQSLILSTSQTTAPDAPPDTTVDQVDDTSIVVRWSRPQAPITGYRIVYSPSV

EGSSTELNLPETANSVTLSDLQPGVQYNITIYAVEENQESTPVVIQQETTGTPRSDTVPSP

RDLQFVEVTDVKVTIMWTPPESAVTGYRVDVIPVNLPGEHGQRLPISRNTFAEVTGLSPG

VTYYFKVFAVSHGRESKPLTAQQTTKLDAPTNLQFVNETDSTVLVRWTPPRAQITGYRL

TVGLTRRGQPRQYNVGPSVSKYPLRNLQPASEYTVSLVAIKGNQESPKATGVFTTLQPG

SSIPPYNTEVTETTIVITWTPAPRIGFKLGVRPSQGGEAPREVTSDSGSIVVSGLTPGVEYV

YTIQVLRDGQERDAPIVNKVVTPLSPPTNLHLEANPDTGVLTVSWERSTTPDITGYRITTT

PTNGQQGNSLEEVVHADQSSCTFDNLSPGLEYNVSVYTVKDDKESVPISDTIIPEVPQLT

DLSFVDITDSSIGLRWTPLNSSTIIGYRITVVAAGEGIPIFEDFVDSSVGYYTVTGLEPGIDY

DISVITLINGGESAPTTLTQQTAVPPPTDLRFTNIGPDTMRVTWAPPPSIDLTNFLVRYSPV

KNEEDVAELSISPSDNAVVLTNLLPGTEYVVSVSSVYEQHESTPLRGRQKTGLDSPTGID

FSDITANSFTVHWIAPRATITGYRIRHHPEHFSGRPREDRVPHSRNSITLTNLTPGTEYVVS

IVALNGREESPLLIGQQSTVSDVPRDLEVVAATPTSLLISWDAPAVTVRYYRITYGETGG

NSPVQEFTVPGSKSTATISGLKPGVDYTITVYAVTGRGDSPASSKPISINYRTEIDKPSQM

QVTDVQDNSISVKWLPSSSPVTGYRVTTTPKNGPGPTKTKTAGPDQTEMTIEGLQPTVE

YVVSVYAQNPSGESQPLVQTAVTNIDRPKGLAFTDVDVDSIKIAWESPQGQVSRYRVTY

SSPEDGIHELFPAPDGEEDTAELQGLRPGSEYTVSVVALHDDMESQPLIGTQSTAIPAPTD

LKFTQVTPTSLSAQWTPPNVQLTGYRVRVTPKEKTGPMKEINLAPDSSSVVVSGLMVAT

KYEVSVYALKDTLTSRPAQGVVTTLENVSPPRRARVTDATETTITISWRTKTETITGFQV

DAVPANGQTPIQRTIKPDVRSYTITGLQPGTDYKIYLYTLNDNARSSPVVIDASTAIDAPS

NLRFLATTPNSLLVSWQPPRARITGYIIKYEKPGSPPREVVPRPRPGVTEATITGLEPGTEY

TIYVIALKNNQKSEPLIGRKKTDELPQLVTLPHPNLHGPEILDVPSTVQKTPFVTHPGYDT

GNGIQLPGTSGQQPSVGQQMIFEEHGFRRTTPPTTATPIRHRPRPYPPNVGEEIQIGHIPRE

DVDYHLYPHGPGLNPNASTGQEALSQTTISWAPFQDTSEYIISCHPVGTDEEPLQFRVPG

TSTSATLTGLTRGATYNVIVEALKDQQRHKVREEVVTVGNSVNEGLNQPTDDSCFDPYT

VSHYAVGDEWERMSESGFKLLCQCLGFGSGHFRCDSSRWCHDNGVNYKIGEKWDRQG

ENGQMMSCTCLGNGKGEFKCDPHEATCYDDGKTYHVGEQWQKEYLGAICSCTCFGGQ

RGWRCDNCRRPGGEPSPEGTTGQSYNQYSQRYHQRTNTNVNCPIECFMPLDVQADRED

SRE
```

Human Fibronectin fragment containing heparin-binding and collagen-binding domains (~70 kDa fragment)

(SEQ ID NO: 140)

```
QAQQMVQPQSPVAVSQSKPGCYDNGKHYQINQQWERTYLGNALVCTCYGGSRGFNCE

SKPEAEETCFDKYTGNTYRVGDTYERPKDSMIWDCTCIGAGRGRISCTIANRCHEGGQS

YKIGDTWRRPHETGGYMLECVCLGNGKGEWTCKPIAEKCFDHAAGTSYVVGETWEKP

YQGWMMVDCTCLGEGSGRITCTSRNRCNDQDTRTSYRIGDTWSKKDNRGNLLQCICTG

NGRGEWKCERHTSVQTTSSGSGPFTDVRAAVYQPQPHPQPPPYGHCVTDSGVVYSVGM
```

```
                          -continued
QWLKTQGNKQMLCTCLGNGVSCQETAVTQTYGGNSNGEPCVLPFTYNGRTFYSCTTEG

RQDGHLWCSTTSNYEQDQKYSFCTDHTVLVQTRGGNSNGALCHFPFLYNNHNYTDCTS

EGRRDNMKWCGTTQNYDADQKFGFCPMAAHEEICTTNEGVMYRIGDQWDKQHDMG

HMMRCTCVGNGRGEWTCIAYSQLRDQCIVDDITYNVNDTFHKRHEEGHMLNCTCFGQ

GRGRWKCDPVDQCQDSETGTFYQIGDSWEKYVHGVRYQCYCYGRGIGEWHCQPLQTY

PSS

Human Fibronectin fragment containing heparin-binding domain (~30 kDa fragment)
                                                                  (SEQ ID NO: 141)
QAQQMVQPQSPVAVSQSKPGCYDNGKHYQINQQWERTYLGNALVCTCYGGSRGENCE

SKPEAEETCFDKYTGNTYRVGDTYERPKDSMIWDCTCIGAGRGRISCTIANRCHEGGQS

YKIGDTWRRPHETGGYMLECVCLGNGKGEWTCKPIAEKCFDHAAGTSYVVGETWEKP

YQGWMMVDCTCLGEGSGRITCTSRNRCNDQDTRTSYRIGDTWSKKDNRGNLLQCICTG

NGRGEWKCER

Human Fibronectin fragment containing collagen-binding domain (~45 kDa fragment)
                                                                  (SEQ ID NO: 142)
HTSVQTTSSGSGPFTDVRAAVYQPQPHPQPPPYGHCVTDSGVVYSVGMQWLKTQGNK

QMLCTCLGNGVSCQETAVTQTYGGNSNGEPCVLPFTYNGRTFYSCTTEGRQDGHLWCS

TTSNYEQDQKYSFCTDHTVLVQTRGGNSNGALCHFPFLYNNHNYTDCTSEGRRDNMK

WCGTTQNYDADQKFGFCPMAAHEEICTTNEGVMYRIGDQWDKQHDMGHMMRCTCV

GNGRGEWTCIAYSQLRDQCIVDDITYNVNDTFHKRHEEGHMLNCTCFGQGRGRWKCD

PVDQCQDSETGTFYQIGDSWEKYVHGVRYQCYCYGRGIGEWHCQPLQTYPSS

Human Fibronectin fragment containing type I repeat 1
                                                                  (SEQ ID NO: 143)
PGCYDNGKHYQINQQWERTYLGNALVCTCYGGSRGFNCESKPEA Human Fibronectin fragment containing type I repeat 2
                                                                  (SEQ ID NO: 144)
ETCFDKYTGNTYRVGDTYERPKDSMIWDCTCIGAGRGRISCTIA Human Fibronectin fragment containing type I repeat 3
                                                                  (SEQ ID NO: 145)
NRCHEGGQSYKIGDTWRRPHETGGYMLECVCLGNGKGEWTCKPI Human Fibronectin fragment containing type I repeat 4
                                                                  (SEQ ID NO: 146)
AEKCFDHAAGTSYVVGETWEKPYQGWMMVDCTCLGEGSGRITCTSR Human Fibronectin fragment containing type I repeat 5
                                                                  (SEQ ID NO: 147)
NRCNDQDTRTSYRIGDTWSKKDNRGNLLQCICTGNGRGEWKCERH Human CNTFR-alpha with predicted signal sequence underlined
                                                                  (SEQ ID NO: 148)
MAAPVPWACCAVLAAAAAVVYAQRHSPQEAPHVQYERLGSDVTLPCGTANWDAAVT

WRVNGTDLAPDLLNGSQLVLHGLELGHSGLYACFHRDSWHLRHQVLLHVGLPPREPVL

SCRSNTYPKGFYCSWHLPTPTYIPNTFNVTVLHGSKIMVCEKDPALKNRCHIRYMHLFST

IKYKVSISVSNALGHNATAITFDEFTIVKPDPPENVVARPVPSNPRRLEVTWQTPSTWPDP

ESFPLKFFLRYRPLILDQWQHVELSDGTAHTITDAYAGKEYIIQVAAKDNEIGTWSDWSV

AAHATPWTEEPRHLTTEAQAAETTTSTTSSLAPPPTTKICDPGELGSGGGPSAPFLVSVPI

TLALAAAAATASSLLI

Human CNTFR-alpha without predicted signal sequence
                                                                  (SEQ ID NO: 149)
QRHSPQEAPHVQYERLGSDVTLPCGTANWDAAVTWRVNGTDLAPDLLNGSQLVLHGL

ELGHSGLYACFHRDSWHLRHQVLLHVGLPPREPVLSCRSNTYPKGFYCSWHLPTPTYIP

NTFNVTVLHGSKIMVCEKDPALKNRCHIRYMHLFSTIKYKVSISVSNALGHNATAITFDE
```

```
FTIVKPDPPENVVARPVPSNPRRLEVTWQTPSTWPDPESFPLKFFLRYRPLILDQWQHVE

LSDGTAHTITDAYAGKEYIIQVAAKDNEIGTWSDWSVAAHATPWTEEPRHLTTEAQAA

ETTTSTTSSLAPPPTTKICDPGELGSGGGPSAPFLVSVPITLALAAAAATASSLLI
```

Human CNTFR-alpha-mature form (SEQ ID NO: 150)

```
QRHSPQEAPHVQYERLGSDVTLPCGTANWDAAVTWRVNGTDLAPDLLNGSQLVLHGL

ELGHSGLYACFHRDSWHLRHQVLLHVGLPPREPVLSCRSNTYPKGFYCSWHLPTPTYIP

NTFNVTVLHGSKIMVCEKDPALKNRCHIRYMHLFSTIKYKVSISVSNALGHNATAITFDE

FTIVKPDPPENVVARPVPSNPRRLEVTWQTPSTWPDPESFPLKFFLRYRPLILDQWQHVE

LSDGTAHTITDAYAGKEYIIQVAAKDNEIGTWSDWSVAAHATPWTEEPRHLTTEAQAA

ETTTSTTSSLAPPPTTKICDPGELGS
```

Human CNTFR-alpha fragment containing Ig-like C2 type domain (SEQ ID NO: 151)

```
QRHSPQEAPHVQYERLGSDVTLPCGTANWDAAVTWRVNGTDLAPDLLNGSQLVLHGL

ELGHSGLYACFHRDSWHLRHQVLLH
```

Human CNTFR-alpha fragment containing FN type III domain 1 (SEQ ID NO: 152)

```
PPREPVLSCRSNTYPKGFYCSWHLPTPTYIPNTFNVTVLHGSKIMVCEKDPALKNRCHIR

YMHLFSTIKYKVSISVSNALGHNATAITFDEFTIVKPDPPENVVARPVPSNPRRLEVT
```

Human CNTFR-alpha fragment containing FN type III domain 2 (SEQ ID NO: 153)

```
WQTPSTWPDPESFPLKFFLRYRPLILDQWQHVELSDGTAHTITDAYAGKEYIIQVAAKD

NEIGTWSDWSVAAHATPWTEEP
```

Hexahistidine peptide tag (SEQ ID NO: 154)

```
HHHHHH
```

Human ILT3 Domain 2 with stem amino acid sequence (aa 124-259) (SEQ ID NO: 155)

```
PTLSALPSPLVTSGKSVTLLCQSRSPMDTFLLIKERAAHPLLHLRSEHGAQQHQAEFPMS

PVTSVHGGTYRCFSSHGFSHYLLSHPSDPLELIVSGSLEDPRPSPTRSVSTAAGPEDQPLM

PTGSVPHSGLRRHWE
```

Hz48A6 heavy chain variable region amino acid sequences
HC-B0 (SEQ ID NO: 156)

```
EVQLVESGGGLVQPGGSLRLSCAASGFTFSSYGMSWVRQAPGKGLEWVATISSGGTYT

FYPDSVKGRFTISRDNAKNSLYLQMNSLRAEDTAVYYCARRGWLLHYYAMDYWGQG

TSVTVSS
```

HC-B1 (SEQ ID NO: 157)

```
EVQLVESGGGLMQPGGSLRLSCAASGFTFSSYGMSWVRQAPGKGLEWVATISSGGTYT

FYPDSVKGRFTISRDNAKNSLYLQMNSLRAEDTAVYYCARRGWLLHYYAMDYWGQG

TSVTVSS
```

HC-C0 (SEQ ID NO: 158)

```
EVQLVESGGGLVQPGGSLRLSCAASGFTFSSYGMSWVRQAPGKGLEWVGTISSGGTYT

FYPDSVKGRFTISRDNSKNTLYLQMNSLRAEDTAVYYCARRGWLLHYYAMDYWGQT

LVTVSS
```

HC-C1 (SEQ ID NO: 159)

```
EVQLVESGGGLVQPGGSLRLSCAASGFTFSSYGMSWVRQAPGKGLEWVATISSGGTYT

FYPDSVKGRFTISRDNSKNTLYLQMNSLRAEDTAVYYCARRGWLLHYYAMDYWGQT
```

-continued

LVTVSSHC-C2

(SEQ ID NO: 160)

EVQLVESGGGLMQPGGSLRLSCAASGFTFSSYGMSWVRQAPGKGLEWVATISSGGTYT

FYPDSVKGRFTISRDNSKNTLYLQMNSLRAEDTAVYYCARRGWLLHYYAMDYWGQGT

LVTVSS

Hz48A6 light chain variable region amino acid sequence
LC-C2

(SEQ ID NO: 161)

DIQLTQSPSFLSASVGDRVTITCRPSESVDSFGNSFMHWFQQKPGKAPKLLIYLSSKLESG

VPSRFSGSGSGTEFTLTISSLQPEDFATYYCQQHNEDPFTFGQGTKVEIK

Hz45G10 heavy chain variable region amino acid sequence
HC-A2

(SEQ ID NO: 162)

EVQLVESGGGLVQPGGSLRLSCAASGFTFSDYGMHWVRQAPGKGLEWVAYIFSGSSTI

YYADTVKGRFTISRDNAKNSLYLQMNSLRAEDTAVYYCARADGRGAMDYWGQGTTV

TVSS

HC-B1

(SEQ ID NO: 163)

EVQLVESGGGLVKPGGSLRLSCAASGFTFSDYGMHWVRQAPGKGLEWVSYIFSGSSTIY

YADTVKGRFTISRDNAKNSLYLQMNSLRAEDTAVYYCARADGRGAMDYWGQGTLVT

VSS

Hz45G10 light chain variable region amino acid sequence
LC-A4

(SEQ ID NO: 164)

DIQMTQSPSSLSASVGDRVTITCRASQDISKFLNWYQQKPGKAPKLLIYYTSRLHSGVPS

RFSGSGSGTDFTFTISSLQPEDIATYFCQQGNTLPWTFGGGTKLEIK

---

What is claimed:

1. A binding agent that specifically binds human immunoglobulin-like transcript 3 (ILT3), comprising:
   (a) a heavy chain variable region (VH) comprising a VH-complementarity determining region (CDR) 1, a VH-CDR2, and a VH-CDR3 from the amino acid sequence of SEQ ID NO: 117 and a light chain variable region (VL) comprising a VL-complementarity determining region (CDR) 1, a VL-CDR2, and a VL-CDR3 from the amino acid sequence of SEQ ID NO: 118;
   (b) a VH comprising a VH-CDR1, a VH-CDR2, and a VH-CDR3 from the amino acid sequence of SEQ ID NO: 119 and a VL comprising a VL-CDR1, a VL-CDR2, and a VL-CDR3 from the amino acid sequence of SEQ ID NO:120;
   (c) a VH comprising a VH-CDR1, a VH-CDR2, and a VH-CDR3 from the amino acid sequence of SEQ ID NO: 109 and a VL comprising a VL-CDR1, a VL-CDR2, and a VL-CDR3 from the amino acid sequence of SEQ ID NO:110;
   (d) a VH comprising a VH-CDR1, a VH-CDR2, and a VH-CDR3 from the amino acid sequence of SEQ ID NO:113 and a VL comprising a VL-CDR1, a VL-CDR2, and a VL-CDR3 from the amino acid sequence of SEQ ID NO:114;
   (e) a VH comprising a VH-CDR1, a VH-CDR2, and a VH-CDR3 from the amino acid sequence of SEQ ID NO:115 and a VL comprising a VL-CDR1, a VL-CDR2, and a VL-CDR3 from the amino acid sequence of SEQ ID NO: 116; or
   (f) a VH comprising a VH-CDR1, a VH-CDR2, and a VH-CDR3 from the amino acid sequence of SEQ ID NO: 121 and a VL comprising a VL-CDR1, a VL-CDR2, and a VL-CDR3 from the amino acid sequence of SEQ ID NO:122.

2. The binding agent of claim 1, wherein:
   (a) the VH comprises the VH-CDR1, the VH-CDR2, and the VH-CDR3 from the amino acid sequence of SEQ ID NO:117; and the VL comprises the VL-CDR1, the VL-CDR2, and the VL-CDR3 from the amino acid sequence of SEQ ID NO: 118, and wherein
      (i) the VH-CDR1 comprises the amino acid sequence of SEQ ID NO:71, the VH-CDR2 comprises the amino acid sequence of SEQ ID NO:72, the VH-CDR3 comprises the amino acid sequence of SEQ ID NO:73, the VL-CDR1 comprises the amino acid sequence of SEQ ID NO: 74, the VL-CDR2 comprises the amino acid sequence of SEQ ID NO:75, and the VL-CDR3 comprises the amino acid sequence of SEQ ID NO:76;
      (ii) the VH-CDR1 comprises the amino acid sequence of SEQ ID NO:77, the VH-CDR2 comprises the amino acid sequence of SEQ ID NO:78, the VH-CDR3 comprises the amino acid sequence of SEQ ID NO:73, the VL-CDR1 comprises the amino acid sequence of SEQ ID NO: 74, the VL-CDR2 comprises the amino acid sequence of SEQ ID NO:75, and the VL-CDR3 comprises the amino acid sequence of SEQ ID NO:76;
      (iii) the VH-CDR1 comprises the amino acid sequence of SEQ ID NO:71, the VH-CDR2 comprises the amino acid sequence of SEQ ID NO:79, the VH-CDR3 comprises the amino acid sequence of SEQ ID NO:73, the VL-CDR1 comprises the amino acid sequence of SEQ ID NO: 74, the VL-CDR2 comprises the amino acid sequence of SEQ ID NO:75, and the VL-CDR3 comprises the amino acid sequence of SEQ ID NO:76;
      (iv) the VH-CDR1 comprises the amino acid sequence of SEQ ID NO:80, the VH-CDR2 comprises the amino acid sequence of SEQ ID NO:72, the VH-CDR3 comprises the amino acid sequence of SEQ ID NO:73, the VL-CDR1 comprises the amino acid sequence of SEQ ID NO: 74, the VL-CDR2 comprises the amino acid sequence of SEQ ID NO:75, and the VL-CDR3 comprises the amino acid sequence of SEQ ID NO:76; or
      (v) the VH-CDR1 comprises the amino acid sequence of SEQ ID NO:81, the VH-CDR2 comprises the amino acid sequence of SEQ ID NO:82, the VH-CDR3 comprises the amino acid sequence of SEQ ID NO:83, the VL-CDR1 comprises the amino acid sequence of SEQ ID NO: 84, the VL-CDR2 comprises the amino acid sequence of SEQ ID NO:85, and the VL-CDR3 comprises the amino acid sequence of SEQ ID NO:86; or (b) the VH comprises the VH-CDR1, the VH-CDR2, and the VH-CDR3 from the amino acid sequence of SEQ ID NO:119; and the VL comprises the VL-CDR1, the VL-CDR2, and the VL-CDR3 from the amino acid sequence of SEQ ID NO:120, and wherein
  (i) the VH-CDR1 comprises the amino acid sequence of SEQ ID NO:27, the VH-CDR2 comprises the amino acid sequence of SEQ ID NO:87, the VH-CDR3 comprises the amino acid sequence of SEQ ID NO:88, the VL-CDR1 comprises the amino acid sequence of SEQ ID NO: 89, the VL-CDR2 comprises the amino acid sequence of SEQ ID NO:90, and the VL-CDR3 comprises the amino acid sequence of SEQ ID NO:91;
  (ii) the VH-CDR1 comprises the amino acid sequence of SEQ ID NO:33, the VH-CDR2 comprises the amino acid sequence of SEQ ID NO:92, the VH-CDR3 comprises the amino acid sequence of SEQ ID NO:88, the VL-CDR1 comprises the amino acid sequence of SEQ ID NO: 89, the VL-CDR2 comprises the amino acid sequence of SEQ ID NO:90, and the VL-CDR3 comprises the amino acid sequence of SEQ ID NO:91;
  (iii) the VH-CDR1 comprises the amino acid sequence of SEQ ID NO:27, the VH-CDR2 comprises the amino acid sequence of SEQ ID NO:93, the VH-CDR3 comprises the amino acid sequence of SEQ ID NO:88, the VL-CDR1 comprises the amino acid sequence of SEQ ID NO: 89, the VL-CDR2 comprises the amino acid sequence of SEQ ID NO:90, and the VL-CDR3 comprises the amino acid sequence of SEQ ID NO:91;
  (iv) the VH-CDR1 comprises the amino acid sequence of SEQ ID NO:36, the VH-CDR2 comprises the amino acid sequence of SEQ ID NO:87, the VH-CDR3 comprises the amino acid sequence of SEQ ID NO:88, the VL-CDR1 comprises the amino acid sequence of SEQ ID NO: 89, the VL-CDR2 comprises the amino acid sequence of SEQ ID NO:90, and the VL-CDR3 comprises the amino acid sequence of SEQ ID NO:91; or
  (v) the VH-CDR1 comprises the amino acid sequence of SEQ ID NO:37, the VH-CDR2 comprises the amino acid sequence of SEQ ID NO:94, the VH-CDR3 comprises the amino acid sequence of SEQ ID NO:95, the VL-CDR1 comprises the amino acid sequence of SEQ ID NO: 96, the VL-CDR2 comprises the amino acid sequence of SEQ ID NO:97, and the VL-CDR3 comprises the amino acid sequence of SEQ ID NO:98; or
(c) the VH comprises the VH-CDR1, the VH-CDR2, and the VH-CDR3 from the amino acid sequence of SEQ ID NO:109; and the VL comprises the VL-CDR1, the VL-CDR2, and the VL-CDR3 from the amino acid sequence of SEQ ID NO:110, and wherein
  (i) the VH-CDR1 comprises the amino acid sequence of SEQ ID NO:11, the VH-CDR2 comprises the amino acid sequence of SEQ ID NO:12, the VH-CDR3 comprises the amino acid sequence of SEQ ID NO:13, the VL-CDR1 comprises the amino acid sequence of SEQ ID NO: 14, the VL-CDR2 comprises the amino acid sequence of SEQ ID NO:15, and the VL-CDR3 comprises the amino acid sequence of SEQ ID NO:16;
  (ii) the VH-CDR1 comprises the amino acid sequence of SEQ ID NO:17, the VH-CDR2 comprises the amino acid sequence of SEQ ID NO:18, the VH-CDR3 comprises the amino acid sequence of SEQ ID NO:13, the VL-CDR1 comprises the amino acid sequence of SEQ ID NO: 14, the VL-CDR2 comprises the amino acid sequence of SEQ ID NO: 15, and the VL-CDR3 comprises the amino acid sequence of SEQ ID NO: 16;
  (iii) the VH-CDR1 comprises the amino acid sequence of SEQ ID NO:11, the VH-CDR2 comprises the amino acid sequence of SEQ ID NO: 19, the VH-CDR3 comprises the amino acid sequence of SEQ ID NO:13, the VL-CDR1 comprises the amino acid sequence of SEQ ID NO: 14, the VL-CDR2 comprises the amino acid sequence of SEQ ID NO: 15, and the VL-CDR3 comprises the amino acid sequence of SEQ ID NO:16;
  (iv) the VH-CDR1 comprises the amino acid sequence of SEQ ID NO:20, the VH-CDR2 comprises the amino acid sequence of SEQ ID NO:12, the VH-CDR3 comprises the amino acid sequence of SEQ ID NO: 13, the VL-CDR1 comprises the amino acid sequence of SEQ ID NO: 14, the VL-CDR2 comprises the amino acid sequence of SEQ ID NO:15, and the VL-CDR3 comprises the amino acid sequence of SEQ ID NO:16; or
  (v) the VH-CDR1 comprises the amino acid sequence of SEQ ID NO:21, the VH-CDR2 comprises the amino acid sequence of SEQ ID NO:22, the VH-CDR3 comprises the amino acid sequence of SEQ ID NO:23, the VL-CDR1 comprises the amino acid sequence of SEQ ID NO: 24, the VL-CDR2 comprises the amino acid sequence of SEQ ID NO:25, and the VL-CDR3 comprises the amino acid sequence of SEQ ID NO:26; or
(d) the VH comprises the VH-CDR1, the VH-CDR2, and the VH-CDR3 from the amino acid sequence of SEQ ID NO: 113; and the VL comprises the VL-CDR1, the VL-CDR2, and the VL-CDR3 from the amino acid sequence of SEQ ID NO:114, and wherein
  (i) the VH-CDR1 comprises the amino acid sequence of SEQ ID NO:43, the VH-CDR2 comprises the amino acid sequence of SEQ ID NO:44, the VH-CDR3 comprises the amino acid sequence of SEQ ID NO:45, the VL-CDR1 comprises the amino acid sequence of SEQ ID NO: 46, the VL-CDR2 comprises the amino acid sequence of SEQ ID NO:47, and the VL-CDR3 comprises the amino acid sequence of SEQ ID NO:48;
  (ii) the VH-CDR1 comprises the amino acid sequence of SEQ ID NO:49, the VH-CDR2 comprises the amino acid sequence of SEQ ID NO:50, the VH-CDR3 comprises the amino acid sequence of SEQ ID NO:45, the VL-CDR1 comprises the amino acid sequence of SEQ ID NO: 46, the VL-CDR2 comprises the amino acid sequence of SEQ ID NO:47, and the VL-CDR3 comprises the amino acid sequence of SEQ ID NO:48;
  (iii) the VH-CDR1 comprises the amino acid sequence of SEQ ID NO:43, the VH-CDR2 comprises the amino acid sequence of SEQ ID NO:51, the VH-CDR3 comprises the amino acid sequence of SEQ ID NO:45, the VL-CDR1 comprises the amino acid sequence of SEQ ID NO: 46, the VL-CDR2 comprises the amino acid sequence of SEQ ID NO:47, and the VL-CDR3 comprises the amino acid sequence of SEQ ID NO:48;
  (iv) the VH-CDR1 comprises the amino acid sequence of SEQ ID NO:52, the VH-CDR2 comprises the amino acid sequence of SEQ ID NO:44, the VH-CDR3 comprises the amino acid sequence of SEQ ID NO:45, the VL-CDR1 comprises the amino acid sequence of SEQ ID NO: 46, the VL-CDR2 comprises the amino acid sequence of SEQ ID NO:47, and the VL-CDR3 comprises the amino acid sequence of SEQ ID NO:48; or (v) the VH-CDR1 comprises the amino acid sequence of SEQ ID NO:53, the VH-CDR2 comprises the amino acid sequence of SEQ ID NO:54, the VH-CDR3 comprises the amino acid sequence of SEQ ID NO:55, the VL-CDR1 comprises the amino acid sequence of SEQ ID NO: 56, the VL-CDR2 comprises the amino acid sequence of SEQ ID NO:57, and the VL-CDR3 comprises the amino acid sequence of SEQ ID NO:58; or (e) the VH comprises the VH-CDR1, the VH-CDR2, and the VH-CDR3 from the amino acid sequence of SEQ ID NO: 115; and the VL comprises the VL-CDR1, the VL-CDR2, and the VL-CDR3 from the amino acid sequence of SEQ ID NO:116, and wherein (i) the VH-CDR1 comprises the amino acid sequence of SEQ ID NO:43, the VH-CDR2 comprises the amino acid sequence of SEQ ID NO:59, the VH-CDR3 comprises the amino acid sequence of SEQ ID NO:60, the VL-CDR1 comprises the amino acid sequence of SEQ ID NO: 61, the VL-CDR2 comprises the amino acid sequence of SEQ ID NO:62, and the VL-CDR3 comprises the amino acid sequence of SEQ ID NO:63;

(ii) the VH-CDR1 comprises the amino acid sequence of SEQ ID NO:49, the VH-CDR2 comprises the amino acid sequence of SEQ ID NO:64, the VH-CDR3 comprises the amino acid sequence of SEQ ID NO:60, the VL-CDR1 comprises the amino acid sequence of SEQ ID NO: 61, the VL-CDR2 comprises the amino acid sequence of SEQ ID NO:62, and the VL-CDR3 comprises the amino acid sequence of SEQ ID NO:63;

(iii) the VH-CDR1 comprises the amino acid sequence of SEQ ID NO:43, the VH-CDR2 comprises the amino acid sequence of SEQ ID NO:65, the VH-CDR3 comprises the amino acid sequence of SEQ ID NO:60, the VL-CDR1 comprises the amino acid sequence of SEQ ID NO: 61, the VL-CDR2 comprises the amino acid sequence of SEQ ID NO:62, and the VL-CDR3 comprises the amino acid sequence of SEQ ID NO:63;

(iv) the VH-CDR1 comprises the amino acid sequence of SEQ ID NO:52, the VH-CDR2 comprises the amino acid sequence of SEQ ID NO:59, the VH-CDR3 comprises the amino acid sequence of SEQ ID NO:60, the VL-CDR1 comprises the amino acid sequence of SEQ ID NO: 61, the VL-CDR2 comprises the amino acid sequence of SEQ ID NO:62, and the VL-CDR3 comprises the amino acid sequence of SEQ ID NO:63; or (v) the VH-CDR1 comprises the amino acid sequence of SEQ ID NO:53, the VH-CDR2 comprises the amino acid sequence of SEQ ID NO:66, the VH-CDR3 comprises the amino acid sequence of SEQ ID NO:67, the VL-CDR1 comprises the amino acid sequence of SEQ ID NO: 68, the VL-CDR2 comprises the amino acid sequence of SEQ ID NO:69, and the VL-CDR3 comprises the amino acid sequence of SEQ ID NO:70; or (f) the VH comprises the VH-CDR1, the VH-CDR2, and the VH-CDR3 from the amino acid sequence of SEQ ID NO:121 and the VL comprises the VL-CDR1, the VL-CDR2, and the VL-CDR3 from the amino acid sequence of SEQ ID NO: 122, and wherein (i) the VH-CDR1 comprises the amino acid sequence of SEQ ID NO:71, the VH-CDR2 comprises the amino acid sequence of SEQ ID NO:99, the VH-CDR3 comprises the amino acid sequence of SEQ ID NO:73, the VL-CDR1 comprises the amino acid sequence of SEQ ID NO: 100, the VL-CDR2 comprises the amino acid sequence of SEQ ID NO:75, and the VL-CDR3 comprises the amino acid sequence of SEQ ID NO:76;

(ii) the VH-CDR1 comprises the amino acid sequence of SEQ ID NO:77, the VH-CDR2 comprises the amino acid sequence of SEQ ID NO:101, the VH-CDR3 comprises the amino acid sequence of SEQ ID NO:73, the VL-CDR1 comprises the amino acid sequence of SEQ ID NO: 100, the VL-CDR2 comprises the amino acid sequence of SEQ ID NO:75, and the VL-CDR3 comprises the amino acid sequence of SEQ ID NO:76;

(iii) the VH-CDR1 comprises the amino acid sequence of SEQ ID NO:71, the VH-CDR2 comprises the amino acid sequence of SEQ ID NO:102, the VH-CDR3 comprises the amino acid sequence of SEQ ID NO:73, the VL-CDR1 comprises the amino acid sequence of SEQ ID NO: 100, the VL-CDR2 comprises the amino acid sequence of SEQ ID NO:75, and the VL-CDR3 comprises the amino acid sequence of SEQ ID NO:76;

(iv) the VH-CDR1 comprises the amino acid sequence of SEQ ID NO:80, the VH-CDR2 comprises the amino acid sequence of SEQ ID NO:99, the VH-CDR3 comprises the amino acid sequence of SEQ ID NO:73, the VL-CDR1 comprises the amino acid sequence of SEQ ID NO: 100, the VL-CDR2 comprises the amino acid sequence of SEQ ID NO:75, and the VL-CDR3 comprises the amino acid sequence of SEQ ID NO:76; or (v) the VH-CDR1 comprises the amino acid sequence of SEQ ID NO:81, the VH-CDR2 comprises the amino acid sequence of SEQ ID NO: 103, the VH-CDR3 comprises the amino acid sequence of SEQ ID NO:83, the VL-CDR1 comprises the amino acid sequence of SEQ ID NO: 104, the VL-CDR2 comprises the amino acid sequence of SEQ ID NO:85, and the VL-CDR3 comprises the amino acid sequence of SEQ ID NO:86.

3. The binding agent of claim 1, wherein:

(a) the VH comprises the amino acid sequence of SEQ ID NO:117, and/or the VL comprises the amino acid sequence of SEQ ID NO:118;

(b) the VH comprises the amino acid sequence of SEQ ID NO:119, and/or the VL comprises the amino acid sequence of SEQ ID NO:120;

(c) the VH comprises the amino acid sequence of SEQ ID NO:109, and/or the VL comprises the amino acid sequence of SEQ ID NO:110;

(d) the VH comprises the amino acid sequence of SEQ ID NO:113, and/or the VL comprises the amino acid sequence of SEQ ID NO:114;

(e) the VH comprises the amino acid sequence of SEQ ID NO:115, and/or the VL comprises the amino acid sequence of SEQ ID NO:116; or (f) the VH comprises the amino acid sequence of SEQ ID NO:121, and/or the VL comprises the amino acid sequence of SEQ ID NO:122.

4. The binding agent of claim 1, wherein:
(a) the VH comprises the amino acid sequence of SEQ ID NO:162, and/or the VL comprises the amino acid sequence of SEQ ID NO:164;
(b) the VH comprises the amino acid sequence of SEQ ID NO:163, and/or the VL comprises the amino acid sequence of SEQ ID NO:164;
(c) the VH comprises the amino acid sequence of SEQ ID NO:156, and/or the VL comprises the amino acid sequence of SEQ ID NO:161;
(d) the VH comprises the amino acid sequence of SEQ ID NO:157, and/or the VL comprises the amino acid sequence of SEQ ID NO:161;
(e) the VH comprises the amino acid sequence of SEQ ID NO:158, and/or the VL comprises the amino acid sequence of SEQ ID NO:161;
(f) the VH comprises the amino acid sequence of SEQ ID NO:159, and/or the VL comprises the amino acid sequence of SEQ ID NO:161; or
(g) the VH comprises the amino acid sequence of SEQ ID NO:160, and/or the VL comprises the amino acid sequence of SEQ ID NO:161.

5. The binding agent of claim 1, which is
(i) a whole antibody;
(ii) an antibody fragment comprising at least one antigen-binding site;
(iii) a chimeric antibody;
(iv) a recombinant antibody;
(v) a humanized antibody;
(vi) a bispecific or multispecific antibody;
(vii) an IgG1 antibody, an IgG2 antibody, or an IgG4 antibody; or
(vii) attached to a half-life extending moiety.

6. The binding agent of claim 5, wherein the antibody fragment is a Fab, a Fab', a F (ab')$_2$, a Fv, an scFv, an (scFv)$_2$, a single chain antibody, a dual variable region antibody, a diabody, or a nanobody.

7. The binding agent of claim 1, comprising
(i) a kappa light chain constant region or a lambda light chain constant region; or
(ii) a human IgG1 constant region and a human kappa light chain constant region.

8. The binding agent of claim 7, wherein the human IgG1 constant region comprises one or more mutations that reduce or eliminate effector functions.

9. The binding agent of claim 1, wherein the binding agent has one or more of the following properties:
(i) binding cynomolgus ILT3;
(ii) binding human and cynomolgus ILT3;
(iii) not binding ILT2, ILT4, ILT5, or LILRB5;
(iv) not binding LILRA1, LILRA2, LILRA4, LILRA5, or LILRA6;
(v) being an ILT3 antagonist;
(vi) inhibiting ILT3 activity;
(vii) inhibiting ILT3 signaling in cells that express ILT3;
(viii) inhibiting binding of ILT3 to APOE;
(ix) inhibiting binding of ILT3 to fibronectin;
(x) inhibiting binding of ILT3 to CNTFR;
(xi) inhibiting ILT3-induced suppression of myeloid cells;
(xii) inhibiting ILT3-induced suppression of myeloid cell activity;
(xiii) restoring FcR activation in myeloid cells that express ILT3; and
(xiv) restoring chemokine production in myeloid cells that express ILT3.

10. The binding agent of claim 9, wherein the binding agent has a $K_D$ for human ILT3 of from 1 µM to 1 pM as assessed by Surface Plasmon Resonance (SPR).

11. A pharmaceutical composition comprising the binding agent of claim 1 and a pharmaceutically acceptable carrier.

12. An isolated polynucleotide or polynucleotides encoding the binding agent of claim 1.

13. A vector or vectors comprising the polynucleotide or polynucleotides of claim 12.

14. An isolated cell comprising the polynucleotide or polynucleotides of claim 12, or a vector or vectors comprising the polynucleotide or polynucleotides of claim 12.

15. A method of making a binding agent that specifically binds human ILT3, the method comprising:
(a) culturing the cell of claim 14 under conditions that result in the expression of the binding agent, and
(b) isolating the binding agent.

16. The method of claim 15, wherein the method further comprises formulating the binding agent as a sterile pharmaceutical composition.

17. A method of (i) disrupting, inhibiting, or blocking the binding of ILT3 to fibronectin or fibronectin-induced ILT3 activity in a mixture of cells or (ii) disrupting, inhibiting, or blocking ILT3-induced suppression of myeloid cells or ILT3-induced suppression of myeloid cell activity, the method comprising contacting the cells or the myeloid cells with the binding agent of claim 1.

18. A method of disrupting, inhibiting, or blocking the binding of ILT3 to fibronectin or fibronectin-induced ILT3 activity in a subject, the method comprising administering to the subject a therapeutically effective amount of the binding agent of claim 1.

19. A method of disrupting, inhibiting, or blocking ILT3-induced suppression of myeloid cells or ILT3-induced suppression of myeloid cell activity in a subject, the method comprising administering to the subject the binding agent of claim 1 in an amount sufficient to activate the myeloid cells.

20. A method of
(i) treating cancer, or inhibiting tumor growth, tumor relapse, or tumor regrowth in a subject,
(ii) increasing or enhancing an immune response to a tumor or tumor cells in a subject, or
(iii) activating myeloid cells in the tumor microenvironment in a subject with a tumor,
the method comprising administering to the subject a therapeutically effective amount of the binding agent of claim 1.

21. The method of claim 20, wherein (i) the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, urinary bladder cancer, brain cancer, esophageal cancer, liver cancer, kidney cancer, sarcoma, or testicular cancer, and/or (ii) the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a sarcoma, or a testicular tumor.

22. The method of claim 20, wherein the cancer is hematologic cancer.

23. The method of claim 22, wherein the hematologic cancer is myelogenous leukemia, acute myeloid leukemia (AML), chronic myeloid leukemia, or myelodysplastic syndrome.

24. The method of claim 20, wherein the binding agent is administered as part of a combination therapy comprising a PD-1 antagonist.

25. The method of claim 24, wherein the PD-1 antagonist is an anti-PD-1 antibody.

26. The method of claim 25, wherein the anti-PD-1 antibody is pembrolizumab.

* * * * *